United States Patent
Johnson

(10) Patent No.: US 9,695,134 B2
(45) Date of Patent: *Jul. 4, 2017

(54) 3,5-DIAMINO-6-CHLORO-N-(N-(4-PHENYLBUTYL)CARBAMIMIDOYL)PYRAZINE-2-CARBOXAMIDE COMPOUNDS

(71) Applicant: PARION SCIENCES, INC., Durham, NC (US)

(72) Inventor: Michael R. Johnson, Chapel Hill, NC (US)

(73) Assignee: Parion Sciences, Inc., Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/592,480

(22) Filed: Jan. 8, 2015

(65) Prior Publication Data

US 2015/0299142 A1 Oct. 22, 2015

Related U.S. Application Data

(63) Continuation of application No. 14/106,098, filed on Dec. 13, 2013, now Pat. No. 9,029,382.

(60) Provisional application No. 61/738,235, filed on Dec. 17, 2012.

(51) Int. Cl.
| | |
|---|---|
| A61K 31/4965 | (2006.01) |
| C07D 241/28 | (2006.01) |
| A61K 45/06 | (2006.01) |
| A61K 9/00 | (2006.01) |
| A61K 47/26 | (2006.01) |
| A61K 33/14 | (2006.01) |

(52) U.S. Cl.
CPC .............. *C07D 241/28* (2013.01); *A61K 9/00* (2013.01); *A61K 9/008* (2013.01); *A61K 9/0075* (2013.01); *A61K 9/0078* (2013.01); *A61K 31/4965* (2013.01); *A61K 33/14* (2013.01); *A61K 45/06* (2013.01); *A61K 47/26* (2013.01)

(58) Field of Classification Search
CPC .................................................. C07D 241/28
See application file for complete search history.

(56) References Cited

U.S. PATENT DOCUMENTS

| | | |
|---|---|---|
| 3,240,780 A | 3/1966 | Cragoe, Jr. et al. |
| 3,249,610 A | 5/1966 | Cragoe, Jr. et al. |
| 3,268,406 A | 8/1966 | Cragoe, Jr. et al. |
| 3,274,191 A | 9/1966 | Cragoe, Jr. et al. |
| 3,274,192 A | 9/1966 | Cragoe, Jr. et al. |
| 3,290,311 A | 12/1966 | Cragoe, Jr. et al. |
| 3,299,063 A | 1/1967 | Cragoe, Jr. et al. |
| 3,300,494 A | 1/1967 | Cragoe, Jr. et al. |
| 3,305,552 A | 2/1967 | Cragoe, Jr. et al. |
| 3,313,813 A | 4/1967 | Cragoe |
| 3,316,266 A | 4/1967 | Tull et al. |
| 3,325,494 A | 6/1967 | Weinstock et al. |
| 3,341,540 A | 9/1967 | Cragoe, Jr. et al. |
| 3,359,269 A | 12/1967 | Cragoe, Jr. et al. |
| 3,360,517 A | 12/1967 | Cragoe, Jr. et al. |
| 3,361,748 A | 1/1968 | Cragoe, Jr. et al. |
| 3,461,123 A | 8/1969 | Jones et al. |
| 3,472,848 A | 10/1969 | Cragoe, Jr. et al. |
| 3,487,082 A | 12/1969 | Cragoe, Jr. et al. |
| 3,491,094 A | 1/1970 | Cragoe, Jr. et al. |
| 3,503,973 A | 3/1970 | Cragoe, Jr. et al. |
| 3,506,662 A | 4/1970 | Cragoe, Jr. et al. |
| 3,507,865 A | 4/1970 | Jones et al. |
| 3,507,866 A | 4/1970 | Jones et al. |
| 3,515,723 A | 6/1970 | Cragoe, Jr. et al. |
| 3,527,758 A | 9/1970 | Cragoe, Jr. et al. |
| 3,531,484 A | 9/1970 | Bicking et al. |
| 3,539,569 A | 11/1970 | Tull et al. |

(Continued)

FOREIGN PATENT DOCUMENTS

| | | |
|---|---|---|
| AU | 2003/211135 A1 | 9/2003 |
| AU | 2004/212962 A1 | 9/2004 |

(Continued)

OTHER PUBLICATIONS

U.S. Appl. No. 11/696,003, filed Apr. 3, 2007, Johnson.

(Continued)

*Primary Examiner* — Brian McDowell
(74) *Attorney, Agent, or Firm* — Wolf, Greenfield & Sacks, P.C.

(57) ABSTRACT

The present invention relates compounds of the formula:

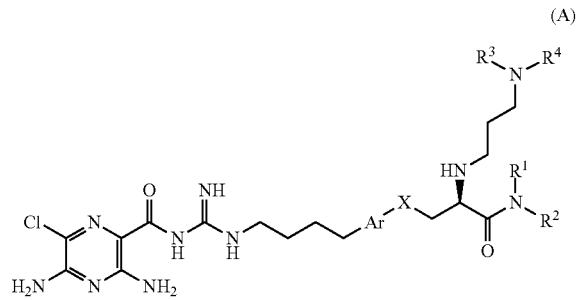

(A)

or pharmaceutically acceptable salts thereof, useful as sodium channel blockers, as well as compositions containing the same, processes for the preparation of the same, and therapeutic methods of use therefore in promoting hydration of mucosal surfaces and the treatment of diseases including cystic fibrosis, chronic obstructive pulmonary disease, asthma, bronchiectasis, acute and chronic bronchitis, emphysema, and pneumonia.

20 Claims, 7 Drawing Sheets

(56) References Cited

U.S. PATENT DOCUMENTS

| | | |
|---|---|---|
| 3,544,568 A | 12/1970 | Cragoe, Jr. et al. |
| 3,544,571 A | 12/1970 | Cragoe, Jr. et al. |
| 3,555,023 A | 1/1971 | Cragoe, Jr. et al. |
| 3,555,024 A | 1/1971 | Cragoe, Jr. et al. |
| 3,573,305 A | 3/1971 | Cragoe, Jr. et al. |
| 3,573,306 A | 3/1971 | Shepard et al. |
| 3,575,975 A | 4/1971 | Cragoe, Jr. et al. |
| 3,577,418 A | 5/1971 | Cragoe, Jr. et al. |
| 3,586,688 A | 6/1971 | Cragoe, Jr. et al. |
| 3,625,950 A | 12/1971 | Cragoe, Jr. et al. |
| 3,660,397 A | 5/1972 | Jones et al. |
| 3,660,400 A | 5/1972 | Cragoe, Jr. et al. |
| 3,668,241 A | 6/1972 | Cragoe, Jr. et al. |
| 3,794,734 A | 2/1974 | Cragoe, Jr. et al. |
| 3,864,401 A | 2/1975 | Schultz et al. |
| 3,894,065 A | 7/1975 | Cragoe, Jr. et al. |
| 3,894,085 A | 7/1975 | Eschenmoser |
| 3,914,253 A | 10/1975 | Cragoe, Jr. et al. |
| 3,928,624 A | 12/1975 | Cragoe, Jr. et al. |
| 3,929,872 A | 12/1975 | Cragoe, Jr. et al. |
| 3,931,239 A | 1/1976 | Cragoe, Jr. et al. |
| 3,935,313 A | 1/1976 | Aron-Samuel et al. |
| 3,948,895 A | 4/1976 | Donald |
| 3,953,476 A | 4/1976 | Cragoe, Jr. et al. |
| 3,956,374 A | 5/1976 | Shepard et al. |
| 3,958,004 A | 5/1976 | Cragoe, Jr. et al. |
| 3,966,966 A | 6/1976 | Cragoe, Jr. et al. |
| 3,974,212 A | 8/1976 | Cragoe, Jr. et al. |
| 3,976,681 A | 8/1976 | Cragoe, Jr. et al. |
| 3,976,686 A | 8/1976 | Cragoe, Jr. et al. |
| 3,979,361 A | 9/1976 | Schultz et al. |
| 3,984,465 A | 10/1976 | Cragoe, Jr. et al. |
| 3,984,552 A | 10/1976 | Cragoe, Jr. et al. |
| 3,987,091 A | 10/1976 | Cragoe, Jr. et al. |
| 3,989,749 A | 11/1976 | Cragoe, Jr. et al. |
| 3,991,087 A | 11/1976 | Cragoe, Jr. et al. |
| 3,991,106 A | 11/1976 | Cragoe, Jr. et al. |
| 4,003,927 A | 1/1977 | Woltersdorf, Jr. et al. |
| 4,006,180 A | 2/1977 | Cragoe, Jr. et al. |
| 4,012,524 A | 3/1977 | Cragoe, Jr. et al. |
| 4,018,802 A | 4/1977 | Cragoe, Jr. et al. |
| 4,020,177 A | 4/1977 | Cragoe, Jr. et al. |
| 4,022,794 A | 5/1977 | Smith et al. |
| 4,025,625 A | 5/1977 | Rooney et al. |
| 4,029,803 A | 6/1977 | Hunter et al. |
| 4,029,816 A | 6/1977 | Cragoe, Jr. et al. |
| 4,033,996 A | 7/1977 | Cragoe, Jr. et al. |
| 4,044,153 A | 8/1977 | Schultz et al. |
| 4,054,652 A | 10/1977 | Rooney et al. |
| 4,055,596 A | 10/1977 | Cragoe, Jr. et al. |
| 4,055,597 A | 10/1977 | Cragoe, Jr. et al. |
| 4,059,087 A | 11/1977 | Tanigami et al. |
| 4,059,601 A | 11/1977 | Cragoe, Jr. et al. |
| 4,059,602 A | 11/1977 | Cragoe, Jr. et al. |
| 4,061,643 A | 12/1977 | Cragoe, Jr. et al. |
| 4,066,675 A | 1/1978 | Cragoe, Jr. et al. |
| 4,066,692 A | 1/1978 | Cragoe, Jr. et al. |
| 4,067,980 A | 1/1978 | Cragoe, Jr. et al. |
| 4,070,464 A | 1/1978 | Cragoe, Jr. et al. |
| 4,070,539 A | 1/1978 | Cragoe, Jr. et al. |
| 4,081,554 A | 3/1978 | Cragoe, Jr. et al. |
| 4,085,117 A | 4/1978 | Cragoe, Jr. et al. |
| 4,085,125 A | 4/1978 | Cragoe, Jr. et al. |
| 4,085,211 A | 4/1978 | Cragoe, Jr. et al. |
| 4,085,219 A | 4/1978 | Cragoe, Jr. et al. |
| 4,087,435 A | 5/1978 | Cragoe, Jr. et al. |
| 4,087,526 A | 5/1978 | Cragoe, Jr. et al. |
| 4,087,542 A | 5/1978 | Cragoe, Jr. et al. |
| 4,091,015 A | 5/1978 | Strike |
| 4,091,105 A | 5/1978 | Rokach et al. |
| 4,091,107 A | 5/1978 | Cragoe, Jr. et al. |
| 4,092,356 A | 5/1978 | Cragoe, Jr. et al. |
| 4,092,414 A | 5/1978 | Cragoe, Jr. et al. |
| 4,096,267 A | 6/1978 | Cragoe, Jr. et al. |
| 4,097,504 A | 6/1978 | Cragoe, Jr. et al. |
| 4,100,294 A | 7/1978 | Cragoe, Jr. et al. |
| 4,102,888 A | 7/1978 | Smith et al. |
| 4,105,769 A | 8/1978 | Rooney et al. |
| 4,108,859 A | 8/1978 | Tong |
| 4,111,877 A | 9/1978 | Dixon et al. |
| 4,112,236 A | 9/1978 | Bicking et al. |
| 4,115,402 A | 9/1978 | Cragoe, Jr. et al. |
| 4,115,573 A | 9/1978 | Cragoe, Jr. et al. |
| 4,126,629 A | 11/1978 | Cragoe, Jr. et al. |
| 4,127,584 A | 11/1978 | Rokach et al. |
| 4,127,587 A | 11/1978 | Wade et al. |
| 4,128,564 A | 12/1978 | Cragoe, Jr. et al. |
| 4,133,885 A | 1/1979 | Bolhofer et al. |
| 4,140,776 A | 2/1979 | Cragoe, Jr. et al. |
| 4,140,861 A | 2/1979 | Cragoe, Jr. et al. |
| 4,145,551 A | 3/1979 | Cragoe, Jr. et al. |
| 4,150,235 A | 4/1979 | Cragoe, Jr. et al. |
| 4,154,742 A | 5/1979 | Cragoe, Jr. et al. |
| 4,155,908 A | 5/1979 | Cragoe, Jr. et al. |
| 4,156,005 A | 5/1979 | Stokker et al. |
| 4,159,279 A | 6/1979 | Smith et al. |
| 4,163,781 A | 8/1979 | Cragoe, Jr. et al. |
| 4,163,794 A | 8/1979 | Cragoe, Jr. et al. |
| 4,166,177 A | 8/1979 | Cragoe, Jr. et al. |
| 4,175,203 A | 11/1979 | Cragoe, Jr. et al. |
| 4,177,285 A | 12/1979 | Cragoe, Jr. et al. |
| 4,178,386 A | 12/1979 | Williams et al. |
| 4,181,661 A | 1/1980 | Rooney et al. |
| 4,181,727 A | 1/1980 | Cragoe, Jr. et al. |
| 4,182,764 A | 1/1980 | Cragoe, Jr. et al. |
| 4,187,315 A | 2/1980 | Cragoe, Jr. et al. |
| 4,189,496 A | 2/1980 | Cragoe, Jr. et al. |
| 4,190,655 A | 2/1980 | DeMarco et al. |
| 4,196,292 A | 4/1980 | Woltersdorf, Jr. et al. |
| 4,203,988 A | 5/1980 | Bolhofer et al. |
| 4,207,329 A | 6/1980 | Williams et al. |
| 4,208,413 A | 6/1980 | Cragoe, Jr. et al. |
| 4,220,654 A | 9/1980 | Bolhofer et al. |
| 4,221,790 A | 9/1980 | Cragoe, Jr. et al. |
| 4,224,447 A | 9/1980 | Woltersdorf, Jr. et al. |
| 4,225,609 A | 9/1980 | Cragoe, Jr. et al. |
| 4,226,867 A | 10/1980 | Cragoe, Jr. et al. |
| 4,229,456 A | 10/1980 | Bolhofer et al. |
| 4,233,452 A | 11/1980 | Williams et al. |
| 4,237,130 A | 12/1980 | Cragoe, Jr. et al. |
| 4,237,144 A | 12/1980 | Cragoe, Jr. et al. |
| 4,246,406 A | 1/1981 | Cragoe, Jr. et al. |
| 4,249,021 A | 2/1981 | Cragoe, Jr. et al. |
| 4,256,758 A | 3/1981 | Cragoe, Jr. et al. |
| 4,260,771 A | 4/1981 | Cragoe, Jr. et al. |
| 4,263,207 A | 4/1981 | Rokach et al. |
| 4,267,341 A | 5/1981 | Rokach et al. |
| 4,272,537 A | 6/1981 | Woltersdorf, Jr. et al. |
| 4,277,602 A | 7/1981 | Woltersdorf et al. |
| 4,282,365 A | 8/1981 | Rokach et al. |
| 4,291,050 A | 9/1981 | Woltersdorf, Jr. et al. |
| 4,292,430 A | 9/1981 | Rokach et al. |
| 4,294,829 A | 10/1981 | Suzuki et al. |
| 4,296,122 A | 10/1981 | Cragoe, Jr. et al. |
| 4,296,237 A | 10/1981 | Cragoe, Jr. et al. |
| 4,298,743 A | 11/1981 | Cragoe, Jr. et al. |
| 4,309,540 A | 1/1982 | Bock et al. |
| 4,316,043 A | 2/1982 | Cragoe, Jr. et al. |
| 4,317,822 A | 3/1982 | Woltersdorf, Jr. et al. |
| 4,317,922 A | 3/1982 | Cragoe, Jr. et al. |
| 4,336,397 A | 6/1982 | Cragoe, Jr. et al. |
| 4,337,258 A | 6/1982 | Rooney et al. |
| 4,337,354 A | 6/1982 | Cragoe, Jr. et al. |
| 4,342,776 A | 8/1982 | Cragoe, Jr. et al. |
| 4,342,782 A | 8/1982 | Cragoe, Jr. |
| 4,349,561 A | 9/1982 | Cragoe, Jr. et al. |
| 4,356,313 A | 10/1982 | Cragoe, Jr. et al. |
| 4,356,314 A | 10/1982 | Cragoe, Jr. et al. |
| 4,362,724 A | 12/1982 | Bock et al. |
| 4,375,475 A | 3/1983 | Willard et al. |
| 4,377,588 A | 3/1983 | Cragoe, Jr. et al. |
| 4,379,791 A | 4/1983 | Cragoe, Jr. et al. |
| 4,389,393 A | 6/1983 | Schor et al. |
| 4,389,417 A | 6/1983 | Bourke et al. |

(56) References Cited

U.S. PATENT DOCUMENTS

| | | |
|---|---|---|
| 4,390,537 A | 6/1983 | Cragoe, Jr. |
| 4,394,385 A | 7/1983 | Cragoe, Jr. |
| 4,394,515 A | 7/1983 | Rokach et al. |
| 4,401,669 A | 8/1983 | Cragoe, Jr. et al. |
| 4,420,615 A | 12/1983 | Bolhofer et al. |
| 4,425,337 A | 1/1984 | Alexander et al. |
| 4,428,956 A | 1/1984 | Cragoe, Jr. et al. |
| 4,428,959 A | 1/1984 | Cragoe, Jr. et al. |
| 4,431,652 A | 2/1984 | Cragoe, Jr. et al. |
| 4,431,660 A | 2/1984 | Cragoe, Jr. et al. |
| 4,432,992 A | 2/1984 | Cragoe, Jr. et al. |
| 4,440,740 A | 4/1984 | Fix et al. |
| 4,448,786 A | 5/1984 | Cragoe, Jr. et al. |
| 4,454,132 A | 6/1984 | Bock et al. |
| 4,459,442 A | 7/1984 | Morris et al. |
| 4,463,208 A | 7/1984 | Cragoe, Jr. et al. |
| 4,464,363 A | 8/1984 | Higuchi et al. |
| 4,465,850 A | 8/1984 | Cragoe, Jr. et al. |
| 4,501,729 A | 2/1985 | Boucher et al. |
| 4,510,322 A | 4/1985 | Blaine et al. |
| 4,536,507 A | 8/1985 | Rokach et al. |
| 4,537,902 A | 8/1985 | Cragoe, Jr. et al. |
| 4,567,289 A | 1/1986 | Willard et al. |
| 4,579,869 A | 4/1986 | Cragoe, Jr. et al. |
| 4,582,842 A | 4/1986 | Cragoe, Jr. et al. |
| 4,594,349 A | 6/1986 | Beyer, Jr. |
| 4,596,821 A | 6/1986 | Cragoe, Jr. et al. |
| 4,604,394 A | 8/1986 | Kaczorowski et al. |
| 4,604,396 A | 8/1986 | Cragoe, Jr. et al. |
| 4,604,403 A | 8/1986 | Cragoe, Jr. et al. |
| 4,605,663 A | 8/1986 | Cragoe, Jr. et al. |
| 4,605,664 A | 8/1986 | Cragoe, Jr. et al. |
| 4,625,047 A | 11/1986 | Cragoe, Jr. et al. |
| 4,634,717 A | 1/1987 | Cragoe, Jr. et al. |
| 4,654,365 A | 3/1987 | Cragoe, Jr. et al. |
| 4,663,322 A | 5/1987 | Beyer, Jr. |
| 4,675,341 A | 6/1987 | Cragoe, Jr. |
| 4,680,414 A | 7/1987 | Cragoe, Jr. et al. |
| 4,699,917 A | 10/1987 | Cragoe, Jr. et al. |
| 4,699,926 A | 10/1987 | Abraham et al. |
| 4,710,513 A | 12/1987 | Willard et al. |
| 4,719,310 A | 1/1988 | Pietruszkiewicz et al. |
| 4,731,381 A | 3/1988 | Abraham et al. |
| 4,731,470 A | 3/1988 | Pietruszkiewicz et al. |
| 4,731,471 A | 3/1988 | Cragoe, Jr. et al. |
| 4,731,472 A | 3/1988 | Pietruszkiewicz et al. |
| 4,731,473 A | 3/1988 | Abraham et al. |
| 4,751,244 A | 6/1988 | Abraham et al. |
| 4,754,061 A | 6/1988 | Cragoe, Jr. et al. |
| 4,769,370 A | 9/1988 | Woltersdorf, Jr. et al. |
| 4,771,076 A | 9/1988 | Cragoe, Jr. et al. |
| 4,775,695 A | 10/1988 | Cragoe, Jr. et al. |
| 4,777,281 A | 10/1988 | Woltersdorf, Jr. et al. |
| 4,778,897 A | 10/1988 | Cragoe, Jr. et al. |
| 4,782,073 A | 11/1988 | Cragoe, Jr. |
| 4,797,391 A | 1/1989 | Woltersdorf, Jr. et al. |
| 4,835,142 A | 5/1989 | Suzuki et al. |
| 4,835,313 A | 5/1989 | Pietruszkiewicz et al. |
| 4,894,376 A | 1/1990 | Morad et al. |
| 4,923,874 A | 5/1990 | McMahon et al. |
| 4,937,232 A | 6/1990 | Bell et al. |
| 4,952,582 A | 8/1990 | Beyer, Jr. |
| 5,132,296 A | 7/1992 | Cherksey |
| 5,182,299 A | 1/1993 | Gullans et al. |
| 5,215,991 A | 6/1993 | Burke |
| 5,242,947 A | 9/1993 | Cherksey et al. |
| 5,292,498 A | 3/1994 | Boucher, Jr. |
| 5,312,820 A | 5/1994 | Ashton et al. |
| 5,384,128 A | 1/1995 | Meezan et al. |
| 5,420,116 A | 5/1995 | Puchelle et al. |
| 5,449,682 A | 9/1995 | Greenlee et al. |
| 5,512,269 A | 4/1996 | Molina y Vedia et al. |
| 5,538,991 A | 7/1996 | Ashton et al. |
| 5,618,557 A | 4/1997 | Wille et al. |
| 5,628,984 A | 5/1997 | Boucher, Jr. |
| 5,635,160 A | 6/1997 | Stutts, III et al. |
| 5,651,957 A | 7/1997 | Molina y Vedia et al. |
| 5,656,256 A | 8/1997 | Boucher et al. |
| 5,683,675 A | 11/1997 | Molina y Vedia et al. |
| 5,707,644 A | 1/1998 | Illum |
| 5,716,931 A | 2/1998 | Molina y Vedia et al. |
| 5,725,842 A | 3/1998 | Boucher, Jr. et al. |
| 5,750,697 A | 5/1998 | Cherksey |
| 5,817,028 A | 10/1998 | Anderson |
| 5,849,706 A | 12/1998 | Molina y Vedia et al. |
| 5,866,610 A | 2/1999 | Lang et al. |
| 5,876,700 A | 3/1999 | Boucher, Jr. et al. |
| 5,902,567 A | 5/1999 | Boucher, Jr. |
| 5,908,611 A | 6/1999 | Gottlieb et al. |
| 5,935,555 A | 8/1999 | Stutts, III et al. |
| 5,955,100 A | 9/1999 | Bosslet et al. |
| 5,962,477 A | 10/1999 | Mak |
| 5,994,336 A | 11/1999 | Zasloff et al. |
| 6,015,828 A | 1/2000 | Cuppoletti |
| 6,022,527 A | 2/2000 | Boucher, Jr. et al. |
| 6,033,688 A | 3/2000 | Mrsny et al. |
| 6,051,576 A | 4/2000 | Ashton et al. |
| 6,071,910 A | 6/2000 | Gleich et al. |
| 6,133,247 A | 10/2000 | Boucher, Jr. |
| 6,136,294 A | 10/2000 | Adjei et al. |
| 6,143,279 A | 11/2000 | Boucher, Jr. et al. |
| 6,153,187 A | 11/2000 | Yacoby-Zeevi |
| 6,159,968 A | 12/2000 | Cuppoletti |
| 6,190,691 B1 | 2/2001 | Mak |
| 6,204,270 B1 | 3/2001 | Ron et al. |
| 6,214,536 B1 | 4/2001 | Boucher, Jr. |
| 6,235,266 B1 | 5/2001 | Stutts, III et al. |
| 6,264,975 B1 | 7/2001 | Boucher, Jr. |
| 6,294,188 B1 | 9/2001 | Ragavan et al. |
| 6,297,226 B1 | 10/2001 | Glasky |
| 6,300,350 B1 | 10/2001 | Belloni et al. |
| 6,323,187 B1 | 11/2001 | Yerxa et al. |
| 6,331,529 B1 | 12/2001 | Yerxa et al. |
| 6,344,475 B1 | 2/2002 | Caplan et al. |
| 6,399,585 B1 | 6/2002 | Larson et al. |
| 6,403,633 B2 | 6/2002 | Illig et al. |
| 6,451,288 B1 | 9/2002 | Boucher, Jr. et al. |
| 6,458,338 B1 | 10/2002 | Adjei et al. |
| 6,475,467 B1 | 11/2002 | Keller et al. |
| 6,475,509 B1 | 11/2002 | Boucher, Jr. |
| 6,476,048 B1 | 11/2002 | Szabo et al. |
| 6,607,741 B2 | 8/2003 | Boucher, Jr. |
| 6,613,345 B2 | 9/2003 | Boucher, Jr. |
| 6,739,172 B2 | 5/2004 | Wagner |
| 6,753,164 B2 | 6/2004 | Ni et al. |
| 6,858,614 B2 | 2/2005 | Johnson |
| 6,858,615 B2 | 2/2005 | Johnson |
| 6,903,105 B2 | 6/2005 | Johnson |
| 6,926,911 B1 | 8/2005 | Boucher, Jr. |
| 6,995,160 B2 | 2/2006 | Johnson |
| 7,026,325 B2 | 4/2006 | Johnson |
| 7,030,117 B2 | 4/2006 | Johnson |
| 7,056,524 B2 | 6/2006 | Boucher, Jr. |
| 7,064,129 B2 | 6/2006 | Johnson et al. |
| 7,186,833 B2 | 3/2007 | Johnson |
| 7,189,719 B2 | 3/2007 | Johnson |
| 7,192,958 B2 | 3/2007 | Johnson |
| 7,192,959 B2 | 3/2007 | Johnson |
| 7,192,960 B2 | 3/2007 | Johnson |
| 7,241,766 B2 | 7/2007 | Johnson |
| 7,247,636 B2 | 7/2007 | Johnson |
| 7,247,637 B2 | 7/2007 | Johnson et al. |
| 7,317,013 B2 | 1/2008 | Johnson |
| 7,332,496 B2 | 2/2008 | Johnson |
| 7,345,044 B2 | 3/2008 | Johnson |
| 7,368,447 B2 | 5/2008 | Johnson et al. |
| 7,368,450 B2 | 5/2008 | Johnson |
| 7,368,451 B2 | 5/2008 | Johnson et al. |
| 7,375,102 B2 | 5/2008 | Fu et al. |
| 7,375,107 B2 | 5/2008 | Johnson |
| 7,388,013 B2 | 6/2008 | Johnson et al. |
| 7,399,766 B2 | 7/2008 | Johnson |
| 7,410,968 B2 | 8/2008 | Johnson et al. |
| 7,553,855 B2 | 6/2009 | Young et al. |

(56) References Cited

U.S. PATENT DOCUMENTS

| | | |
|---|---|---|
| 7,745,442 B2 | 6/2010 | Johnson et al. |
| 7,807,834 B2 | 10/2010 | Johnson et al. |
| 7,820,678 B2 | 10/2010 | Johnson |
| 7,842,697 B2 | 11/2010 | Johnson |
| 7,868,010 B2 | 1/2011 | Johnson et al. |
| 7,875,619 B2 | 1/2011 | Johnson |
| 7,956,059 B2 | 6/2011 | Johnson |
| 7,981,898 B2 | 7/2011 | Johnson et al. |
| 8,008,494 B2 | 8/2011 | Johnson |
| 8,022,210 B2 | 9/2011 | Johnson |
| 8,058,278 B2 | 11/2011 | Johnson et al. |
| 8,124,607 B2 | 2/2012 | Johnson |
| 8,143,256 B2 | 3/2012 | Johnson |
| 8,163,758 B2 | 4/2012 | Johnson et al. |
| 8,198,286 B2 | 6/2012 | Johnson |
| 8,211,895 B2 | 7/2012 | Johnson et al. |
| 8,227,474 B2 | 7/2012 | Johnson |
| 8,261,047 B2 | 9/2012 | Moyer |
| 8,288,391 B2 | 10/2012 | Johnson et al. |
| 8,314,105 B2 | 11/2012 | Johnson |
| 8,324,218 B2 | 12/2012 | Johnson |
| 8,431,579 B2 | 4/2013 | Johnson et al. |
| 8,507,497 B2 | 8/2013 | Johnson et al. |
| 8,551,534 B2 | 10/2013 | Boucher et al. |
| 8,575,176 B2 | 11/2013 | Johnson |
| 8,669,262 B2 | 3/2014 | Johnson |
| 8,846,688 B2 | 9/2014 | Johnson |
| 8,980,898 B2 | 3/2015 | Johnson et al. |
| 9,072,738 B2 | 7/2015 | Johnson |
| 2003/0135716 A1 | 7/2003 | Vinitzky |
| 2003/0195160 A1 | 10/2003 | Johnson |
| 2003/0199456 A1 | 10/2003 | Johnson |
| 2004/0116415 A1 | 6/2004 | Sun et al. |
| 2004/0162296 A1 | 8/2004 | Johnson |
| 2004/0195160 A1 | 10/2004 | Max et al. |
| 2004/0198744 A1 | 10/2004 | Johnson |
| 2004/0198745 A1 | 10/2004 | Johnson |
| 2004/0198746 A1 | 10/2004 | Johnson |
| 2004/0198747 A1 | 10/2004 | Johnson |
| 2004/0198748 A1 | 10/2004 | Johnson |
| 2004/0198749 A1 | 10/2004 | Johnson |
| 2004/0199456 A1 | 10/2004 | Flint et al. |
| 2004/0204424 A1 | 10/2004 | Johnson |
| 2004/0204425 A1 | 10/2004 | Johnson |
| 2004/0229884 A1 | 11/2004 | Johnson |
| 2005/0059676 A1 | 3/2005 | Johnson |
| 2005/0080091 A1 | 4/2005 | Johnson et al. |
| 2005/0080092 A1 | 4/2005 | Johnson |
| 2005/0080093 A1 | 4/2005 | Johnson et al. |
| 2005/0090505 A1 | 4/2005 | Johnson et al. |
| 2005/0113388 A1 | 5/2005 | Johnson |
| 2005/0113389 A1 | 5/2005 | Johnson |
| 2005/0113390 A1 | 5/2005 | Johnson |
| 2005/0228182 A1 | 10/2005 | Johnson et al. |
| 2005/0234072 A1 | 10/2005 | Johnson et al. |
| 2006/0040954 A1 | 2/2006 | Johnson |
| 2006/0052394 A1 | 3/2006 | Johnson et al. |
| 2006/0052395 A1 | 3/2006 | Johnson et al. |
| 2006/0063780 A1 | 3/2006 | Johnson |
| 2006/0142306 A1 | 6/2006 | Johnson |
| 2006/0142581 A1 | 6/2006 | Johnson |
| 2006/0205738 A1 | 9/2006 | Johnson et al. |
| 2007/0018640 A1 | 1/2007 | Guzik et al. |
| 2007/0021439 A1 | 1/2007 | Johnson |
| 2007/0032509 A1 | 2/2007 | Johnson et al. |
| 2007/0265280 A1 | 11/2007 | Johnson |
| 2008/0076782 A1 | 3/2008 | Johnson |
| 2008/0090841 A1 | 4/2008 | Johnson et al. |
| 2008/0096896 A1 | 4/2008 | Johnson |
| 2008/0103148 A1 | 5/2008 | Johnson |
| 2008/0167466 A1 | 7/2008 | Johnson et al. |
| 2008/0171879 A1 | 7/2008 | Johnson |
| 2008/0171880 A1 | 7/2008 | Johnson et al. |
| 2008/0176863 A1 | 7/2008 | Johnson et al. |
| 2008/0177072 A1 | 7/2008 | Johnson |
| 2008/0200476 A1 | 8/2008 | Johnson |
| 2008/0249109 A1 | 10/2008 | Johnson et al. |
| 2008/0293740 A1 | 11/2008 | Johnson et al. |
| 2009/0018144 A1 | 1/2009 | Johnson et al. |
| 2009/0062308 A1 | 3/2009 | Johnson |
| 2009/0076273 A1 | 3/2009 | Johnson |
| 2009/0082287 A1 | 3/2009 | Johnson et al. |
| 2009/0104272 A1 | 4/2009 | Boucher et al. |
| 2009/0214444 A1 | 8/2009 | Johnson |
| 2009/0227530 A1 | 9/2009 | Johnson |
| 2009/0227594 A1 | 9/2009 | Johnson |
| 2009/0253714 A1 | 10/2009 | Johnson et al. |
| 2009/0324724 A1 | 12/2009 | Johnson |
| 2010/0074881 A1 | 3/2010 | Boucher et al. |
| 2010/0130547 A1 | 5/2010 | Zhang et al. |
| 2010/0144661 A1 | 6/2010 | Johnson |
| 2010/0267746 A1 | 10/2010 | Johnson |
| 2011/0003832 A1 | 1/2011 | Johnson et al. |
| 2011/0008268 A1 | 1/2011 | Johnson et al. |
| 2011/0046158 A1 | 2/2011 | Johnson et al. |
| 2011/0144338 A1 | 6/2011 | Johnson et al. |
| 2011/0195973 A1 | 8/2011 | Johnson |
| 2012/0044272 A1 | 2/2012 | Han et al. |
| 2012/0116083 A1 | 5/2012 | Johnson |
| 2012/0220606 A1 | 8/2012 | Johnson et al. |
| 2013/0012692 A1 | 1/2013 | Johnson |
| 2013/0060034 A1 | 3/2013 | Johnson |
| 2013/0178482 A1 | 7/2013 | Johnson |
| 2013/0324559 A1 | 12/2013 | Johnson et al. |
| 2014/0031371 A1 | 1/2014 | Johnson |
| 2014/0096765 A1 | 4/2014 | Boucher et al. |
| 2014/0107133 A1 | 4/2014 | Johnson |
| 2014/0142118 A1 | 5/2014 | Johnson |
| 2014/0170244 A1 | 6/2014 | Johnson |
| 2014/0171447 A1 | 6/2014 | Johnson |
| 2014/0179625 A1 | 6/2014 | Johnson |
| 2015/0166487 A1 | 6/2015 | Johnson |
| 2015/0307530 A1 | 10/2015 | Johnson et al. |
| 2015/0376145 A1 | 12/2015 | Johnson |
| 2015/0376146 A1 | 12/2015 | Johnson |

FOREIGN PATENT DOCUMENTS

| | | |
|---|---|---|
| CN | 101534813 A | 9/2009 |
| FR | 1 525 670 A | 5/1968 |
| FR | 1 525 671 A | 5/1968 |
| GB | 1145934 A | 3/1969 |
| GB | 1158399 A | 7/1969 |
| JP | 2005/530692 A | 10/2005 |
| JP | 2006/518389 A | 8/2006 |
| JP | 2007/517764 A | 7/2007 |
| JP | 2010/502738 A | 1/2010 |
| WO | WO 00/23023 A1 | 4/2000 |
| WO | WO 01/05773 A1 | 1/2001 |
| WO | WO 01/28584 A1 | 4/2001 |
| WO | WO 2011/156355 A1 | 12/2001 |
| WO | WO 03/070182 A2 | 8/2003 |
| WO | WO 03/070182 A3 | 8/2003 |
| WO | WO 03/070184 A2 | 8/2003 |
| WO | WO 2004/073629 A2 | 9/2004 |
| WO | WO 2005/016879 A2 | 2/2005 |
| WO | WO 2005/018560 A2 | 3/2005 |
| WO | WO 2005/018644 A1 | 3/2005 |
| WO | WO 2005/025496 A2 | 3/2005 |
| WO | WO 2005/034847 A2 | 4/2005 |
| WO | WO 2005/044180 A2 | 5/2005 |
| WO | WO 2006/022935 A1 | 3/2006 |
| WO | WO 2006/023573 A2 | 3/2006 |
| WO | WO 2006/023617 A2 | 3/2006 |
| WO | WO 2007/018640 A1 | 2/2007 |
| WO | WO 2007/071396 A2 | 6/2007 |
| WO | WO 2007/071400 A1 | 6/2007 |
| WO | WO 2007/146867 A2 | 12/2007 |
| WO | WO 2007/146869 A1 | 12/2007 |
| WO | WO 2007/146870 A1 | 12/2007 |
| WO | WO 2008/030217 A2 | 3/2008 |
| WO | WO 2008/031028 A2 | 3/2008 |
| WO | WO 2008/031048 A2 | 3/2008 |
| WO | WO 2008/124491 A1 | 10/2008 |

(56) References Cited

FOREIGN PATENT DOCUMENTS

| WO | WO 2008/124496 A1 | 10/2008 |
|---|---|---|
| WO | WO 2008/135557 A1 | 11/2008 |
| WO | WO 2009/049159 A1 | 4/2009 |
| WO | WO 2009/074575 A2 | 6/2009 |
| WO | WO 2009/138378 A1 | 11/2009 |
| WO | WO 2009/139948 A1 | 11/2009 |
| WO | WO 2009/150137 A2 | 12/2009 |
| WO | WO 2013/003386 A1 | 1/2013 |
| WO | WO 2013/003444 A1 | 1/2013 |

OTHER PUBLICATIONS

U.S. Appl. No. 12/171,867, filed Jul. 11, 2008, Johnson, et al.
U.S. Appl. No. 12/171,897, filed Jul. 11, 2008, Johnson, et al.
U.S. Appl. No. 14/106,156, filed Dec. 13, 2013, Johnson.
U.S. Appl. No. 14/458,898, filed Aug. 13, 2014, Johnson, et al.
U.S. Appl. No. 14/577,098, filed Dec. 19, 2014, Johnson.
U.S. Appl. No. 14/564,299, filed Dec. 9, 2014, Johnson, et al.
U.S. Appl. No. 14/594,744, filed Jan. 12, 2015, Johnson.
International Search Report and Written Opinion issued Mar. 3, 2014 in PCT/US2013/075093.
A.J. Hirsch, et al., "Design, Synthesis and Structure-Activity Relationships of Novel 2-Substituted Pyrazinoylguanidine Epithelial Sodium Channel Blockers. Drugs for Cystic Fibrosis and Chronic Bronchitis" Journal of Medicinal Chemistry, vol. 49, XP008122316, Jun. 13, 2006, pp. 4098-4115.
U.S. Appl. No. 14/727,189, filed Jun. 1, 2015, Johnson.
PCT/US2004/26808, Apr. 15, 2005, International Search Report and Written Opinion.
PCT/US2005/17740, Aug. 31, 2005, International Search Report and Written Opinion.
PCT/US2007/077907, Mar. 27, 2008, International Search Report and Written Opinion.
PCT/US2007/077880, Sep. 15, 2008, International Search Report and Written Opinion.
PCT/US2007/070857, Dec. 6, 2007, International Search Reprot and Written Opinion.
PCT/US/2007/070861, Nov. 21, 2007, International Search Report and Written Opinion.
PCT/US2013/075244, Feb. 17, 2014, International Search Report and Written Opinion.
PCT/US2003/004823, May 10, 2004, International Search Report.
PCT/US2004/004451, Aug. 27, 2004, International Search Report and Written Opinion.
PCT/US2004/026880, Apr. 15, 2005, International Search Report and Wirtten Opinion.
PCT/US2009/035286, Oct. 21, 2009, International Search Report and Written Opinion.
PCT/US2004/026885, Jan. 31, 2005, International Search Report and Written Opinion.
PCT/US2006/015957, Oct. 5, 2006, International Search Report and Written Opinion.
PCT/US2005/02934, Mar. 21, 2006, International Search Report and Written Opinion.
PCT/US2013/075108, Feb. 6, 2014, International Search Report and Written Opinion.
PCT/US2012/044272, Sep. 20, 2012, International Search Report and Written Opinion.
PCT/US2003/004817, Aug. 21, 2003, International Search Report.
International Search Report and Written Opinion, mailed Apr. 15, 2005, in connection with Application No. PCT/US2004/026808.
International Search Report and Written Opinion, mailed Aug. 31, 2005, in connection with Application No. PCT/US2005/017740.
International Search Report and Written Opinion, mailed Mar. 27, 2008, in connection with Application No. PCT/US2007/077907.
International Search Report and Written Opinion, mailed Sep. 15, 2008, in connection with Application No. PCT/US2007/077880.
International Search Report and Written Opinion, mailed Dec. 6, 2007, in connection with Application No. PCT/US2007/070857.
International Search Report and Written Opinion, mailed Nov. 21, 2007, in connection with Application No. PCT/US/2007/070861.
International Search Report and Written Opinion, mailed Feb. 17, 2014, in connection with for Application No. PCT/US2013/075244.
International Search Report, mailed May 10, 2004, in connection with Application No. PCT/US2003/004823.
International Search Report and Written Opinion, mailed Aug. 27, 2004, in connection with Application No. PCT/US2004/004451.
International Search Report and Written Opinion, mailed Apr. 15, 2005, in connection with Application No. PCT/US2004/026880.
International Search Report and Written Opinion, mailed Oct. 21, 2009, in connection with Application No. PCT/US2009/035286.
International Search Report and Written Opinion, mailed Jan. 31, 2005, in connection with Application No. PCT/US2004/026885.
International Search Report and Written Opinion, mailed Oct. 5, 2006, in connection with Application No. PCT/US2006/015957.
International Search Report and Written Opinion, mailed Mar. 21, 2006, in connection with Application No. PCT/US2005/029345.
International Search Report and Written Opinion, mailed Feb. 6, 2014, in connection with Application No. PCT/US2013/075108.
International Search Report and Written Opinion, mailed Sep. 20, 2012, in connection with Application No. PCT/US2012/044272.
International Search Report, mailed Aug. 21, 2003, in connection with Application No. PCT/US2003/004817.
[No Author Listed] Deterministic effects and stochastic effects. Hong Kong Observatory. Last accessed on Mar. 21, 2016 and available at: http://www.hko.gov.hk/education/dbcp/rad_health/eng/r4_1.htm. 2 pages.
Barbry et al., [3H]phenamil binding protein of the renal epithelium Na+ channel. Purification, affinity labeling, and functional reconstitution. Biochemistry. Jan. 30, 1990;29(4):1039-45.
Barbry et al., Biochemical identification of two types of phenamil binding sites associated with amiloride-sensitive Na+ channels. Biochemistry. May 2, 1989;28(9):3744-9.
Barrett et al., Chloride secretion by the intestinal epithelium: molecular basis and regulatory aspects. Annu Rev Physiol. 2000;62:535-72.
Bennett et al., Effect of uridine 5'-triphosphate plus amiloride on mucociliary clearance in adult cystic fibrosis. Am J Respir Crit Care Med. Jun. 1996;153(6 Pt 1):1796-801.
Bicking et al., Pyrazine Diuretics. I. N-Amidino-3-amino-6-halopyrazinecarboxamides. J. Med. Chem. 1965; 8(5):638-42.
Borisy et al., Systematic discovery of multicomponent therapeutics. Proc Natl Acad Sci U S A. Jun. 24, 2003;100(13):7977-82. Epub Jun. 10, 2003.
Boucher, Airway surface dehydration in cystic fibrosis: pathogenesis and therapy. Annu Rev Med. 2007;58:157-70.
Boucher, Cystic fibrosis: a disease of vulnerability to airway surface dehydration. Trends Mol Med. Jun. 2007;13(6):231-40. Epub May 23, 2007.
Boucher, Evidence for airway surface dehydration as the initiating event in CF airway disease. J Intern Med. Jan. 2007;261(1):5-16.
Chawla et al., Curr. Res. & Info. Pharm. Sci. CRIPS. 2004; 5(1): 9-12.
Cline et al., Predicting the quality of powders for inhalation from surface energy and area. Pharm Res. Sep. 2002;19(9):1274-7.
Clunes et al., Front-runners for pharmacotherapeutic correction of the airway ion transport defect in cystic fibrosis. Curr Opin Pharmacol. Jun. 2008;8(3):292-9. doi: 10.1016/j.coph.2008.04.006. Epub May 28, 2008.
Cocks et al., Amiloride analogues cause endothelium-dependent relaxation in the canine coronary artery in vitro: possible role of Na+/Ca2+ exchange. Br J Pharmacol. Sep. 1988; 95(1): 67-76.
Cohn et al., In vitro activity of amiloride combined with tobramycin against Pseudomonas isolates from patients with cystic fibrosis. Antimicrob Agents Chemother. Mar. 1988;32(3):395-6.
Cohn et al., In vitro antimicrobial activity of amiloride analogs against Pseudomonas. Chemotherapy. 1992;38(4):232-7.
Collard et al., Prevention of ventilator-associated pneumonia: an evidence based systematic review. Ann Intern Med. Mar. 18, 2003;138(6):494-501.

(56) References Cited

OTHER PUBLICATIONS

Cragoe et al., Chapter 2: An Overview of the Structure-Activity Relations in the Amiloride Series. Amiloride and its Analogs. 1992; 9-24.
Cragoe et al., Chapter 3. The Synthesis of Amiloride and its Analogs. 1992; 24-38.
Cragoe et al., Chapter 7: Diuretic Agents. Annual Reports in Medicinal Chemistry. 1965; 67-77.
Cragoe et al., Chapter 7: Diuretic Agents. Annual Reports in Medicinal Chemistry. 1966; 59-68.
Cragoe et al., Pyrazine diuretics. II. N-amidino-3-amino-5-substituted 6-halopyrazinecarboxamides. J Med Chem. Jan. 1967;10(1):66-75.
Donaldson et al., Mucociliary clearance as an outcome measure for cystic fibrosis clinical research. Proc Am Thorac Soc. Aug. 1, 2007;4(4):399-405.
Donaldson et al., Mucus clearance and lung function in cystic fibrosis with hypertonic saline. N Engl J Med. Jan. 19, 2006;354(3):241-50.
Dorwald, Side Reactions in Organic Synthesis: A Guide to Successful Synthesis Design. Weinheim: Wiley-VCH Verlag GmbH & Co. KGaA, 2005, Preface.
Elkins et al., A controlled trial of long-term inhaled hypertonic saline in patients with cystic fibrosis. N Engl J Med. Jan. 19, 2006;354(3):229-40.
Epand et al., Reversal of intrinsic multidrug resistance in Chinese hamster ovary cells by amiloride analogs. Br J Cancer. Feb. 1991;63(2):247-51.
Giannakou et al., Characterization of the *Drosophila melanogaster* alkali-metal/proton exchanger (NHE) gene family J Exp Biol. Nov. 2001;204(Pt 21):3703-16.
Giunta et al., Amiloride, a diuretic with in vitro antimicrobial activity. Pharmacol Res Commun. Aug. 1984;16(8):821-9.
Goralski et al., Osmolytes and ion transport modulators: new strategies for airway surface rehydration. Curr Opin Pharmacol. Jun. 2010;10(3):294-9. doi: 10.1016/j.coph.2010.04.003. Epub May 1, 2010.
Gowen et al., Increased nasal potential difference and amiloride sensitivity in neonates with cystic fibrosis. J Pediatr. Apr. 1986;108(4):517-21.
Hackam et al., Translation of research evidence from animals to humans JAMA. Oct. 11, 2006;296(14):1731-2.
Hirsh et al., Design, synthesis, and structure-activity relationships of novel 2-substituted pyrazinoylguanidine epithelial sodium channel blockers: drugs for cystic fibrosis and chronic bronchitis. J Med Chem. Jul. 13, 2006;49(14):4098-115.
Hirsh et al., Evaluation of second generation amiloride analogs as therapy for cystic fibrosis lung disease. J Pharmacol Exp Ther. Dec. 2004;311(3):929-38. Epub Jul. 23, 2004.
Hirsh et al., Pharmacological properties of N-(3,5-diamino-6-chloropyrazine-2-carbonyl)-N'-4-[4-(2,3-dihydroxypropoxy)phenyl]butyl-guanidine methanesulfonate (552-02), a novel epithelial sodium channel blocker with potential clinical efficacy for cystic fibrosis lung disease. J Pharmacol Exp Ther. Apr. 2008;325(1):77-88. doi: 10.1124/jpet.107.130443. Epub Jan. 24, 2008.
Hoffman et al., Effects of Topically Delivered Benzamil and Amiloride on Nasal Potential Difference in Cystic Fibrosis. Am, J, Resp. Crit. Care Med. 1998; 157:1844-9.
http://www.biology-online.org/dictionary/Oligosaccharide, last accessed on Mar. 20, 2008.
http://www.faqs.org/health/topics/96/Bronchodilators.html, last accessed on Nov. 22, 2009.
Jones et al., Pharmacokinetics of amiloride after inhalation and oral administration in adolescents and adults with cystic fibrosis. Pharmacotherapy. Mar.-Apr. 1997;17(2):263-70.
Jordan, Nature Reviews:Drug Discovery. 2003; 2:205.
Kellerman, P2Y(2) receptor agonists: a new class of medication targeted at improved mucociliary clearance. Chest. May 2002;121(5 Suppl):201S-205S.

Kleyman et al., Amiloride and its analogs as tools in the study of ion transport. J Membr Biol. Oct. 1988;105(1):1-21.
Kleyman et al., Distinct epitopes on amiloride. II. Variably restricted epitopes defined by monoclonal anti-amiloride antibodies. Am J Physiol. Feb. 1991;260(2 Pt 1):C271-6.
Kleyman et al., New amiloride analogue as hapten to raise anti-amiloride antibodies. Am J Physiol. Jan. 1986;250(1 Pt 1):C165-70.
Kleyman et al., The cellular pool of Na+ channels in the amphibian cell line A6 is not altered by mineralocorticoids. Analysis using a new photoactive amiloride analog in combination with anti-amiloride antibodies. J Biol Chem. Jul. 15, 1989;264(20):11995-2000.
Knowles et al, A pilot study of aerosolized amiloride for the treatment of lung disease in cystic fibrosis. N Engl J Med. Apr. 26, 1990;322(17):1189-94.
Knowles et al., Aerosolized amiloride as treatment of cystic fibrosis lung disease: a pilot study. Adv Exp Med Biol. 1991;290:119-28; discussion 129-32.
Knowles et al., Chapter 20. Amiloride in Cystic Fibrosis: Safety, Pharmacokinetics, and Efficacy in the Treatment of Pulmonary Disease. 1992; 301-16.
Kyle et al., Sodium channel blockers. J Med Chem. May 31, 2007;50(11):2583-8. Epub May 10, 2007.
Lammas et al., ATP-induced killing of mycobacteria by human macrophages is mediated by purinergic P2Z(P2X7) receptors. Immunity. Sep. 1997;7(3):433-44.
Li et al., Stereoselective blockade of amphibian epithelial sodium channels by amiloride analogs. J Pharmacol Exp Ther. Dec. 1993;267(3):1081-4.
Mastronarde et al., Amiloride inhibits cytokine production in epithelium infected with respiratory syncytial virus. Am J Physiol. Aug. 1996;271(2 Pt 1):L201-7.
Mentz et al., Deposition, clearance, and effects of aerosolized amiloride in sheep airways. Am Rev Respir Dis. Nov. 1986;134(5):938-43.
Olivier et al., Acute safety and effects on mucociliary clearance of aerosolized uridine 5'-triphosphate +/− amiloride in normal human adults. Am J Respir Crit Care Med. Jul. 1996;154(1):217-23.
O'Neil et al., The Merck Index. An Encyclopedia of Chemicals, Drugs, and Biologicals. 2006; 69-70.
Padmanabhan et al., Solution-phase, parallel synthesis and pharmacological evaluation of acylguanidine derivatives as potential sodium channel blockers. Bioorg Med Chem Lett. Dec. 17, 2001;11(24):3151-5.
Paisley et al., Regulation of airway mucosal hydration. Expert Rev Clin Pharmacol. May 2010;3(3):361-9. doi: 10.1586/ecp.10.19.
Rogister et al., Novel inhibitors of the sodium-calcium exchanger: benzene ring analogues of N-guanidino substituted amiloride derivatives. Eur J Med Chem. Jul.-Aug. 2001;36(7-8):597-614.
Sabater et al., Aerosolization of P2Y(2)-receptor agonists enhances mucociliary clearance in sheep. J Appl Physiol (1985). Dec. 1999;87(6):2191-6.
Shah, Chapter 7, Progress in the Treatment of Pulmonary Disease in Cystic Fibrosis. Annual Reports in Medicinal Chemistry. 2001; 36:67-76.
Shryock et al., Adenosine and adenosine receptors in the cardiovascular system: biochemistry, physiology, and pharmacology. Am J Cardiol. Jun. 19, 1997;79(12A):2-10. Abstract only.
Smith et al., Chapter 7. Diuretics, Annual Reports in Medicinal Chemistry. 1978; 13:61-70.
Smith et al., Chapter 8. Diuretics, Annual Reports in Medicinal Chemistry. 1976; 11:71-9.
Sood et al., Increasing concentration of inhaled saline with or without amiloride: effect on mucociliary clearance in normal subjects. Am J Respir Crit Care Med. Jan. 15, 2003;167(2):158-63. Epub Oct. 31, 2002.
Strader et al., Structural basis of beta-adrenergic receptor function. FASEB J. May 1989;3(7):1825-32.
Strosberg et al., Structure and function of the beta 3-adrenergic receptor. Annu Rev Pharmacol Toxicol. 1997;37:421-50.
Tarran et al., Rationale for hypertonic saline therapy for cystic fibrosis lung disease. Semin Respir Crit Care Med. Jun. 2007;28(3):295-302.

(56) References Cited

OTHER PUBLICATIONS

Tarran et al., The CF salt controversy: in vivo observations and therapeutic approaches. Mol Cell. Jul. 2001;8(1):149-58.
Taylor et al., A Facile Route to "Open Chain" Analogues of DDATHF. Heterocycles. 1989;28(2):1169-78.
Thelin et al., The epithelium as a target for therapy in cystic fibrosis. Curr Opin Pharmacol. Jun. 2007;7(3):290-5. Epub May 1, 2007.
Tomkiewicz et al., Amiloride inhalation therapy in cystic fibrosis. Influence on ion content, hydration, and rheology of sputum. Am Rev Respir Dis. Oct. 1993;148(4 Pt 1):1002-7.
Velly et al., Effects of amiloride and its analogues on [3H]batrachotoxinin-A 20-alpha benzoate binding, [3H]tetracaine binding and 22Na influx. Eur J Pharmacol. Apr. 27, 1988;27;149(1-2):97-105.
Wark et al., Nebulised hypertonic saline for cystic fibrosis. The Cochrane Collaboration, The Cochrane Library. 2008; 4:1-35.
Windscheif et al., Substituted Dipyridlethenes and -ethynes and Key Pyridine Building Blocks. Synthesis. 1994; 87-92.
Wolff, Justus Liebigs Annalen der Chemie. 1913; 394: 23-59.
Worlitzsch et al., Effects of Reduced Mucus Oxygen Concentration in Airway Pseudomonas Infections of Cystic Fibrosis Patients. The Journal of Clinical Investigation. 2002; 109(3):317-36.
Yin et al., Conversion of the 2,2,6,6-tetramethylpiperidine moiety to a 2,2-dimethylpyrrolidine by cytochrome P450: evidence for a mechanism involving nitroxide radicals and heme iron. Biochemistry. May 11, 2004;43(18):5455-66.
Zhou et al., Preventive but not late amiloride therapy reduces morbidity and mortality of lung disease in betaENaC-overexpressing mice. Am J Respir Crit Care Med. Dec. 15, 2008;178(12):1245-56. doi: 10.1164/rccm.200803-442OC. Epub Oct. 10, 2008.

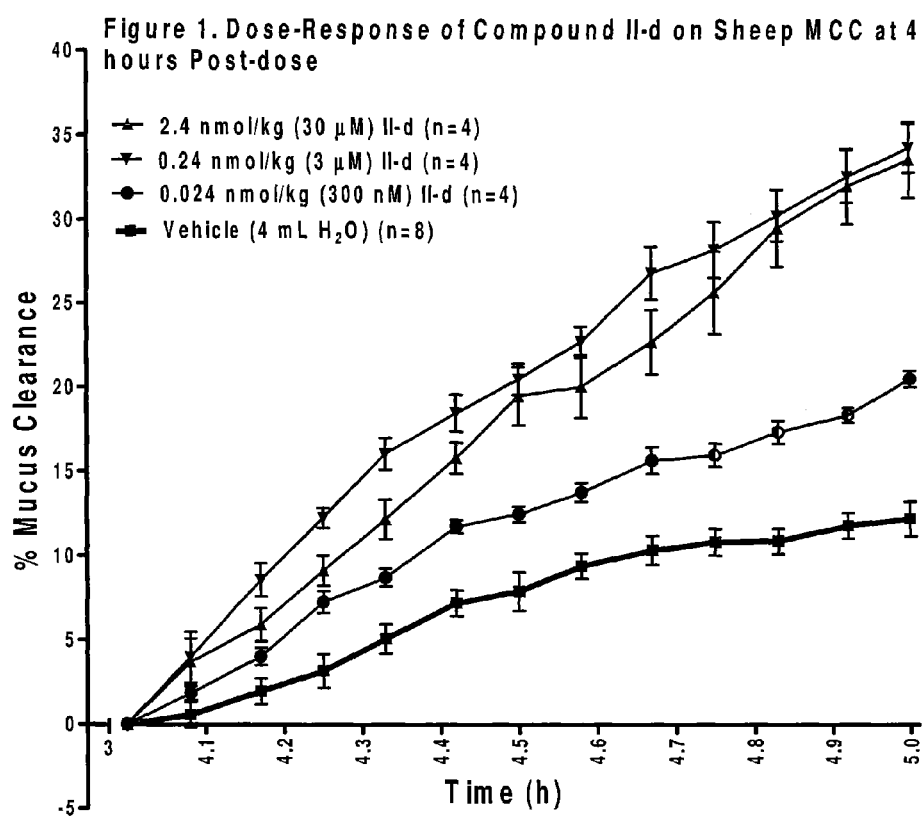
Figure 1. Dose-Response of Compound II-d on Sheep MCC at 4 hours Post-dose

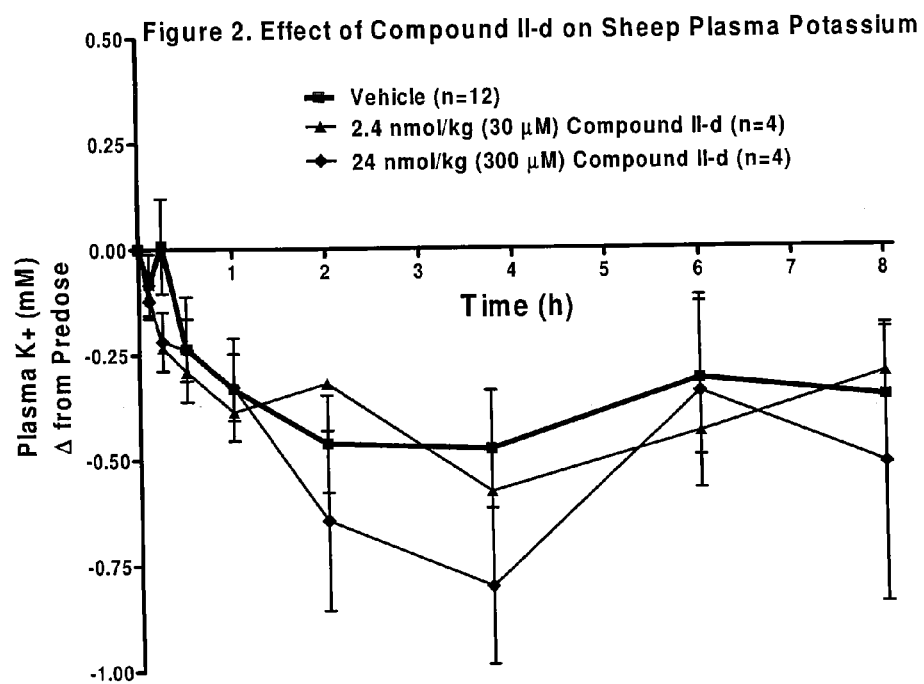

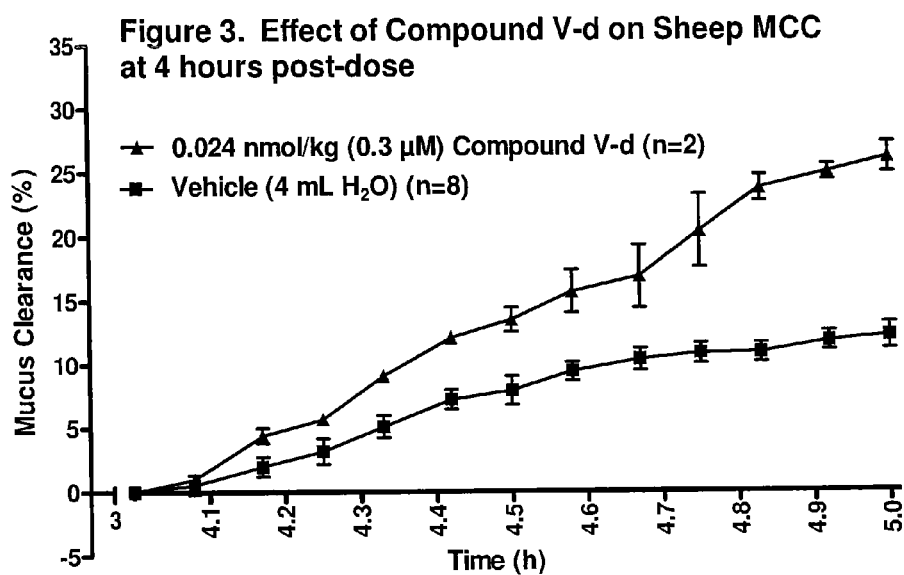
Figure 3. Effect of Compound V-d on Sheep MCC at 4 hours post-dose

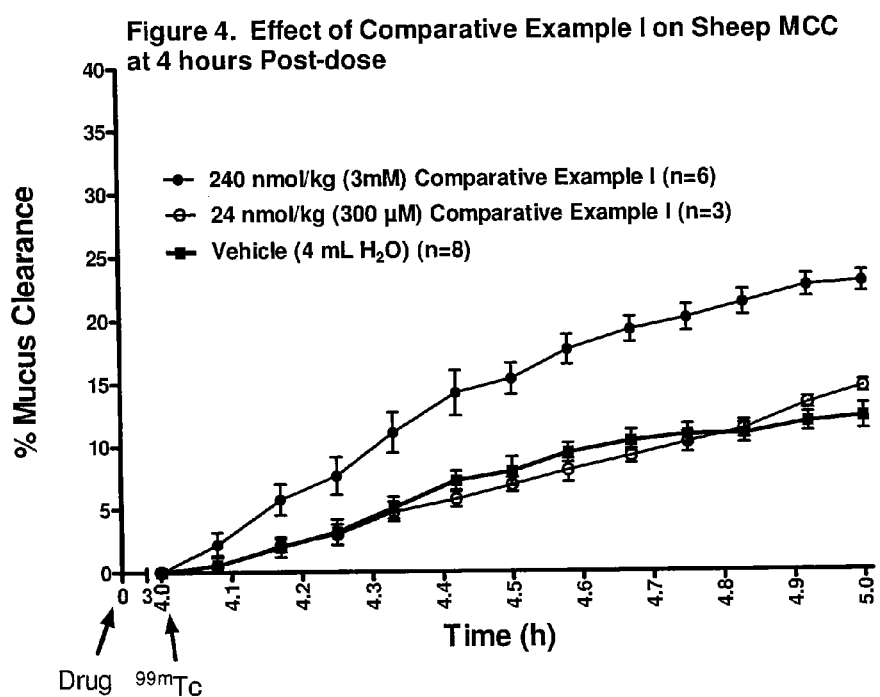

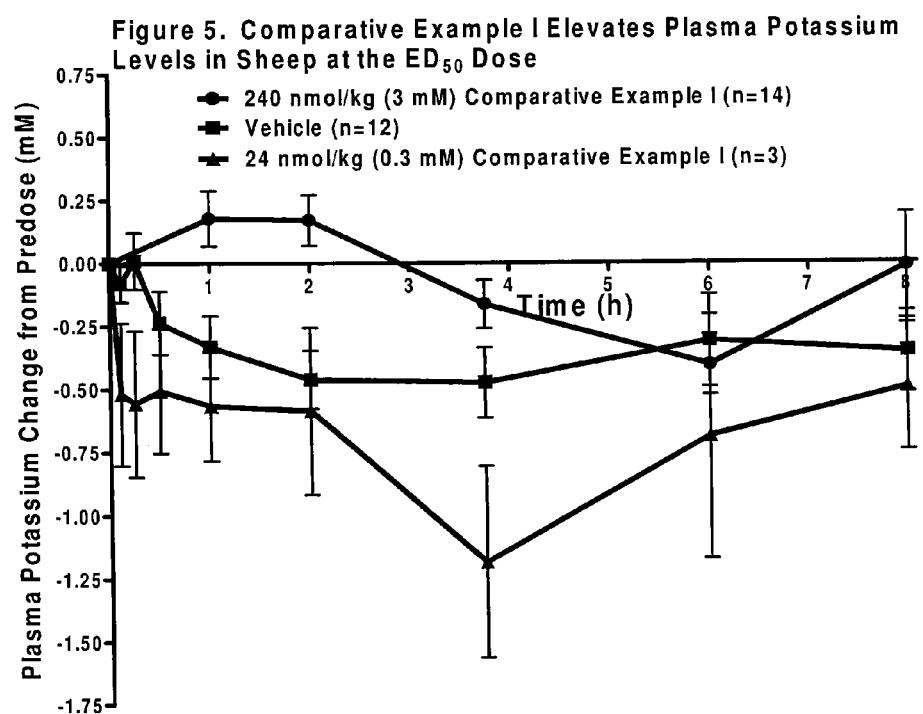
Figure 5. Comparative Example I Elevates Plasma Potassium Levels in Sheep at the $ED_{50}$ Dose

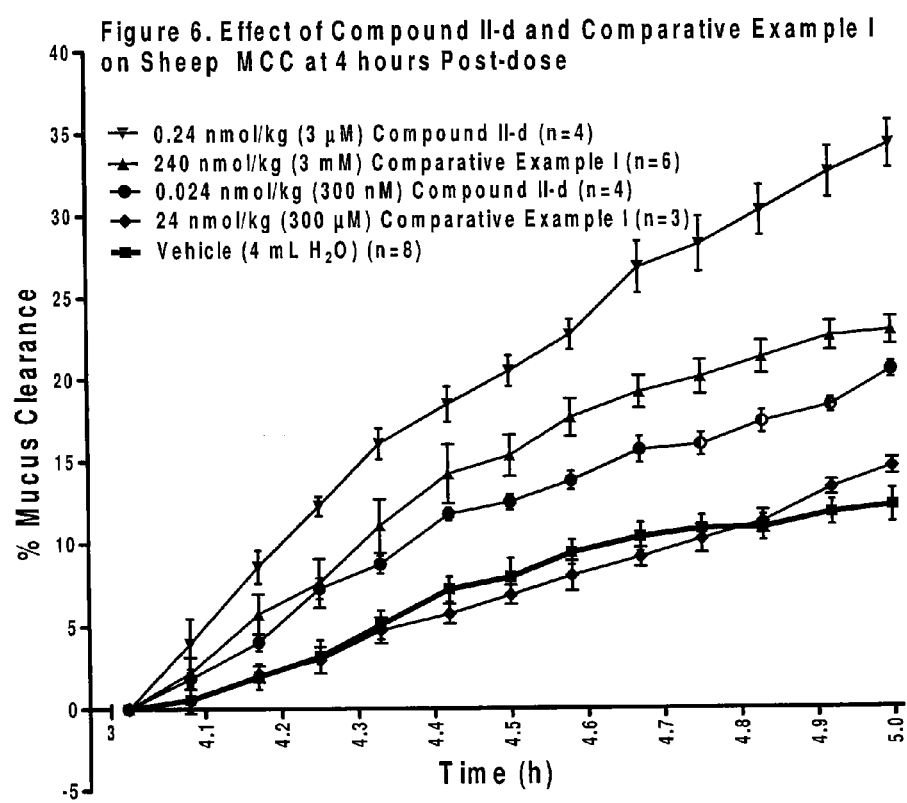
Figure 6. Effect of Compound II-d and Comparative Example I on Sheep MCC at 4 hours Post-dose

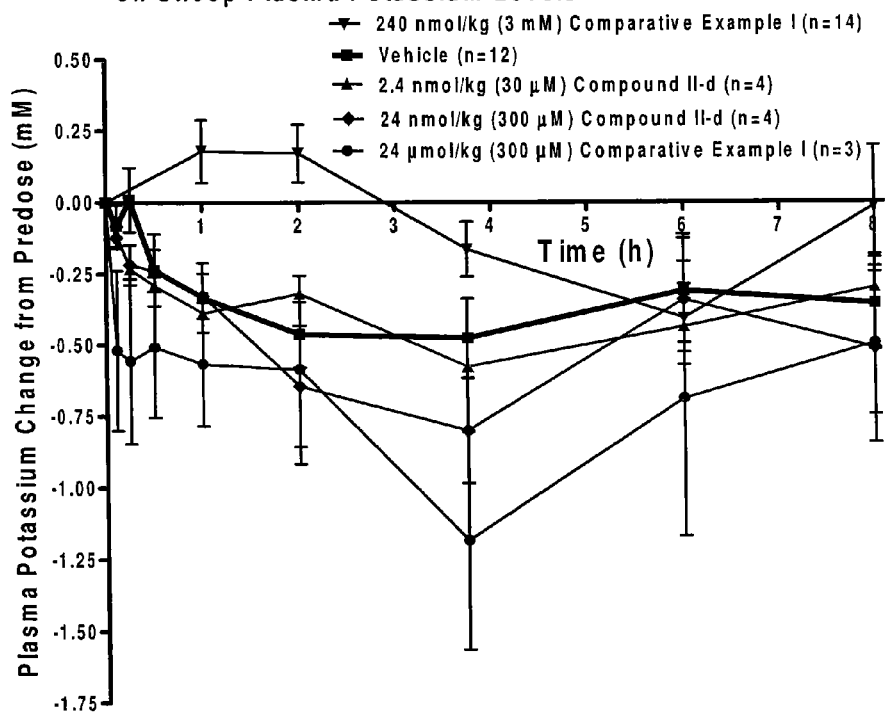

3,5-DIAMINO-6-CHLORO-N-(N-(4-PHENYLBUTYL)CARBAMIMIDOYL) PYRAZINE-2-CARBOXAMIDE COMPOUNDS

CONTINUING APPLICATION INFORMATION

This application is a Continuation of application Ser. No. 14/106,098, filed on Dec. 13, 2013, allowed, which claims benefit to Provisional Application No. 61/738,235, filed on Dec. 17, 2012, both of which are incorporated herein by reference.

FIELD OF THE INVENTION

The present invention relates to novel substituted 3,5-diamino-6-chloro-N—(N-(4-arylbutyl)carbamimidoyl)pyrazine-2-carboxamide compounds, particularly including substituted 3,5-diamino-6-chloro-N—(N-(4-phenylbutyl)carbamimidoyl)pyrazine-2-carboxamide compounds, such as 3,5-diamino-N—(N-(4-(4-((S)-4-amino-3-(3-(bis((2S,3R,4R,5R)-2,3,4,5,6-pentahydroxyhexyl)amino)propylamino)-4-oxobutyl)phenyl)butyl)carbamimidoyl)-6-chloropyrazine-2-carboxamide and its enantiomers and pharmaceutically acceptable salts, useful as sodium channel blockers, compositions containing the same, therapeutic methods and uses for the same and processes for preparing the same.

BACKGROUND OF THE INVENTION

The mucosal surfaces at the interface between the environment and the body have evolved a number of "innate defenses", i.e., protective mechanisms. A principal form of such innate defense is to cleanse these surfaces with liquid. Typically, the quantity of the liquid layer on a mucosal surface reflects the balance between epithelial liquid secretion, often reflecting anion ($Cl^-$ and/or $HCO_3^-$) secretion coupled with water (and a cation counter-ion), and epithelial liquid absorption, often reflecting $Na^+$ absorption, coupled with water and counter anion ($Cl^-$ and/or $HCO_3^-$). Many diseases of mucosal surfaces are caused by too little protective liquid on those mucosal surfaces created by an imbalance between secretion (too little) and absorption (relatively too much). The defective salt transport processes that characterize these mucosal dysfunctions reside in the epithelial layer of the mucosal surface.

One approach to replenish the protective liquid layer on mucosal surfaces is to "re-balance" the system by blocking $Na^+$ channels and liquid absorption. The epithelial protein that mediates the rate-limiting step of $Na^+$ and liquid absorption is the epithelial $Na^+$ channel ("ENaC"). ENaC is positioned on the apical surface of the epithelium, i.e. the mucosal surface-environmental interface. Ideally, to inhibit ENaC mediated $Na^+$ and liquid absorption, an ENaC blocker of the amiloride class will be delivered to the mucosal surface and maintained at this site to achieve maximum therapeutic benefit.

The use of ENaC blockers has been reported for a variety of diseases which are ameliorated by increased mucosal hydration. In particular, the use of ENaC blockers in the treatment of respiratory diseases such as cystic fibrosis (CF), and COPD, including chronic bronchitis (CB) and emphysema, which reflect the body's failure to clear mucus normally from the lungs and ultimately result in chronic airway infection has been reported. See, *Evidence for airway surface dehydration as the initiating event in CF airway disease*, R. C. Boucher, Journal of Internal Medicine, Vol. 261, Issue 1, January 2007, pages 5-16; and *Cystic fibrosis: a disease of vulnerability to airway surface dehydration*, R. C. Boucher, Trends in Molecular Medicine, Vol. 13, Issue 6, June 2007, pages 231-240.

Data indicate that the initiating problem in both CB and CF is the failure to clear mucus from airway surfaces. The failure to clear mucus reflects an imbalance in the quantities of mucus as airway surface liquid (ASL) on airway surfaces. This imbalance results in a relative reduction in ASL which leads to mucus concentration, reduction in the lubricant activity of the periciliary liquid (PCL), mucus adherence to the airway surface, and failure to clear mucus via ciliary activity to the mouth. The reduction in mucus clearance leads to chronic bacterial colonization of mucus adherent to airway surfaces. The chronic retention of bacteria, inability of local antimicrobial substances to kill mucus-entrapped bacteria on a chronic basis, and the consequent chronic inflammatory response to this type of surface infection, are manifest in CB and CF.

There is currently a large, unmet medical need for products that specifically treat the variety of diseases which are ameliorated by increased mucosal hydration, including CB, COPD and CF, among others. The current therapies for CB, COPD and CF focus on treating the symptoms and/or the late effects of these diseases. However, none of these therapies effectively treat the fundamental problem of the failure to clear mucus from the lung.

R. C. Boucher, in U.S. Pat. No. 6,264,975, describes the use of pyrazinoylguanidine sodium channel blockers for hydrating mucosal surfaces typified by the well-known diuretics amiloride, benzamil, and phenamil. However, these compounds are relatively impotent, considering the limited mass of drug that can be inhaled to the lung; (2) rapidly absorbed, and thereby exhibiting undesirably short half-life on the mucosal surface; and (3) are freely dissociable from ENaC. More potent drugs with longer half-lives on the mucosal surface are needed.

Too little protective surface liquid on other mucosal surfaces is a common pathophysiology of a number of diseases. For example, in xerostomia (dry mouth) the oral cavity is depleted of liquid due to a failure of the parotid sublingual and submandibular glands to secrete liquid despite continued $Na^+$ (ENaC) transport mediated liquid absorption from the oral cavity. Keratoconjunctivitis sira (dry eye) is caused by failure of lacrimal glands to secrete liquid in the face of continued $Na^+$ dependent liquid absorption on conjunctional surfaces. In rhinosinusitis, there is an imbalance between mucin secretion and relative ASL depletion. Failure to secrete Cl— (and liquid) in the proximal small intestine, combined with increased $Na^+$ (and liquid) absorption in the terminal ileum leads to the distal intestinal obstruction syndrome (DIOS). In older patients excessive $Na^+$ (and volume) absorption in the descending colon produces constipation and diverticulitis.

The published literature includes a number of patent applications and granted patents directed toward pyrazinoylguanidine analogs as sodium channel blockers. Examples of such publications include PCT Publication Nos. WO2003/070182, WO2003/070184, WO2004/073629, WO2005/025496, WO2005/016879, WO2005/018644, WO2006/022935, WO2006/023573, WO2006/023617, WO2007/018640, WO2007/146869, WO2008/031028, WO2008/031048, and U.S. Pat. Nos. 6,858,614, 6,858,615, 6,903,105, 6,995,160, 7,026,325, 7,030,117, 7,064,129, 7,186,833, 7,189,719, 7,192,958, 7,192,959, 7,192,960, 7,241,766, 7,247,636, 7,247,637, 7,317,013, 7,332,496, 7,345,044, 7,368,447, 7,368,450, 7,368,451, 7,375,107, 7,388,013, 7,399,766, 7,410,968, 7,745,442, 7,807,834, 7,820,678, 7,842,697, 7,868,010, 7,875,619, 7,956,059, 7,981,898, 8,008,494, 8,022,210, 8,058,278, 8,124,607, 8,143,256, 8,163,758, 8,198,286, and 8,211,895.

There remains a need for novel sodium channel blocking compounds with enhanced potency and effectiveness on mucosal tissues. There also remains the need for novel sodium channel blocking compounds that provide therapeutic effect, but minimize or eliminate the onset or progression of hyperkalemia in recipients.

SUMMARY OF THE INVENTION

This invention provides compounds of Formula (A):

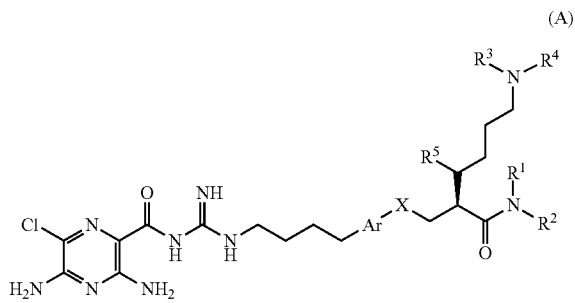

wherein Ar is a moiety selected from the group of:

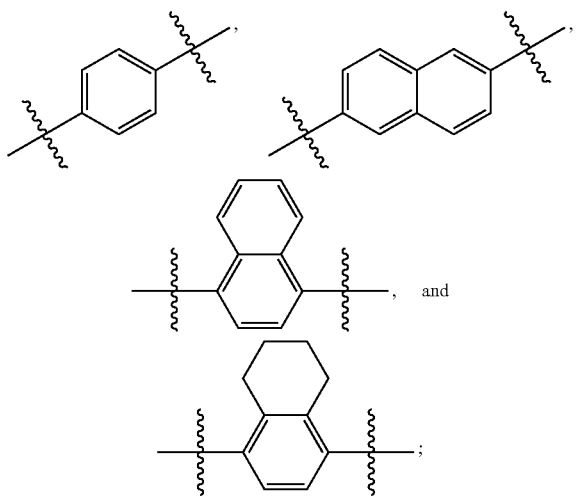

X is selected from —CH$_2$—, —O—, or —S—;

R$^1$ and R$^2$ are independently selected from H and C$_1$-C$_6$ alkyl;

or R$^1$ and R$^2$ together with the nitrogen atom to which they are bound form a 5-membered or 6-membered heterocyclic ring optionally containing one additional ring heteroatom selected from N or O;

R$^3$ is an alkyl group having from 3 to 8 carbon atoms or a polyhydroxylated alkyl group having from 3 to 8 carbon atoms;

R$^4$ is a polyhydroxylated alkyl group having from 3 to 8 carbon atoms; and

R$^5$ is selected from H or C$_1$-C$_3$ alkyl;

or a pharmaceutically acceptable salt thereof.

The invention also provides solvates and hydrates, individual stereoisomers, including optical isomers (enantiomers and diastereomers) and geometric isomers (cis-/trans-isomerism), mixtures of stereoisomers, and tautomers of 3,5-diamino-N—(N-(4-(4-((S)-4-amino-3-(3-(bis((2S,3R,4R,5R)-2,3,4,5,6-pentahydroxyhexyl)amino)propylamino)-4-oxobutyl)phenyl) butyl)carbamimidoyl)-6-chloropyrazine-2-carboxamide, or a pharmaceutically acceptable salt thereof, as well as pharmaceutical compositions comprising the compound, or a pharmaceutically acceptable salt thereof, its use in methods of treatment, and methods for its preparation.

BRIEF DESCRIPTION OF THE DRAWINGS

A more complete appreciation of the invention and many of the advantages thereof may be readily obtained by reference to the information herein in conjunction with the following figures:

FIG. 1 is a graph demonstrating a 4-hour dose response of Compound II-d compared to vehicle.

FIG. 2 is a graph of the effect od Compound II-d on sheep plasma.

FIG. 3 is a graph demonstrating the effect of Compound II-d on Sheep MCC 4 hours post-dose.

FIG. 4 is a graph demonstrating the effect of Comparative Example 1 on Sheep MCC 4 hours post-dose.

FIG. 5 is a graph demonstrating the effect of Comparative Example 1 on plasma potassium in sheep.

FIG. 6 is a graph demonstrating the effect of Compound II-d and Comparative Example 1 on Sheep MCC 4 hours post-dose.

FIG. 7. is a graph demonstrating the effect of Compound II-d and Comparative Example 1 on plasma potassium in sheep.

DETAILED DESCRIPTION OF THE INVENTION

Also provided are embodiments comprising twelve groups of compounds independently represented by Formulas (B), (C), (D), (E), (F), (G), (H), (I), (J), (K), (L), and (M):

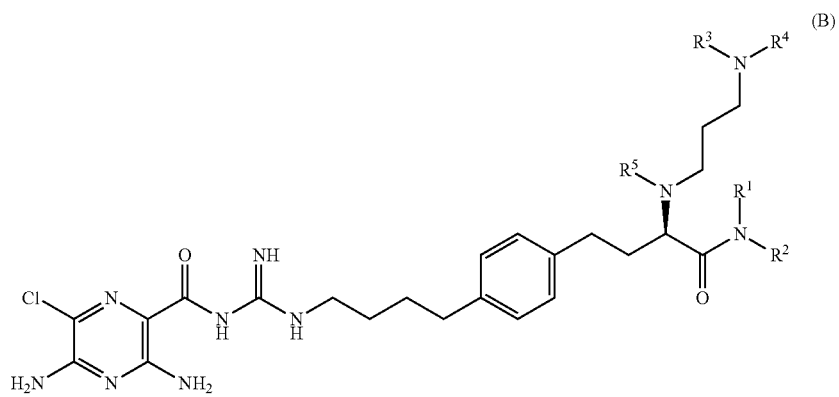

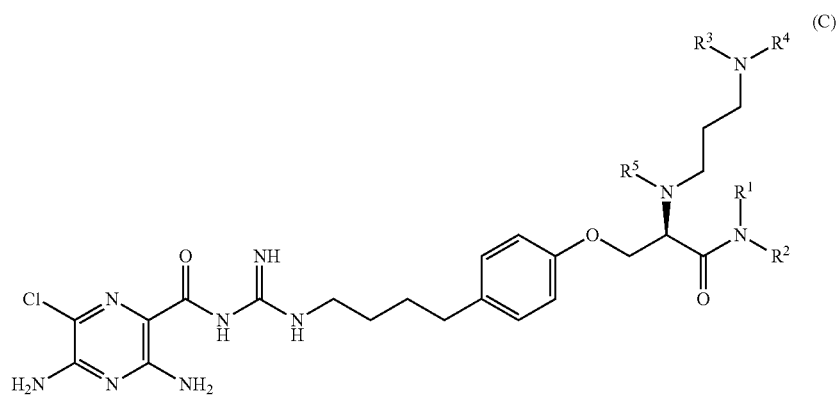
(C)
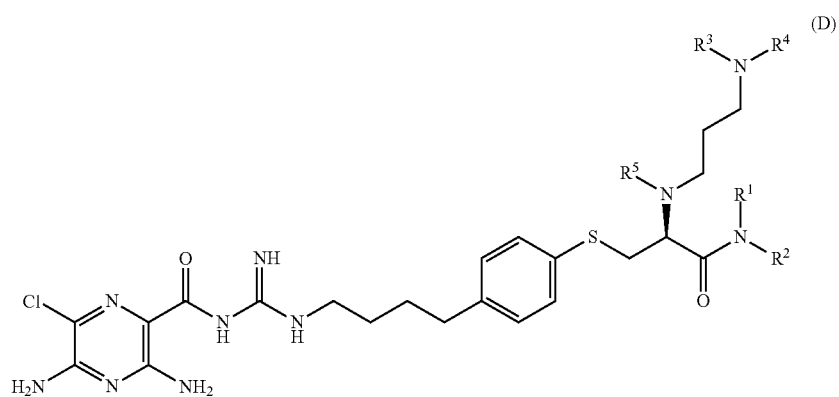
(D)
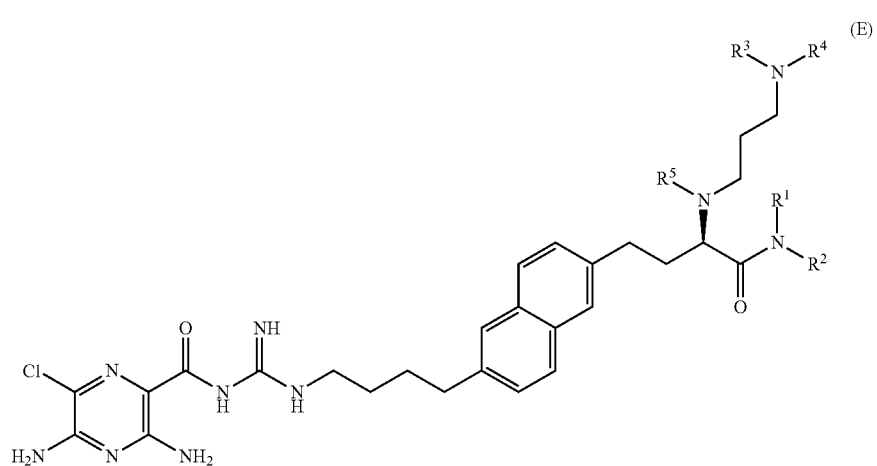
(E)
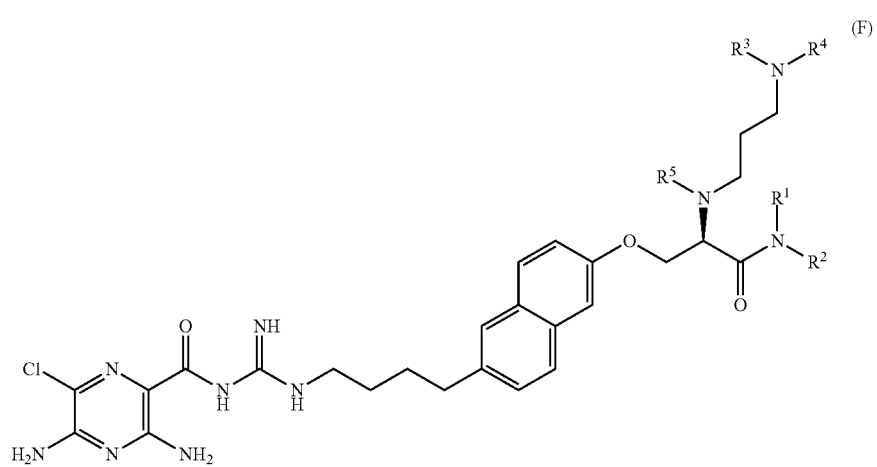
(F)

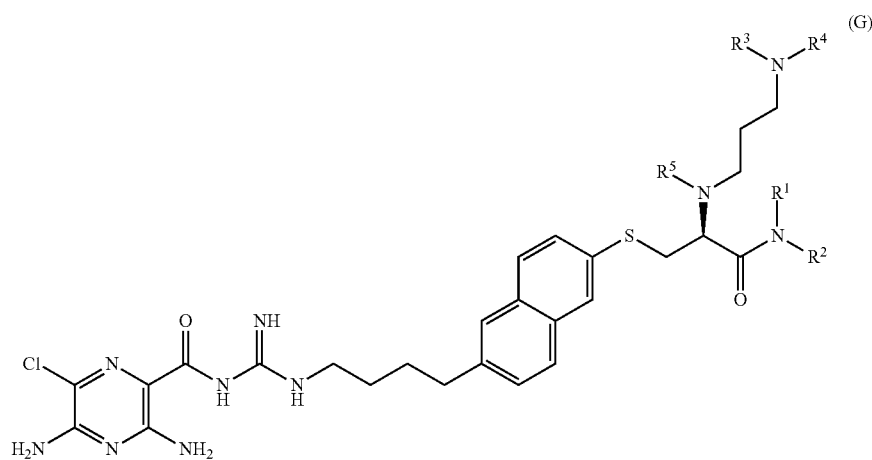
(G)
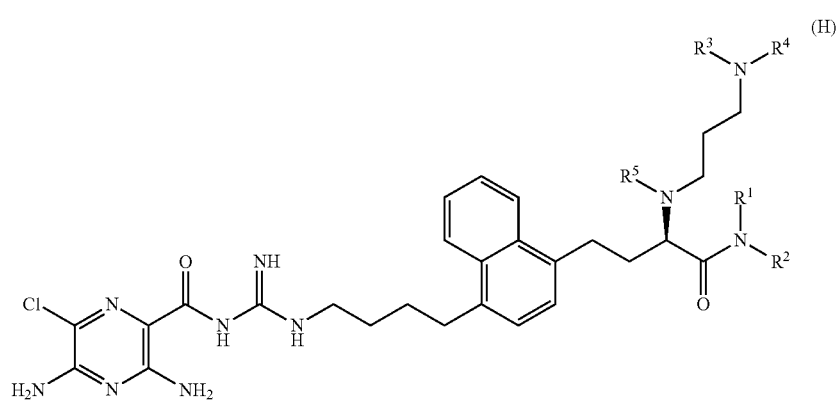
(H)
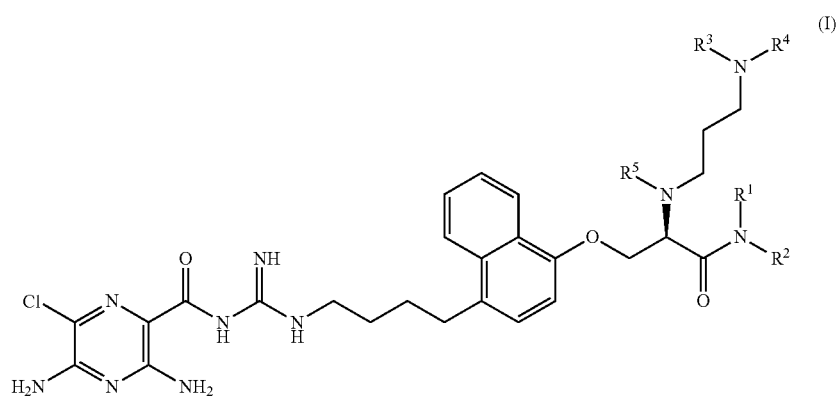
(I)
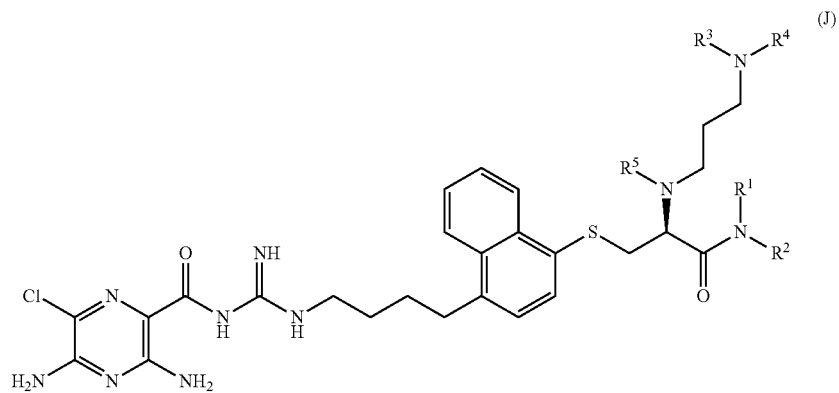
(J)

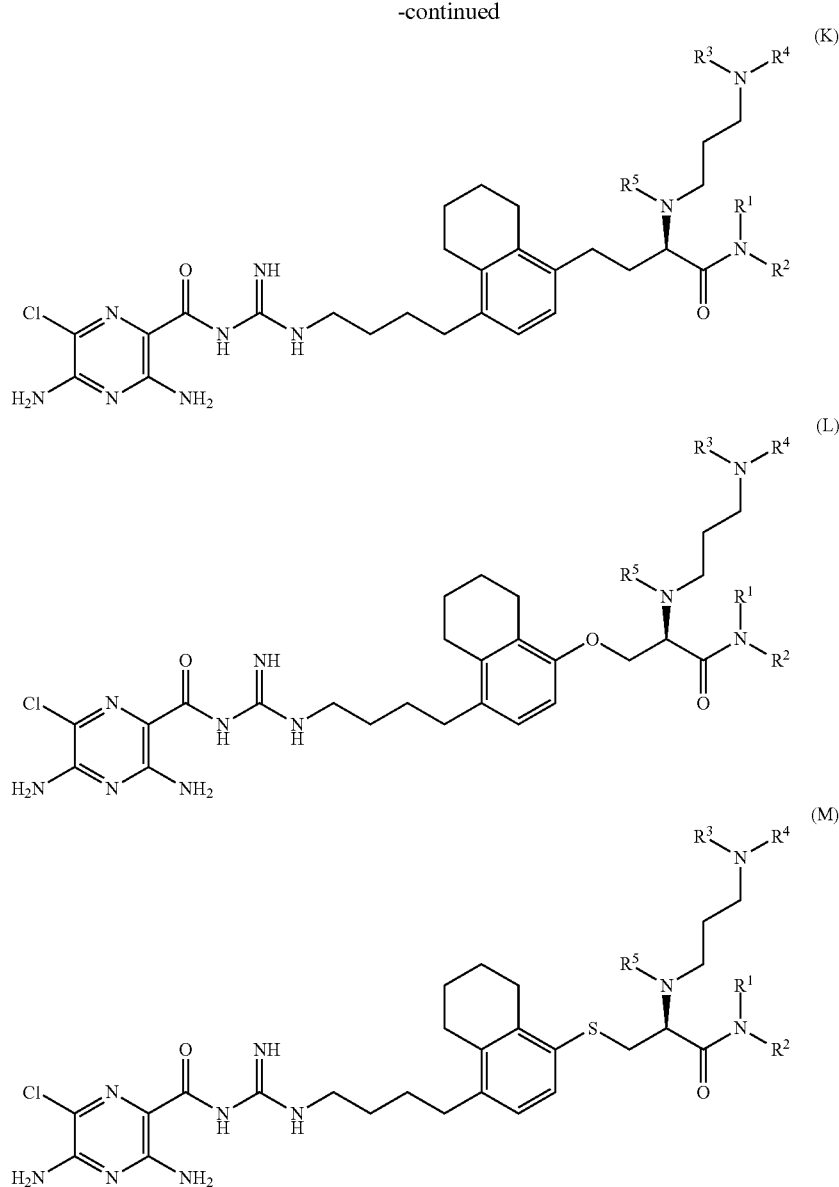

wherein, in each group (B), (C), (D), (E), (F), (G), (H), (I), (J), (K), (L), and (M):

$R^1$ and $R^2$ are independently selected from H and $C_1$-$C_6$ alkyl;

or $R^1$ and $R^2$ together with the nitrogen atom to which they are bound form a 5-membered or 6-membered heterocyclic ring optionally containing one additional ring heteroatom selected from N or O; $R^3$ is an alkyl group having from 3 to 8 carbon atoms or a polyhydroxylated alkyl group having from 3 to 8 carbon atoms;

$R^4$ is a polyhydroxylated alkyl group having from 3 to 8 carbon atoms; and $R^5$ is selected from H or $C_1$-$C_3$ alkyl;

or a pharmaceutically acceptable salt thereof.

Within each group of compounds represented by Formulas (A), (B), (C), (D), (E), (F), (G), (H), (I), (J), (K), (L), and (M) there is a further group of compounds wherein:

$R^1$ and $R^2$ are independently selected from H and $C_1$-$C_6$ alkyl;

$R^3$ and $R^4$ are each, independently, a polyhydroxylated alkyl group having from 3 to 8 carbon atoms;

$R^5$ is selected from H or $C_1$-$C_3$ alkyl;

or a pharmaceutically acceptable salt thereof.

Within each group of compounds represented by Formulas (A), (B), (C), (D), (E), (F), (G), (H), (I), (J), (K), (L), and (M) there is a further group of compounds wherein:

$R^1$ and $R^2$ are independently selected from H and $C_1$-$C_3$ alkyl;

$R^3$ is an alkyl group having from 3 to 8 carbon atoms; and $R^4$ is a polyhydroxylated alkyl group having from 3 to 8 carbon atoms;

$R^5$ is selected from H or $C_1$-$C_3$ alkyl;

or a pharmaceutically acceptable salt thereof.

Also within each group of compounds represented by Formulas (A), (B), (C), (D), (E), (F), (G), (H), (I), (J), (K), (L), and (M) there is a further group of compounds wherein:

$R^1$ and $R^2$ are, independently, selected from H and —$CH_3$;

$R^3$ is an alkyl group having from 3 to 8 carbon atoms or a polyhydroxylated alkyl group having from 3 to 8 carbon atoms;

$R^4$ is a polyhydroxylated alkyl group having from 3 to 8 carbon atoms; and $R^5$ is selected from H or $C_1$-$C_3$ alkyl;

or a pharmaceutically acceptable salt thereof.

Within each group of compounds represented by Formulas (A), (B), (C), (D), (E), (F), (G), (H), (I), (J), (K), (L), and (M) there is also a further group of compounds wherein:

$R^1$ and $R^2$ are, independently, selected from H and —$CH_3$;

$R^3$ is an alkyl group having from 3 to 8 carbon atoms;

$R^4$ is a polyhydroxylated alkyl group having from 3 to 8 carbon atoms; and $R^5$ is selected from H or $C_1$-$C_3$ alkyl;

or a pharmaceutically acceptable salt thereof.

Further within each group of compounds represented by Formulas (A), (B), (C), (D), (E), (F), (G), (H), (I), (J), (K), (L), and (M) there is a further group of compounds wherein:

$R^1$ and $R^2$ are, independently, selected from H and —$CH_3$;

$R^3$ and $R^4$ are each, independently, a polyhydroxylated alkyl group having from 3 to 8 carbon atoms; and $R^5$ is selected from H or $C_1$-$C_3$ alkyl;

or a pharmaceutically acceptable salt thereof.

Included within each group of compounds represented by Formulas (A), (B), (C), (D), (E), (F), (G), (H), (I), (J), (K), (L), and (M) there is a further group of compounds wherein:

$R^1$ and $R^2$ are H;

$R^3$ is an alkyl group having from 3 to 8 carbon atoms or a polyhydroxylated alkyl group having from 3 to 8 carbon atoms;

$R^4$ is a polyhydroxylated alkyl group having from 3 to 8 carbon atoms; and $R^5$ is selected from H or $C_1$-$C_3$ alkyl;

or a pharmaceutically acceptable salt thereof.

Also within each group of compounds represented by Formulas (A), (B), (C), (D), (E), (F), (G), (H), (I), (J), (K), (L), and (M) there is a further group of compounds wherein:

$R^1$ and $R^2$ are H;

$R^3$ is an alkyl group having from 3 to 8 carbon atoms;

$R^4$ is a polyhydroxylated alkyl group having from 3 to 8 carbon atoms; and $R^5$ is selected from H or $C_1$-$C_3$ alkyl;

or a pharmaceutically acceptable salt thereof.

Still further within each group of compounds represented by Formulas (A), (B), (C), (D), (E), (F), (G), (H), (I), (J), (K), (L), and (M) there is a further group of compounds wherein $R^1$ and $R^2$ are H; and $R^3$ and $R^4$ are each, independently, a polyhydroxylated alkyl group having from 3 to 8 carbon atoms; and $R^5$ is selected from H or $C_1$-$C_3$ alkyl; or a pharmaceutically acceptable salt thereof.

Within each of the groups described above there is a further group wherein $R^5$ is H; or a pharmaceutically acceptable salt thereof. Within each of the groups described above there is also a further group wherein $R^5$ is —$CH_3$; or a pharmaceutically acceptable salt thereof.

The 5-membered or 6-membered heterocyclic rings optionally containing one additional ring heteroatom selected from N or O formed by $R^1$ and $R^2$, together with the nitrogen atom to which they are bound, include pyrrolidinyl, piperidinyl, piperazinyl, and morpholinyl rings.

Polyhydroxylated alkyl groups of this invention are those in which an alkyl chain of from 3 to 8 carbon atoms substituted by two or more hydroxyl groups. Examples of polyhydroxylated alkyl groups are butane-1,4-diol; butane-1,2,2-triol; butane-1,1,2,3,-tetraol; pentane-1,2,3,4-tetraol; hexane-1,2,3,4,5-pentaol; heptane-1,2,3,4,5,6-hexaol; and octane-1,2,3,4,5,6,7-heptaol.

One embodiment within each group of compounds described herein are those compounds in which the polyhydroxylated alkyl group has the formula —$CH_2$—$(CHR^5)_n$—H, wherein n is an integer selected from 2, 3, 4, 5, 6, or 7, and $R^5$ is independently in each instance H or OH, with the proviso that at least two of the $R^5$ groups are OH.

Another embodiment within each group of compounds described herein are those compounds in which the polyhydroxylated alkyl group has the formula —$CH_2$—CHOH—$(CHR^6)_m$—H, wherein m is an integer selected from 1, 2, 3, 4, 5, or 6, and $R^6$ is independently in each instance H or OH, with the proviso that at least one of the $R^6$ groups is OH.

A further embodiment within each group of compounds described herein comprises compounds in which the polyhydroxylated alkyl group has the formula —$CH_2$—$(CHOH)_n$—$CH_2OH$, wherein n is an integer selected from 1, 2, 3, 4, 5, or 6. Another embodiment within each group of compounds described herein comprises compounds in which n is an integer selected from 2, 3, 4, or 5. Another embodiment within each group comprises compounds in which n is an integer selected from 3, 4, or 5.

In another embodiment within each group of compounds described herein, the chain represented by the $R^4$ formula —$CH_2$—$(CHOH)_n$—$CH_2OH$ is 2,3,4,5,6-pentahydroxyhexane, having the formula:

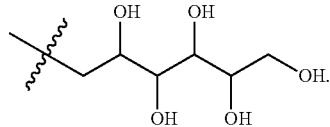 [SMILES: *CC(O)C(O)C(O)C(O)CO]

In a further embodiment within each group of compounds described herein, the chain represented by the $R^4$ formula —$CH_2$—$(CHOH)_n$—$CH_2OH$ is of the formula:

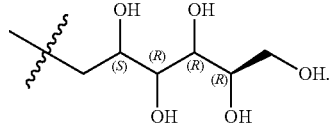

Within each of the groups independently represented by the compounds of Formulas (A), (B), (C), (D), (E), (F), (G), (H), (I), (J), (K), (L), and (M), there is a further embodiment wherein: $R^1$ is H; $R^2$ is H or $C_1$-$C_3$ alkyl;

$R^3$ is an alkyl group having from 4 to 8 carbon atoms or a polyhydroxylated alkyl group having from 4 to 8 carbon atoms; and $R^4$ is a polyhydroxylated alkyl group of the formula —$CH_2$—$(CHOH)_n$—$CH_2OH$; and n in each instance is independently an integer selected from 1, 2, 3, 4, 5, or 6;

or a pharmaceutically acceptable salt thereof.

Within each of the groups independently represented by the compounds of Formulas (A), (B), (C), (D), (E), (F), (G), (H), (I), (J), (K), (L), and (M), there is still a further embodiment wherein: $R^1$ and $R^2$ are H; $R^3$ is an alkyl group having from 5 to 7 carbon atoms; $R^4$ is a polyhydroxylated alkyl group of the formula —CH$_2$—(CHOH)$_n$—CH$_2$OH; and n is an integer selected from 1, 2, 3, 4, 5, or 6; or a pharmaceutically acceptable salt thereof.

Within each of the groups described herein there is a further embodiment wherein R$^4$ is a polyhydroxylated alkyl group of the formula —CH$_2$—(CHOH)$_n$—CH$_2$OH and n is an integer selected from 3, 4, or 5. In a further embodiment within each group, R$^4$ is a polyhydroxylated alkyl group of the formula —CH$_2$—(CHOH)$_n$—CH$_2$OH and n is 4.

Within each of the groups independently represented by the compounds of Formulas (A), (B), (C), (D), (E), (F), (G), (H), (I), (J), (K), (L), and (M), there is still a further embodiment wherein: R$^1$ and R$^2$ are H; R$^3$ is an alkyl group having 6 carbon atoms; R$^4$ is a polyhydroxylated alkyl group of the formula —CH$_2$—(CHOH)$_n$—CH$_2$OH; and n is 4; or a pharmaceutically acceptable salt thereof.

Also provided is the compound 3,5-diamino-N—(N-(4-(4-(4-amino-3-(3-(bis(2,3,4,5,6-pentahydroxyhexyl)amino) propylamino)-4-oxobutyl)phenyl)butyl) carbamimidoyl)-6-chloropyrazine-2-carboxamide, of Formula (B-1):

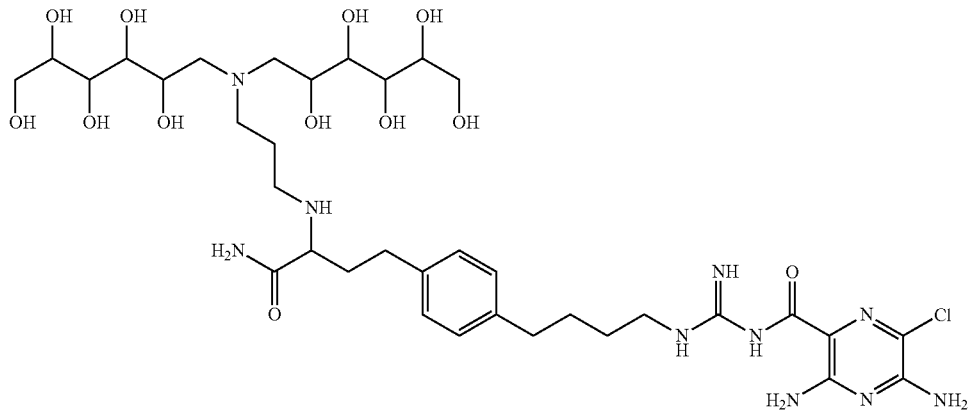

(B-1)

or a pharmaceutically acceptable salt form thereof.

In another embodiment, the compound of Formula (A) is 3,5-diamino-N—(N-(4-(4-((S)-4-amino-3-(3-(bis((2S,3R,4R,5R)-2,3,4,5,6-pentahydroxyhexyl)amino)propylamino)-4-oxobutyl)phenyl)butyl)carbamimidoyl)-6-chloropyrazine-2-carboxamide, having the formula (B-2):

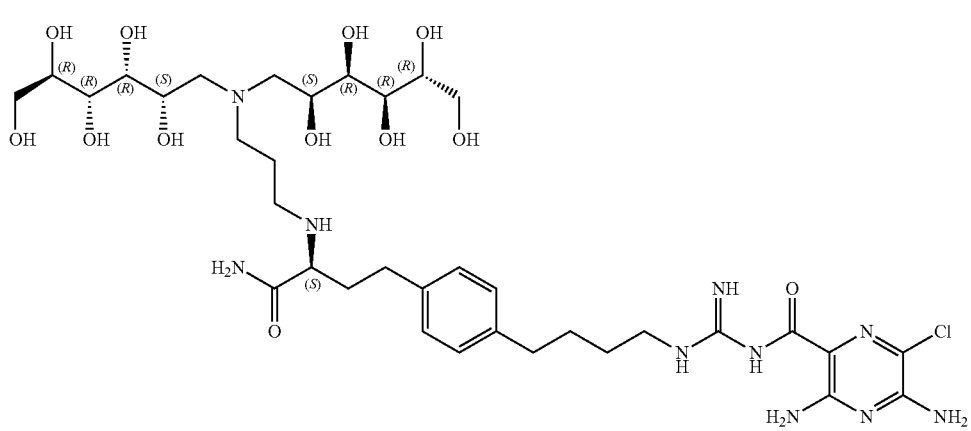

(B-2)

or a pharmaceutically acceptable salt thereof.

Also provided is the compound 3,5-diamino-N—(N-(4-(4-(4-amino-3-(3-(hexyl(2,3,4,5,6-pentahydroxyhexyl)amino)propylamino)-4-oxobutyl)phenyl)butyl) carbamimidoyl)-6-chloropyrazine-2-carboxamide, of Formula (B-3):

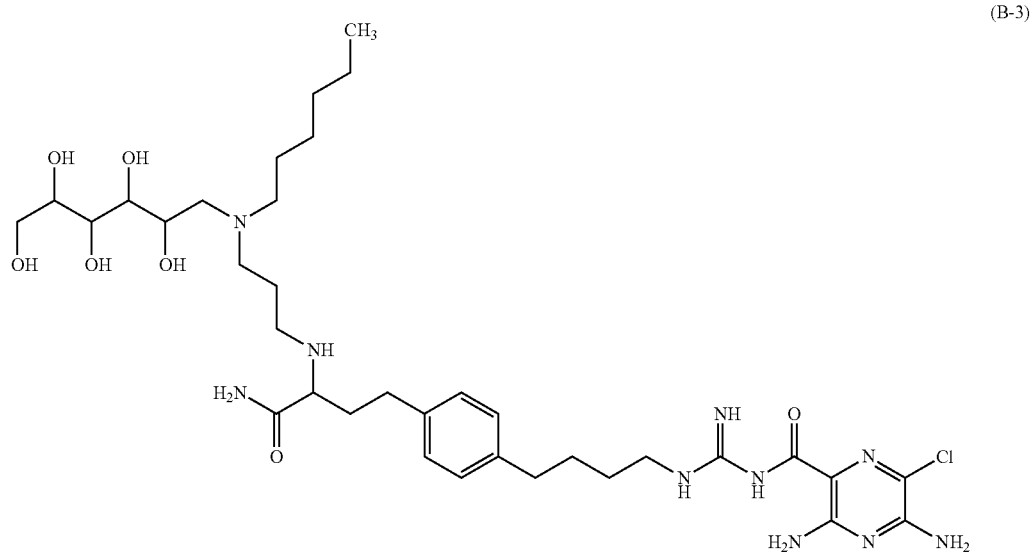 [SMILES: CCCCCCN(CCCNC(CCc1ccc(CCCCNC(=N)NC(=O)c2nc(Cl)c(N)nc2N)cc1)C(N)=O)CC(O)C(O)C(O)C(O)CO]

(B-3)

or a pharmaceutically acceptable salt thereof.

In another embodiment, the compound is 3,5-diamino-N—(N-(4-(4-((S)-4-amino-3-(3-(hexyl((2S,3R,4R,5R)-2,3,4,5,6-pentahydroxyhexyl)amino) propylamino)-4-oxobutyl) phenyl)butyl)carbamimidoyl)-6-chloropyrazine-2-carboxamide, having formula (B-4):

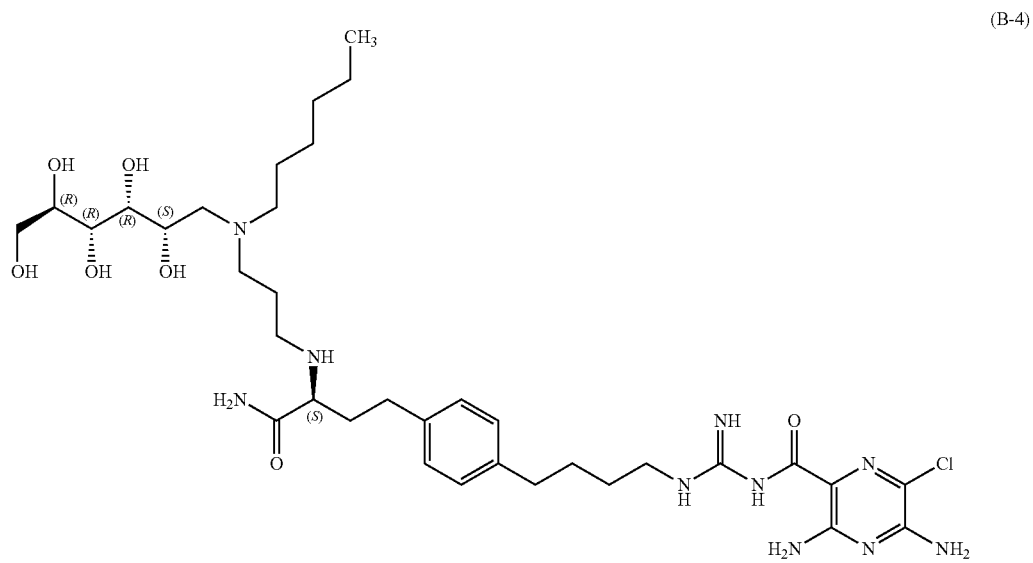

(B-4)

or a pharmaceutically acceptable salt thereof.

Other compounds of this invention include those of formulas (E-1), (E-2), (E-3), and (E-4), or a pharmaceutically acceptable salt thereof:

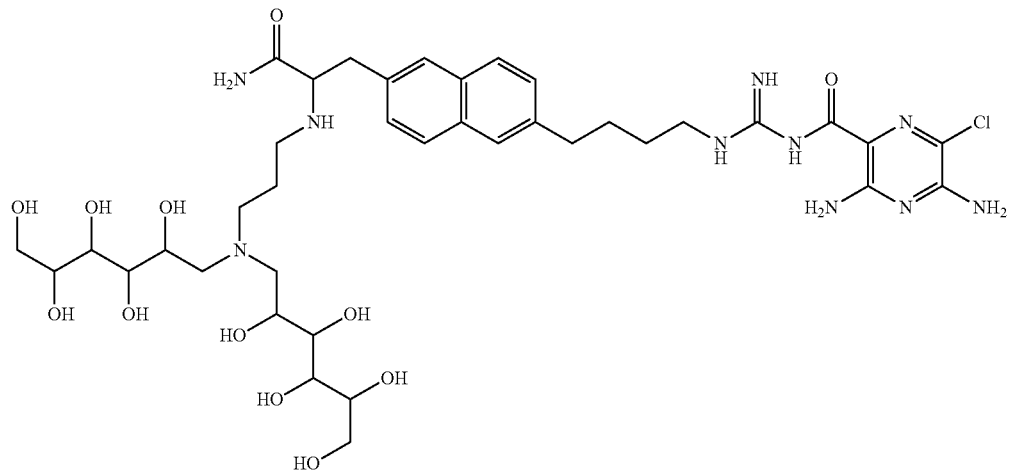
3,5-diamino-N—(N-(4-(6-(3-amino-2-(3-(bis(2,3,4,5,6-pentahydroxyhexyl)amino)propylamino)-3-oxopropyl)naphthalen-2-yl)butyl)carbamimidoyl)-6-chloropyrazine-2-carboxamide;
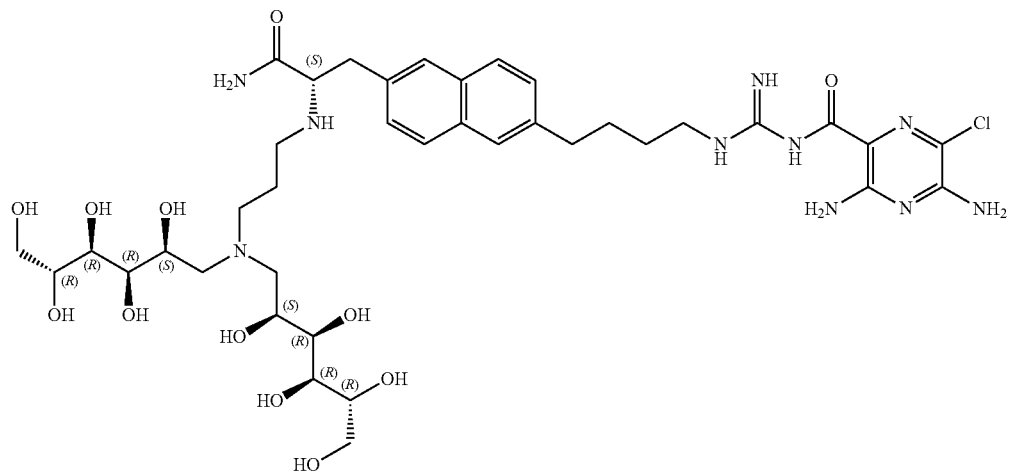
3,5-diamino-N—(N-(4-(6-((S)-3-amino-2-(3-(bis((2S,3R,4R,5R)-2,3,4,5,6-pentahydroxyhexyl)amino)propylamino)-3-oxopropyl)naphthalen-2-yl)butyl)carbamimidoyl)-6-chloropyrazine-2-carboxamide;

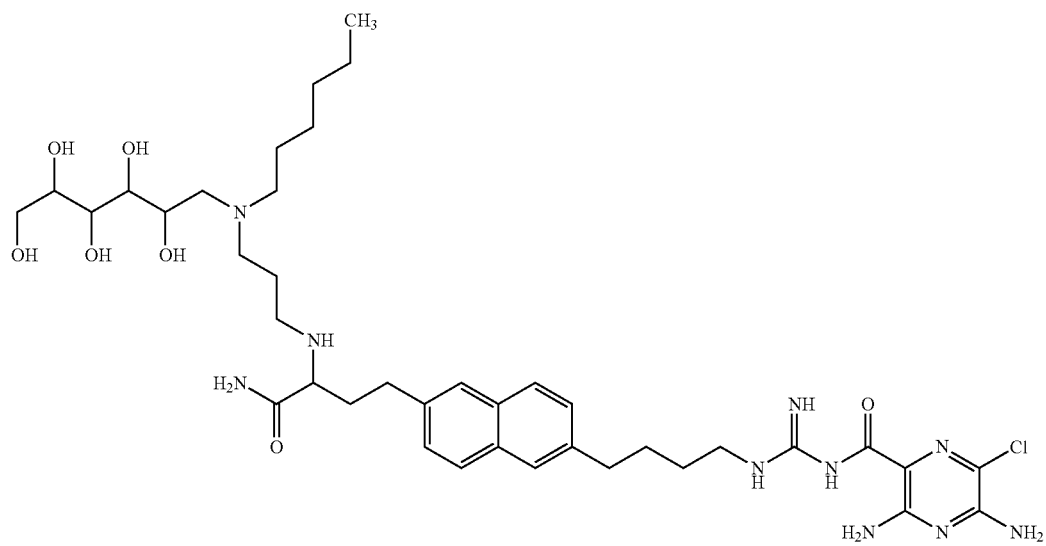

(E-3)

3,5-diamino-N—(N-(4-(6-(4-amino-3-(3-(hexyl(2,3,4,5,6-pentahydroxyhexyl)amino)propylamino)-4-oxobutyl)naphthalen-2-yl)butyl)carbamimidoyl)-6-chloropyrazine-2-carboxamide; and

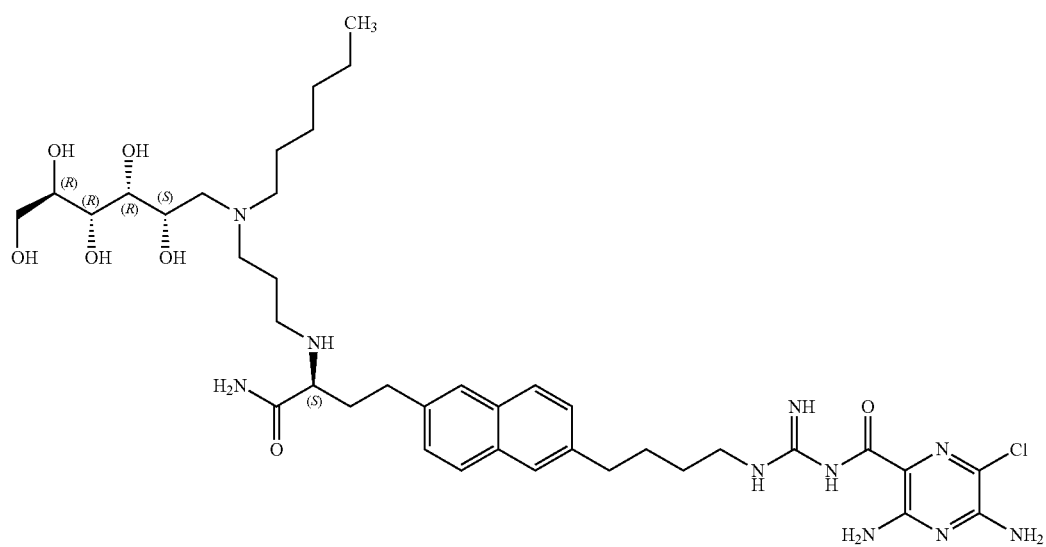

(E-4)

3,5-diamino-N—(N-(4-(6-((S)-4-amino-3-(3-(hexyl((2S,3R,4R,5R)-2,3,4,5,6-pentahydroxyhexyl)amino)propylamino)-4-oxobutyl)naphthalen-2-yl)butyl)carbamimidoyl)-6-chloropyrazine-2-carboxamide.

Further compounds of this invention include those of formulas (H-1), (H-2), (H-3), and (H-4), or a pharmaceutically acceptable salt thereof:

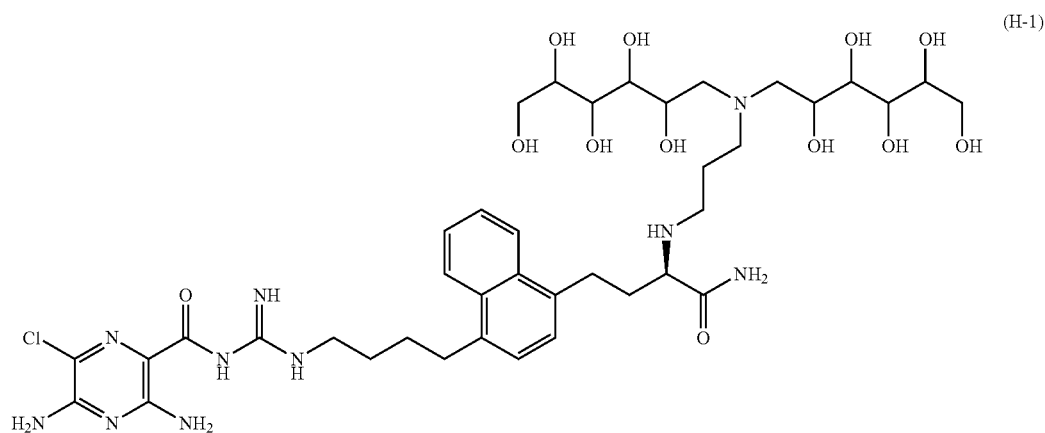 [SMILES: N=C(NCCCCc1ccc(CC[C@@H](NCCCN(CC(O)C(O)C(O)C(O)CO)CC(O)C(O)C(O)C(O)CO)C(N)=O)c2ccccc12)NC(=O)c1nc(Cl)c(N)nc1N]
(H-1)
3,5-diamino-N—(N-(4-(4-((3R)-4-amino-3-(3-(bis(2,3,4,5,6-pentahydroxyhexyl)amino)propylamino)-4-oxobutyl)naphthalen-1-yl) butyl)carbamimidoyl)-6-chloropyrazine-2-carboxamide; and
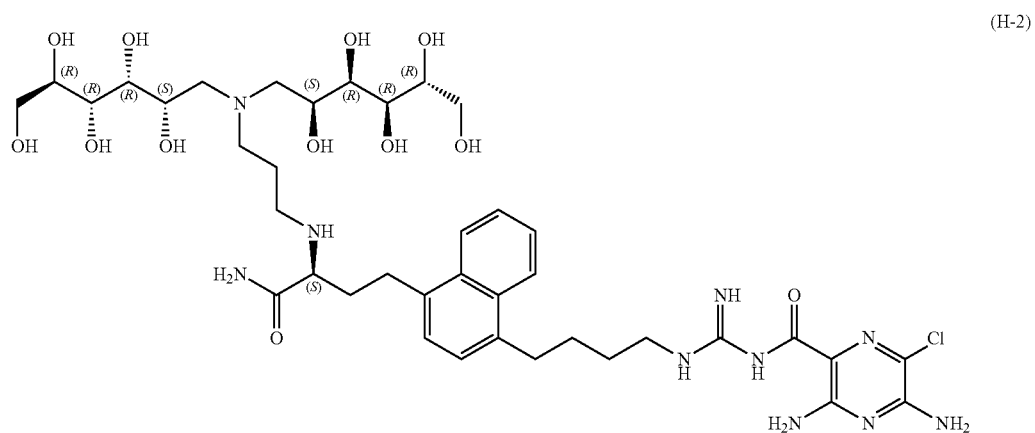
(H-2)
3,5-diamino-N—(N-(4-(4-((S)-4-amino-3-(3-(bis((2S,3R,4R,5R)-2,3,4,5,6-pentahydroxyhexyl)amino)propylamino)-4-oxobutyl)naphthalen-1-yl)butyl)carbamimidoyl)-6-chloropyrazine-2-carboxamide; and

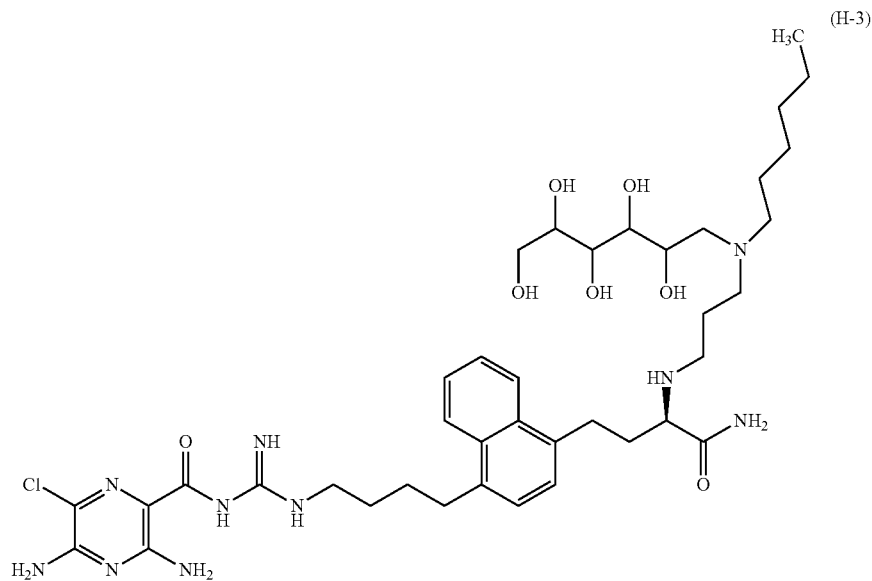 [SMILES: CCCCCCN(CCCN[C@H](CCc1ccc(CCCCNC(=N)NC(=O)c2nc(Cl)c(N)nc2N)c2ccccc12)C(N)=O)CC(O)C(O)C(O)C(O)CO]

(H-3)

3,5-diamino-N—(N-(4-(4-((3R)-4-amino-3-(3-(hexyl(2,3,4,5,6-pentahydroxyhexyl)amino)propylamino)-4-oxobutyl)naphthalen-1-yl)butyl)carbamimidoyl)-6-chloropyrazine-2-carboxamide; and

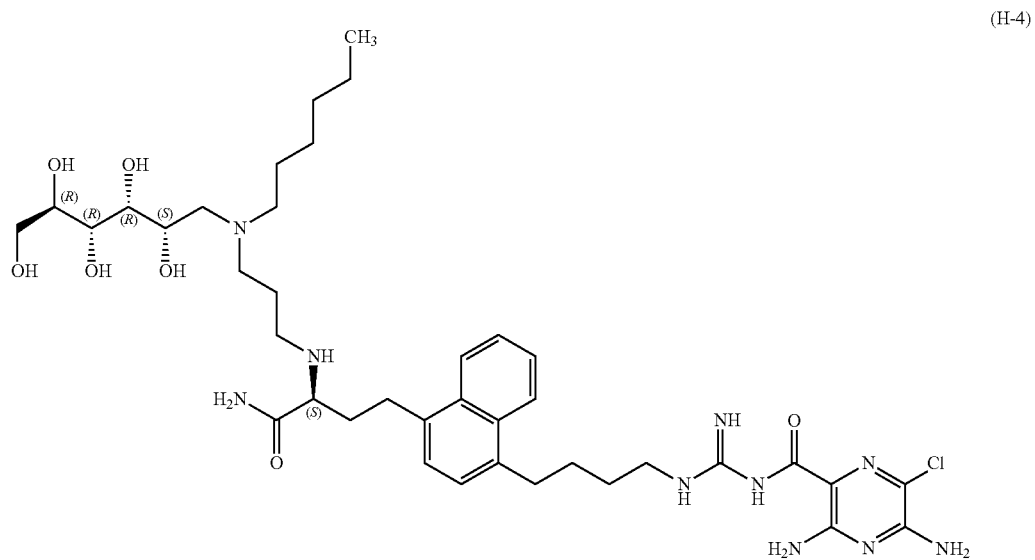

(H-4)

3,5-diamino-N—(N-(4-(4-((S)-4-amino-3-(3-(hexyl((2S,3R,4R,5R)-2,3,4,5,6-pentahydroxyhexyl)amino)propylamino)-4-oxobutyl)naphthalen-1-yl)butyl)carbamimidoyl)-6-chloropyrazine-2-carboxamide.

Additional compounds of this invention include those of formulas (K-1), (K-2), (K-3), and (K-4), or a pharmaceutically acceptable salt thereof:

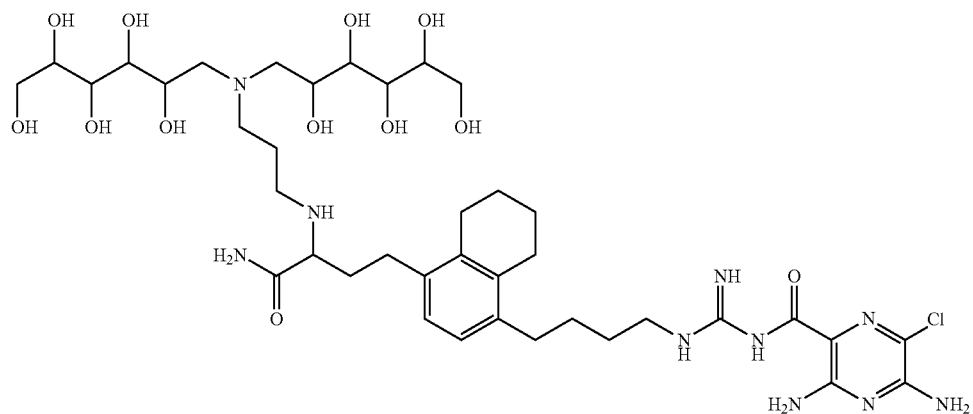

3,5-diamino-N—(N-(4-(4-(4-amino-3-(3-(bis(2,3,4,5,6-pentahydroxyhexyl)amino)propylamino)-4-oxobutyl)-5,6,7,8-tetrahydronaphthalen-1-yl)butyl)carbamimidoyl)-6-chloropyrazine-2-carboxamide;

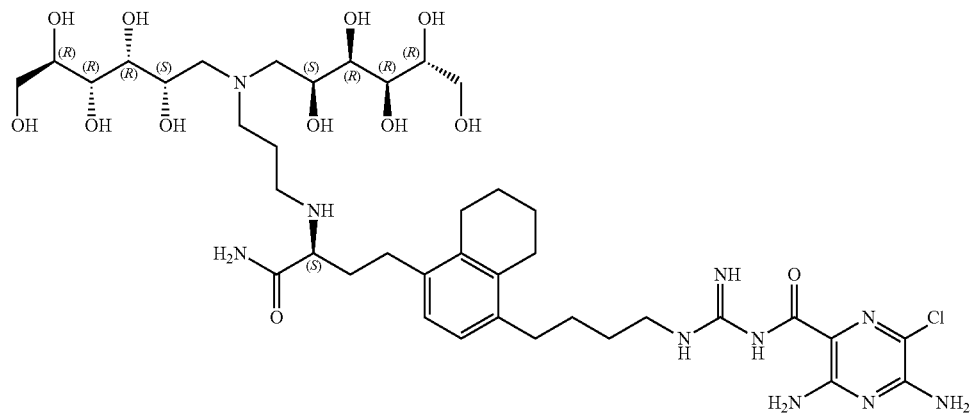

3,5-diamino-N—(N-(4-(4-((S)-4-amino-3-(3-(bis((2S,3R,4R,5R)-2,3,4,5,6-pentahydroxyhexyl)amino)propylamino)-4-oxobutyl)-5,6,7,8-tetrahydronaphthalen-1-yl)butyl)carbamimidoyl)-6-chloropyrazine-2-carboxamide;

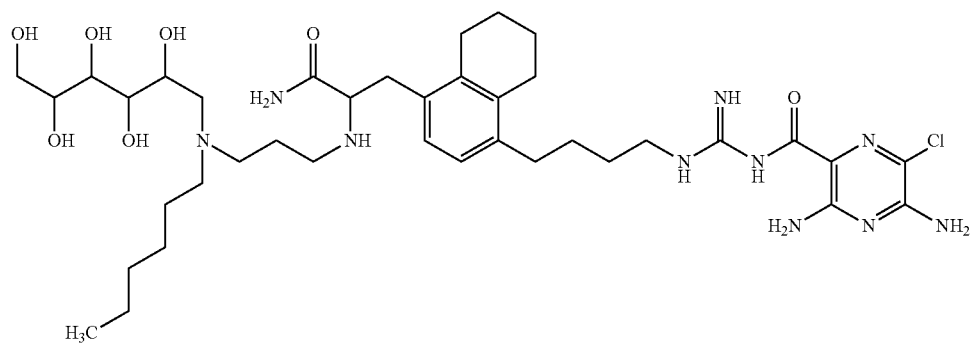

3,5-diamino-N—(N-(4-(4-(3-amino-2-(3-(hexyl(2,3,4,5,6-pentahydroxyhexyl)amino)propylamino)-3-oxopropyl)-5,6,7,8-tetrahydronaphthalen-1-yl)butyl)carbamimidoyl)-6-chloropyrazine-2-carboxamide; and

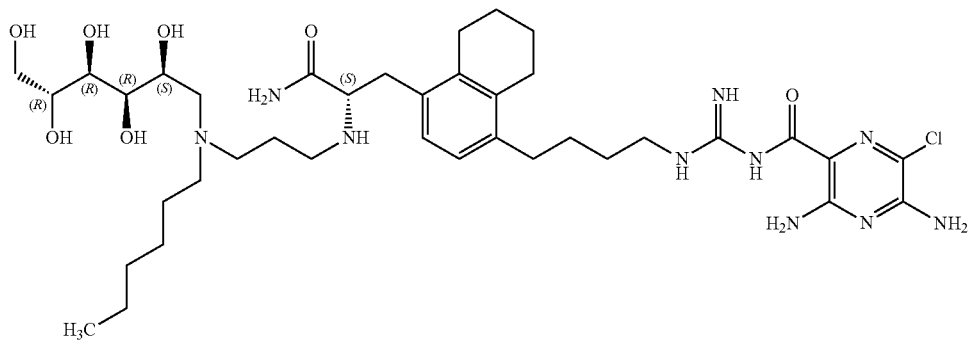

(K-4)

3,5-diamino-N—(N-(4-(4-(((S)-3-amino-2-(3-(hexyl((2S,3R,4R,5R)-2,3,4,5,6-pentahydroxyhexyl)amino)propylamino)-3-oxopropyl)-5,6,7,8-tetrahydronaphthalen-1-yl)butyl)carbamimidoyl)-6-chloropyrazine-2-carboxamide.

As used herein, the following terms are defined as indicated.

"A compound of the invention" means a compound of Formula (A) or a salt thereof, particularly a pharmaceutically acceptable salt thereof.

"A compound of Formula (A)" means a compound having the structural formula designated herein as Formula (A). Compounds of Formula (A) include solvates and hydrates (i.e., adducts of a compound of Formula (A) with a solvent). In those embodiments wherein a compound of Formula (A) includes one or more chiral centers, the phrase is intended to encompass each individual stereoisomer including optical isomers (enantiomers and diastereomers) and geometric isomers (cis-/trans-isomerism) and mixtures of stereoisomers. In addition, compounds of Formula (A) also include tautomers of the depicted formula(s).

Throughout the description and examples, compounds are named using standard IUPAC naming principles, where possible, including the use of the ChemDraw Ultra 11.0 software program for naming compounds, sold by CambridgeSoft Corp./PerkinElmer.

In some chemical structure representations where carbon atoms do not have a sufficient number of attached variables depicted to produce a valence of four, the remaining carbon substituents needed to provide a valence of four should be assumed to be hydrogen. Similarly, in some chemical structures where a bond is drawn without specifying the terminal group, such bond is indicative of a methyl (Me, —CH$_3$) group, as is conventional in the art.

The compounds of Formula I, may be in the form of a free base or a salt, particularly a pharmaceutically acceptable salt. For a review of pharmaceutically acceptable salts see Berge et al., *J. Pharma Sci.* (1977) 66:1-19.

Pharmaceutically acceptable salts formed from inorganic or organic acids include for example, hydrochloride, hydrobromide, hydroiodide, sulfate, bisulfate, nitrate, sulfamate, phosphate, hydrogen phosphate, acetate, trifluoroacetate, maleate, malate, fumarate, lactate, tartrate, citrate, formate, gluconate, succinate, pyruvate, tannate, ascorbate, palmitate, salicylate, stearate, phthalate, alginate, polyglutamate, oxalate, oxaloacetate, saccharate, benzoate, alkyl or aryl sulfonates (e.g., methanesulfonate, ethanesulfonate, benzenesulfonate, p-toluenesulfonate or naphthalenesulfonate) and isothionate; complexes formed with amino acids such as lysine, arginine, glutamic acid, glycine, serine, threonine, alanine, isoleucine, leucine and the like. The compounds of the invention may also be in the form of salts formed from elemental anions such as chlorine, bromine or iodine.

For therapeutic use, salts of active ingredients of the compounds of Formula (A) will be pharmaceutically acceptable, i.e. they will be salts derived from a pharmaceutically acceptable acid. However, salts of acids which are not pharmaceutically acceptable may also find use, for example, in the preparation or purification of a pharmaceutically acceptable compound. Trifluoroacetate salts, for example, may find such use. All salts, whether or not derived from a pharmaceutically acceptable acid, are within the scope of the present invention.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space. "Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography. "Enantiomers" refer to two stereoisomers of a compound which are non-superimposable mirror images of one another.

Stereochemical definitions and conventions used herein generally follow S. P. Parker, Ed., MCGRAW-HILL DICTIONARY OF CHEMICAL TERMS (1984) McGraw-Hill Book Company, New York; and Eliel, E. and Wilen, S., STEREOCHEMISTRY OF ORGANIC COMPOUNDS (1994) John Wiley & Sons, Inc., New York.

Use of the wavy or undulating symbol (∼∼∼) in the structures herein is understood to indicate a point through which the structure shown is bonded to another portion of a molecule.

Many organic compounds exist in optically active forms, i.e., they have the ability to rotate the plane of plane-polarized light. In describing an optically active compound, the prefixes D and L or R and S are used to denote the absolute configuration of the molecule about its chiral center(s). A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species.

The term "tautomers" refers to a type of stereoisomer in which migration of a hydrogen atom results in two or more structures. The compounds of Formula (A) may exist in different tautomeric forms. One skilled in the art will recognize that amidines, amides, guanidines, ureas, thioureas, heterocycles and the like can exist in tautomeric forms. By way of example and not by way of limitation, compounds of Formula (A) can exist in various tautomeric forms as shown below:

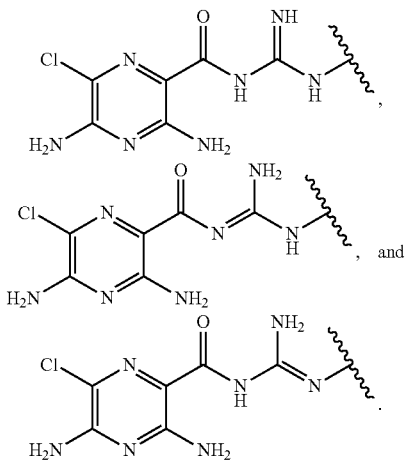

All possible tautomeric forms of the amidines, amides, guanidines, ureas, thioureas, heterocycles and the like of all of the embodiments of Formula (A) are within the scope of the instant invention. Tautomers exist in equilibrium and thus the depiction of a single tautomer in the formulas provided will be understood by those skilled in the art to refer equally to all possible tautomers.

It is to be noted that all enantiomers, diastereomers, and racemic mixtures, tautomers, polymorphs, pseudopolymorphs of compounds within the scope of Formula (A) and pharmaceutically acceptable salts thereof are embraced by the present invention. All mixtures of such enantiomers and diastereomers, including enantiomerically enriched mixtures and diastereomerically enriched mixtures are within the scope of the present invention. Enantiomerically enriched mixtures are mixtures of enantiomers wherein the ratio of the specified enantiomer to the alternative enantiomer is greater than 50:50. More particularly, an enantiomerically enriched mixture comprises at least about 75% of the specified enantiomer, and preferably at least about 85% of the specified enantiomer. In one embodiment, the enantiomerically enriched mixture is substantially free of the other enantiomer. Similarly, diastereomerically enriched mixtures are mixtures of diastereomers wherein amount of the specified diastereomer is greater than the amount of each alternative diastereomer. More particularly, a diastereomerically enriched mixture comprises at least about 75% of the specified diastereomer, and preferably at least about 85% of the specified diastereomer. In one embodiment, the diastereomerically enriched mixture is substantially free of all other diastereomers. The term "substantially free of" will be understood by those skilled in the art to indicate less than a 5% presence of other diastereomers, preferably less than 1%, more preferably less than 0.1%. In other embodiments no other diastereomers will be present or the amount of any other diastereomers present will be below the level of detection. Stereoisomers may be separated by techniques known in the art, including high performance liquid chromatography (HPLC) and crystallization of chiral salts.

A single stereoisomer, e.g. an enantiomer, substantially free of its stereoisomer may be obtained by resolution of the racemic mixture using a method such as formation of diastereomers using optically active resolving agents ("Stereochemistry of Carbon Compounds," (1962) by E. L. Eliel, McGraw Hill; Lochmuller, C. H., (1975) *J. Chromatogr.*, 113:(3) 283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions.

In one embodiment, the present invention provides an enantiomerically enriched mixture of, or a composition comprising an enantiomerically enriched mixture of, 3,5-diamino-N—(N-(4-(4-(((S)-4-amino-3-(3-(bis((2S,3R,4R,5R)-2,3,4,5,6-pentahydroxyhexyl)amino)propylamino)-4-oxobutyl)phenyl)butyl)carbamimidoyl)-6-chloropyrazine-2-carboxamide, having the formula (B-2), or a pharmaceutically acceptable salt thereof, as the predominant isomer.

Another embodiment provides an enantiomerically enriched mixture of, or a composition comprising an enantiomerically enriched mixture of, 3,5-diamino-N—(N-(4-(4-(((S)-4-amino-3-(3-(hexyl((2S,3R,4R,5R)-2,3,4,5,6-pentahydroxyhexyl)amino) propylamino)-4-oxobutyl)phenyl)butyl)carbamimidoyl)-6-chloropyrazine-2-carboxamide, having the formula (B-4), or a pharmaceutically acceptable salt thereof, as the predominant isomer.

Another embodiment provides an enantiomerically enriched mixture of, or a composition comprising an enantiomerically enriched mixture of, 3,5-diamino-N—(N-(4-(4-(((R)-4-amino-3-(3-(bis((2R,3S,4S,5S)-2,3,4,5,6-pentahydroxyhexyl)amino)propylamino)-4-oxobutyl)naphthalen-1-yl)butyl)carbamimidoyl)-6-chloropyrazine-2-carboxamide, having the formula (H-2), or a pharmaceutically acceptable salt thereof, as the predominant isomer.

A further embodiment provides an enantiomerically enriched mixture of, or a composition comprising an enantiomerically enriched mixture of, 3,5-diamino-N—(N-(4-(4-(((R)-4-amino-3-(3-(hexyl((2R,3S,4S,5S)-2,3,4,5,6-pentahydroxyhexyl)amino) propylamino)-4-oxobutyl)naphthalen-1-yl)butyl)carbamimidoyl)-6-chloropyrazine-2-carboxamide, having the formula (H-4), or a pharmaceutically acceptable salt thereof, as the predominant isomer.

Other embodiments comprise the enantiomerically enriched mixtures or compositions comprising, respectively, the compounds of formulas (B-2), (B-4), (H-2), and (H-4), or a pharmaceutically acceptable salt thereof, as the predominant isomer in each of their respective mixtures.

Other embodiments comprise the enantiomerically enriched mixtures or compositions comprising, respectively, the compounds of formulas (B-2), (B-4), (H-2), and (H-4), or a pharmaceutically acceptable salt thereof, substantially free of other isomers in each of their respective mixtures.

A compound of Formula (A) and pharmaceutically acceptable salts thereof may exist as different polymorphs or pseudopolymorphs. As used herein, crystalline polymorphism means the ability of a crystalline compound to exist in different crystal structures. The crystalline polymorphism may result from differences in crystal packing (packing polymorphism) or differences in packing between different conformers of the same molecule (conformational polymorphism). As used herein, crystalline pseudopolymorphism also includes the ability of a hydrate or solvate of a compound to exist in different crystal structures. The pseudopolymorphs of the instant invention may exist due to differences in crystal packing (packing pseudopolymorphism) or due to differences in packing between different conformers of the same molecule (conformational pseudopolymorphism). The instant invention comprises all polymorphs and pseudopolymorphs of the compounds of Formula (A) and pharmaceutically acceptable salts thereof.

A compound of Formula (A) and pharmaceutically acceptable salts thereof may also exist as an amorphous solid. As used herein, an amorphous solid is a solid in which there is no long-range order of the positions of the atoms in the solid. This definition applies as well when the crystal size is two nanometers or less. Additives, including solvents, may be used to create the amorphous forms of the instant invention. The instant invention, including all pharmaceutical compositions, methods of treatment, combination products, and uses thereof described herein, comprises all amorphous forms of the compounds of Formula (A) and pharmaceutically acceptable salts thereof.

Uses

The compounds of the invention exhibit activity as sodium channel blockers. Without being bound by any particular theory, it is believed that the compounds of the invention may function in vivo by blocking epithelial sodium channels present in mucosal surfaces and thereby reduce the absorption of water by the mucosal surfaces. This effect increases the volume of protective liquids on mucosal surfaces, and rebalances the system.

As a consequence, the compounds of the invention are useful as medicaments, particularly for the treatment of clinical conditions for which a sodium channel blocker may be indicated. Such conditions include pulmonary conditions such as diseases associated with reversible or irreversible airway obstruction, chronic obstructive pulmonary disease (COPD), including acute exacerbations of COPD, asthma, bronchiectasis (including bronchiectasis due to conditions other than cystic fibrosis), acute bronchitis, chronic bronchitis, post-viral cough, cystic fibrosis, emphysema, pneumonia, panbronchiolitis, and transplant-associated bronchiolitis, including lung- and bone marrow-transplant associated bronchiolitis, in a human in need thereof. The compounds of the invention may also be useful for treating ventilator-associated tracheobronchitis and/or preventing ventilator-associated pneumonia in ventilated patients. The present invention comprises methods for treating each of these conditions in a mammal in need thereof, preferably in a human in need thereof, each method comprising administering to said mammal a pharmaceutically effective amount of a compound of the present invention, or a pharmaceutically acceptable salt thereof. Also provided are (a) a method for reducing exacerbations of COPD in a mammal in need thereof; (b) a method for reducing exacerbations of CF in a mammal in need thereof; (c) a method of improving lung function (FEV1) in a mammal in need thereof, (d) a method of improving lung function (FEV1) in a mammal experiencing COPD, (e) a method of improving lung function (FEV1) in a mammal experiencing CF, (f) a method of reducing airway infections in a mammal in need thereof.

Also provided is a method of stimulating, enhancing or improving mucociliary clearance in a mammal, the method comprising administering to a mammal in need thereof a pharmaceutically effective amount of a compound of Formula (A), or a pharmaceutically acceptable salt thereof. Mucociliary clearance will be understood to include the natural mucociliary actions involved in the transfer or clearance of mucus in the airways, including the self-clearing mechanisms of the bronchi. Therefore, also provided is a method of improving mucus clearance in the airways of a mammal in need thereof.

Additionally, sodium channel blockers may be indicated for the treatment of conditions which are ameliorated by increased mucosal hydration in mucosal surfaces other than pulmonary mucosal surfaces. Examples of such conditions include dry mouth (xerostomia), dry skin, vaginal dryness, sinusitis, rhinosinusitis, nasal dehydration, including nasal dehydration brought on by administering dry oxygen, dry eye, Sjogren's disease, otitis media, primary ciliary dyskinesia, distal intestinal obstruction syndrome, esophagitis, constipation, and chronic diverticulitis. The compounds of the invention can also be used for promoting ocular or corneal hydration.

The compounds of the present invention may also be useful in methods for obtaining a sputum sample from a human. The method may be carried out by administering a compound of the invention to at least one lung of the patient, and then inducing and collecting a sputum sample from that human.

Accordingly, in one aspect, the present invention provides a method for the treatment of a condition in a mammal, such as a human, for which a sodium channel blocker is indicated.

In other embodiments, the present invention provides each of the methods described herein with the additional benefit of minimizing or eliminating hyperkalemia in the recipient of the method. Also provided are embodiments comprising each of the methods described herein wherein an improved therapeutic index is achieved.

The terms "treat", "treating" and "treatment", as used herein refers to reversing, alleviating, inhibiting the progress of, or preventing the disorder or condition or one or more symptoms of such disorder or condition.

All therapeutic methods described herein are carried out by administering an effective amount of a compound of the invention, a compound of Formula (A) or a pharmaceutically acceptable salt thereof, to a subject (typically mammal and preferably human) in need of treatment.

In one embodiment the invention provides a method for the treatment of a condition which is ameliorated by increased mucosal hydration in a mammal, particularly a human in need thereof. In one embodiment the invention provides a method for the treatment of a disease associated with reversible or irreversible airway obstruction in a mammal, particularly a human, in need thereof. In one particular embodiment the present invention provides a method for the treatment of chronic obstructive pulmonary disease (COPD) in a mammal, particularly a human in need thereof. In one particular embodiment the present invention provides a method for reducing the frequency, severity or duration of acute exacerbation of COPD or for the treatment of one or more symptoms of acute exacerbation of COPD in a mammal, particularly a human in need thereof. In one embodiment the invention provides a method for the treatment of asthma in a mammal, particularly a human, in need thereof.

In one embodiment the invention provides a method for the treatment of bronchiectasis (including bronchiectasis due to conditions other than cystic fibrosis) in a mammal, particularly a human, in need thereof. In one embodiment the invention provides a method for the treatment of bronchitis, including acute and chronic bronchitis in a mammal, particularly a human, in need thereof. In one embodiment the invention provides a method for the treatment of post-viral cough in a mammal, particularly a human, in need thereof. In one embodiment the invention provides a method for the treatment of cystic fibrosis in a mammal, particularly a human, in need thereof. In one embodiment the invention provides a method for the treatment of emphysema in a mammal, particularly a human in need thereof. In one embodiment the invention provides a method for the treatment of pneumonia in a mammal, particularly a human in need thereof. In one embodiment the invention provides a method for the treatment of panbronchiolitis in a mammal, particularly a human in need thereof. In one embodiment the invention provides a method for the treatment of transplant-associated bronchiolitis, including lung- and bone marrow-transplant associated bronchiolitis in a mammal, particularly a human in need thereof. In one embodiment the invention provides a method for treating ventilator-associated tracheobronchitis and/or preventing ventilator-associated pneumonia in a ventilated human in need thereof.

This invention provides specific methods for treating a disease selected from the group of reversible or irreversible airway obstruction, chronic obstructive pulmonary disease (COPD), asthma, bronchiectasis (including bronchiectasis due to conditions other than cystic fibrosis), acute bronchitis, chronic bronchitis, post-viral cough, cystic fibrosis, emphysema, pneumonia, panbronchiolitis, transplant-associate bronchiolitis, and ventilator-associated tracheobronchitis or preventing ventilator-associated pneumonia in a human in need thereof, each method comprising administering to said human an effective amount of a compound of formula (B-2), or a pharmaceutically acceptable salt thereof. In further embodiments for each method of treatment, the pharmaceutically acceptable salt form is a hydrochloride salt or a hydroxynaphthoate salt of the compound of formula (B-2). In another embodiment within each method of treatment, the freebase of the compound of formula (B-2) is used.

In one embodiment the invention provides a method for the treatment of dry mouth (xerostomia) in a mammal, particularly a human in need thereof. In one embodiment the invention provides a method for the treatment of dry skin in a mammal, particularly a human in need thereof. In one embodiment the invention provides a method for the treatment of vaginal dryness in a mammal, particularly a human in need thereof. In one embodiment the invention provides a method for the treatment of sinusitis, rhinosinusitis, or nasal dehydration, including nasal dehydration brought on by administering dry oxygen, in a mammal, particularly a human in need thereof. In one embodiment the invention provides a method for the treatment of dry eye, or Sjogren's disease, or promoting ocular or corneal hydration in a mammal, particularly a human in need thereof. In one embodiment the invention provides a method for the treatment of otitis media in a mammal, particularly a human in need thereof. In one embodiment the invention provides a method for the treatment of primary ciliary dyskinesia, in a mammal, particularly a human in need thereof. In one embodiment the invention provides a method for the treatment of distal intestinal obstruction syndrome, esophagitis, constipation, or chronic diverticulitis in a mammal, particularly a human in need thereof.

There is also provided a compound of the invention for use in medical therapy, particularly for use in the treatment of condition in a mammal, such as a human, for which a sodium channel blocker is indicated. All therapeutic uses described herein are carried out by administering an effective amount of a compound of the invention to the subject in need of treatment. In one embodiment there is provided a compound of the invention for use in the treatment of a pulmonary condition such as a disease associated with reversible or irreversible airway obstruction in a mammal, particularly a human, in need thereof. In one particular embodiment there is provided a compound of the invention for use in the treatment of chronic obstructive pulmonary disease (COPD) in a mammal, particularly a human in need thereof. In one embodiment, there is provided a compound of the invention for use in reducing the frequency, severity or duration of acute exacerbation of COPD or for the treatment of one or more symptoms of acute exacerbation of COPD, in a mammal, particularly a human, in need thereof. In one embodiment there is provided a compound of the invention for use in the treatment of asthma in a mammal, particularly a human, in need thereof. In one embodiment there is provided a compound for use in the treatment of bronchiectasis, including bronchiectasis due to conditions other than cystic fibrosis, or bronchitis, including acute bronchitis and chronic bronchitis, in a mammal, particularly a human, in need thereof. In one embodiment there is provided a compound for use in the treatment of post-viral cough, in a mammal, particularly a human, in need thereof. In one embodiment there is provided a compound for use in the treatment of cystic fibrosis in a mammal, particularly a human in need thereof. In one embodiment there is provided a compound of the invention for use in the treatment of emphysema in a mammal, particularly a human, in need thereof. In one embodiment there is provided a compound of the invention for use in the treatment of pneumonia in a mammal, particularly a human, in need thereof. In one embodiment there is provided a compound of the invention for use in the treatment of panbronchiolitis or transplant-associated bronchiolitis, including lung- and bone marrow-transplant associated bronchiolitis in a mammal, particularly a human, in need thereof. In one embodiment there is provided a compound of the invention for use in the treatment of ventilator-associated tracheobronchitis or preventing ventilator-associated pneumonia in a ventilated human in need thereof.

In one embodiment there is provided a compound of the invention for use in the treatment of a condition ameliorated by increased mucosal hydration in mucosal surfaces of a mammal, particularly a human, in need thereof. In one embodiment there is provided a compound for use in the treatment of dry mouth (xerostomia) in a mammal, particularly a human, in need thereof. In one embodiment there is provided a compound for use in the treatment of dry skin in a mammal, particularly a human, in need thereof. In one embodiment there is provided a compound for use in the treatment of vaginal dryness in a mammal, particularly a human in need thereof. In one embodiment there is provided a compound of the invention for use in the treatment of sinusitis, rhinosinusitis, or nasal dehydration, including nasal dehydration brought on by administering dry oxygen in a mammal, particularly a human, in need thereof. In one embodiment there is provided a compound of the invention for use in the treatment of dry eye, or Sjogren's disease or promoting ocular or corneal hydration in a mammal, particularly a human, in need thereof. In one embodiment there is provided a compound of the invention for use in the treatment of otitis media in a mammal, particularly a human, in need thereof. In one embodiment there is provided a compound of the invention for use in the treatment of primary ciliary dyskinesia in a mammal, particularly a human, in need thereof. In one embodiment there is provided a compound of the invention for use in the treatment of distal intestinal obstruction syndrome, esophagitis, constipation, or chronic diverticulitis in a mammal, particularly a human, in need thereof.

The present invention also provides the use of a compound of the invention in the manufacture of a medicament for the treatment of a condition in a mammal, such as a human, for which a sodium channel blocker is indicated. In one embodiment is provided the use of a compound of the invention in the manufacture of a medicament for the treatment of diseases associated with reversible or irreversible airway obstruction, chronic obstructive pulmonary disease (COPD), acute exacerbations of COPD, asthma, bronchiectasis (including bronchiectasis due to conditions other than cystic fibrosis), bronchitis (including acute bronchitis and chronic bronchitis), post-viral cough, cystic fibrosis, emphysema, pneumonia, panbronchiolitis, transplant-associated bronchiolitis, (including lung- and bone marrow-transplant associated bronchiolitis), ventilator-associated tracheobronchitis or preventing ventilator-associated pneumonia.

In one particular embodiment is provided the use of a compound of the invention in the manufacture of a medicament for the treatment of a condition ameliorated by increased mucosal hydration in mucosal surfaces, treatment of dry mouth (xerostomia), dry skin, vaginal dryness, sinusitis, rhinosinusitis, nasal dehydration, including nasal dehydration brought on by administering dry oxygen, treatment of dry eye, Sjogren's disease, promoting ocular or corneal hydration, treatment of otitis media, primary ciliary dyskinesia, distal intestinal obstruction syndrome, esophagitis, constipation, or chronic diverticulitis The terms "effective amount", "pharmaceutically effective amount", "effective dose", and "pharmaceutically effective dose" as used herein, refer to an amount of compound of the invention which is sufficient in the subject to which it is administered, to elicit the biological or medical response of a cell culture, tissue, system, or mammal (including human) that is being sought, for instance by a researcher or clinician. The term also includes within its scope, amounts effective to enhance normal physiological function. In one embodiment, the effective amount is the amount needed to provide a desired level of drug in the secretions and tissues of the airways and lungs, or alternatively, in the bloodstream of a subject to be treated to give an anticipated physiological response or desired biological effect when such a composition is administered by inhalation. For example an effective amount of a compound of the invention for the treatment of a condition for which a sodium channel blocker is indicated is sufficient in the subject to which it is administered to treat the particular condition. In one embodiment an effective amount is an amount of a compound of the invention which is sufficient for the treatment of COPD or cystic fibrosis in a human.

The precise effective amount of the compounds of the invention will depend on a number of factors including but not limited to the species, age and weight of the subject being treated, the precise condition requiring treatment and its severity, the bioavailability, potency, and other properties of the specific compound being administered, the nature of the formulation, the route of administration, and the delivery device, and will ultimately be at the discretion of the attendant physician or veterinarian. Further guidance with respect to appropriate dose may be found in considering conventional dosing of other sodium channel blockers, such as amiloride, with due consideration also being given to any differences in potency between amiloride and the compounds of the present invention.

A pharmaceutically effective dose administered topically to the airway surfaces of a subject (e.g., by inhalation) of a compound of the invention for treatment of a 70 kg human may be in the range of from about 10 ng to about 10 mg. In another embodiment, the pharmaceutically effective dose may be from about 0.1 to about 1000 µg. Typically, the daily dose administered topically to the airway surfaces will be an amount sufficient to achieve dissolved concentration of active agent on the airway surfaces of from about $10^{-9}$, $10^{-8}$, or $10^{-7}$ to about $10^{-4}$, $10^{-3}$, $10^{-2}$, or $10^{-1}$ Moles/liter, more preferably from about $10^{-9}$ to about $10^{-4}$ Moles/liter. The selection of the specific dose for a patient will be determined by the attendant physician, clinician or veterinarian of ordinary skill in the art based upon a number of factors including those noted above. In one particular embodiment the dose of a compound of the invention for the treatment of a 70 kg human will be in the range of from about 10 nanograms (ng) to about 10 mg. In another embodiment, the effective dose would be from about 0.1 µg to about 1,000 µg. In one embodiment, the dose of a compound of the invention for the treatment of a 70 kg human will be in the range of from about 0.5 µg to about 0.5 mg. In further embodiments the dose will be independently selected from a) about 0.1 µg to about 60 µg; b) from about 0.1 µg to about 50 µg; b) from about 0.1 to about 30 µg; c) from about 0.1 µg to about 20 µg; d) from about 0.1 µg to about 10 µg; e) from about 0.1 µg to about 5 µg; f) from about 10 µg to about 40 µg; g) from about 15 µg to about 50 µg; or h) from about 15 µg to about 30 µg, respectively.

It will be understood that in each of these dose ranges, all incremental doses in the range are included. For instance, the 0.5-50 µg range includes individual doses independently selected from the group of: 0.1 µg, 0.2 µg, 0.3 µg, 0.4 µg, 0.5 µg, 0.6 µg, 0.7 µg, 0.8 µg, 0.9 µg, 1.0 µg, 1.1 µg, 1.2 µg, 1.3 µg, 1.4 µg, 1.5 µg, 1.6 µg, 1.7 µg, 1.8 µg, 1.9 µg, 2.0 µg, 2.1 µg, 2.2 µg, 2.3 µg, 2.4 µg, 2.5 µg, 2.6 µg, 2.7 µg, 2.8 µg, 2.9 µg, 3.0 µg, 3.1 µg, 3.2 µg, 3.3 µg, 3.4 µg, 3.5 µg, 3.6 µg, 3.7 µg, 3.8 µg, 3.9 µg, 4.0 µg, 4.1 µg, 4.2 µg, 4.3 µg, 4.4 µg, 4.5 µg, 4.6 µg, 4.7 µg, 4.8 µg, 4.9 µg, 5.0 µg, 5.1 µg, 5.2 µg, 5.3 µg, 5.4 µg, 5.5 µg, 5.6 µg, 5.7 µg, 5.8 µg, 5.9 µg, 6.0 µg, 6.1 µg, 6.2 µg, 6.3 µg, 6.4 µg, 6.5 µg, 6.6 µg, 6.7 µg, 6.8 µg, 6.9 µg, 7.0 µg, 7.1 µg, 7.2 µg, 7.3 µg, 7.4 µg, 7.5 µg, 7.6 µg, 7.7 µg, 7.8 µg, 7.9 µg, 8.0 µg, 8.1 µg, 8.2 µg, 8.3 µg, 8.4 µg, 8.5 µg, 8.6 µg, 8.7 µg, 8.8 µg, 8.9 µg, 9.0 µg, 9.1 µg, 9.2 µg, 9.3 µg, 9.4 µg, 9.5 µg, 9.6 µg, 9.7 µg, 9.8 µg, 9.9 µg, 10.0 µg, 10.1 µg, 10.2 µg, 10.3 µg, 10.4 µg, 10.5 µg, 10.6 µg, 10.7 µg, 10.8 µg, 10.9 µg, 11.0 µg, 11.1 µg, 11.2 µg, 11.3 µg, 11.4 µg, 11.5 µg, 11.6 µg, 11.7 µg, 11.8 µg, 11.9 µg, 12.0 µg, 12.1 µg, 12.2 µg, 12.3 µg, 12.4 µg, 12.5 µg, 12.6 µg, 12.7 µg, 12.8 µg, 12.9 µg, 13.0 µg, 13.1 µg, 13.2 µg, 13.3 µg, 13.4 µg, 13.5 µg, 13.6 µg, 13.7 µg, 13.8 µg, 13.9 µg, 14.0 µg, 14.1 µg, 14.2 µg, 14.3 µg, 14.4 µg, 14.5 µg, 14.6 µg, 14.7 µg, 14.8 µg, 14.9 µg, 15.0 µg, 15.1 µg, 15.2 µg, 15.3 µg, 15.4 µg, 15.5 µg, 15.6 µg, 15.7 µg, 15.8 µg, 15.9 µg, 16.0 µg, 16.1 µg, 16.2 µg, 16.3 µg, 16.4 µg, 16.5 µg, 16.6 µg, 16.7 µg, 16.8 µg, 16.9 µg, 17.0 µg, 17.1 µg, 17.2 µg, 17.3 µg, 17.4 µg, 17.5 µg, 17.6 µg, 17.7 µg, 17.8 µg, 17.9 µg, 18.0 µg, 18.1 µg, 18.2 µg, 18.3 µg, 18.4 µg, 18.5 µg, 18.6 µg, 18.7 µg, 18.8 µg, 18.9 µg, 19.0 µg, 19.1 µg, 19.2 µg, 19.3 µg, 19.4 µg, 19.5 µg, 19.6 µg, 19.7 µg, 19.8 µg, 19.9 µg, 20.0 µg, 20.1 µg, 20.2 µg, 20.3 µg, 20.4 µg, 20.5 µg, 20.6 µg, 20.7 µg, 20.8 µg, 20.9 µg, 21.0 µg, 21.1 µg, 21.2 µg, 21.3

μg, 21.4 μg, 21.5 μg, 21.6 μg, 21.7 μg, 21.8 μg, 21.9 μg, 22.0 μg, 22.1 μg, 22.2 μg, 22.3 μg, 22.4 μg, 22.5 μg, 22.6 μg, 22.7 μg, 22.8 μg, 22.9 μg, 23.0 μg, 23.1 μg, 23.2 μg, 23.3 μg, 23.4 μg, 23.5 μg, 23.6 μg, 23.7 μg, 23.8 μg, 23.9 μg, 24.0 μg, 24.1 μg, 24.2 μg, 24.3 μg, 24.4 μg, 24.5 μg, 24.6 μg, 24.7 μg, 24.8 μg, 24.9 μg, 25.0 μg, 25.1 μg, 25.2 μg, 25.3 μg, 25.4 μg, 25.5 μg, 25.6 μg, 25.7 μg, 25.8 μg, 25.9 μg, 26.0 μg, 26.1 μg, 26.2 μg, 26.3 μg, 26.4 μg, 26.5 μg, 26.6 μg, 26.7 μg, 26.8 μg, 26.9 μg, 27.0 μg, 27.1 μg, 27.2 μg, 27.3 μg, 27.4 μg, 27.5 μg, 27.6 μg, 27.7 μg, 27.8 μg, 27.9 μg, 28.0 μg, 28.1 μg, 28.2 μg, 28.3 μg, 28.4 μg, 28.5 μg, 28.6 μg, 28.7 μg, 28.8 μg, 28.9 μg, 29.0 μg, 29.1 μg, 29.2 μg, 29.3 μg, 29.4 μg, 29.5 μg, 29.6 μg, 29.7 μg, 29.8 μg, 29.9 μg, 30.0 μg, 30.1 μg, 30.2 μg, 30.3 μg, 30.4 μg, 30.5 μg, 30.6 μg, 30.7 μg, 30.8 μg, 30.9 μg, 31.0 μg, 31.1 μg, 31.2 μg, 31.3 μg, 31.4 μg, 31.5 μg, 31.6 μg, 31.7 μg, 31.8 μg, 31.9 μg, 32.0 μg, 32.1 μg, 32.2 μg, 32.3 μg, 32.4 μg, 32.5 μg, 32.6 μg, 32.7 μg, 32.8 μg, 32.9 μg, 33.0 μg, 33.1 μg, 33.2 μg, 33.3 μg, 33.4 μg, 33.5 μg, 33.6 μg, 33.7 μg, 33.8 μg, 33.9 μg, 34.0 μg, 34.1 μg, 34.2 μg, 34.3 μg, 34.4 μg, 34.5 μg, 34.6 μg, 34.7 μg, 34.8 μg, 34.9 μg, 35.0 μg, 35.1 μg, 35.2 μg, 35.3 μg, 35.4 μg, 35.5 μg, 35.6 μg, 35.7 μg, 35.8 μg, 35.9 μg, 36.0 μg, 36.1 μg, 36.2 μg, 36.3 μg, 36.4 μg, 36.5 μg, 36.6 μg, 36.7 μg, 36.8 μg, 36.9 μg, 37.0 μg, 37.1 μg, 37.2 μg, 37.3 μg, 37.4 μg, 37.5 μg, 37.6 μg, 37.7 μg, 37.8 μg, 37.9 μg, 38.0 μg, 38.1 μg, 38.2 μg, 38.3 μg, 38.4 μg, 38.5 μg, 38.6 μg, 38.7 μg, 38.8 μg, 38.9 μg, 39.0 μg, 39.1 μg, 39.2 μg, 39.3 μg, 39.4 μg, 39.5 μg, 39.6 μg, 39.7 μg, 39.8 μg, 39.9 μg, 40.0 μg, 40.1 μg, 40.2 μg, 40.3 μg, 40.4 μg, 40.5 μg, 40.6 μg, 40.7 μg, 40.8 μg, 40.9 μg, 41.0 μg, 41.1 μg, 41.2 μg, 41.3 μg, 41.4 μg, 41.5 μg, 41.6 μg, 41.7 μg, 41.8 μg, 41.9 μg, 42.0 μg, 42.1 μg, 42.2 μg, 42.3 μg, 42.4 μg, 42.5 μg, 42.6 μg, 42.7 μg, 42.8 μg, 42.9 μg, 43.0 μg, 43.1 μg, 43.2 μg, 43.3 μg, 43.4 μg, 43.5 μg, 43.6 μg, 43.7 μg, 43.8 μg, 43.9 μg, 44.0 μg, 44.1 μg, 44.2 μg, 44.3 μg, 44.4 μg, 44.5 μg, 44.6 μg, 44.7 μg, 44.8 μg, 44.9 μg, 45.0 μg, 45.1 μg, 45.2 μg, 45.3 μg, 45.4 μg, 45.5 μg, 45.6 μg, 45.7 μg, 45.8 μg, 45.9 μg, 46.0 μg, 46.1 μg, 46.2 μg, 46.3 μg, 46.4 μg, 46.5 μg, 46.6 μg, 46.7 μg, 46.8 μg, 46.9 μg, 47.0 μg, 47.1 μg, 47.2 μg, 47.3 μg, 47.4 μg, 47.5 μg, 47.6 μg, 47.7 μg, 47.8 μg, 47.9 μg, 48.0 μg, 48.1 μg, 48.2 μg, 48.3 μg, 48.4 μg, 48.5 μg, 48.6 μg, 48.7 μg, 48.8 μg, 38.9 μg, 49.0 μg, 49.1 μg, 49.2 μg, 49.3 μg, 49.4 μg, 49.5 μg, 49.6 μg, 49.7 μg, 49.8 μg, 39.9 μg, and 50 μg.

The foregoing suggested doses may be adjusted using conventional dose calculations if the compound is administered via a different route. Determination of an appropriate dose for administration by other routes is within the skill of those in the art in light of the foregoing description and the general knowledge in the art.

Delivery of an effective amount of a compound of the invention may entail delivery of a single dosage form or multiple unit doses which may be delivered contemporaneously or separate in time over a designated period, such as 24 hours. A dose of a compound of the invention (alone or in the form of a composition comprising the same) may be administered from one to ten times per day. Typically, a compound of the invention (alone or in the form of a composition comprising the same) will be administered four, three, two, or one time(s) per day (24 hours).

The compounds of Formula (A) of the present invention are also useful for treating airborne infections. Examples of airborne infections include, for example, RSV. The compounds of Formula (A) of the present invention are also useful for treating an anthrax infection. The present invention relates to the use of the compounds of Formula (A) of the present invention for prophylactic, post-exposure prophylactic, preventive or therapeutic treatment against diseases or conditions caused by pathogens. In a preferred embodiment, the present invention relates to the use of the compounds of Formula (A) for prophylactic, post-exposure prophylactic, preventive or therapeutic treatment against diseases or conditions caused by pathogens which may be used in bioterrorism.

In recent years, a variety of research programs and biodefense measures have been put into place to deal with concerns about the use of biological agents in acts of terrorism. These measures are intended to address concerns regarding bioterrorism or the use of microorganisms or biological toxins to kill people, spread fear, and disrupt society. For example, the National Institute of Allergy and Infectious Diseases (NIAID) has developed a Strategic Plan for Biodefense Research which outlines plans for addressing research needs in the broad area of bioterrorism and emerging and reemerging infectious diseases. According to the plan, the deliberate exposure of the civilian population of the United States to *Bacillus anthracis* spores revealed a gap in the nation's overall preparedness against bioterrorism. Moreover, the report details that these attacks uncovered an unmet need for tests to rapidly diagnose, vaccines and immunotherapies to prevent, and drugs and biologics to cure disease caused by agents of bioterrorism.

Much of the focus of the various research efforts has been directed to studying the biology of the pathogens identified as potentially dangerous as bioterrorism agents, studying the host response against such agents, developing vaccines against infectious diseases, evaluating the therapeutics currently available and under investigation against such agents, and developing diagnostics to identify signs and symptoms of threatening agents. Such efforts are laudable but, given the large number of pathogens which have been identified as potentially available for bioterrorism, these efforts have not yet been able to provide satisfactory responses for all possible bioterrorism threats. Additionally, many of the pathogens identified as potentially dangerous as agents of bioterrorism do not provide adequate economic incentives for the development of therapeutic or preventive measures by industry. Moreover, even if preventive measures such as vaccines were available for each pathogen which may be used in bioterrorism, the cost of administering all such vaccines to the general population is prohibitive.

Until convenient and effective treatments are available against every bioterrorism threat, there exists a strong need for preventative, prophylactic or therapeutic treatments which can prevent or reduce the risk of infection from pathogenic agents.

The present invention provides such methods of prophylactic treatment. In one aspect, a prophylactic treatment method is provided comprising administering a prophylactically effective amount of the compounds of Formula (A) to an individual in need of prophylactic treatment against infection from one or more airborne pathogens. A particular example of an airborne pathogen is anthrax.

In another aspect, a prophylactic treatment method is provided for reducing the risk of infection from an airborne pathogen which can cause a disease in a human, said method comprising administering an effective amount of the compounds of Formula (A) to the lungs of the human who may be at risk of infection from the airborne pathogen but is asymptomatic for the disease, wherein the effective amount of a sodium channel blocker and osmolye are sufficient to reduce the risk of infection in the human. A particular example of an airborne pathogen is anthrax.

In another aspect, a post-exposure prophylactic treatment or therapeutic treatment method is provided for treating infection from an airborne pathogen comprising administering an effective amount of the compounds of Formula (A) to the lungs of an individual in need of such treatment against infection from an airborne pathogen. The pathogens which may be protected against by the prophylactic post exposure, rescue and therapeutic treatment methods of the invention include any pathogens which may enter the body through the mouth, nose or nasal airways, thus proceeding into the lungs. Typically, the pathogens will be airborne pathogens, either naturally occurring or by aerosolization. The pathogens may be naturally occurring or may have been introduced into the environment intentionally after aerosolization or other method of introducing the pathogens into the environment. Many pathogens which are not naturally transmitted in the air have been or may be aerosolized for use in bioterrorism. The pathogens for which the treatment of the invention may be useful includes, but is not limited to, category A, B and C priority pathogens as set forth by the NIAID. These categories correspond generally to the lists compiled by the Centers for Disease Control and Prevention (CDC). As set up by the CDC, Category A agents are those that can be easily disseminated or transmitted person-to-person, cause high mortality, with potential for major public health impact. Category B agents are next in priority and include those that are moderately easy to disseminate and cause moderate morbidity and low mortality. Category C consists of emerging pathogens that could be engineered for mass dissemination in the future because of their availability, ease of production and dissemination and potential for high morbidity and mortality. Particular examples of these pathogens are anthrax and plague. Additional pathogens which may be protected against or the infection risk therefrom reduced include influenza viruses, rhinoviruses, adenoviruses and respiratory syncytial viruses, and the like. A further pathogen which may be protected against is the coronavirus which is believed to cause severe acute respiratory syndrome (SARS).

The present invention also relates to the use of sodium channel blockers of Formula I, or a pharmaceutically acceptable salt thereof, for preventing, mitigating, and/or treating deterministic health effects to the respiratory tract caused by exposure to radiological materials, particularly respirable aerosols containing radionuclides from nuclear attacks, such as detonation of radiological dispersal devices (RDD), or accidents, such as nuclear power plant disasters. As such, provided herein is a method for preventing, mitigating, and/or treating deterministic health effects to the respiratory tract and/or other bodily organs caused by respirable aerosols containing radionuclides in a recipient in need thereof, including in a human in need thereof, said method comprising administering to said human an effective amount of a compound of Formula (A), or a pharmaceutically acceptable salt thereof.

A major concern associated with consequence management planning for exposures of members of the public to respirable aerosols containing radionuclides from nuclear attacks, such as detonation of radiological dispersal devices (RDD), or accidents, such as nuclear power plant disasters is how to prevent, mitigate or treat potential deterministic health effects to the respiratory tract, primarily the lung. It is necessary to have drugs, techniques and procedures, and trained personnel prepared to manage and treat such highly internally contaminated individuals.

Research has been conducted to determine ways in which to prevent, mitigate or treat potential damage to the respiratory tract and various organs in the body that is caused by internally deposited radionuclides. To date, most of the research attention has focused on strategies designed to mitigate health effects from internally deposited radionuclides by accelerating their excretion or removal. These strategies have focused on soluble chemical forms that are capable of reaching the blood stream and are deposited at remote systemic sites specific to a given radioelement. Such approaches will not work in cases where the deposited radionuclide is in relatively insoluble form. Studies have shown that many, if not most of the physicochemical forms of dispersed radionuclides from RDDs, will be in relatively insoluble form.

The only method known to effectively reduce the radiation dose to the lungs from inhaled insoluble radioactive aerosols is bronchoalveolar lavage or BAL. This technique, which was adapted from that already in use for the treatment of patients with alveolar proteinosis, has been shown to be a safe, repeatable procedure, even when performed over an extended period of time. Although there are variations in procedure, the basic method for BAL is to anaesthetize the subject, followed by the slow introduction of isotonic saline into a single lobe of the lung until the function residual capacity is reached. Additional volumes are then added and drained by gravity.

The results of studies using BAL on animals indicate that about 40% of the deep lung content can be removed by a reasonable sequence of BALs. In some studies, there was considerable variability among animals in the amount of radionuclide recovered. The reasons for the variability are currently not understood.

Further, based on a study on animals, it is believed that a significant dose reduction from BAL therapy results in mitigation of health effects due to inhalation of insoluble radionuclides. In the study, adult dogs inhaled insoluble $^{144}$Ce-FAP particles. Two groups of dogs were given lung contents of $^{144}$Ce known to cause radiation pneumonitis and pulmonary fibrosis (about 2 MBq/kg body mass), with one group being treated with 10 unilateral lavages between 2 and 56 days after exposure, the other untreated. A third group was exposed at a level of $^{144}$Ce comparable to that seen in the BAL-treated group after treatment (about 1 MBq/kg), but these animals were untreated. All animals were allowed to live their lifespans, which extended to 16 years. Because there is variability in initial lung content of $^{144}$Ce among the dogs in each group, the dose rates and cumulative doses for each group overlap. Nevertheless, the effect of BAL in reducing the risk from pneumonitis/fibrosis was evident from the survival curves. In the untreated dogs with lung contents of 1.5-2.5 MBq/kg, the mean survival time was 370±65 d. For the treated dogs, the mean survival was 1270±240 d, which was statistically significantly different. The third group, which received lung contents of $^{144}$Ce of 0.6-1.4 MBq had a mean survival time of 1800±230, which was not statistically different from the treated group. Equally important to the increased survival, the dogs in the high-dose untreated group died from deterministic effects to lung (pneumonitis/fibrosis) while the treated dogs did not. Instead, the treated dogs, like the dogs in the low-dose untreated group, mostly had lung tumors (hemangiosarcoma or carcinoma). Therefore, the reduction in dose resulting from BAL treatment appears to have produced biological effects in lung that were predictable based on the radiation doses that the lungs received.

Based on these results, it is believed that decreasing the residual radiological dose further by any method or combination of methods for enhancing the clearance of particles from the lung would further decrease the probability of health effects to lung. However, BAL is a procedure that has many drawbacks. BAL is a highly invasive procedure that must be performed at specialized medical centers by trained pulmonologists. As such, a BAL procedure is expensive. Given the drawbacks of BAL, it is not a treatment option that would be readily and immediately available to persons in need of accelerated removal of radioactive particles, for example, in the event of a nuclear attack. In the event of a nuclear attack or a nuclear accident, immediate and relatively easily administered treatment for persons who have been exposed or who are at risk of being exposed is needed. Sodium channel blockers administered as an inhalation aerosol have been shown to restore hydration of airway surfaces. Such hydration of airway surfaces aids in clearing accumulated mucus secretions and associated particulate matter from the lung. As such, without being bound by any particular theory, it is believed that sodium channel blockers can be used to accelerate the removal of radioactive particles from airway passages.

As discussed above, the greatest risk to the lungs following a radiological attack, such as a dirty bomb, results from the inhalation and retention of insoluble radioactive particles. As a result of radioactive particle retention, the cumulative exposure to the lung is significantly increased, ultimately resulting in pulmonary fibrosis/pneumonitis and potentially death. Insoluble particles cannot be systemically cleared by chelating agents because these particles are not in solution. To date, the physical removal of particulate matter through BAL is the only therapeutic regimen shown to be effective at mitigating radiation-induced lung disease. As discussed above, BAL is not a realistic treatment solution for reducing the effects of radioactive particles that have been inhaled into the body. As such, it is desirable to provide a therapeutic regimen that effectively aids in clearing radioactive particles from airway passages and that, unlike BAL, is relatively simple to administer and scalable in a large-scale radiation exposure scenario. In addition, it is also desirable that the therapeutic regimen be readily available to a number of people in a relatively short period of time.

In an aspect of the present invention, a method for preventing, mitigating, and/or treating deterministic health effects to the respiratory tract and/or other bodily organs caused by respirable aerosols containing radionuclides comprises administering an effective amount of a sodium channel blocker of Formula (A) or a pharmaceutically acceptable salt thereof to an individual in need. In a feature of this aspect, the sodium channel blocker is administered in conjunction with an osmolyte. With further regard to this feature, the osmolyte is hypertonic saline (HS). In a further feature, the sodium channel blocker and the osmolyte are administered in conjunction with an ion transport modulator. With further regard to this feature, the ion transport modulator may be selected from the group consisting of β-agonists, CFTR potentiators, purinergic receptor agonists, lubiprostones, and protease inhibitors. In another feature of this aspect, the radionuclides are selected from the group consisting of Colbalt-60, Cesium-137, Iridium-192, Radium-226, Phosphorus-32, Strontium-89 and 90, Iodine-125, Thallium-201, Lead-210, Thorium-234, Uranium-238, Plutonium, Cobalt-58, Chromium-51, Americium, and Curium. In a further feature, the radionuclides are from a radioactive disposal device. In yet another feature, the sodium channel blocker or pharmaceutically acceptable salt thereof is administered in an aerosol suspension of respirable particles which the individual inhales. In an additional feature, the sodium channel blocker or a pharmaceutically acceptable salt thereof is administered post-exposure to the radionuclides.

Compositions

While it is possible for a compound of the invention to be administered alone, in some embodiments it is preferable to present it in the form of a composition, particularly a pharmaceutical composition (formulation). Thus, in another aspect, the invention provides compositions, and particularly pharmaceutical compositions (such as an inhalable pharmaceutical composition) comprising a pharmaceutically effective amount of a compound of the invention as an active ingredient, and a pharmaceutically acceptable excipient, diluent or carrier. The term "active ingredient" as employed herein refers to any compound of the invention or combination of two or more compounds of the invention in a pharmaceutical composition. Also provided are specific embodiments in which a pharmaceutical composition comprises a pharmaceutically effective amount of a compound of this invention, including compounds selected from those of Formulas (A), (B), (C), (D), (E), (F), (G), (H), (I), (J), (K), (L), (M), (B-1), (B-2), (B-3), (B-4), (E-1), (E-2), (E-3), (E-4), (H-1), (H-2), (H-3), (H-4), (K-1), (K-2), (K-3), and (K-4), or a pharmaceutically acceptable salt thereof, independently or in combination, and a pharmaceutically acceptable excipient, diluent or carrier.

In some embodiments, the pharmaceutical composition comprises a pharmaceutically effective amount of a compound selected from those of Formulas (A), (B), (C), (D), (E), (F), (G), (H), (I), (J), (K), (L), (M), (B-1), (B-2), (B-3), (B-4), (E-1), (E-2), (E-3), (E-4), (H-1), (H-2), (H-3), (H-4), (K-1), (K-2), (K-3), and (K-4), or a pharmaceutically acceptable salt thereof, independently or in combination, in a diluent.

In separate embodiments, the pharmaceutical composition comprises a pharmaceutically effective amount of a compound selected from those of Formulas (A), (B), (C), (D), (E), (F), (G), (H), (I), (J), (K), (L), (M), (B-1), (B-2), (B-3), (B-4), (E-1), (E-2), (E-3), (E-4), (H-1), (H-2), (H-3), (H-4), (K-1), (K-2), (K-3), and (K-4), or a pharmaceutically acceptable salt thereof, in hypertonic saline, sterile water, and hypertonic saline, respectively, wherein the saline concentration can be as described herein. In one embodiment the saline concentration is 0.17% w/v and in another it is 2.8% w/v.

Also provided is a kit comprising i) a pharmaceutically effective amount of a compound of Formula selected from those of Formulas (A), (B), (C), (D), (E), (F), (G), (H), (I), (J), (K), (L), (M), (B-1), (B-2), (B-3), (B-4), (E-1), (E-2), (E-3), (E-4), (H-1), (H-2), (H-3), (H-4), (K-1), (K-2), (K-3), and (K-4), or a pharmaceutically acceptable salt thereof; ii) one or more pharmaceutically acceptable excipients, carriers, or diluents; iii) instructions for administering the compound of group i) and the excipients, carriers, or diluents of group ii) to a subject in need thereof; and; iv) a container. A subject in need thereof includes any subject in need of the methods of treatment described herein, particularly including a human subject in need thereof. Further embodiments also comprise an aerosolization device selected from the group of a nebulizer, including vibrating mesh nebulizers and jet nebulizers, a dry powder inhaler, including active and passive dry powder inhalers, and a metered dose inhaler, including pressurized, dry powder, and soft mist metered dose inhalers. Also provided are independent embodiments wherein the pharmaceutically effective amount of a compound as described herein, or a pharmaceutically acceptable salt thereof, comprises one of the individual single effective doses described herein or one of the dose ranges described herein.

In one embodiment a kit comprises i) from about 10 ng to about 10 mg of a compound selected from those of Formulas (A), (B), (C), (D), (E), (F), (G), (H), (I), (J), (K), (L), (M), (B-1), (B-2), (B-3), (B-4), (E-1), (E-2), (E-3), (E-4), (H-1), (H-2), (H-3), (H-4), (K-1), (K-2), (K-3), and (K-4), or a pharmaceutically acceptable salt thereof, per dose; ii) from about 1 to about 5 mL of diluent per dose; iii) instructions for administering the compound of group i) and the diluent of group ii) to a subject in need thereof; and; iv) a container. In a further embodiment, the diluent is from about 1 to about 5 mL of a saline solution, as described herein, per dose. In a further embodiment, the diluent is from about 1 to about 5 mL of a hypotonic saline solution per dose. In another embodiment, the diluent is from about 1 to about 5 mL of a hypertonic saline solution per dose. In a still further embodiment, the diluent is from about 1 to about 5 mL of sterile water per dose.

Also provided is a kit comprising i) a solution comprising a pharmaceutically effective amount of a compound selected from those of Formulas (A), (B), (C), (D), (E), (F), (G), (H), (I), (J), (K), (L), (M), (B-1), (B-2), (B-3), (B-4), (E-1), (E-2), (E-3), (E-4), (H-1), (H-2), (H-3), (H-4), (K-1), (K-2), (K-3), and (K-4), or a pharmaceutically acceptable salt thereof; dissolved in a pharmaceutically acceptable diluent; iii) instructions for administering the solution of group i) to a subject in need thereof; and iii) a container.

Also provided is a kit comprising i) a solution comprising from about 10 ng to about 10 mg of a compound selected from those of Formulas (A), (B), (C), (D), (E), (F), (G), (H), (I), (J), (K), (L), (M), (B-1), (B-2), (B-3), (B-4), (E-1), (E-2), (E-3), (E-4), (H-1), (H-2), (H-3), (H-4), (K-1), (K-2), (K-3), and (K-4), or a pharmaceutically acceptable salt thereof; dissolved in a pharmaceutically acceptable diluent; iii) instructions for administering the solution of group i) to a subject in need thereof; and iii) a container. In a further embodiment, the diluent is from about 1 to about 5 mL of a saline solution, as described herein, per dose.

Another embodiment comprises a kit comprising i) a pharmaceutically effective amount of a compound selected from those of Formulas (A), (B), (C), (D), (E), (F), (G), (H), (I), (J), (K), (L), (M), (B-1), (B-2), (B-3), (B-4), (E-1), (E-2), (E-3), (E-4), (H-1), (H-2), (H-3), (H-4), (K-1), (K-2), (K-3), and (K-4), or a pharmaceutically acceptable salt thereof; in a dry powder formulation suitable for inhalation ii) optionally, one or more pharmaceutically acceptable excipients or carriers suitable for inhalation; iii) instructions for administering the compound of group i) and the excipients or carriers of group ii) to a subject in need thereof; and; iv) a container. In a further embodiment, the kit also comprises a dry powder inhaler suitable for delivering the dry powder formulation to a recipient. The dry powder inhaler may be, in additional embodiments, a single-dose inhaler or a multi-dose inhaler.

Further embodiments of each of the kits described herein includes those in which the concentration of the compound selected from those of Formulas (A), (B), (C), (D), (E), (F), (G), (H), (I), (J), (K), (L), (M), (B-1), (B-2), (B-3), (B-4), (E-1), (E-2), (E-3), (E-4), (H-1), (H-2), (H-3), (H-4), (K-1), (K-2), (K-3), and (K-4), or a pharmaceutically acceptable salt thereof, per dose, is one of the effective dose ranges described herein, including a) from about 0.1 µg to about 1,000 µg; b) from about 0.5 µg to about 0.5 mg; and c) from about 0.5 µg to about 50 µg.

For each of the kits described above there is an additional embodiment in which the diluent is hypertonic saline of the concentrations described herein. In another embodiment for each kit the diluent is hypotonic saline of the concentrations described herein. In a further embodiment for each kit, the diluent is sterile water suitable for inhalation.

The pharmaceutically acceptable excipient(s), diluent(s) or carrier(s) must be acceptable in the sense of being compatible with the other ingredients of the formulation and not deleterious to the recipient thereof. Generally, the pharmaceutically acceptable excipient(s), diluent(s) or carrier(s) employed in the pharmaceutical formulation are "non-toxic" meaning that it/they is/are deemed safe for consumption in the amount delivered in the formulation and "inert" meaning that it/they does/do not appreciable react with or result in an undesired effect on the therapeutic activity of the active ingredient(s). Pharmaceutically acceptable excipients, diluents and carriers are conventional in the art and may be selected using conventional techniques, based upon the desired route of administration. See, REMINGTON'S, PHARMACEUTICAL SCIENCES, Lippincott Williams & Wilkins; 21$^{st}$ Ed (May 1, 2005). Preferably, the pharmaceutically acceptable excipient(s), diluent(s) or carrier(s) are Generally Regarded As Safe (GRAS) according to the FDA.

Pharmaceutical compositions according to the invention include those suitable for oral administration; parenteral administration, including subcutaneous, intradermal, intramuscular, intravenous and intraarticular; topical administration, including topical administration to the skin, eyes, ears, etc; vaginal or rectal administration; and administration to the respiratory tract, including the nasal cavities and sinuses, oral and extrathoracic airways, and the lungs, including by use of aerosols which may be delivered by means of various types of dry powder inhalers, pressurized metered dose inhalers, softmist inhalers, nebulizers, or insufflators. The most suitable route of administration may depend upon, several factors including the patient and the condition or disorder being treated.

The formulations may be presented in unit dosage form or in bulk form as for example in the case of formulations to be metered by an inhaler and may be prepared by any of the methods well known in the art of pharmacy. Generally, the methods include the step of bringing the active ingredient into association with the carrier, diluent or excipient and optionally one or more accessory ingredients. In general the formulations are prepared by uniformly and intimately bringing into association the active ingredient with one or more liquid carriers, diluents or excipients or finely divided solid carriers, diluents or excipients, or both, and then, if necessary, shaping the product into the desired formulation.

In one preferred embodiment, the composition is an inhalable pharmaceutical composition which is suitable for inhalation and delivery to the endobronchial space. Typically, such composition is in the form of an aerosol comprising particles for delivery using a nebulizer, pressurized metered dose inhaler (MDI), softmist inhaler, or dry powder inhaler (DPI). The aerosol formulation used in the methods of the present invention may be a liquid (e.g., solution) suitable for administration by a nebulizer, softmist inhaler, or MDI, or a dry powder suitable for administration by an MDI or DPI.

Aerosols used to administer medicaments to the respiratory tract are typically polydisperse; that is they are comprised of particles of many different sizes. The particle size distribution is typically described by the Mass Median Aerodynamic Diameter (MMAD) and the Geometric Standard Deviation (GSD). For optimum drug delivery to the endobronchial space the MMAD is in the range from about 1 to about 10 urn and preferably from about 1 to about 5 µm, and the GSD is less than 3, and preferably less than about 2. Aerosols having a MMAD above 10 µm are generally too large when inhaled to reach the lungs. Aerosols with a GSD greater than about 3 are not preferred for lung delivery as they deliver a high percentage of the medicament to the oral cavity. To achieve these particle sizes in powder formulation, the particles of the active ingredient may be size reduced using conventional techniques such as micronisation or spray drying. Non-limiting examples of other processes or techniques that can be used to produce respirable particles include spray drying, precipitation, supercritical fluid, and freeze drying. The desired fraction may be separated out by air classification or sieving. In one embodiment, the particles will be crystalline. For liquid formulations, the particle size is determined by the selection of a particular model of nebulizer, softmist inhaler, or MDI.

Aerosol particle size distributions are determined using devices well known in the art. For example a multi-stage Anderson cascade impactor or other suitable method such as those specifically cited within the US Pharmacopoeia Chapter 601 as characterizing devices for aerosols emitted from metered-dose and dry powder inhalers.

Dry powder compositions for topical delivery to the lung by inhalation may be formulated without excipient or carrier and instead including only the active ingredients in a dry powder form having a suitable particle size for inhalation. Dry powder compositions may also contain a mix of the active ingredient and a suitable powder base (carrier/diluent/excipient substance) such as mono-, di- or poly-saccharides (e.g., lactose or starch). Lactose is typically the preferred excipient for dry powder formulations. When a solid excipient such as lactose is employed, generally the particle size of the excipient will be much greater than the active ingredient to aid the dispersion of the formulation in the inhaler.

Non-limiting examples of dry powder inhalers include reservoir multi-dose inhalers, pre-metered multi-dose inhalers, capsule-based inhalers and single-dose disposable inhalers. A reservoir inhaler contains a large number of doses (e.g. 60) in one container. Prior to inhalation, the patient actuates the inhaler which causes the inhaler to meter one dose of medicament from the reservoir and prepare it for inhalation. Examples of reservoir DPIs include but are not limited to the Turbohaler® by AstraZeneca and the ClickHaler® by Vectura.

In a pre-metered multi-dose inhaler, each individual dose has been manufactured in a separate container, and actuation of the inhaler prior to inhalation causes a new dose of drug to be released from its container and prepared for inhalation. Examples of multidose DPI inhalers include but are not limited to Diskus® by GSK, Gyrohaler® by Vectura, and Prohaler® by Valois. During inhalation, the inspiratory flow of the patient accelerates the powder out of the device and into the oral cavity. For a capsule inhaler, the formulation is in a capsule and stored outside the inhaler. The patient puts a capsule in the inhaler, actuates the inhaler (punctures the capsule), then inhales. Examples include the Rotohaler™ (GlaxoSmithKline), Spinhaler™ (Novartis), HandiHaler™ (IB), TurboSpin™ (PH&T). With single-dose disposable inhalers, the patient actuates the inhaler to prepare it for inhalation, inhales, then disposes of the inhaler and packaging. Examples include the Twincer™ (U Groningen), OneDose™ (GFE), and Manta Inhaler™ (Manta Devices).

Generally, dry powder inhalers utilize turbulent flow characteristics of the powder path to cause the excipient-drug aggregates to disperse, and the particles of active ingredient are deposited in the lungs. However, certain dry powder inhalers utilize a cyclone dispersion chamber to produce particles of the desired respirable size. In a cyclone dispersion chamber, the drug enters a coin shaped dispersion chamber tangentially so that the air path and drug move along the outer circular wall. As the drug formulation moves along this circular wall it bounces around and agglomerates are broken apart by impact forces. The air path spirals towards the center of the chamber exiting vertically. Particles that have small enough aerodynamic sizes can follow the air path and exit the chamber. In effect, the dispersion chamber works like a small jet mill. Depending on the specifics of the formulation, large lactose particles may be added to the formulation to aid in the dispersion through impact with the API particles.

The Twincer™ single-dose disposable inhaler appears to operate using a coin-shaped cyclone dispersion chamber referred to as an "air classifier." See, U.S. Published Patent Application No. 2006/0237010 to Rijksuniversiteit Groningen. Papers published by the University of Groningen, have stated that a 60 mg dose of pure micronized colistin sulfomethate could be effectively delivered as an inhalable dry powder utilizing this technology.

In preferred embodiments, the aerosol formulation is delivered as a dry powder using a dry powder inhaler wherein the particles emitted from the inhaler have an MMAD in the range of about 1 μm to about 5 μm and a GSD about less than 2.

Examples of suitable dry powder inhalers and dry powder dispersion devices for use in the delivery of compounds and compositions according to the present invention include but are not limited to those disclosed in U.S. Pat. No. 7,520,278; U.S. Pat. No. 7,322,354; U.S. Pat. No. 7,246,617; U.S. Pat. No. 7,231,920; U.S. Pat. No. 7,219,665; U.S. Pat. No. 7,207,330; U.S. Pat. No. 6,880,555; U.S. Pat. No. 5,522,385; U.S. Pat. No. 6,845,772; U.S. Pat. No. 6,637,431; U.S. Pat. No. 6,329,034; U.S. Pat. No. 5,458,135; U.S. Pat. No. 4,805,811; and U.S. Published Patent Application No. 2006/0237010.

In one embodiment, the pharmaceutical formulation according to the invention is a dry powder for inhalation which is formulated for delivery by a Diskus®-type device. The Diskus® device comprises an elongate strip formed from a base sheet having a plurality of recesses spaced along its length and a lid sheet hermetically but peelably sealed thereto to define a plurality of containers, each container having therein an inhalable formulation containing a predetermined amount of active ingredient either alone or in admixture with one or more carriers or excipients (e.g., lactose) and/or other therapeutically active agents. Preferably, the strip is sufficiently flexible to be wound into a roll. The lid sheet and base sheet will preferably have leading end portions which are not sealed to one another and at least one of the leading end portions is constructed to be attached to a winding means. Also, preferably the hermetic seal between the base and lid sheets extends over their whole width. To prepare the dose for inhalation, the lid sheet may preferably be peeled from the base sheet in a longitudinal direction from a first end of the base sheet.

In one embodiment, the pharmaceutical formulation according to the invention is a dry powder for inhalation which is formulated for delivery using a single-dose disposable inhaler, and particularly the Twincer™ inhaler. The Twincer™ inhaler comprises a foil laminate blister with one or more recesses and a lid sheet hermetically but peelably sealed thereto to define a plurality of containers. Each container has therein an inhalable formulation containing a predetermined amount of active ingredient(s) either alone or in admixture with one or more carriers or excipients (e.g., lactose). The lid sheet will preferably have a leading end portion which is constructed to project from the body of the inhaler. The patient would operate the device and thereby administer the aerosol formulation by 1) removing the outer packaging overwrap, 2) pulling the foil tab to uncover the drug in the blister and 3) inhaling the drug from the blister.

In another embodiment, the pharmaceutical formulation according to the invention is a dry powder for inhalation wherein the dry powder is formulated into microparticles as described in PCT Publication No. WO2009/015286 or WO2007/114881, both to NexBio. Such microparticles are generally formed by adding a counter ion to a solution containing a compound of the invention in a solvent, adding an antisolvent to the solution; and gradually cooling the solution to a temperature below about 25° C., to form a composition containing microparticles comprising the compound. The microparticles comprising the compound may then be separated from the solution by any suitable means such as sedimentation, filtration or lyophillization. Suitable counterions, solvents and antisolvents for preparing microparticles of the compounds of the invention are described in WO2009/015286.

In another embodiment, a pharmaceutical composition according to the invention is delivered as a dry powder using a metered dose inhaler. Non-limiting examples of metered dose inhalers and devices include those disclosed in U.S. Pat. No. 5,261,538; U.S. Pat. No. 5,544,647; U.S. Pat. No. 5,622,163; U.S. Pat. No. 4,955,371; U.S. Pat. No. 3,565,070; U.S. Pat. No. 3,361,306 and U.S. Pat. No. 6,116,234 and U.S. Pat. No. 7,108,159. In a preferred embodiment, a compound of the invention is delivered as a dry powder using a metered dose inhaler wherein the emitted particles have an MMAD that is in the range of about 1 µm to about 5 µm and a GSD that is less than about 2.

Liquid aerosol formulations for delivery to the endobronchial space or lung by inhalation may for example be formulated as aqueous solutions or suspensions or as aerosols delivered from pressurized packs, such as metered dose inhalers, with the use of suitable liquefied propellants, softmist inhalers, or nebulizers. Such aerosol compositions suitable for inhalation can be either a suspension or a solution and generally contain the active ingredient(s) together with a pharmaceutically acceptable carrier or diluent (e.g., water (distilled or sterile), saline, hypertonic saline, or ethanol) and optionally one or more other therapeutically active agents.

Aerosol compositions for delivery by pressurized metered dose inhalers typically further comprise a pharmaceutically acceptable propellant. Examples of such propellants include fluorocarbon or hydrogen-containing chlorofluorocarbon or mixtures thereof, particularly hydrofluoroalkanes, e.g., dichlorodifluoromethane, trichlorofluoromethane, dichlorotetrafluoroethane, especially 1,1,1,2-tetrafluoroethane, 1,1,1,2,3,3,3,-heptafluoro-n-propane or a mixture thereof. The aerosol composition may be excipient free or may optionally contain additional formulation excipients well known in the art such as surfactants e.g., oleic acid or lecithin and cosolvents e.g., ethanol. Pressurized formulations will generally be retained in a canister (e.g., an aluminum canister) closed with a valve (e.g., a metering valve) and fitted into an actuator provided with a mouthpiece.

In another embodiment, a pharmaceutical composition according to the invention is delivered as a liquid using a metered dose inhaler. Non-limiting examples of metered dose inhalers and devices include those disclosed in U.S. Pat. Nos. 6,253,762, 6,413,497, 7,601,336, 7,481,995, 6,743,413, and 7,105,152. In a preferred embodiment, a compound of the invention is delivered as a dry powder using a metered dose inhaler wherein the emitted particles have an MMAD that is in the range of about 1 µm to about 5 µm and a GSD that is less than about 2.

In one embodiment the aerosol formulation is suitable for aerosolization by a jet nebulizer, or ultrasonic nebulizer including static and vibrating porous plate nebulizers. Liquid aerosol formulations for nebulization may be generated by solubilizing or reconstituting a solid particle formulation or may be formulated with an aqueous vehicle with the addition of agents such as acid or alkali, buffer salts, and isotonicity adjusting agents. They may be sterilized by in-process techniques such as filtration, or terminal processes such as heating in an autoclave or gamma irradiation. They may also be presented in non-sterile form.

Patients can be sensitive to the pH, osmolality, and ionic content of a nebulized solution. Therefore these parameters should be adjusted to be compatible with the active ingredient and tolerable to patients. The most preferred solution or suspension of active ingredient will contain a chloride concentration >30 mM at pH 4.5-7.4, preferably 5.0-5.5, and an osmolality of from about 800-1600 mOsm/kg. The pH of the solution can be controlled by either titration with common acids (hydrochloric acid or sulfuric acid, for example) or bases (sodium hydroxide, for example) or via the use of buffers. Commonly used buffers include citrate buffers, such as citric acid/sodium citrate buffers, acetate buffers, such as acetic acid/sodium acetate buffers, and phosphate buffers. Buffer strengths can range from 2 mM to 50 mM.

Useful acetate, phosphate, and citrate buffers include sodium acetate, sodium acetate trihydrate, ammonium acetate, potassium acetate, sodium phosphate, sodium phosphate dibasic, disodium hydrogen phosphate, potassium dihydrogen phosphate, potassium hydrogen phosphate, potassium phosphate, sodium citrate, and potassium citrate. Other buffers which may be utilized include sodium hydroxide, potassium hydroxide, ammonium hydroxide, aminomethylpropanol, tromethamine, tetrahydroxypropyl ethylenediamine, citric acid, acetic acid, hydroxytricarboxylic acid or a salt thereof, such as a citrate or sodium citrate salt thereof, lactic acid, and salts of lactic acid including sodium lactate, potassium lactate, lithium lactate, calcium lactate, magnesium lactate, barium lactate, aluminum lactate, zinc lactate, silver lactate, copper lactate, iron lactate, manganese lactate, ammonium lactate, monoethanolamine, diethanolamine, triethanolamine, diisopropanolamine, as well as combinations thereof, and the like.

Such formulations may be administered using commercially available nebulizers or other atomizer that can break the formulation into particles or droplets suitable for deposition in the respiratory tract. Non-limiting examples of nebulizers which may be employed for the aerosol delivery of a composition of the invention include pneumatic jet nebulizers, vented or breath-enhanced jet nebulizers, or ultrasonic nebulizers including static or vibrating porous plate nebulizers. Commercially available nebulizers include the Aeroneb® Go nebulizer (Aerogen) and the eFlow nebulizer (Pari Pharma).

A jet nebulizer utilizes a high velocity stream of air blasting up through a column of water to generate droplets. Particles unsuitable for inhalation impact on walls or aerodynamic baffles. A vented or breath enhanced nebulizer works in essentially the same way as a jet nebulizer except that inhaled air passes through the primary droplet generation area to increase the output rate of the nebulizer while the patient inhales.

In an ultrasonic nebulizer, vibration of a piezoelectric crystal creates surface instabilities in the drug reservoir that cause droplets to be formed. In porous plate nebulizers pressure fields generated by sonic energy force liquid through the mesh pores where it breaks into droplets by Rayleigh breakup. The sonic energy may be supplied by a vibrating horn or plate driven by a piezoelectric crystal, or by the mesh itself vibrating. Non-limiting examples of atomizers include any single or twin fluid atomizer or nozzle that produces droplets of an appropriate size. A single fluid atomizer works by forcing a liquid through one or more holes, where the jet of liquid breaks up into droplets. Twin fluid atomizers work by either forcing both a gas and liquid through one or more holes, or by impinging a jet of liquid against another jet of either liquid or gas.

The choice of nebulizer which aerosolizes the aerosol formulation is important in the administration of the active ingredient(s). Different nebulizers have differing efficiencies based their design and operation principle and are sensitive to the physical and chemical properties of the formulation. For example, two formulations with different surface tensions may have different particle size distributions. Additionally, formulation properties such as pH, osmolality, and permeant ion content can affect tolerability of the medication, so preferred embodiments conform to certain ranges of these properties.

In a preferred embodiment, the formulation for nebulization is delivered to the endobronchial space as an aerosol having an MMAD between about 1 μm and about 5 μm and a GSD less than 2 using an appropriate nebulizer. To be optimally effective and to avoid upper respiratory and systemic side effects, the aerosol should not have a MMAD greater than about 5 μm and should not have a GSD greater than about 2. If an aerosol has an MMAD larger than about 5 μm or a GSD greater than about 2 a large percentage of the dose may be deposited in the upper airways decreasing the amount of drug delivered to the desired site in the lower respiratory tract. If the MMAD of the aerosol is smaller than about 1 μm then a large percentage of the particles may remain suspended in the inhaled air and may then be exhaled during expiration.

The compounds of the invention may also be administered by transbronchoscopic lavage.

Formulations suitable for oral administration may be presented as discrete units such as capsules, cachets or tablets, each containing a predetermined amount of the active ingredient; as a powder or granules; as a solution or suspension in an aqueous liquid or a non-aqueous liquid; or as an oil-in-water liquid emulsion or a water-in-oil liquid emulsion. The active ingredient may also be presented as a sachet, bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binders, lubricant, inert diluent, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein.

Formulations for topical administration in the mouth, for example buccally or sublingually, include lozenges, comprising the active ingredient in a flavored base such as sucrose and *acacia* or tragacanth, and pastilles comprising the active ingredient in a base such as gelatin and glycerin or sucrose and *acacia*.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example saline or water-for-injection, immediately prior to use. Extemporaneous injection solutions and suspensions may be prepared from sterile powders, granules and tablets of the kind previously described.

Oral fluids such as solutions, syrups and elixirs can be prepared in dosage unit form so that a given quantity contains a predetermined amount of the active ingredient. Syrups can be prepared by dissolving the active ingredient in a suitably flavored aqueous solution, while elixirs are prepared through the use of a pharmaceutically acceptable alcoholic vehicle. Suspensions can be formulated by dispersing the active ingredient in a pharmaceutically acceptable vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be incorporated into oral liquid compositions.

Liposome delivery systems such as small unilamellar vesicles, large unilamellar vesicles and multilamellar vesicles may also be employed as delivery means for the compounds of the invention. Liposomes may be formed from a variety of phospholipids such as cholesterol, stearylamine and phosphatidylcholines.

Pharmaceutical compositions for topical administration may be formulated as ointments, creams, suspensions, lotions, powders, solutions, pastes, gels, sprays, aerosols or oils. Compositions designed for the treatment of the eyes or other external tissues, for example the mouth and skin, may be applied as a topical ointment or cream. When formulated as an ointment, the active ingredient may be employed with either a paraffinic or a water-miscible ointment base. Alternatively, the active ingredient may be formulated in a cream with an oil-in-water cream base or a water-in-oil base.

Other compositions designed for topical administration to the eyes or ears include eye drops and ear drops wherein the active ingredient is dissolved or suspended in a suitable carrier, such as for example an aqueous solvent, including saline.

Compositions designed for nasal administration include aerosols, solutions, suspensions, sprays, mists and drops. Aerosolable formulations for nasal administration may be formulated in much the same ways as aerosolable formulations for inhalation with the condition that particles of non-respirable size will be preferred in formulations for nasal administration. Typically, particles of about 5 microns in size, up to the size of visible droplets may be employed. Thus, for nasal administration, a particle size in the range of 10-500 μm may be used to ensure retention in the nasal cavity.

Transdermal patches may also be employed, which are designed to remain in contact with the epidermis of the patient for an extended period of time and promote the absorption of the active ingredient there through.

Compositions for vaginal or rectal administration include ointments, creams, suppositories and enemas, all of which may be formulated using conventional techniques.

In another aspect, the invention provides a method of promoting hydration of mucosal surfaces or restoring mucosal defense in a human in need thereof, comprising administering to the human a pharmaceutical composition comprising a compound of the invention, wherein said compound is administered in an effective amount. In one preferred embodiment, the method comprises administering the pharmaceutical composition as an inhalable composition comprising an amount of a compound of the invention that is sufficient to achieve dissolved concentration of the compound on the airway surfaces of from about $10^{-9}$, $10^{-8}$, or $10^{-7}$ to about $10^{-4}$, $10^{-3}$, $10^{-2}$, or $10^{-1}$ Moles/liter, more preferably from about $10^{-9}$ to about $10^{-4}$ Moles/liter.

In another aspect, the invention provides a method of treating any one of: a disease associated with reversible or irreversible airway obstruction, chronic obstructive pulmonary disease (COPD), asthma, bronchiectasis (including bronchiectasis due to conditions other than cystic fibrosis), acute bronchitis, chronic bronchitis, post-viral cough, cystic fibrosis, emphysema, pneumonia, panbronchiolitis, transplant-associate bronchiolitis, and ventilator-associated tracheobronchitis or preventing ventilator-associated pneumonia in a human in need thereof, comprising administering to the human a pharmaceutical composition comprising a compound of the invention, wherein said compound is administered in an effective amount. In one preferred embodiment, the method comprises administering the pharmaceutical composition as an inhalable composition comprising an amount of a compound of the invention that is sufficient to achieve dissolved concentration of the compound on the airway surfaces of from about $10^{-9}$, $10^{-9}$, or $10^{-7}$ to about $10^{-4}$, $10^{-3}$, $10^{-2}$, or $10^{-1}$ Moles/liter, more preferably from about $10^{-9}$ to about $10^{-4}$ Moles/liter.

In another aspect, the invention provides a method of treating any one of dry mouth (xerostomia), dry skin, vaginal dryness, sinusitis, rhinosinusitis, or nasal dehydration, including nasal dehydration brought on by administering dry oxygen, dry eye or Sjogren's disease, promoting ocular or corneal hydration, treating distal intestinal obstruction syndrome, treating otitis media, primary ciliary diskinesia, distal intestinal obstruction syndrome, esophagitis, constipation, or chronic diverticulitis in a human in need thereof, comprising administering to the human a pharmaceutical composition comprising a compound of the invention, wherein said compound is administered in an effective amount.

Preferred unit dosage formulations for the compounds of the invention are those containing an effective amount of the active ingredient or an appropriate fraction thereof.

It should be understood that in addition to the ingredients particularly mentioned above, the formulations of this invention may include other agents conventional in the art having regard to the type of formulation in question for example those suitable for oral administration may include flavoring agents.

The compositions of the present invention may be formulated for immediate, controlled or sustained release as desired for the particular condition being treated and the desired route of administration. For example, a controlled release formulation for oral administration may be desired for the treatment of constipation in order to maximize delivery of the active agent to colon. Such formulations and suitable excipients for the same are well known in the art of pharmacy. Because the free base of the compound is generally less soluble in aqueous solutions than the salt, compositions comprising a free base of a compound of Formula (A) may be employed to provide more sustained release of active agent delivered by inhalation to the lungs. An active agent present in the lungs in particulate form which has not dissolved into solution is not available to induce a physiological response, but serves as a depot of bioavailable drug which gradually dissolves into solution. As another example, a formulation may employ both a free base and salt form of a compound of the invention to provide both immediate release and sustained release of the active ingredient for dissolution into the mucus secretions of, for example, the nose.

Combinations

The compounds of the invention may be formulated and/or used in combination with other therapeutically active agents. Examples of other therapeutically active agents which may be formulated or used in combination with the compounds of the invention include but are not limited to osmolytes, anti-inflammatory agents, anticholinergic agents, β-agonists (including selective $β_2$-agonists), P2Y2 receptor agonists, peroxisome proliferator-activated receptor (PPAR) delta agonists, other epithelial sodium channel blockers (ENaC receptor blockers), cystic fibrosis transmembrane conductance regulator (CFTR) modulators, kinase inhibitors, antiinfective agents, antihistamines, non-antibiotic anti-inflammatory macrolides, elastase and protease inhibitors, and mucus or mucin modifying agents, such as surfactants. In addition, for cardiovascular indications, the compounds of the invention may be used in combination with beta blockers, ACE inhibitors, HMGCoA reductase inhibitors, calcium channel blockers and other cardiovascular agents.

The present invention thus provides, as another aspect, a composition comprising an effective amount of a compound of the invention and one or more other therapeutically active agents selected from osmolytes, anti-inflammatory agents, anticholinergic agents, β-agonists (including selective $β_2$-agonists), P2Y2 receptor agonists, PPAR delta agonists, ENaC receptor blockers, cystic fibrosis transmembrane conductance regulator (CFTR) modulators, kinase inhibitors, antiinfective agents, antihistamines, non-antibiotic anti-inflammatory macrolides, elastase and protease inhibitors, and mucus or mucin modifying agents, such as surfactants. The present invention thus provides, as another aspect, a composition comprising an effective amount of a compound of the invention and one or more other therapeutically active agents selected from beta blockers, ACE inhibitors, HMG-CoA reductase inhibitors, and calcium channel blockers. Use of the compounds of the invention in combination with one or more other therapeutically active agents (particularly osmolytes) may lower the dose of the compound of the invention that is required to sufficiently hydrate mucosal surfaces, thereby reducing the potential for undesired side-effects attributable to systemic blocking of sodium channels such as for example in the kidneys.

"Osmolytes" according to the present invention are molecules or compounds that are osmotically active. "Osmotically active" molecules and compounds are membrane-impermeable (i.e., essentially non-absorbable) on the airway or pulmonary epithelial surface. The terms "airway surface" and "pulmonary surface," as used herein, include pulmonary airway surfaces such as the bronchi and bronchioles, alveolar surfaces, and nasal and sinus surfaces. Suitable osmolytes include ionic osmolytes (i.e., salts), and non-ionic osmolytes (i.e., sugars, sugar alcohols, and organic osmolytes). In general, osmolytes (both ionic and non-ionic) used in combination with the compounds of the invention are preferably osmolytes that do not promote, or in fact deter or retard bacterial growth. Osmolytes suitable for use in the present invention may be in racemic form or in the form of an enantiomer, diastereomer, tautomer, polymorph or pseudopolymorph.

Examples of ionic osmolytes useful in the present invention include any salt of a pharmaceutically acceptable anion and a pharmaceutically acceptable cation. Preferably, either (or both) of the anion and cation are osmotically active and not subject to rapid active transport, in relation to the airway surfaces to which they are administered. Such compounds include but are not limited to anions and cations that are contained in FDA approved commercially marketed salts, see, e.g., *Remington: The Science and Practice of Pharmacy*, Vol. II, pg. 1457 (19$^{th}$ Ed. 1995), and can be used in any combination as known in the art.

Specific examples of pharmaceutically acceptable osmotically active anions include but are not limited to, acetate, benzenesulfonate, benzoate, bicarbonate, bitartrate, bromide, calcium edetate, camsylate (camphorsulfonate), carbonate, chloride, citrate, dihydrochloride, edetate, edisylate (1,2-ethanedisulfonate), estolate (lauryl sulfate), esylate (1,2-ethanedisulfonate), fumarate, gluceptate, gluconate, glutamate, glycollylarsanilate (p-glycollamidophenylarsonate), hexylresorcinate, hydrabamine (N,N'-Di(dehydroabietyl)ethylenediamine), hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, nitrite, pamoate (embonate), pantothenate, phosphate or diphosphate, polygalacturonate, salicylate, stearate, subacetate, succinate, sulfate, tannate, tartrate, teoclate (8-chlorotheophyllinate), triethiodide, bicarbonate, etc. Preferred anions include chloride, sulfate, nitrate, gluconate, iodide, bicarbonate, bromide, and phosphate.

Specific examples of pharmaceutically acceptable osmotically active cations include but are not limited to, organic cations such as benzathine (N,N'-dibenzylethylenediamine), chloroprocaine, choline, diethanolamine, ethylenediamine, meglumine (N-methyl D-glucamine), procaine, D-lysine, L-lysine, D-arginine, L-arginine, triethylammonium, N-methyl D-glycerol, and the like; and metallic cations such as aluminum, calcium, lithium, magnesium, potassium, sodium, zinc, iron, ammonium, and the like. Preferred organic cations include 3-carbon, 4-carbon, 5-carbon and 6-carbon organic cations. Preferred cations include sodium, potassium, choline, lithium, meglumine, D-lysine, ammonium, magnesium, and calcium.

Specific examples of ionic osmolytes that may be used in combination with a compound of the invention include but are not limited to, sodium chloride (particularly hypertonic saline), potassium chloride, choline chloride, choline iodide, lithium chloride, meglumine chloride, L-lysine chloride, D-lysine chloride, ammonium chloride, potassium sulfate, potassium nitrate, potassium gluconate, potassium iodide, ferric chloride, ferrous chloride, potassium bromide, and combinations of any two or more of the foregoing. In one embodiment, the present invention provides a combination of a compound of the invention and two different osmotically active salts. When different salts are used, one of the anion or cation may be the same among the differing salts. Hypertonic saline is a preferred ionic osmolyte for use in combination with the compounds of the invention. Non-ionic osmolytes include sugars, sugar-alcohols, and organic osmolytes.

Sugars and sugar-alcohols useful as osmolytes in the present invention include but are not limited to 3-carbon sugars (e.g., glycerol, dihydroxyacetone); 4-carbon sugars (e.g., both the D and L forms of erythrose, threose, and erythrulose); 5-carbon sugars (e.g., both the D and L forms of ribose, arabinose, xylose, lyxose, psicose, fructose, sorbose, and tagatose); and 6-carbon sugars (e.g., both the D and L forms of altose, allose, glucose, mannose, gulose, idose, galactose, and talose, and the D and L forms of allo-heptulose, allo-hepulose, gluco-heptulose, manno-heptulose, gulo-heptulose, ido-heptulose, galacto-heptulose, talo-heptulose). Additional sugars useful in the practice of the present invention include raffinose, raffinose series oligosaccharides, and stachyose. Both the D and L forms of the reduced form of each sugar/sugar alcohol are also suitable for the present invention. For example, glucose, when reduced, becomes sorbitol; an osmolyte within the scope of the invention. Accordingly, sorbitol and other reduced forms of sugar/sugar alcohols (e.g., mannitol, dulcitol, arabitol) are suitable osmolytes for use in the present invention. Mannitol is a preferred non-ionic osmolyte for use in combination with the compounds of the invention.

"Organic osmolytes" is generally used to refer to molecules that control intracellular osmolality in the kidney. See e.g., J. S. Handler et al., *Comp. Biochem. Physiol*, 117, 301-306 (1997); M. Burg, *Am. J. Physiol*. 268, F983-F996 (1995). Organic osmolytes include but are not limited to three major classes of compounds: polyols (polyhydric alcohols), methylamines, and amino acids. Suitable polyol organic osmolytes include but are not limited to, inositol, myo-inositol, and sorbitol. Suitable methylamine organic osmolytes include but are not limited to, choline, betaine, carnitine (L-, D- and DL forms), phosphorylcholine, lyso-phosphorylcholine, glycerophosphorylcholine, creatine, and creatine phosphate. Suitable amino acid organic osmolytes include but are not limited to, the D- and L-forms of glycine, alanine, glutamine, glutamate, aspartate, proline and taurine. Additional organic osmolytes suitable for use in the present invention include tihulose and sarcosine. Mammalian organic osmolytes are preferred, with human organic osmolytes being most preferred. However, certain organic osmolytes are of bacterial, yeast, and marine animal origin, and these compounds may also be employed in the present invention.

Osmolyte precursors may be used in combination with the compounds of the invention An "osmolyte precursor" as used herein refers to a compound which is converted into an osmolyte by a metabolic step, either catabolic or anabolic. Examples of osmolyte precursors include but are not limited to, glucose, glucose polymers, glycerol, choline, phosphatidylcholine, lyso-phosphatidylcholine and inorganic phosphates, which are precursors of polyols and methylamines. Precursors of amino acid osmolytes include proteins, peptides, and polyamino acids, which are hydrolyzed to yield osmolyte amino acids, and metabolic precursors which can be converted into osmolyte amino acids by a metabolic step such as transamination. For example, a precursor of the amino acid glutamine is poly-L-glutamine, and a precursor of glutamate is poly-L-glutamic acid.

Chemically modified osmolytes or osmolyte precursors may also be employed. Such chemical modifications involve linking the osmolyte (or precursor) to an additional chemical group which alters or enhances the effect of the osmolyte or osmolyte precursor (e.g., inhibits degradation of the osmolyte molecule). Such chemical modifications have been utilized with drugs or prodrugs and are known in the art. (See, for example, U.S. Pat. Nos. 4,479,932 and 4,540,564; Shek, E. et al., *J. Med. Chem.* 19:113-117 (1976); Bodor, N. et al., *J. Pharm. Sci.* 67:1045-1050 (1978); Bodor, N. et al., *J. Med. Chem.* 26:313-318 (1983); Bodor, N. et al., *J. Pharm. Sci.* 75:29-35 (1986).

Preferred osmolytes for use in combination with the compounds of the invention include sodium chloride, particular hypertonic saline, and mannitol.

For the formulation of 7% and >7% hypertonic saline, formulations containing bicarbonate anions may be particularly useful, especially for respiratory disorders with cystic fibrosis transmembrane conductance regulator (CFTR) dysfunction such as CF or COPD. Recent findings indicate that, although the relative ratio of $HCO_3^-$ conductance/$Cl^-$ conductance is between 0.1 and 0.2 for single CFTR channels activated with cAMP and ATP, the ratio in the sweat duct can range from virtually 0 to almost 1.0, depending on conditions of stimulation. That is, combining cAMP+cGMP+α-ketoglutarate can yield CFTR $HCO_3^-$ conductance almost equal to that of $Cl^-$ conductance (Quiton et al. Physiology, Vol. 22, No. 3, 212-225, June 2007). Furthermore, formulations of 7% and >7% hypertonic saline containing bicarbonate anions may be particularly useful due to better control of the pH in the airway surface liquid. First, it has shown that that airway acidification occurs in CF (Tate et al. 2002) and that absent CFTR-dependent bicarbonate secretion can lead to an impaired capacity to respond to airway conditions associated with acidification of airway surface liquid layer (Coakley et al. 2003). Second, addition of HS solution without bicarbonate to the surface of the lung may further dilute the bicarbonate concentrations, and potentially reduce the pH or the ability to respond to airway acidification within the airway surface liquid layer. Therefore addition of bicarbonate anions to HS may help maintain or improve the pH of airway surface liquid layer in CF patients.

Due to this evidence, inclusion of bicarbonate anion in the formulation of 7% or >7% hypertonic saline administered by the method of this invention would be particularly useful. Formulations containing up to 30 to 200 mM concentrations of bicarbonate anions are of particular interest for 7% or >7% HS solutions.

Hypertonic saline is understood to have a salt concentration greater than that of normal saline (NS), i.e. greater than 9 g/L or 0.9% w/v, and hypotonic saline has a salt concentration less than that of normal saline, such as from about 1 g/L or 0.1% w/v to about 8 g/L or 0.8% w/v. Hypertonic saline solutions useful in the formulations and methods of treatment herein may have a salt concentration from about 1% to about 23.4% (w/v). In one embodiment the hypertonic saline solution has a salt concentration from about 60 g/L (6% w/v) to about 100 g/L (10% w/v). In another embodiment, the saline solution has a salt concentration from about 70 g/L (7% w/v) to about 100 g/L (10% w/v). In further embodiments, the saline solution has salt concentrations of a) from about 0.5 g/L (0.05% w/v) to about 70 g/L (7% w/v); b) from about 1 g/L (0.1% w/v) to about 60 g/L (6% w/v); c) from about 1 g/L (0.1% w/v) to about 50 g/L (5% w/v); d) from about 1 g/L (0.1% w/v) to about 40 g/L (4% w/v); e) from about 1 g/L (0.1% w/v) to about 30 g/L (3% w/v); and f) from about 1 g/L (0.1% w/v) to about 20 g/L (2% w/v).

Specific concentrations of saline solutions useful in the formulations and methods of treatment herein include, independently, those having salt concentrations of 1 g/L (0.1% w/v), 2 g/L (0.2% w/v), 3 g/L (0.3% w/v), 4 g/L (0.4% w/v), 5 g/L (0.5% w/v), 6 g/L (0.6% w/v), 7 g/L (0.7% w/v), 8 g/L (0.8% w/v), 9 g/L (0.9% w/v), 10 g/L (1% w/v), 20 g/L (2% w/v), 30 g/L (3% w/v), 40 g/L (4% w/v), 50 g/L (5% w/v), 60 g/L (6% w/v), 70 g/L (7% w/v), 80 g/L (8% w/v), 90 g/L (9% w/v), 100 g/L (10% w/v), 110 g/L (11% w/v), 120 g/L (12% w/v), 130 g/L (13% w/v), 140 g/L (14% w/v), 150 g/L (15% w/v), 160 g/L (16% w/v), 170 g/L (17% w/v), 180 g/L (18% w/v), 190 g/L (19% w/v), 200 g/L (20% w/v), 210 g/L (21% w/v), 220 g/L (22% w/v), and 230 g/L (23% w/v). Saline concentrations between each of these listed concentrations/percentages may also be used, such as saline of 1.7 g/L (0.17% w/v), 1.25 g/L (1.25% w/v), 1.5 g/L (1.5% w/v), 25 g/L (2.5% w/v), 28 g/L (2.8% w/v), 35 g/L (3.5% w/v), 45 g/L (4.5% w/v), and 75 g/L (7.5% w/v).

Specific useful concentration of hypotonic saline solutions include those from about 0.12 g/L (0.012% w/v) to about 8.5 g/L (0.85% w/v). Any concentration within this range may be used, such as, on a w/v basis, 0.05%, 0.1%, 0.15%, 0.2%, 0.225% (¼ NS), 0.25%, 0.3% (⅓ NS), 0.35%, 0.4%, 0.45% (½ NS), 0.5%, 0.55%, 0.6% (⅔ NS), 0.65%, 0.675% (¾ NS), 0.7%, 0.75%, and 0.8%.

Each of the ranges and specific concentrations of saline described herein may be used with the formulations, methods of treatment, regimens, and kits described herein.

Also intended within the scope of this invention are chemically modified osmolytes or osmolyte precursors. Such chemical modifications involve linking to the osmolyte (or precursor) an additional chemical group which alters or enhances the effect of the osmolyte or osmolyte precursor (e.g., inhibits degradation of the osmolyte molecule). Such chemical modifications have been utilized with drugs or prodrugs and are known in the art. (See, for example, U.S. Pat. Nos. 4,479,932 and 4,540,564; Shek, E. et al., J. Med. Chem. 19:113-117 (1976); Bodor, N. et al., J. Pharm. Sci. 67:1045-1050 (1978); Bodor, N. et al., J. Med. Chem. 26:313-318 (1983); Bodor, N. et al., J. Pharm. Sci. 75:29-35 (1986), each incorporated herein by reference.

Suitable anti-inflammatory agents for use in combination with the compounds of the invention include corticosteroids and non-steroidal anti-inflammatory drugs (NSAIDs), particularly phosphodiesterase (PDE) inhibitors. Examples of corticosteroids for use in the present invention include oral or inhaled corticosteroids or prodrugs thereof. Specific examples include but are not limited to ciclesonide, desisobutyryl-ciclesonide, budesonide, flunisolide, mometasone and esters thereof (e.g., mometasone furoate), fluticasone propionate, fluticasone furoate, beclomethasone, methyl prednisolone, prednisolone, dexamethasone, 6α,9α-difluoro-17α-[(2-furanylcarbonyl)oxy]-11β-hydroxy-16α-methyl-3-oxo-androsta-1,4-diene-17β-carbothioic acid S-fluoromethyl ester, 6α,9α-difluoro-11β-hydroxy-16α-methyl-3-oxo-17α-propionyloxy-androsta-1,4-diene-17β-carbothioic acid S-(2-oxo-tetrahydro-furan-3S-yl) ester, beclomethasone esters (e.g., the 17-propionate ester or the 17,21-dipropionate ester, fluoromethyl ester, triamcinolone acetonide, rofleponide, or any combination or subset thereof. Preferred corticosteroids for formulation or use in combination with the compounds of the invention are selected from ciclesonide, desisobutyryl-ciclesonide, budesonide, mometasone, fluticasone propionate, and fluticasone furoate, or any combination or subset thereof.

NSAIDs for use in the present invention include but are not limited to sodium cromoglycate, nedocromil sodium, phosphodiesterase (PDE) inhibitors (e.g., theophylline, aminophylline, PDE4 inhibitors, mixed PDE3/PDE4 inhibitors or mixed PDE4/PDE7 inhibitors), leukotriene antagonists, inhibitors of leukotriene synthesis (e.g., 5 LO and FLAP inhibitors), inducible nitric oxide synthase (iNOS) inhibitors, protease inhibitors (e.g., tryptase inhibitors, neutrophil elastase inhibitors, and metalloprotease inhibitors) β2-integrin antagonists and adenosine receptor agonists or antagonists (e.g., adenosine 2a agonists), cytokine antagonists (e.g., chemokine antagonists) or inhibitors of cytokine synthesis (e.g., prostaglandin D2 (CRTh2) receptor antagonists). Examples of leukotriene modifiers suitable for administration by the method of this invention include montelukast, zileuton, panlukast, and zafirlukast.

The PDE4 inhibitor, mixed PDE3/PDE4 inhibitor or mixed PDE4/PDE7 inhibitor may be any compound that is known to inhibit the PDE4 enzyme or which is discovered to act as a PDE4 inhibitor, and which are selective PDE4 inhibitors (i.e., compounds which do not appreciably inhibit other members of the PDE family). Examples of specific PDE4 inhibitors for formulation and use in combination with the compounds of the present invention include but are not limited to roflumilast, pumafentrine, arofylline, cilomilast, tofimilast, oglemilast, tolafentrine, piclamilast, ibudilast, apremilast, 2-[4-[6,7-diethoxy-2,3-bis(hydroxymethyl)-1-naphthalenyl]-2-pyridinyl]-4-(3-pyridinyl)-1(2H)-phthalazinone (T2585), N-(3,5-dichloro-4-pyridinyl)-1-[(4-fluorophenyl)methyl]-5-hydroxy-α-oxo-1H-indole-3-acetamide (AWD-12-281, 4-[(2R)-2-[3-(cyclopentyloxy)-4-methoxyphenyl]-2-phenylethyl]-pyridine (CDP-840), 2-[4-[[[[2-(1,3-benzodioxol-5-yloxy)-3-pyridinyl]carbonyl]amino]methyl]-3-fluorophenoxy]-(2R)-propanoic acid (CP-671305), N-(4,6-dimethyl-2-pyrimidinyl)-4-[4,5,6,7-tetrahydro-2-(4-methoxy-3-methylphenyl)-5-(4-methyl-1-piperazinyl)-1H-indol-1-yl]-benzenesulfonamide, (2E)-2-butenedioate (YM-393059), 9-[(2-fluorophenyl)methyl]-N-methyl-2-(trifluoromethyl)-9H-purin-6-amine (NCS-613), N-(2,5-dichloro-3-pyridinyl)-8-methoxy-5-quinolinecarboxamide (D-4418), N-[(3R)-9-amino-3,4,6,7-tetrahydro-4-oxo-1-phenylpyrrolo[3,2,1-][1,4]benzodiazepin-3-yl]-3H-purin-6-amine (PD-168787), 3-[[3-(cyclopentyloxy)-4-methoxyphenyl]methyl]-N-ethyl-8-(1-methylethyl)-3H-purin-6-amine hydrochloride (V-11294A), N-(3,5-dichloro-1-oxido-4-pyridinyl)-8-methoxy-2-(trifluoromethyl)-5-quinolinecarboxamide (Sch351591), 5-[3-(cyclopentyloxy)-4-methoxyphenyl]-3-[(3-methylphenyl)methyl]-(3S,5S)-2-piperidinone HT-0712), 5-(2-((1R,4R)-4-amino-1-(3-(cyclopentyloxy)-4-methyoxyphenyl)cyclohexyl) ethynyl)-pyrimidine-2-amine,cis-[4-cyano-4-(3-cyclopropylmethoxy-4-difluoromethoxy phenyl) cyclohexan-1-ol], and 4-[6,7-diethoxy-2,3-bis(hydroxymethyl)-1-naphthalenyl]-1-(2-methoxyethyl)-2(1H)-pyridinone (T-440), 6-({3-[(Dimethylamino)carbonyl]phenyl}sulfonyl)-8-methyl-4-{[3-methyloxy)phenyl]amino}-3-quinolinecarboxamide (GSK256066), and any combination or subset thereof.

Anticholinergic agents for formulation or use in combination with the compounds of the invention include but are not limited to muscarinic receptor antagonists, particularly including pan antagonists and antagonists of the $M_3$ receptors. Exemplary compounds include the alkaloids of the belladonna plants, such as atropine, scopolamine, homatropine, hyoscyamine, and the various forms including salts thereof (e.g., anhydrous atropine, atropine sulfate, atropine oxide or HCl, methylatropine nitrate, homatropine hydrobromide, homatropine methyl bromide, hyoscyamine hydrobromide, hyoscyamine sulfate, scopolamine hydrobromide, scopolamine methyl bromide), or any combination or subset thereof.

Additional anticholinergics for formulation and use in combination with the methantheline, propantheline bromide, anisotropine methyl bromide or Valpin 50, aclidinium bromide, glycopyrrolate (Robinul), isopropamide iodide, mepenzolate bromide, tridihexethyl chloride, hexocyclium methylsulfate, cyclopentolate HCl, tropicamide, trihexyphenidyl CCl, pirenzepine, telenzepine, and methoctramine, or any combination or subset thereof.

Preferred anticholinergics for formulation and use in combination with the compounds of the invention include ipratropium (bromide), oxitropium (bromide) and tiotropium (bromide), aclidinium (bromide), or any combination or subset thereof.

Examples of β-agonists for formulation and use in combination with the compounds of the invention include but are not limited to salmeterol, R-salmeterol, and xinafoate salts thereof, albuterol (also known as salbutamol) or R-albuterol (free base or sulfate), levalbuterol, formoterol (fumarate), fenoterol, procaterol, pirbuterol, metaprterenol, terbutaline and salts thereof, and any combination or subset thereof.

$P2Y_2$ receptor agonists for formulation and use in combination with the compounds of the invention may be employed in an amount effective to stimulate chloride and water secretion by airway surfaces, particularly nasal airway surfaces. Suitable $P2Y_2$ receptor agonists are known in the art and are described for example, in columns 9-10 of U.S. Pat. No. 6,264,975, and also U.S. Pat. Nos. 5,656,256 and 5,292,498.

$P2Y_2$ agonists that can be administered by the methods of this invention include $P2Y_2$ receptor agonists such as ATP, UTP, UTP-.gamma.-S and dinucleotide $P2Y_2$ receptor agonists (e.g. denufosol or diquafosol) or a pharmaceutically acceptable salt thereof. The $P2Y_2$ receptor agonist is typically included in an amount effective to stimulate chloride and water secretion by airway surfaces, particularly nasal airway surfaces. Suitable $P2Y_2$ receptor agonists are described in, but are not limited to, U.S. Pat. No. 6,264,975, U.S. Pat. No. 5,656,256, U.S. Pat. No. 5,292,498, U.S. Pat. No. 6,348,589, U.S. Pat. No. 6,818,629, U.S. Pat. No. 6,977,246, U.S. Pat. No. 7,223,744, U.S. Pat. No. 7,531,525 and U.S. Pat. AP. 2009/0306009 each of which is incorporated herein by reference.

Combination therapies and formulations herein can include adenosine 2b (A2b) agonists, also, including 2-[6-amino-3,5-dicyano-4-[4-(cyclopropylmethoxy) phenyl]pyridin-2-ylsulfanyl]acetamide (BAY 60-6583), NECA (N-ethylcarboxamidoadenosine), (S)-PHPNECA, LUF-5835 and LUF-5845. A2b agonists that may be used are described by Volpini et al., *Journal of Medicinal Chemistry* 45 (15): 3271-9 (2002); Volpini et al., *Current Pharmaceutical Design* 8 (26): 2285-98 (2002); Baraldi et al., *Journal of Medicinal Chemistry* 47 (6): Cacciari et al., 1434-47 (2004); *Mini Reviews in Medicinal Chemistry* 5 (12): 1053-60 (December 2005); Baraldi et al., *Current Medicinal Chemistry* 13 (28): 3467-82 (2006); Beukers et al., *Medicinal Research Reviews* 26 (5): 667-98 (September 2006); Elzein et al., *Bioorganic & Medicinal Chemistry Letters* 16 (2): 302-6 (January 2006); Carotti, et al., *Journal of Medicinal Chemistry* 49 (1): 282-99 (January 2006); Tabrizi et al., *Bioorganic & Medicinal Chemistry* 16 (5): 2419-30 (March 2008); and Stefanachi, et al., *Bioorganic & Medicinal Chemistry* 16 (6): 2852-69 (March 2008).

Examples of other ENaC receptor blockers for formulation and use in combination with the compounds of the invention include but are not limited to amiloride and derivatives thereof such as those compounds described in U.S. Pat. No. 6,858,615, and PCT Publication Nos. WO2003/070182, WO2004/073629, WO2005/018644, WO2006/022935, WO2007/018640, and WO2007/146869.

Small molecule ENaC blockers are capable of directly preventing sodium transport through the ENaC channel pore. ENaC blocker that can be administered in the combinations herein include, but are not limited to, amiloride, benzamil, phenamil, and amiloride analogues as exemplified by U.S. Pat. No. 6,858,614, U.S. Pat. No. 6,858,615, U.S. Pat. No. 6,903,105, U.S. Pat. No. 6,995,160, U.S. Pat. No. 7,026,325, U.S. Pat. No. 7,030,117, U.S. Pat. No. 7,064,129, U.S. Pat. No. 7,186,833, U.S. Pat. No. 7,189,719, U.S. Pat. No. 7,192,958, U.S. Pat. No. 7,192,959, U.S. Pat. No. 7,241,766, U.S. Pat. No. 7,247,636, U.S. Pat. No. 7,247,637, U.S. Pat. No. 7,317,013, U.S. Pat. No. 7,332,496, U.S. Pat. No. 7,345,044, U.S. Pat. No. 7,368,447, U.S. Pat. No. 7,368,450, U.S. Pat. No. 7,368,451, U.S. Pat. No. 7,375,107, U.S. Pat. No. 7,399,766, U.S. Pat. No. 7,410,968, U.S. Pat. No. 7,820,678, U.S. Pat. No. 7,842,697, U.S. Pat. No. 7,868,010, U.S. Pat. No. 7,875,619.

ENaC proteolysis is well described to increase sodium transport through ENaC. Protease inhibitors block the activity of endogenous airway proteases, thereby preventing ENaC cleavage and activation. Proteases that cleave ENaC include furin, meprin, matriptase, trypsin, channel associated proteases (CAPs), and neutrophil elastases. Protease inhibitors that can inhibit the proteolytic activity of these proteases that can be administered in the combinations herein include, but are not limited to, camostat, prostasin, furin, aprotinin, leupeptin, and trypsin inhibitors.

Combinations herein may include one or more suitable nucleic acids (or polynucleic acid), including but not limited to antisense oligonucleotide, siRNA, miRNA, miRNA mimic, antagomir, ribozyme, aptamer, and decoy oligonucleotide nucleic acids. See, e.g., US Patent Application Publication No. 20100316628. In general, such nucleic acids may be from 17 or 19 nucleotides in length, up to 23, 25 or 27 nucleotides in length, or more. Examples include, but are not limited to, those described in U.S. Pat. No. 7,517,865 and US Patent Applications Nos. 20100215588; 20100316628; 20110008366; and 20110104255. In general, the siRNAs are from 17 or 19 nucleotides in length, up to 23, 25 or 27 nucleotides in length, or more.

CFTR activity modulating compounds that can be administered in the combinations of this invention include, but are not limited to, compounds described in US 2009/0246137 A1, US 2009/0253736 A1, US 2010/0227888 A1, U.S. Pat. No. 7,645,789, US 2009/0246820 A1, US 2009/0221597 A1, US 2010/0184739 A1, US 2010/0130547 A1, US 2010/0168094 A1 and issued patent: U.S. Pat. No. 7,553,855; U.S. Pat. No. 7,772,259 B2, U.S. Pat. No. 7,405,233 B2, US 2009/0203752, U.S. Pat. No. 7,499,570, as well as Kalydeco™ (ivacaftor).

Mucus or mucin modifying agents useful in the combinations and methods herein include reducing agents, surfactants and detergents, expectorants, and deoxyribonuclease agents.

Mucin proteins are organized into high molecular weight polymers via the formation of covalent (disulfide) and non-covalent bonds. Disruption of the covalent bonds with reducing agents is a well-established method to reduce the viscoelastic properties of mucus in vitro and is predicted to minimize mucus adhesiveness and improve clearance in vivo. Reducing agents are known to decrease mucus viscosity in vitro and commonly used as an aid to processing sputum samples. Examples of reducing agents include sulfide containing molecules or phosphines capable of reducing protein di-sulfide bonds including, but not limited to, N-acetyl cysteine, N-acystelyn, carbocysteine, glutathione, dithiothreitol, thioredoxin containing proteins, and tris (2-carboxyethyl) phosphine.

N-acetyl cysteine (NAC) is approved for use in conjunction with chest physiotherapy to loosen viscid or thickened airway mucus. Clinical studies evaluating the effects of oral or inhaled NAC in CF and COPD have reported improvements in the rheologic properties of mucus and trends toward improvements in lung function and decreases in pulmonary exacerbations. However, the preponderance of clinical data suggests that NAC is at best a marginally effective therapeutic agent for treating airway mucus obstruction when administered orally or by inhalation. A recent Cochrane review of the existing clinical literature on the use of NAC found no evidence to support the efficacy of NAC for CF.

NAC is a relative inefficient reducing agent which is only partially active on the airway surface. Very high concentrations of NAC (200 mM or 3.26%) are required to fully reduce Muc5B, a major gel-forming airway mucin, in vitro. Furthermore, in the pH environment of the airway surface (measured in the range of pH 6.0 to 7.2 in CF and COPD airways), NAC exists only partially in its reactive state as a negatively charge thiolate. Thus, in the clinic, NAC is administered at very high concentrations. However, it is predicted that current aerosol devices will not be able to achieve therapeutic concentrations of even a 20% Mucomyst solution on distal airway surfaces within the relatively short time domains (7.5-15 minutes) typically used.

In non-clinical studies, $^{14}$C-tabled NAC, administered by inhalation, exhibits rapid elimination from the lungs with a half-life ranging from 6 to 36 minutes[12]

NAC is administered as a highly concentrated, hypertonic inhalation solution (20% or 1.22 molar) and has been reported to cause bronchoconstriction and cough. In many cases, it is recommended that NAC be administered with a bronchodilator to improve the tolerability of this agent.

Thus, reducing agents such as NAC are not well suited for bolus aerosol administration. However, it is anticipated that delivery of reducing agents by pulmonary aerosol infusion would increase the effectiveness, while allowing for a decrease in the concentration of reducing agent in the inhalation solution (predicted to increase tolerability).

Surfactants and detergents are spreading agents shown to decrease mucus viscoelasticity, improving mucus clearability. Examples of surfactants include dipalmitoylphosphatidylcholine (DPPC), PF, palmitic acid, palmitoyl-oleoylphosphatidylglycerol, surfactant-associated proteins (e.g. SP-A, B, or C), or may be animal derived (e.g. from cow or calf lung lavage or extracted from minced pig lung) or combinations thereof. See, e.g., U.S. Pat. Nos. 7,897,577; 5,876, 970; 5,614,216; 5,100,806; and 4,312,860. Examples of surfactant products include Exosurf® Neonatal (colfosceril palmitate), Pumactant® (DPPC and egg phosphatidylglycerol), KL-4 surfactant, Venticute® (lusulptide, rSP-C surfactant), Alveofact® (bovactant), Curosurf® (poractant alfa), Infasurf® (calfactant), Newfacten® (modified bovine surfactant), Surface®, Netsurf™ (nonionic alcohol ethoxylate surfactant) and Survanta® (beractant). Examples of detergents include, but are not limited to, Tween-80 and triton-X 100.

Any suitable expectorant can be used, including but not limited to guaifenesin (see, e.g., U.S. Pat. No. 7,345,051). Any suitable deoxyribonuclease can be used, including but not limited to Dornase Alpha. (see, e.g., U.S. Pat. No. 7,482,024). Examples of kinase inhibitors include inhibitors of NFkB, PI3K (phosphatidylinositol 3-kinase), p38-MAP kinase and Rho kinase.

Antiinfective agents for formulation and use in combination with the compounds of the invention include antivirals and antibiotics. Examples of suitable antivirals include Tamiflu® (oseltamivir) and Relenza® (zanamivir). Examples of suitable antibiotics include but are not limited to aztreonam (arginine or lysine), fosfomycin, and aminoglycosides such as tobramycin, or any combination or subset thereof. Additional anti-infective agents that may be used herein include aminoglycosides, Daptomycin, Fluoroquinolones, Ketolides, Carbapenems, Cephalosporins, Erythromycin, Linezolid, Penicillins, Azithromycin, Clindamycin, Oxazolidinones, Tetracyclines, and Vancomycin.

Examples of useful carbapenam antibiotics are impenam, panipenam, meropenam, biapenam, MK-826 (L-749,345), DA-1131, ER-35786, lenapenam, S-4661, CS-834 (prodrug of R-95867), KR-21056 (prodrug of KR-21012), L-084 (prodrug of LJC 11036) and Ceftolozane (CXA-101).

Antihistamines (i.e., H1-receptor antagonists) for formulation and use in combination with the compounds of the invention include but are not limited to: ethanolamines such as diphenhydramine HCl, carbinoxamine maleate, doxylamine, clemastine fumarate, and dimenhydrinate; ethylenediamines such as pyrilamine maleate (metpyramine), tripelennamine HCl, tripelennamine citrate, and antazoline; alkylamines such as pheniramine, chiorpheniramine, bromopheniramine, dexchlorpheniramine, triprolidine and acrivastine; pyridines such as methapyrilene, piperazines such as hydroxyzine HCl, hydroxyzine pamoate, cyclizine HCl, cyclizine lactate, meclizine HCl and cetirizine HCl; piperidines such as astemisole, levocabastine HCl, loratadine, descarboethoxyloratadine, terfenadine, and fexofenadine HCl; tri- and tetracyclics such as promethazine, chlorpromethazine trimeprazine and azatadine; and azelastine HCl, or any combination or subset thereof.

Examples of other classes of therapeutic agents suitable for use in the combinations and methods herein include antivirals such as ribavirin, anti-fungal agents such as amphotericin, intraconazole and voriconazole, anti-rejection drugs such as cyclosporine, tacrolimus and sirolimus, bronchodilators including but not limited to anticholinergic agents such as atrovent, siRNAs, gene therapy vectors, aptamers, endothelin-receptor antagonists, alpha-1-antitrypsin and prostacyclins.

In the above-described methods of treatment and uses, a compound of the invention may be employed alone, or in combination with one or more other therapeutically active agents. Typically, any therapeutically active agent that has a therapeutic effect in the disease or condition being treated with the compound of the invention may be utilized in combination with the compounds of the invention, provided that the particular therapeutically active agent is compatible with therapy employing a compound of the invention. Typical therapeutically active agents which are suitable for use in combination with the compounds of the invention include agents described above.

In one preferred embodiment, the compounds of the invention are used in combination with one or more osmolytes, particularly hypertonic saline or mannitol.

In another aspect, the invention provides methods for treatment and uses as described above, which comprise administering an effective amount of a compound of the invention and at least one other therapeutically active agent. The compounds of the invention and at least one additional therapeutically active agent may be employed in combination concomitantly or sequentially in any therapeutically appropriate combination. The administration of a compound of the invention with one or more other therapeutically active agents may be by administration concomitantly in 1) a unitary pharmaceutical composition, such as the compositions described above, or 2) separate pharmaceutical compositions each including one or more of the component active ingredients. The components of the combination may be administered separately in a sequential manner wherein the compound of the invention is administered first and the other therapeutically active agent is administered second or vice versa.

In the embodiments wherein the compound of the invention is administered in combination with one or more osmolytes, the administration of each component is preferably concomitant, and may be in a unitary composition or separate compositions. In one embodiment, the compound of the invention and one or more osmolytes are administered concomitantly by transbronchoscopic lavage. In another embodiment, the compound of the invention and one or more osmolytes are administered concomitantly by inhalation.

When a compound of the invention is used in combination with another therapeutically active agent, the dose of each compound may differ from that when the compound of the invention is used alone. Appropriate doses will be readily determined by one of ordinary skill in the art. The appropriate dose of the compound of the invention, the other therapeutically active agent(s) and the relative timings of administration will be selected in order to achieve the desired combined therapeutic effect, and are within the expertise and discretion of the attendant physician, clinician or veterinarian.

Experimental Procedures

The present invention also provides processes for preparing the compounds of the invention and to the synthetic intermediates useful in such processes, as described in detail below.

Certain abbreviations and acronyms are used in describing the synthetic processes and experimental details. Although most of these would be understood by one skilled in the art, the following table contains a list of many of these abbreviations and acronyms.

ABBREVIATION MEANING

AcOH Acetic Acid
AIBN Azobisisobutyronitrile
DIAD Diisopropyl azidodicarboxylate
DIPEA N,N-Diisopropylethylamine
Cbz carboxybenzyl
DCE dichloroethane
DCM dichloromethane
DMF dimethylformamide
DMSO dimethylsulfoxide
Et Ethyl
EtOAc or EA ethyl acetate
EtOH Ethanol
ESI electrospray ionization
HATU 2-(1H-7-Azabenzotriazol-1-yl)-1,1,3,3-tetramethyluronium hexafluorophosphate
HPLC High performance liquid chromatography
iCBF Isobutyl chloroformate
iPrOH Isopropyl alcohol
i.t. or IT intratracheal
Me Methyl
MeOH methanol
m/z or m/e mass to charge ratio
MH$^+$ mass plus 1
MH$^-$ mass minus 1
MIC minimal inhibitory concentration
MS or ms mass spectrum
MTBE methyl t-butyl ether
NaCNBH3 sodium cyanoborohydride
NMM N-methyl morpholine
rt or r.t. room temperature
R$_f$ Retardation factor
t-Bu tert-butyl
TEA triethylamine THF tetrahydrofuran
TLC or tlc thin layer chromatography
δ parts per million down field from tetramethylsilane
Cbz Benzyloxycarbonyl, i.e. —(CO)O-benzyl
AUC Area under the curve or peak
$t_R$ Retention time
GC-MS Gas chromatography-mass spectrometry
wt % Percent by weight
h Hours
min Minutes
MHz megahertz
TFA Trifluoroacetic acid
UV Ultraviolet
Boc tert-butyloxycarbonyl
Ph₃P Triphenylphosphine The compounds of Formula (A) may be synthesized using techniques known in the art. A representative synthetic procedure is illustrated in Scheme 1 below.

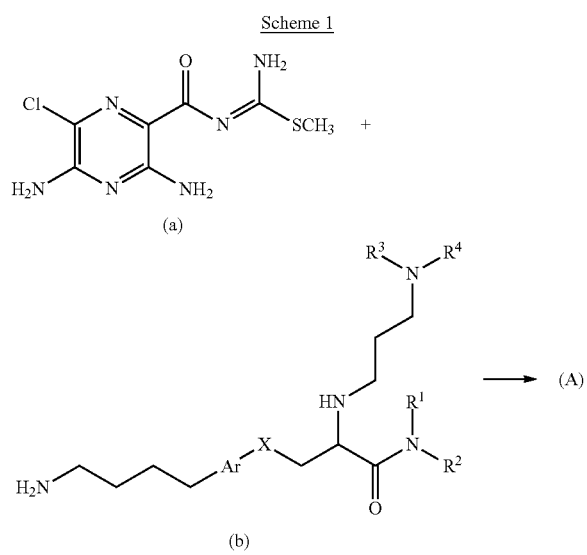

These procedures are described in, for example, E. J. Cragoe, "The Synthesis of Amiloride and Its Analogs" (Chap 3) in Amiloride and Its Analogs, pp. 25-36. Other processes for preparing amiloride analogs are described in, for example, U.S. Pat. No. 3,318,813, to Cragoe, particularly at methods A, B, C, and D of the '813 patent. Still other processes which may be adapted for the preparation of the compounds of the invention are described in PCT Publication Nos. WO2003/07182, WO2005/108644, WO2005/022935, U.S. Pat. No. 7,064,129, U.S. Pat. No. 6,858,615, U.S. Pat. No. 6,903,105, WO 2004/073629, WO 2007/146869, and WO 2007/018640.

Generally, the compounds of the invention may be conveniently prepared by treating a compound of Formula (a) with an amine of Formula (b). More specifically, compounds of Formula (a) are treated with the amine of Formula (b) in a suitable solvent such as methanol, ethanol, or tetrahydrofuran, and a base such as triethylamine (TEA), or diisoproylethylamine (DIPEA), with heating to elevated temperature, e.g., 70° C. Further purification, resolution of stereoisomers, crystallization and/or preparation of salt forms may be carried out using conventional techniques.

As will be apparent to those skilled in the art, in certain instances, the starting or intermediate compounds in the synthesis may possess other functional groups which provide alternate reactive sites. Interference with such functional groups may be avoided by utilization of appropriate protecting groups, such as amine or alcohol protecting groups, and where applicable, appropriately prioritizing the synthetic steps. Suitable protecting groups will be apparent to those skilled in the art. Methods are well known in the art for installing and removing such protecting groups and such conventional techniques may be employed in the processes of the instant invention as well.

The following specific examples which are provided herein for purposes of illustration only and do not limit the scope of the invention, which is defined by the claims.

Material and methods. All reagent and solvents were purchased from Aldrich Chemical Corp. Chem-Impex International Inc. and TCI chemical industry Co. Ltd. NMR spectra were obtained on either a Bruker AC 400 ($^1$H NMR at 400 MHz and $^{13}$C NMR at 100 MHz) or a Bruker AC 300 ($^1$H NMR at 300 MHz and $^{13}$C NMR at 75 MHz). Proton spectra were referenced to tetramethylsilane as an internal standard and the carbon spectra were referenced to CDCl₃, CD₃OD, or DMSO-d₆ (purchased from Aldrich or Cambridge Isotope Laboratories, unless otherwise specified). Flash chromatography was performed on a Combiflash system (Combiflash Rf, Teledyne Isco) charged with silica gel column (Redi Sep. Rf, Teledyne Isco) or reverse phase column (High performance C18 Gold column). ESI Mass spectra were obtained on a Shimadzu LCMS-2010 EV Mass Spectrometer. HPLC analyses were obtained using a Waters XTerra MS C18 5 μm 4.6×150 mm Analytical Column detected at 220 nm (unless otherwise specified) on a Shimadzu Prominence HPLC system. The following time program was used with a flow rate of 1.0 mL per minute:

| Time (min) | Percent A ($H_2O$ with 0.05% TFA) | Percent B ($CH_3CN$ with 0.05% TFA) |
|---|---|---|
| 2.50 | 90 | 10 |
| 20.00 | 10 | 90 |
| 30.00 | 10 | 90 |
| 32.50 | 90 | 10 |

UPLC analyses were obtained using a Waters ACQUITY UPLC HSS T3 1.8 μm 2.1×100 mm Analytical Column detected at 220 nm (unless otherwise specified) on a Shimadzu Prominence UFLC system. The following time program was used with a flow rate of 0.3 mL per minute:

| Time (min) | Percent A ($H_2O$ with 0.05% $NH_4COOH$ and 0.1% HCOOH) | Percent B ($CH_3CN$/Water 80:20% with 0.05% $NH_4COOH$ and 0.1% HCOOH) |
|---|---|---|
| 1.00 | 90 | 10 |
| 4.00 | 30 | 70 |
| 5.00 | 30 | 70 |
| 5.50 | 90 | 10 |
| 6.50 | 90 | 10 |

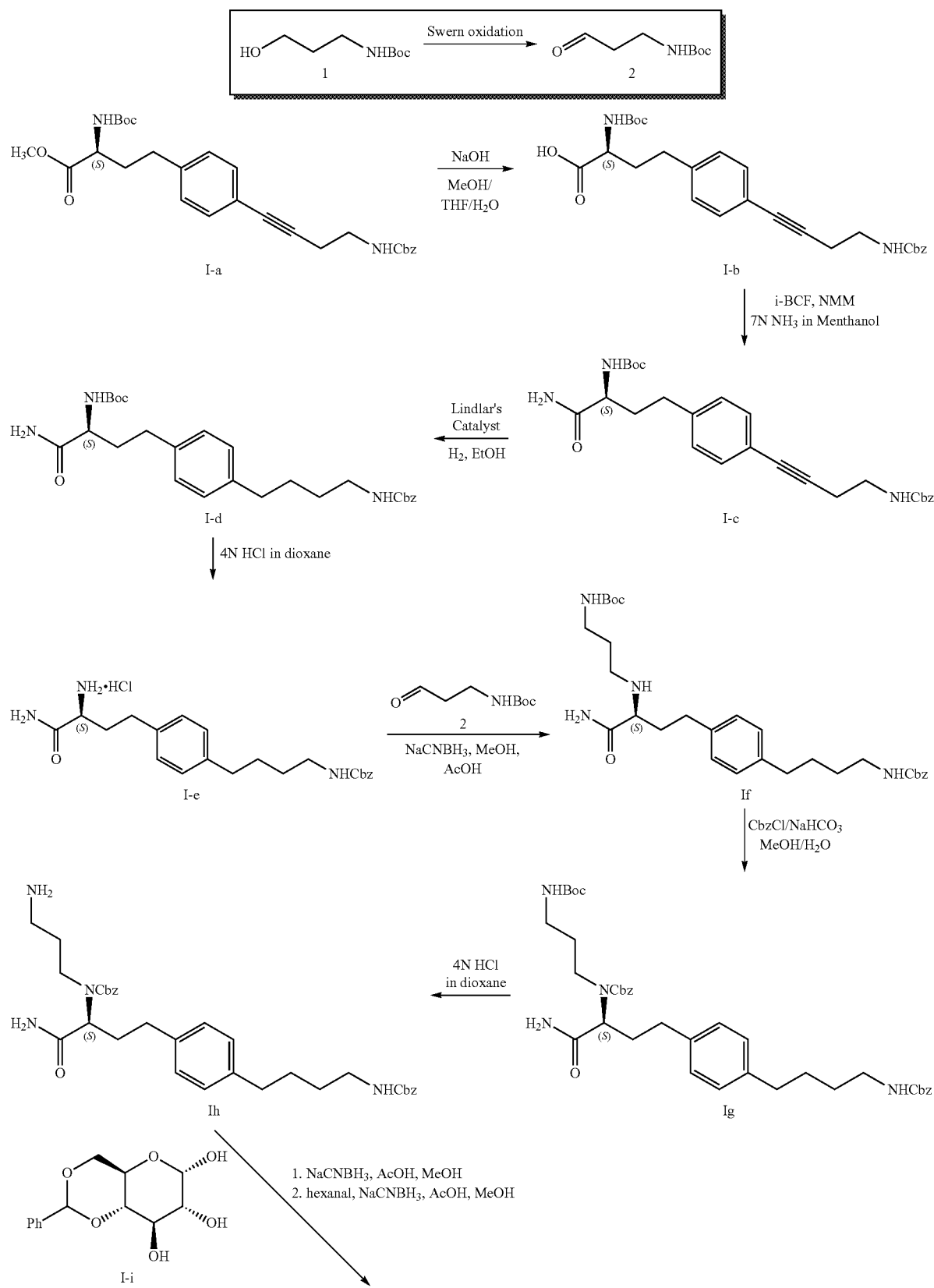

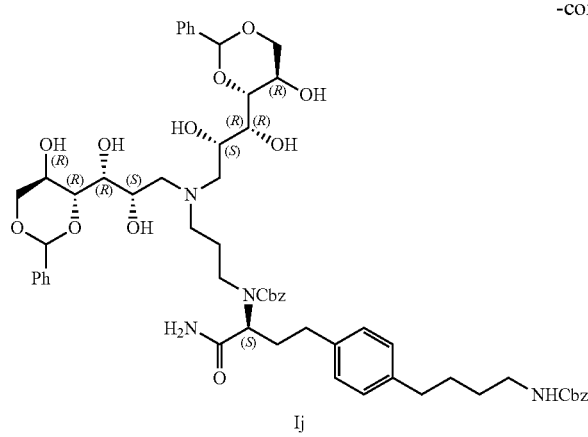
Ij

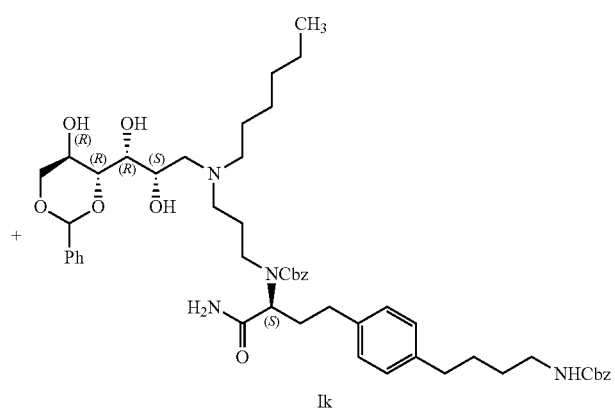
Ik

Preparation of tert-butyl 3-oxopropylcarbamate (2)

To a solution of oxalyl chloride (8.56 mL, 98.15 mmol) in CH$_2$Cl$_2$ (200 mL) was added DMSO (8.70 mL, 122.5 mmol) at −78° C. After 30 min, compound 1 (8.60 g, 49.90 mmol) was added at −78° C. and the reaction mixture was stirred for another 30 min. Triethylamine (41 mL, 294 mmol) was added and the reaction mixture was continued to be stirred at −78° C. for 30 min, then allowed to be warmed to 0° C. and stirred for 1 h. The reaction mixture was partitioned between CH$_2$Cl$_2$ (300 mL) and water (300 mL). The aqueous layer was separated and extracted with CH$_2$Cl$_2$ (2×300 mL). The combined organic extracts were dried over Na$_2$SO$_4$ and concentrated. The residue was purified by column chromatography (silica gel, 49:1 CHCl$_3$/MeOH) to afford aldehyde 2 as a yellow liquid: $^1$H NMR (300 MHz, CD$_3$OD) δ 9.80 (s, 1H), 4.94-4.82 (br s, 1H), 3.42 (dd, J=12.1 Hz, 6.0 Hz, 2H), 2.70 (t, J=6.0 Hz, 2H), 1.43 (s, 9H).

Preparation of (S)-4-(4-(4-(benzyloxycarbonylamino)but-1-ynyl)phenyl)-2-(tert-butoxycarbonylamino)butanoic acid (I-b)

To a solution of methyl ester I-a (5.00 g, 10.12 mmol) in THF/MeOH/H$_2$O (60 mL/60 mL/20 mL) was added NaOH (2.40 g, 60.72 mmol) and the reaction mixture was stirred at room temperature for 2 h. The pH value was adjusted to 9 with 1 N aq HCl and organic solvent was removed. The pH value of residue was adjusted to 5, and the suspension was partitioned between CH$_2$Cl$_2$ (500 mL) and water (500 mL). The aqueous layer was separated and extracted with CH$_2$Cl$_2$ (2×500 mL). The combined organic extracts were dried over Na$_2$SO$_4$ and concentrated to afford compound I-b as a brown solid: $^1$H NMR (400 MHz, DMSO-d6) δ ☐7.37-7.30 (m, 5H), 7.27 (d, J=8.4 Hz, 2H), 7.14 (d, J=8.4 Hz, 2H), 6.73 (brs, 1H), 5.03 (s, 2H), 3.75-3.69 (m, 1H), 3.21 (q, J=6.4 Hz, 2H), 2.60-2.47 (m, 4H), 1.97-1.76 (m, 2H), 1.38 (s, 9H).

Preparation of (S)-4-(4-(4-(benzyloxycarbonylamino)but-1-ynyl)phenyl)-2-(tert-butoxycarbonylamino)butanoic amide (I-c)

To a solution of acid I-b (4.40 g, 9.10 mmol) in THF (60 mL) was added NMM (1.50 mL, 13.65 mmol) and i-BCF (1.55 mL, 11.91 mmol) at 0° C. The reaction mixture was stirred at the same temperature for 2 h and NH$_3$ (7.0 N in methanol, 13 mL, 91 mmol) was added dropwise. The reaction mixture was continued to be stirred at 0° C. for 2 h, then allowed to be warmed to room temperature and stirred for 16 h. After concentration, the residue was partitioned between CH$_2$Cl$_2$ (300 mL) and water (300 mL). The aqueous layer was separated and extracted with CH$_2$Cl$_2$ (2×300 mL). The combined organic extracts were dried over Na$_2$SO$_4$ and concentrated. The residue was purified by column chromatography (silica gel, 30:1 CHCl$_3$/MeOH) to afford amide I-c as a yellow solid: $^1$H NMR (400 MHz, CD$_3$OD) δ 7.36-7.24 (m, 7H), 7.13 (d, J=8.4 Hz, 2H), 5.08 (s, 2H), 4.02-3.96 (m, 1H), 2.72-2.56 (m, 2H), 2.57 (t, J=7.1 Hz, 2H), 2.07-1.86 (m, 4H), 1.45 (s, 9H).

Preparation of Compound (I-d)

A suspension of I-c (3.40 g, 7.0 mmol) and 10% Lindlar's Catalyst (2.00 g) in EtOH (100 mL) was subjected to hydrogenation conditions (1 atm) for 36 h at room temperature. The reaction mixture was filtered through celite and washed with MeOH. The filtrate was concentrated in vacuum and the residue was purified by column chromatography (silica gel, 95:5 CHCl$_3$/CH$_3$OH) to afford compound I-d as a yellow solid: $^1$H NMR (300 MHz, CD$_3$OD) δ 7.35-7.23 (m, 5H), 7.21-7.12 (m, 2H), 7.07 (s, 2H), 5.04 (s, 2H), 4.06-3.94 (m, 1H), 3.21 (t, J=7.0 Hz, 1H), 3.11 (t, J=7.0 Hz, 1H), 2.77-2.46 (m, 4H), 2.10-1.77 (m, 4H), 1.67-1.51 (m, 2H), 1.45 (s, 9H).

Preparation of Compound (I-e)

Compound I-d (2.9 g, 6.0 mmol) was dissolved in 4 N HCl in dioxane (20 mL) at room temperature and the solution was stirred for 1 h. The solvent was removed in vacuum to give compound I-e as a white solid: $^1$H NMR (300 MHz, CD$_3$OD) δ 7.34-7.23 (m, 5H), 7.22-7.14 (m, 2H), 7.11 (s, 2H), 5.05 (s, 2H), 3.98-3.90 (m, 1H), 3.21 (t, J=7.0 Hz, 1H), 3.11 (t, J=7.0 Hz, 1H), 2.69 (dd, J=17 Hz, 8.0 Hz, 2H), 2.57 (t, J=6.9 Hz, 1H), 2.50 (ddd, J=9.3 Hz, 7.5 Hz, 2.1 Hz, 1H), 2.00-2.04 (m, 3H), 1.67-1.45 (m, 3H).

Preparation of Compound (I-f)

To a solution of compound 1-e (2.40 g, 5.72 mmol) and aldehyde 2 (1.2 g, 6.87 mmol) in MeOH (35 mL) was added acetic acid (0.5 mL) and the reaction mixture was stirred at room temperature for 10 min. Then sodium cyanoborohydride (540 mg, 8.58 mmol) was added and the solution was continued to be stirred at room temperature for 3 h. Additional compound 2 (0.3 equiv), AcOH (0.5 equiv), and NaCNBH₃ (0.5 equiv) were added and the solution was continued to be stirred at room temperature for 12 h. After concentration, the residue was partitioned between EtOAc (300 mL) and saturated NaHCO₃ (300 mL). The aqueous layer was separated and extracted with EtOAc (2×300 mL). The combined organic extracts were dried over Na₂SO₄ and concentrated. The residue (crude I-f, 3.50 g) was directly used for the next step without further purification.

Preparation of Compound (I-g)

To a solution of compound I-f (crude, 3.50 g) in MeOH (25 mL) was added saturated NaHCO₃ (25 mL) at 0° C. and the solution was stirred for 10 min. Benzyl chloroformate (1.75 mL) was added dropwise and the reaction mixture was stirred for 2 h at 0° C., then allowed to be warmed to room temperature and stirred for 1 h. After concentration, the residue was dissolved in CH₂Cl₂ (200 mL), then washed with water (300 mL) and brine (300 mL). The organic layer was dried over Na₂SO₄ and concentrated. The residue (crude 1-g, 3.50 g) was directly used for the next step without further purification.

Preparation of Compound (I-h)

Compound I-g (crude, 3.50 g) was dissolved in 4 N HCl in dioxane (30 mL) at room temperature and the solution was stirred for 1 h. After concentration, the residue was neutralized with aqueous NH₄OH and purified by column chromatography (silica gel, 16:1 CHCl₃/MeOH) to afford compound I-h as a yellow solid: ¹H NMR (300 MHz, CD₃OD) ☐7.45-7.22 (m, 10H), 7.21-6.99 (m, 4H), 5.15 (s, 2H), 5.04 (s, 2H), 4.54-4.36 (m, 1H), 3.55-3.39 (m, 2H), 3.21 (t, J=7.2 Hz, 1H), 3.11 (t, J=7.2 Hz, 1H), 2.97-2.80 (m, 2H), 2.56 (t, J=7.2 Hz, 2H), 2.52-2.44 (m, 4H), 2.28-2.01 (m, 2H), 1.91 (t, J=6.6 Hz, 2H), 1.64-1.43 (m, 2H).

Preparation of Compound I-j and I-k

To a solution of compound I-h (1.15 g, 2.00 mmol) and triol Ii (2.68 g, 10.0 mmol) in methanol (35 mL) was added acetic acid (0.91 mL) and the reaction mixture was stirred at room temperature for 10 min. Sodium cyanoborohydride (880 mg, 14.0 mmol) was added and the solution was continued to be stirred at room temperature for 2 h. Additional compound I-i (6.0 equiv), AcOH (8.0 equiv), and NaCNBH₃ (8.0 equiv) were added and the solution was continued to be stirred at room temperature for 16 h. Hexanal (0.36 mL, 3.00 mmol), AcOH (0.91 mL), and NaCNBH₃ (0880 mg, 14.0 mmol) were added and the reaction mixture was stirred for 2 h. After concentration, the residue was partitioned between EtOAc (300 mL) and saturated NaHCO₃ (200 mL). The aqueous layer was separated and extracted with EtOAc (2×300 mL). The combined organic extracts were dried over Na₂SO₄ and concentrated. The residue was purified by C-18 reverse phase Gold column to afford compound I-j and compound I-k as white solids.

Data for benzyl 2-((1-amino-4-(4-(4-(benzyloxycarbonylamino)butyl)phenyl)-1-oxobutan-2-yl)(3-(((2S,3R)-2,3-dihydroxy-3-((2S,4R,5R)-5-hydroxy-2-phenyl-1,3-dioxan-4-yl)propyl)((2S,3R)-2,3-dihydroxy-3-((4R,5R)-5-hydroxy-2-phenyl-1,3-dioxan-4-yl)propyl)amino)propyl)amino)acetate (compound I-j)

¹H NMR (400 MHz, CD₃OD) δ 7.53-7.39 (m, 4H), 7.37-7.22 (m, 16H), 7.18-6.94 (m, 4H), 5.52-5.37 (m, 2H), 5.09 (s, 2H), 5.04 (s, 2H), 4.21 (dd, J=11 Hz, 5.5 Hz, 2H) 4.01-3.89 (m, 4H), 3.88-3.81 (m, 2H), 3.75-3.64 (m, 3H), 3.57 (t, J=9.5 Hz, 2H), 3.19 (t, J=7.1 Hz, 1H), 3.09 (t, J=6.4 Hz, 2H), 2.75-2.40 (m, 12H), 2.25-2.08 (m, 1H), 2.04-1.86 (m, 1H), 1.85-1.65 (m, 3H), 1.63-1.53 (m, 1H), 1.52-1.40 (m, 1H).

Data for benzyl 2-((1-amino-4-(4-(4-(benzyloxycarbonylamino)butyl)phenyl)-1-oxobutan-2-yl)(3-(((2S,3R)-2,3-dihydroxy-3-((4R,5R)-5-hydroxy-2-phenyl-1,3-dioxan-4-yl)propyl)(hexyl)amino)propyl)amino)acetate (compound I-k)

¹H NMR (400 MHz, CD₃OD) of I-k, δ 7.58-7.22 (m, 15H), 7.20-6.95 (m, 4H), 5.53-5.43 (m, 1H), 5.11 (s, 2H), 5.05 (s, 2H), 4.22 (dd, J=9.7 Hz, 4.8 Hz, 1H) 4.00-3.83 (m, 4H), 3.80-3.69 (m, 1H), 3.59 (t, J=10.6 Hz, 1H), 3.20 (t, J=6.8 Hz, 1H), 3.10 (t, J=5.8 Hz, 2H), 2.77-2.62 (m, 1H), 2.61-2.31 (m, 10H), 2.27-2.14 (m, 1H), 2.06-1.89 (m, 1H), 1.86-1.54 (m, 3H), 1.53-1.44 (m, 1H), 1.41-1.00 (m, 10H), 0.85 (t, J=5.9 Hz, 3H).

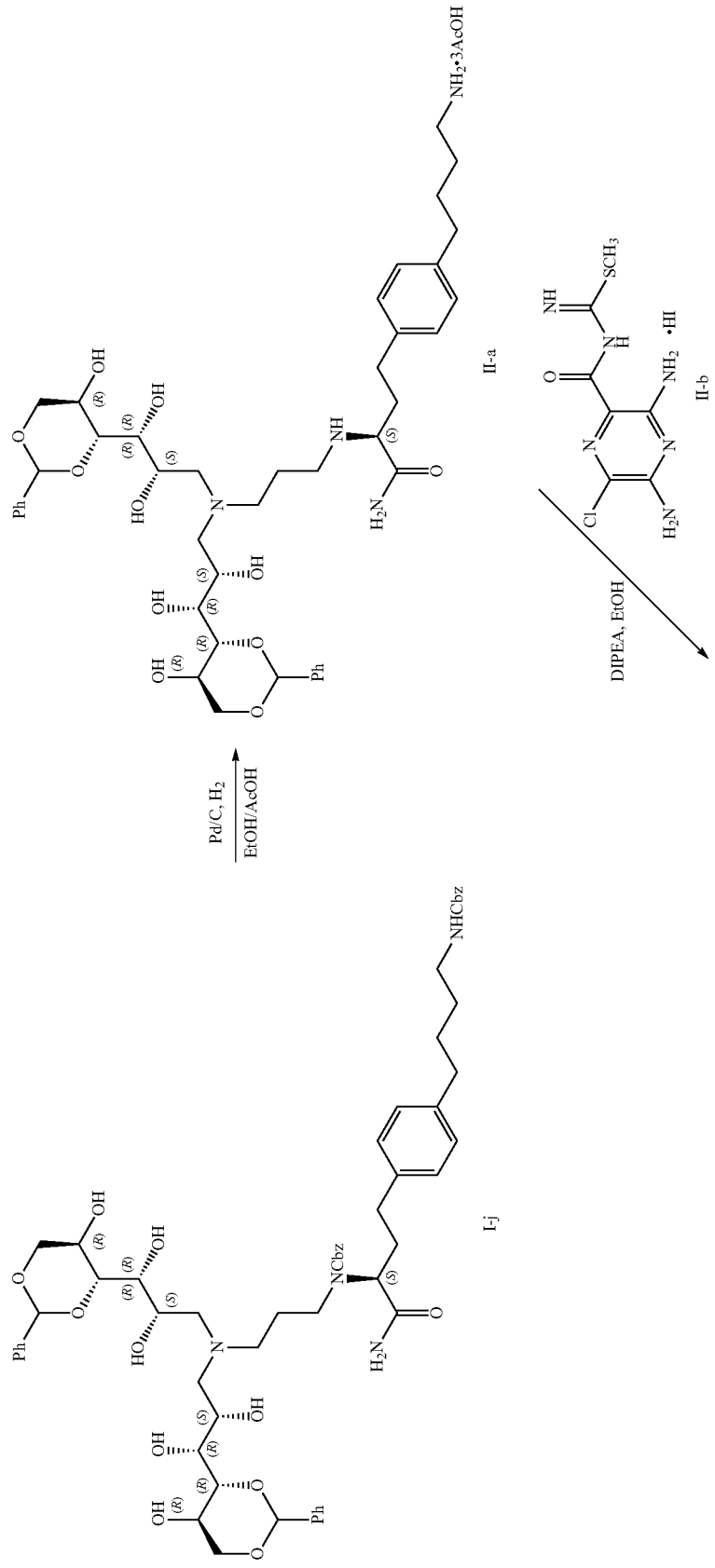
Scheme II. Preparation of the Hydrochloride Salt of 3,5-diamino-N-(N-(4-(4-((S)-4-amino-3-(3-(bis((2S,3R,4R,5R)-2,3,4,5,6-pentahydroxyhexyl)amino)-4-oxobutyl)phenyl)butyl)carbamimidoyl)-6-chloropyrazine-2-carboxamide (II-d).

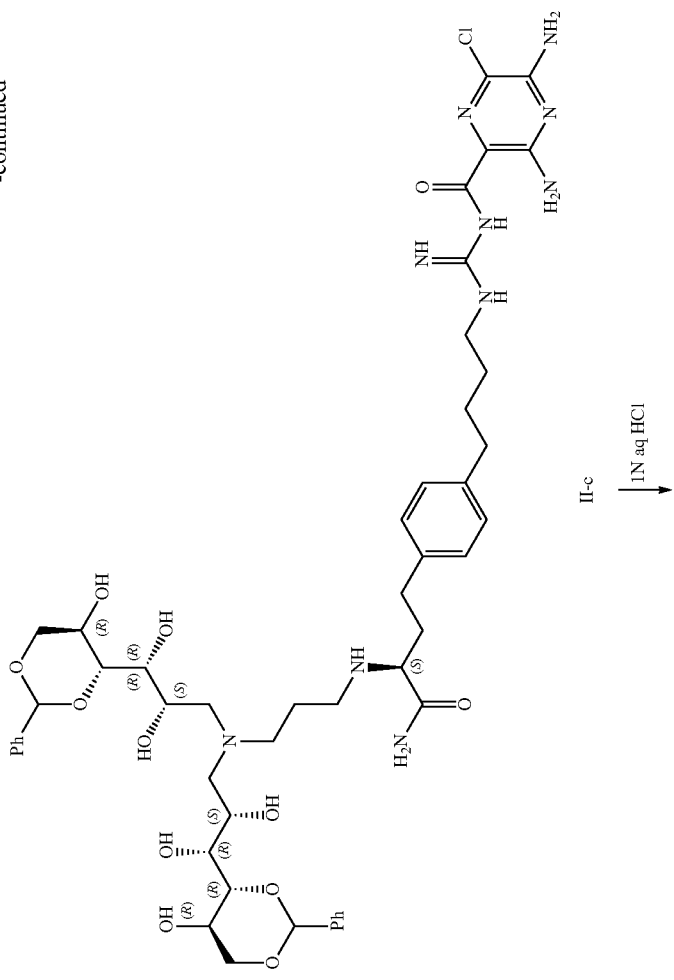

-continued
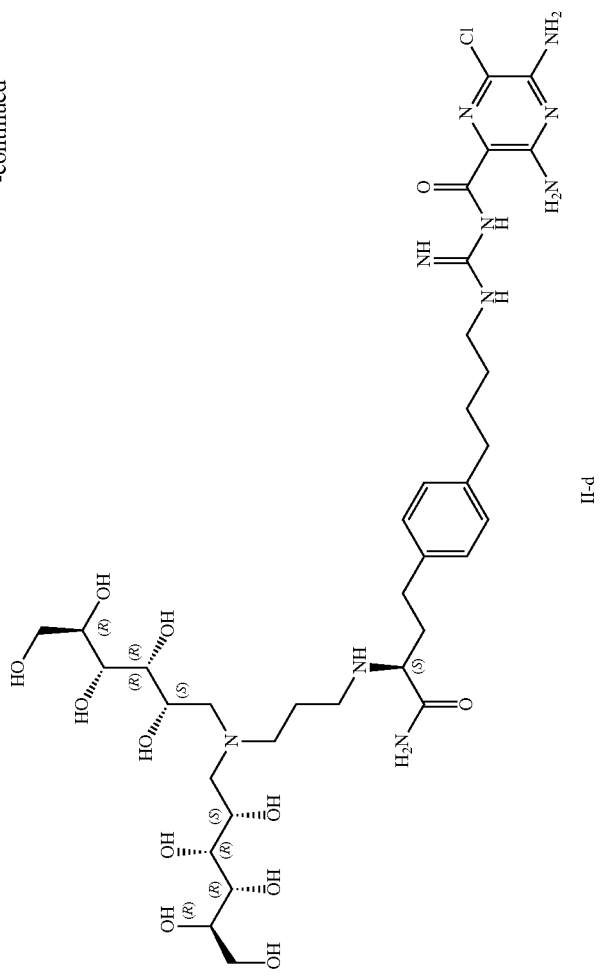
II-d

Preparation of Compound II-a

A suspension of I-j (700 mg, 0.65) and 10% Pd/C (300 mg) in EtOH/AcOH (40 mL/4 mL) was subjected to hydrogenation conditions (1 atm) for 16 h at room temperature. The reaction mixture was filtered through celite and washed with MeOH. The filtrate was concentrated in vacuum to afford compound II-a as a white solid: $^1$H NMR (400 MHz, CD$_3$OD) δ 7.47-7.40 (m, 4H), 7.35-7.26 (m, 7H), 7.10-7.07 (m, 3H), 5.49 (s, 2H), 4.24 (dd, J=10.7 Hz, 5.4 Hz, 1H), 4.18-4.09 (m, 2H), 4.00-3.88 (m, 3H), 3.87-3.82 (m, 2H), 3.77-3.69 (m, 2H), 3.59 (t, J=10.0 Hz, 2H), 3.54-3.46 (m, 1H), 3.06 (dd, J=12.7 Hz, J=9.0 Hz, 1H), 3.00-2.93 (m, 1H), 2.92 (t, J=8.1 Hz, 2H), 2.83-2.71 (m, 4H), 2.66-2.51 (m, 4H), 2.06-1.85 (m, 4H), 1.95 (s, 9H), 1.73-1.57 (m, 4H), 1.38-1.00 (m, 2H).

Preparation of Compound II-c

To a solution of compound II-a (650 mg, 0.65 mmol) and methyl 3,5-diamino-6-chloropyrazine-2-carbonylcarbamimidothioate hydroiodic acid salt (II-b, 409 mg, 1.05 mmol) in EtOH (25 mL) was added DIPEA (0.92 mL, 5.20 mmol) at room temperature. The reaction mixture was heated at 70° C. in a sealed tube for 2 h, then cooled to room temperature, and concentrated in vacuum. The residue was purified by column chromatography (silica gel, 9:1 CH$_2$Cl$_2$/MeOH, 80:18:2 CHCl$_3$/CH$_3$OH/NH$_4$OH) to afford compound II-c as a yellow solid: $^1$H NMR (400 MHz, CD$_3$OD) δ 7.48-7.41 (m, 4H), 7.35-7.26 (m, 6H), 7.10 (brs, 4H), 5.45 (s, 2H), 4.22 (dd, J=10.7 Hz, 5.2 Hz, 2H), 4.00-3.90 (m, 4H), 4.00-3.88 (m, 2H), 3.85 (dd, J=5.4 Hz, 3.0 Hz, 2H), 3.71 (t, J=2.3 Hz, 1H), 3.69 (t, J=2.3 Hz, 1H), 3.58 (t, J=11.4 Hz, 2H), 3.25 (t, J=7.6 Hz, 2H), 3.05 (t, J=6.7 Hz, 1H), 2.73-2.41 (m, 6H), 1.89-1.77 (m, 2H), 1.75-1.53 (m, 6H).

Preparation of the Hydrochloride Salt of 3,5-diamino-N—(N-(4-(4-(((S)-4-amino-3-(3-(bis((2S,3R,4R,5R)-2,3,4,5,6-pentahydroxyhexyl)amino)propylamino)-4-oxobutyl)phenyl)butyl)carbamimidoyl)-6-chloropyrazine-2-carboxamide (II-d)

A solution of compound II-c (260 mg, 0.25 mmol) in 1 N aq HCl (25 mL) was stirred at room temperature for 2 h. The solvent was removed and the residue was purified by C-18 reverse phase Gold column to afford compound II-d as a yellow hygroscopic solid: $^1$H NMR (400 MHz, CD$_3$OD) δ 7.23-7.12 (m, 4H), 4.29-4.18 (m, 2H), 4.05 (t, J=6.2 Hz, 1H), 3.90-3.84 (m, 2H), 3.82-3.79 (m, 1H), 3.78-3.76 (m, 1H), 3.74-3.63 (m, 6H), 3.61-3.40 (m, 8H), 3.34 (t, J=6.8 Hz, 2H), 3.26-3.08 (m, 2H), 2.76-2.61 (m, 4H), 2.36-2.25 (m, 2H), 2.24-2.15 (m, 2H), 1.81-1.67 (m, 4H).

Scheme III. Preparation of the Hydrochloride Salt of 3,5-diamino-N-(N-(4-(4-(4-((S)-4-amino-3-(3-(hexyl((2S,3R,4R,5R)-2,3,4,5,6-pentahydroxyhexyl)amino)propylamino)-4-oxobutyl)phenyl)butyl)carbamimidoyl)-6-chloropyrazine-2-carboxamide (II-d):
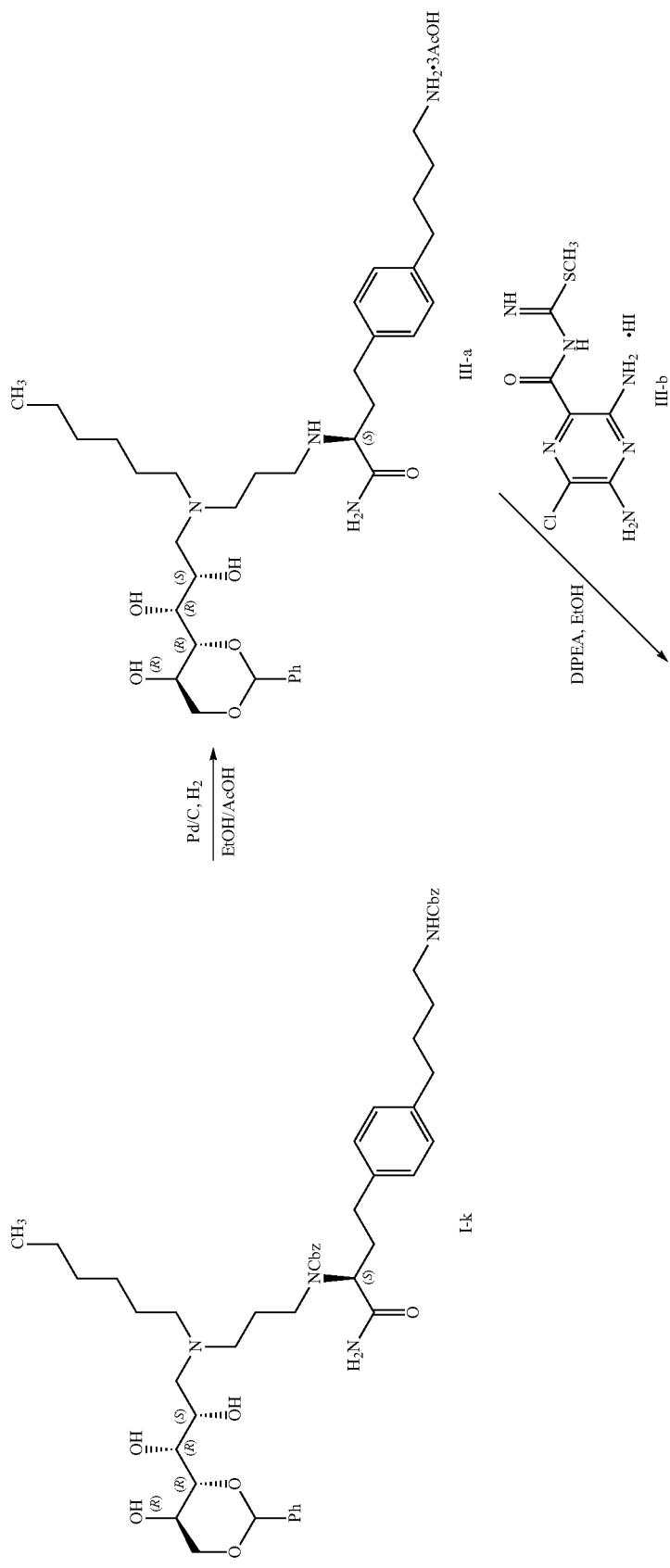

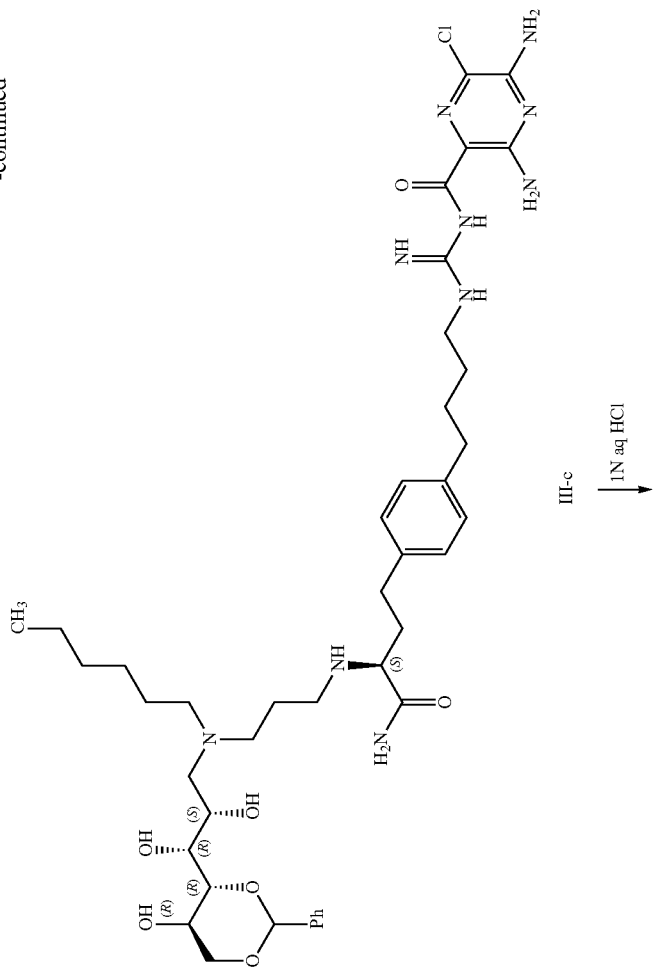

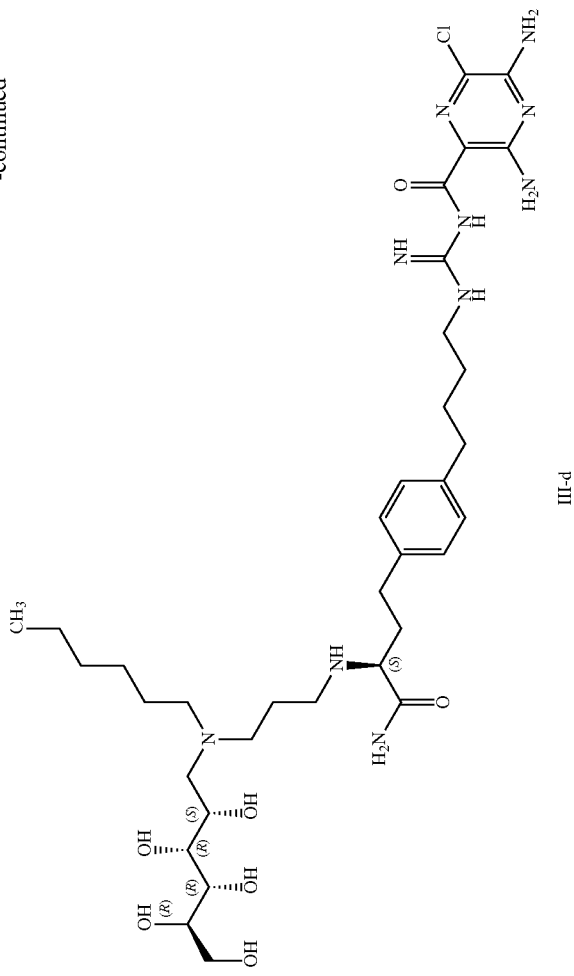

Preparation of III-a—(2S)-4-(4-(4-aminobutyl)phenyl)-2-(3-(((2S,3R)-2,3-dihydroxy-3-((4R,5R)-5-hydroxy-2-phenyl-1,3-dioxan-4-yl)propyl)(hexyl)amino)propylamino) butanamide triacetate A suspension of I-k (450 mg, 0.54) and 10% Pd/C (200 mg) in EtOH/AcOH (20 mL/2 mL) was subjected to hydrogenation conditions (1 atm) for 6 h at room temperature. The reaction mixture was filtered through celite and washed with MeOH. The filtrate was concentrated in vacuum to afford compound III-a as a white solid: $^1$H NMR (400 MHz, CD$_3$OD) δ 7.50-7.43 (m, 2H), 7.36-7.30 (m, 3H), 7.13-7.09 (m, 4H), 5.54 (s, 1H), 4.25 (dd, J=10.7 Hz, 5.1 Hz, 2H), 4.17 (ddd, J=9.3 Hz, 5.8 Hz, 3.1 Hz, 1H), 3.98 (dd, J=9.5 Hz, 5.3 Hz, 1H), 3.91 (dd, J=5.6 Hz, 1.8 Hz, 1H), 3.78 (dd, J=9.5 Hz, 2.2 Hz, 1H), 3.62 (t, J=10.4 Hz, 1H), 3.29-3.16 (m, 2H), 3.14-3.0 (m, 2H), 3.04-2.94 (m, 1H), 2.90 (t, J=7.1 Hz, 2H), 2.72 (t, J=5.3 Hz, 2H), 2.67-2.57 (m, 4H), 1.94 (s, 9H), 1.91-1.84 (m, 2H), 1.83-1.76 (m, 2H), 1.73-1.54 (m, 6H), 1.33-1.15 (m, 7H), 0.86 (t, J=8.1 Hz, 3H) □

Preparation of III-c—3,5-diamino-N—(N-(4-(4-((3S)-4-amino-3-(3-(((2S,3R)-2,3-dihydroxy-3-((4R,5R)-5-hydroxy-2-phenyl-1,3-dioxan-4-yl)propyl)(hexyl)amino) propylamino)-4-oxobutyl)phenyl)butyl)carbamimidoyl)-6-chloropyrazine-2-carboxamide To a solution of compound III-a (400 mg, 0.48 mmol) and methyl 3,5-diamino-6-chloropyrazine-2-carbonylcarbamimidothioate hydroiodic acid salt (III-b, 302 mg, 0.77 mmol) in EtOH (15 mL) was added DIPEA (0.68 mL, 3.84 mmol) at room temperature. The reaction mixture was heated at 70° C. in a sealed tube for 2 h, then cooled to room temperature, and concentrated in vacuo. The residue was purified by column chromatography (silica gel, 9:1 CH$_2$Cl$_2$/MeOH, 80:18:2 CHCl$_3$/CH$_3$OH/NH$_4$OH) to afford compound III-c as a yellow solid: $^1$H NMR (400 MHz, CD$_3$OD) δ 7.46 (dd, J=8.0 Hz, 4.6 Hz, 2H), 7.33-7.28 (m, 3H), 7.11 (brs, 4H), 5.52 (s, 1H), 4.23 (dd, J=10.8 Hz, 5.2 Hz, 1H), 4.02-3.92 (m, 2H), 3.89 (dd, J=5.3 Hz, 2.1 Hz, 1H), 3.75 (dd, J=9.3 Hz, 2.2 Hz, 1H), 3.60 (t, J=10.5 Hz, 1H), 3.29-3.21 (m, 2H), 3.07 (t, J=7.1 Hz, 1H), 2.76 (dd, J=12.7 Hz, 5.6 Hz, 2H), 2.68-2.41 (m, 10H), 1.93-1.78 (m, 2H), 1.76-1.53 (m, 6H), 1.47-1.37 (m, 2H), 1.32-1.16 (m, 6H), 0.86 (t, J=8.1 Hz, 3H).

Preparation of the Hydrochloride Salt of 3,5-diamino-N—(N-(4-(4-((S)-4-amino-3-(3-(hexyl((2S,3R,4R,5R)-2,3,4,5,6-pentahydroxyhexyl)amino)propylamino)-4-oxobutyl)phenyl)butyl)carbamimidoyl)-6-chloropyrazine-2-carboxamide (III-d)

A solution of compound III-c (230 mg, 0.27 mmol) in 1 N aq HCl (20 mL) was stirred at room temperature for 3 h. The solvent was removed and the residue was purified by C-18 reverse phase Gold column to afford compound III-d as a yellow hygroscopic solid: $^1$H NMR (400 MHz, CD$_3$OD) δ 7.16 (s, 4H), 4.18 (dd, J=12.0 Hz, 5.6 Hz, 1H), 4.03-3.95 (m, 1H), 3.84 (dd, J=4.9 Hz, 1.2 Hz, 1H), 3.78 (dd, J=10.5 Hz, 3.0 Hz, 1H), 3.74-3.63 (m, 3H), 3.42-3.32 (m, 6H), 3.28-3.21 (m, 2H), 3.19-3.04 (m, 2H), 2.76-2.62 (m, 4H), 2.30-2.13 (m, 4H), 1.84-1.65 (m, 6H), 1.46-1.32 (m, 6H), 0.93 (t, J=7.2 Hz, 3H).

Scheme IV. Preparation of Intermediates IV-x and IV-y.

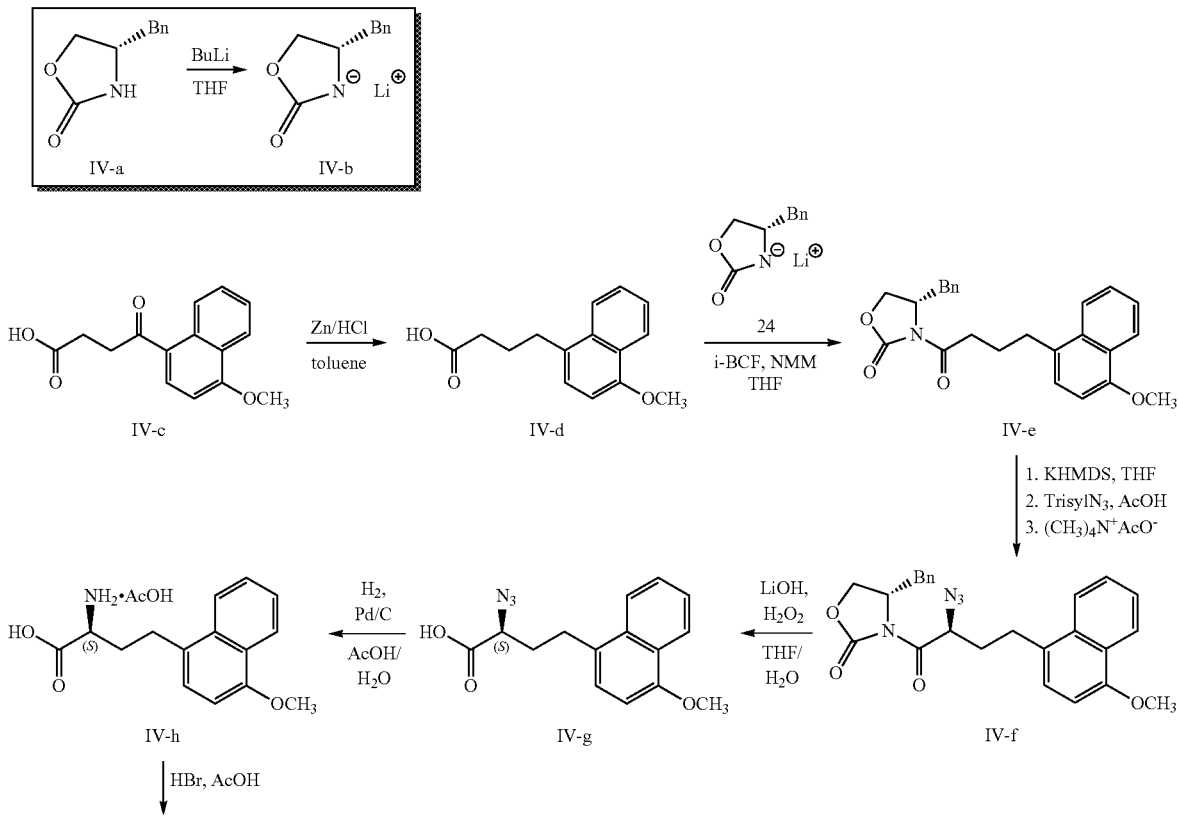

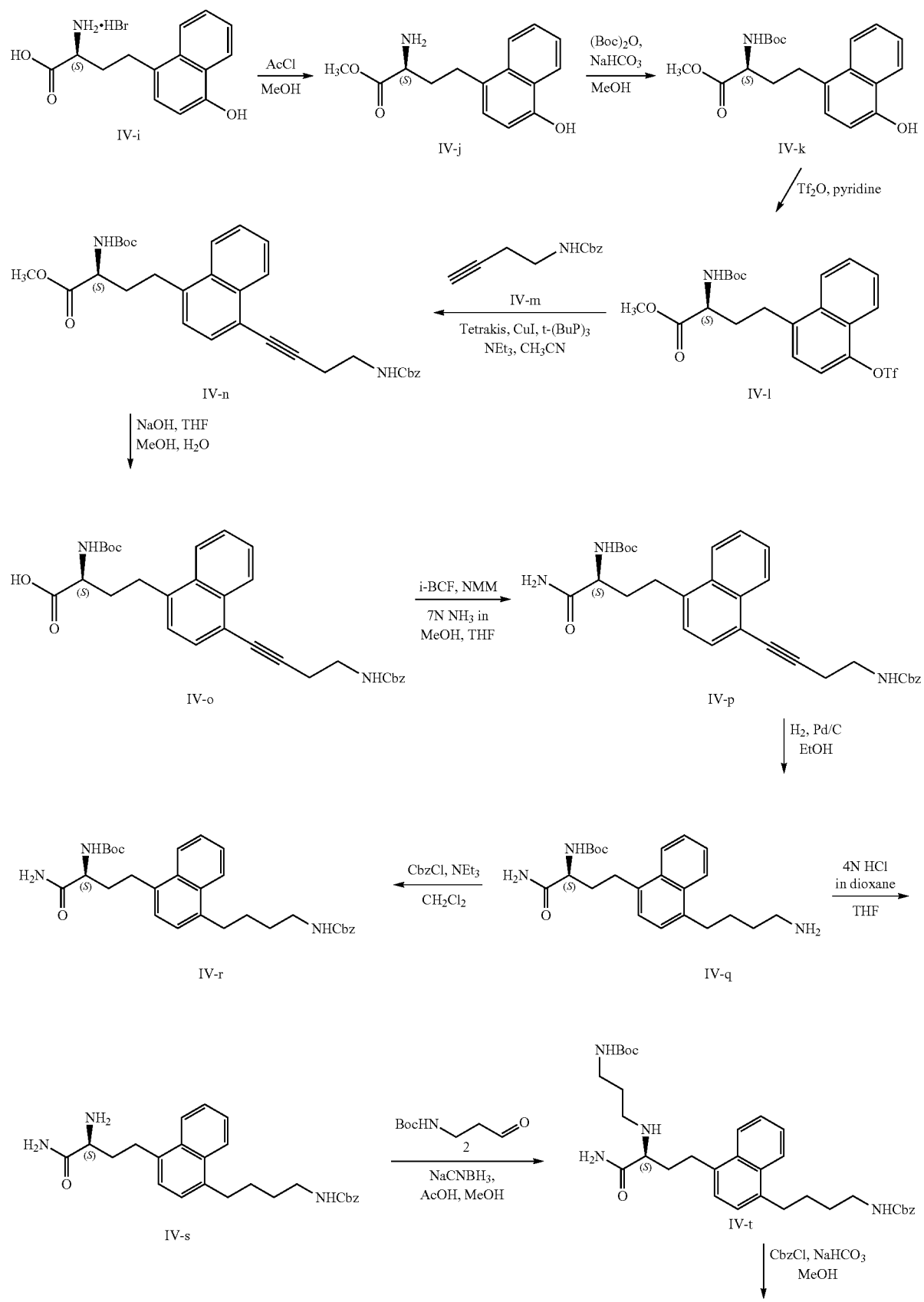

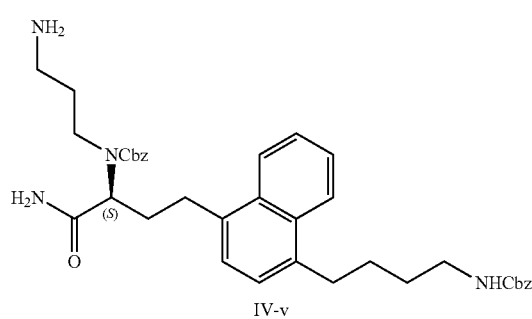

IV-v

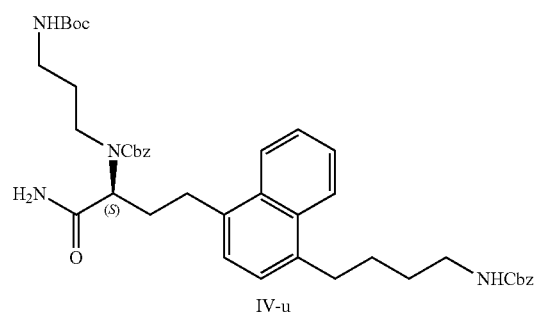

IV-u

4N HCl in dioxane, THF

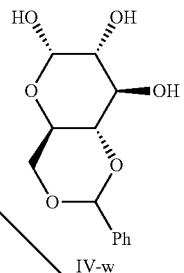

IV-w

NaCN(BH₃), AcOH, MeOH

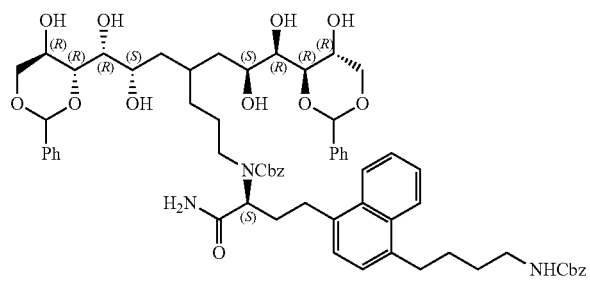

IV-x

+

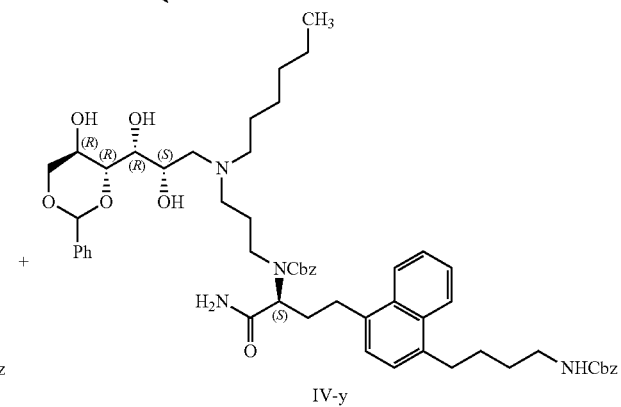

IV-y

Preparation of Compound
IV-d—4-(4-methoxynaphthalen-1-yl)butanoic acid

To a solution of 4-(4-methoxynaphthalen-1-yl)-4-oxobutanoic acid, compound IV-c (100 g, 387.5 mmol), in toluene (500 mL) and concentrated hydrochloric acid (500 mL) was added Zn dust (251 g, 3.87 mol) portion wise at room temperature. The reaction mixture was heated to reflux for 2 h, cooled down to room temperature and filtered through celite. After the filtrate was concentrated to 50%, the resulting precipitate was filtered and dried to afford compound IV-d as an off-white solid: $^1$H NMR (400 MHz, DMSO-$d_6$) δ 12.05 (s, 1H), 8.18 (dd, J=8.0 Hz, 1.2 Hz, 1H), 8.04 (d, J=8.0 Hz, 1H), 7.58-7.47 (m, 2H), 7.26 (d, J=7.6 Hz, 1H), 6.89 (d, J=8.0 Hz, 1H), 3.94 (s, 3H), 2.96 (t, J=7.6 Hz, 2H), 2.30 (t, J=7.6 Hz, 2H), 1.85 (t, J=7.6 Hz, 2H).

Preparation of Compound IV-e—(S)-4-benzyl-3-(4-(4-methoxynaphthalen-1-yl) butanoyl)oxazolidin-2-one To a solution of compound IV-d (43.5 g, 245.9 mmol) in dry THF (500 mL) was added n-butyl lithium drop wise at −78° C. and the reaction mixture was stirred for 45 min to give a solution of compound IV-b. To a separate solution of compound IV-d (50.0 g, 204.9 mmol) in dry THF (100 mL) was added NMM (25.0 g, 245.9 mmol) and i-BCF (30.7 g, 245.9 mmol) drop wise at 0° C. The reaction mixture was stirred for another 30 min at the same temperature, and then the prepared solution of compound IV-b was added slowly at 0° C. The reaction mixture was stirred for another 3 h at room temperature, quenched with satd NH₄Cl, concentrated to remove THF, and partitioned between EtOAc (1000 mL) and water (1000 mL). The aqueous layer was separated and extracted with EtOAc (2×1000 mL). The combined organic extracts were dried over Na₂SO₄ and concentrated. The residue was purified by column chromatography (silica gel, 30:70 EtOAc/hexanes) to afford compound IV-e as a white solid: $^1$H NMR (400 MHz, DMSO-$d_6$) δ 8.19 (d, J=8.3, 1H), 8.09 (d, J=8.3, 1H), 7.60-7.48 (m, 2H), 7.31-7.19 (m, 6H), 6.91 (d, J=7.8 Hz, 1H), 4.69-4.63 (m, 1H), 4.31 (t, J=8.6 Hz, 1H), 4.16 (dd, J=8.8 Hz, 2.8 Hz, 1H), 3.95 (s, 3H), 3.03-2.99 (m, 2H), 2.95-2.89 (m, 2H), 1.98-1.93 (m, 2H).

Preparation of Compound IV-f—(S)-3-((S)-2-azido-4-(4-methoxynaphthalen-1-yl) butanoyl)-4-benzyloxazolidin-2-one To a solution of compound IV-e (10.0 g, 24.81 mmol) in dry THF (70 mL) was added KHMDS (6.40 g, 32.3 mmol)

portion wise at −78° C. After the resulting mixture was stirred for 30 min, trisyl azide (11.5 g, 37.2 mmol) was added and the reaction mixture was stirred for 2-3 min. Acetic acid (9.0 g, 148.8 mmol) followed by tetramethyl ammonium acetate (13.2 g, 99.24 mmol) was added slowly at the same temperature. The reaction mixture was allowed to be warmed to 27° C., stirred for 16 h, quenched with satd NaHCO$_3$ (300 mL), concentrated to remove THF and extracted with EtOAc (2×300 mL). The combined organic extracts were dried over Na$_2$SO$_4$ and concentrated. The residue was purified by column chromatography (silica gel, 30:70 EtOAc/Hexane) to afford compound IV-f as a colorless oil: $^1$H NMR (300 MHz, CDCl$_3$) δ 8.30 (t, J=6.1 Hz, 1H), 7.99 (d, J=8.3 Hz, 1H), 7.56-7.47 (m, 2H), 7.37-7.28 (m, 3H), 7.20-7.16 (m, 2H), 6.74 (d, J=7.8 Hz, 1H), 5.12-5.08 (m, 1H), 4.54-4.49 (m, 1H), 4.16-4.11 (m, 2H), 3.98 (s, 3H), 3.33-3.27 (m, 3H), 2.84-2.77 (m, 1H), 2.35-2.04 (m, 2H).

Preparation of Compound IV-g—(S)-2-azido-4-(4-methoxynaphthalen-1-yl)butanoic acid To a solution of compound IV-f (6.10 g, 13.7 mmol) in THF/H$_2$O (70 mL/30 mL) was added H$_2$O$_2$ (2.80 g, 82.2 mmol) followed by LiOH (1.15 g, 27.4 mmol) portion wise at 0° C. The reaction mixture was stirred for 3 h at the same temperature, quenched with satd Na$_2$SO$_3$ (200 mL), concentrated under reduced pressure to remove THF and washed with CH$_2$Cl$_2$ (200 mL). The aqueous layer was acidified with 1N aq HCl and extracted with CH$_2$Cl$_2$ (2×250 mL). The combined organic extracts were dried over Na$_2$SO$_4$, concentrated and washed with MTBE to afford compound IV-g as an off-white solid: $^1$H NMR (400 MHz, DMSO-d$_6$) δ 13.15 (s, 1H), 8.19 (dd, J=8.0 Hz, 1.2 Hz, 1H), 8.00 (d, J=8.4 Hz, 1H), 7.60-7.48 (m, 2H), 7.29 (d, J=7.8 Hz, 1H), 6.90 (d, J=7.8 Hz, 1H), 4.21-4.18 (m, 1H), 3.94 (s, 3H), 3.07-3.04 (m, 2H), 2.13-1.89 (m, 2H).

Preparation of Compound IV-h—(S)-2-amino-4-(4-methoxynaphthalen-1-yl)butanoic acid acetate A suspension of compound IV-g (3.20 g, 11.2 mmol) and 10% Pd/C (1.60 g) in AcOH/H$_2$O (80 mL/20 mL) was subjected to hydrogenation conditions (1 atm) for 3 h at room temperature. The reaction mixture was filtered through celite and washed with MeOH. The filtrate was concentrated in vacuum to afford acetic salt IV-h as a yellow solid: $^1$H NMR (300 MHz, DMSO-d$_6$) δ 13.15 (s, 1H), 8.18 (d, J=8.1 Hz, 1H), 8.08 (d, J=8.1 Hz, 1H), 7.57-7.46 (m, 2H), 7.28 (d, J=7.6 Hz, 1H), 6.89 (d, J=7.8 Hz, 1H), 3.93 (s, 3H), 3.04 (t, J=6.9 Hz, 2H), 2.08-1.90 (m, 2H).

Preparation of Compound IVA—(S)-2-amino-4-(4-hydroxynaphthalen-1-yl)butanoic acid hydrobromide To a solution of compound IV-h (2.80 g, 10.81 mmol) in acetic acid (30 mL) was added hydrobromic acid (30 mL) drop wise at room temperature and the reaction mixture was refluxed for 4 h. The reaction mixture was cooled to room temperature and concentrated. The residue was diluted with H$_2$O (15 mL), slightly basified with ammonia and crystallized over night to afford compound IV-i as a brown solid: ESI-MS m/z 246 [C$_{14}$H$_{15}$NO$_3$+H]$^+$.

Preparation of Compound IV-j—(S)-methyl 2-amino-4-(4-hydroxynaphthalen-1-yl)butanoate Acetyl chloride (13.5 g, 171.4 mmol) was added to dry methanol (70 mL) at 0° C. and then compound IV-i (6.00 g, 24.48 mmol) was added. The reaction mixture was refluxed for 4 h and concentrated. The residue was partitioned between CH$_2$Cl$_2$ (300 mL) and saturated NaHCO$_3$ (300 mL). The aqueous layer was separated and extracted with CH$_2$Cl$_2$ (2×300 mL). The combined organic extracts were dried over Na$_2$SO$_4$ and concentrated to afford compound IV-j as a colorless oil: ESI-MS m/z 260 [C$_{15}$H$_{17}$NO$_3$+H]$^+$.

Preparation of Compound IV-k—(S)-methyl 2-(tert-butoxycarbonylamino)-4-(4-hydroxynaphthalen-1-yl)butanoate To a solution of compound IV-j (4.80 g, 18.53 mmol) in MeOH/H$_2$O (40 mL/10 mL) was added NaHCO$_3$ (6.20 g, 74.13 mmol) and Boc$_2$O (4.85 g, 22.2 mmol) at 0° C. The resulting mixture was allowed to warm to room temperature and stirred for 3 h. The reaction mixture was partitioned between CH$_2$Cl$_2$ (200 mL) and water (200 mL). The aqueous layer was separated and extracted with CH$_2$Cl$_2$ (2×200 mL). The combined organic extracts were washed with brine, dried over Na$_2$SO$_4$ and concentrated to give compound IV-k as a colorless oil: $^1$H NMR (300 MHz, DMSO-d$_6$) δ 9.91 (s, 1H), 8.15 (dd, J=8.0 Hz, 1.2 Hz, 1H), 7.98 (d, J=8.3 Hz, 1H), 7.52-7.41 (m, 3H), 7.13 (d, J=7.7 Hz, 1H), 6.77 (d, J=7.6 Hz, 1H), 4.05-3.99 (m, 1H), 3.66 (s, 3H), 3.04-2.86 (m, 2H), 1.97-1.91 (m, 2H), 1.42 (s, 9H).

Preparation of Compound IV-l—(S)-methyl 2-(tert-butoxycarbonylamino)-4-(4-(trifluoromethylsulfonyloxy)naphthalen-1-yl)butanoate To a solution of compound IV-k (9.50 g, 26.46 mmol) in pyridine (50 mL) was added triflic anhydride (8.90 g, 282.1 mmol) at 0° C., and the reaction mixture was stirred at room temperature for 2.5 h. After concentration, the reaction mixture was partitioned between CH$_2$Cl$_2$ (300 mL) and water (300 mL). The aqueous layer was separated and extracted with CH$_2$Cl$_2$ (2×300 mL). The combined organic extracts were washed with brine, dried over Na$_2$SO$_4$ and concentrated to afford compound IV-1 as a brown oil: ESI-MS m/z 492 [C$_{21}$H$_{24}$F$_3$NO$_7$S+H]$^+$.

Preparation of Compound IV-n—(S)-methyl 4-(4-(4-(benzyloxycarbonylamino)but-1-ynyl)naphthalen-1-yl)-2-(tert-butoxycarbonylamino)butanoate To a solution of compound IV-l (6.00 g, 12.21 mmol) in anhydrous CH$_3$CN (100 mL) was added TEA (4.93 g, 48.8 mmol), 10% (t-Bu)$_3$P in hexanes (0.50 g, 2.44 mmol), benzyl but-3-ynylcarbamate (IV-m, 3.70 g, 18.3 mmol) and CuI (0.11 g, 0.61 mmol) at room temperature. The resulting mixture was degassed with Argon for 3 min and Pd(PPh$_3$)$_4$ (1.40 g, 1.22 mmol) was added rapidly in one portion. After degassing with Argon for 5 min, the resulting mixture was refluxed for 5 h. The reaction mixture was concentrated in vacuum and the residue was purified by column (silica gel, 40:60 hexanes/EA) to afford compound IV-n as a brown oil: $^1$H NMR (300 MHz, CDCl$_3$) δ 8.35-8.31 (m, 1H), 7.97-7.94 (m, 1H), 7.54-7.50 (m, 3H), 7.37-7.29 (m, 6H), 5.29-5.13 (m, 4H), 4.44 (br s, 1H), 3.73 (s, 3H), 3.56-3.49 (m, 2H), 3.14-3.07 (m, 2H), 2.79 (t, J=6.6 Hz, 2H), 2.10-1.98 (m, 2H), 1.42 (s, 9H).

Preparation of Compound IV-o—(S)-4-(4-(4-(benzyloxycarbonylamino)but-1-ynyl)naphthalen-1-yl)-2-(tert-butoxycarbonylamino)butanoic acid To a solution of methyl ester IV-n (3.40 g, 6.25 mmol) in THF/MeOH/H$_2$O (30 mL/30 mL/10 mL) was added NaOH (0.75 g, 18.7 mmol) and the reaction mixture was stirred at room temperature for 3 h. The pH value was adjusted to 9 with 1 N aq HCl and organic solvent was removed. The pH value was adjusted to 5, and the suspension was partitioned between $CH_2Cl_2$ (200 mL) and water (200 mL). The aqueous layer was separated and extracted with $CH_2Cl_2$ (2×200 mL). The combined organic extracts were dried over $Na_2SO_4$ and concentrated to afford compound IV-o as a brown solid: $^1H$ NMR (300 MHz, $CDCl_3$) δ 8.28 (t, J=7.0 Hz, 1H), 7.91 (br s, 1H), 7.45 (d, J=6.9 Hz, 3H), 7.34-7.29 (m, 6H), 7.15 (d, J=6.3 Hz, 1H), 5.29-5.12 (m, 4H), 4.31 (br s, 1H), 3.51 (d, J=6.2 Hz, 2H), 3.06 (br s, 1H), 2.76 (t, J=6.2 Hz, 2H), 2.30-2.04 (m, 2H), 1.42 (s, 9H).

Preparation of Compound IV-p—(S)-4-(4-(4-(benzyloxycarbonylamino)but-1-ynyl)naphthalen-1-yl)-2-(tert-butoxycarbonylamino)butanoic acid To a solution of acid IV-o (2.90 g, 5.47 mmol) in THF (40 mL) was added NMM (0.82 g, 8.2 mmol) and i-BCF (0.97 g, 7.11 mmol) at 0° C. The reaction mixture was stirred at the same temperature for 30 min and $NH_3$ (7.0 N in methanol, 6.0 mL, 43.7 mmol) was added dropwise. The reaction mixture was continued to be stirred at 0° C. for 2 h, allowed to be warmed to room temperature and stirred for 16 h. After concentration, the residue was partitioned between $CH_2Cl_2$ (100 mL) and water (100 mL). The aqueous layer was separated and extracted with $CH_2Cl_2$ (2×100 mL). The combined organic extracts were dried over $Na_2SO_4$ and concentrated. The residue was washed with MTBE to afford amide IV-p as a yellow solid: $^1H$ NMR (400 MHz, DMSO-$d_6$) δ 8.29 (br s, 1H), 8.13 (br s, 1H), 7.59-7.53 (m, 3H), 7.34-7.28 (m, 9H), 7.03 (t, J=7.2 Hz, 1H), 5.05 (s, 2H), 3.98 (br s, 1H), 3.31 (br s, 2H), 3.13-3.01 (m, 3H), 2.72 (t, J=6.6 Hz, 2H), 1.98-1.84 (m, 2H), 1.42 (s, 9H).

Preparation of Compound IV-q—(S)-tert-butyl 1-amino-4-(4-(4-aminobutyl)naphthalen-1-yl)-1-oxobutan-2-ylcarbamate A suspension of compound IV-p (2.30 g, 4.34 mmol) and 10% Pd/C (1.20 g) in EtOH (50 mL) was subjected to hydrogenation conditions (1 atm) for 16 h at room temperature. The reaction mixture was filtered through celite and washed with EtOH. The filtrate was concentrated in vacuum and washed with MTBE/hexanes to afford acetic salt IV-q as an off-white solid: $^1H$ NMR (400 MHz, $CDCl_3$) δ 8.05-8.01 (m, 2H), 7.50-7.42 (m, 2H), 7.24-7.20 (m, 2H), 6.22 (br s, 1H), 5.50 (br s, 1H), 5.16 (d, J=8.0 Hz, 1H), 4.20 (br s, 1H), 3.12 (t, J=8.1 Hz, 2H), 3.04 (t, J=7.5 Hz, 2H), 2.71 (t, J=7.0 Hz, 2H), 2.34-2.24 (m, 1H), 2.07-1.98 (m, 1H), 1.80-1.70 (m, 6H), 1.45 (s, 9H).

Preparation of Compound IV-r

To a stirred solution of compound IV-q (1.4 g, 3.50 mmol) in dry $CH_2Cl_2$ (25 mL) was added TEA (0.53 g, 5.25 mmol) and CbzCl (0.65 g, 3.85 mmol) at 0° C. The reaction mixture was stirred for 2 h at room temperature and partitioned between $CH_2Cl_2$ (100 mL) and water (100 mL). The aqueous layer was separated and extracted with $CH_2Cl_2$ (2×100 mL). The combined organic extracts were washed with brine, dried over $Na_2SO_4$ and concentrated to afford compound IV-r as a yellow oil: ESI-MS m/z 534 $[C_{31}H_{39}N_3O_5+H]^+$.

Preparation of Compound IV-s

To a solution of compound IV-r (1.75 g, 3.28 mmol) in dry THF (10 mL) was added 4 N HCl in dioxane (20 mL) and the reaction mixture was stirred for 6 h at room temperature. The solvent was removed in vacuum and the residue was washed with MTBE to afford compound IV-s as an off-white solid: $^1H$ NMR (400 MHz, MeOD-$d_3$) δ 8.07-8.03 (m, 2H), 7.53-7.49 (m, 2H), 7.31-7.27 (m, 7H), 5.05 (s, 2H), 4.05 (t, J=6.2 Hz, 1H), 3.20-3.14 (m, 6H), 2.26-2.22 (m, 2H), 1.76-1.59 (m, 4H).

Preparation of Compound IV-t

To a solution of compound IV-s (1.2 g, 2.77 mmol) and aldehyde 2 (0.95 g, 5.54 mmol) in MeOH (25 mL) was added acetic acid (0.5 mL) and the reaction mixture was stirred at room temperature for 10 min. Sodium cyanoborohydride (0.25 g, 4.15 mmol) was added and the solution was continued to be stirred at room temperature for 16 h. Additional compound 2 (0.3 equiv), AcOH (0.3 equiv), and $NaCNBH_3$ (0.3 equiv) were added over the period of 3 h and this addition was repeated four times until LC-MS showed >90% consumption of amine. After concentration, the residue was partitioned between EtOAc (300 mL) and saturated $NaHCO_3$ (200 mL). The aqueous layer was separated and extracted with EtOAc (2×300 mL). The combined organic extracts were dried over $Na_2SO_4$ and concentrated to afford IV-t, which was used in the next step without further purification.

Preparation of Compound IV-u

To a solution of compound IV-t (crude, 850 mg) in MeOH/$H_2O$ (25 mL/12 mL) was added $NaHCO_3$ (0.36 g, 4.32 mmol) at 0° C. and the solution was stirred for 10 min. Benzyl chloroformate (0.50 g, 2.88 mmol)) was added drop wise and the reaction mixture was stirred for 2 h at 0° C., then allowed to be warmed to room temperature and stirred for 1 h. After concentration, the residue was dissolved in $CH_2Cl_2$ (200 mL), then washed with water (300 mL) and brine (300 mL). The organic layer was dried over $Na_2SO_4$ and concentrated to afford IV-u, which was used in the next step without further purification.

Preparation of Compound IV-v

Compound IV-u (crude, 750 mg) was dissolved in 4 N HCl in dioxane (10 mL) at room temperature and the solution was stirred for 2 h. After concentration, the residue was washed with MTBE and neutralized with aqueous $NH_4OH$ to afford compound IV-v as an off-white solid: $^1H$ NMR (400 MHz, $CD_3OD$) δ 8.06 (br s, 2H), 7.48-7.46 (m, 2H), 7.31-7.19 (m, 11H), 5.48 (s, 2H), 5.13-5.04 (m, 4H), 3.34-3.32 (m, 3H), 3.15 (t, J=6.9 Hz, 4H), 3.04 (t, J=7.5 Hz, 2H), 2.58-2.40 (m, 3H), 2.12 (br s, 1H), 1.76-1.57 (m, 6H).

Preparation of Compound IV-x and Compound IV-y

To a solution of compound IV-v (710 mg, 1.13 mmol) and triol IV-w (1.52 g, 5.68 mmol) in methanol (50 mL) was added acetic acid (1.00 mL) and the reaction mixture was stirred at room temperature for 30 min. Sodium cyanoborohydride (490 mg, 7.91 mmol) was added and the solution was continued to be stirred at room temperature for 16 h. Additional compound IV-w (16.0 equiv), AcOH (20.0 equiv), and $NaCNBH_3$ (20.0 equiv) were added and the solution was continued to be stirred at room temperature for 72 h. Hexanal (0.45 g, 4.52 mmol), AcOH (0.91 mL), and $NaCNBH_3$ (350 mg, 5.65 mmol) were added and the reaction mixture was stirred for 4 h. After concentration, the residue was partitioned between EtOAc (300 mL) and saturated NaHCO$_3$ (200 mL). The aqueous layer was separated and extracted with EtOAc (2×300 mL). The combined organic extracts were dried over Na$_2$SO$_4$ and concentrated. The residue was purified by C-18 reverse phase Gold column to afford compound IV-x and compound IV-y as white solids:

Data for benzyl 2-(((S)-1-amino-4-(4-(4-(benzyloxycarbonylamino)butyl)naphthalen-1-yl)-1-oxobutan-2-yl)(3-(bis((2S,3R)-2,3-dihydroxy-3-((4R,5R)-5-hydroxy-2-phenyl-1,3-dioxan-4-yl)propyl)amino)propyl)amino)acetate (Compound IV-x)

ESI-MS m/z 1130 [C$_{63}$H$_{76}$N$_4$O$_{15}$+H]$^+$.

Data for benzyl 2-(((S)-1-amino-4-(4-(4-(benzyloxycarbonylamino)butyl)naphthalen-1-yl)-1-oxobutan-2-yl)(3-(((2S,3R)-2,3-dihydroxy-3-((4R,5R)-5-hydroxy-2-phenyl-1,3-dioxan-4-yl)propyl)(hexyl)amino)propyl)amino)acetate (Compound IV-y)

ESI-MS m/z 962 [C$_{56}$H$_{72}$N$_4$O$_{10}$+H]$^+$.

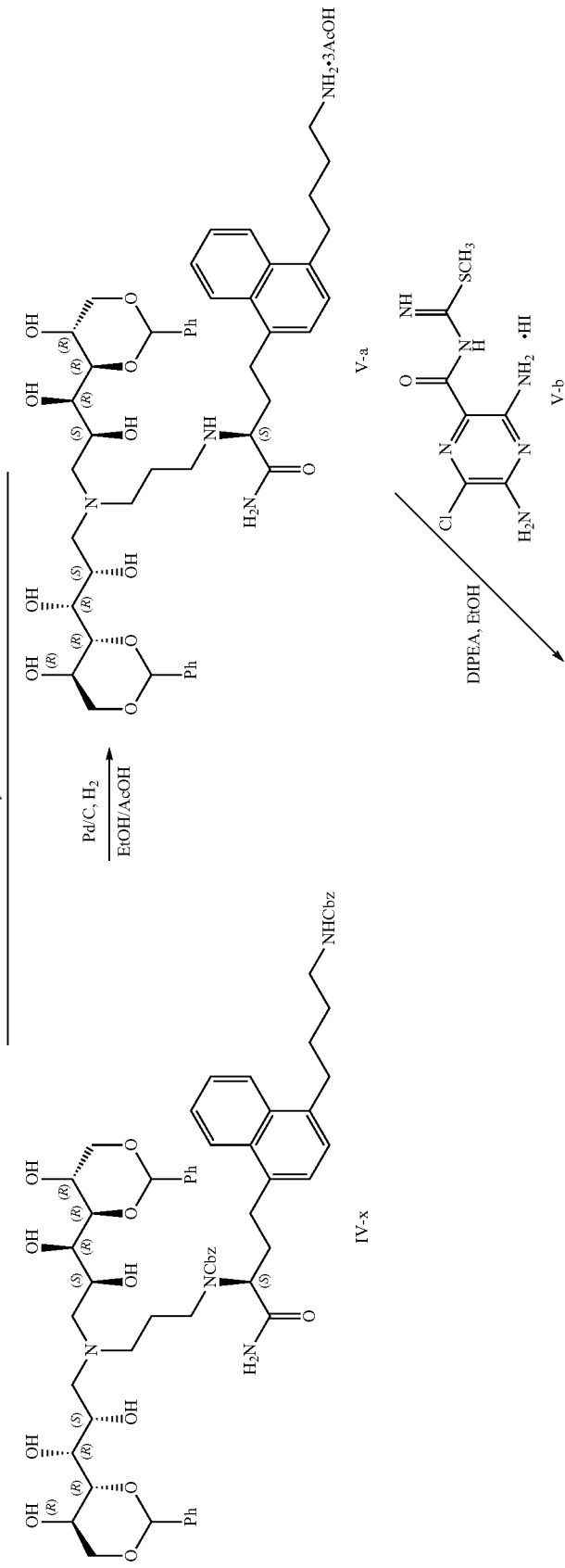

-continued
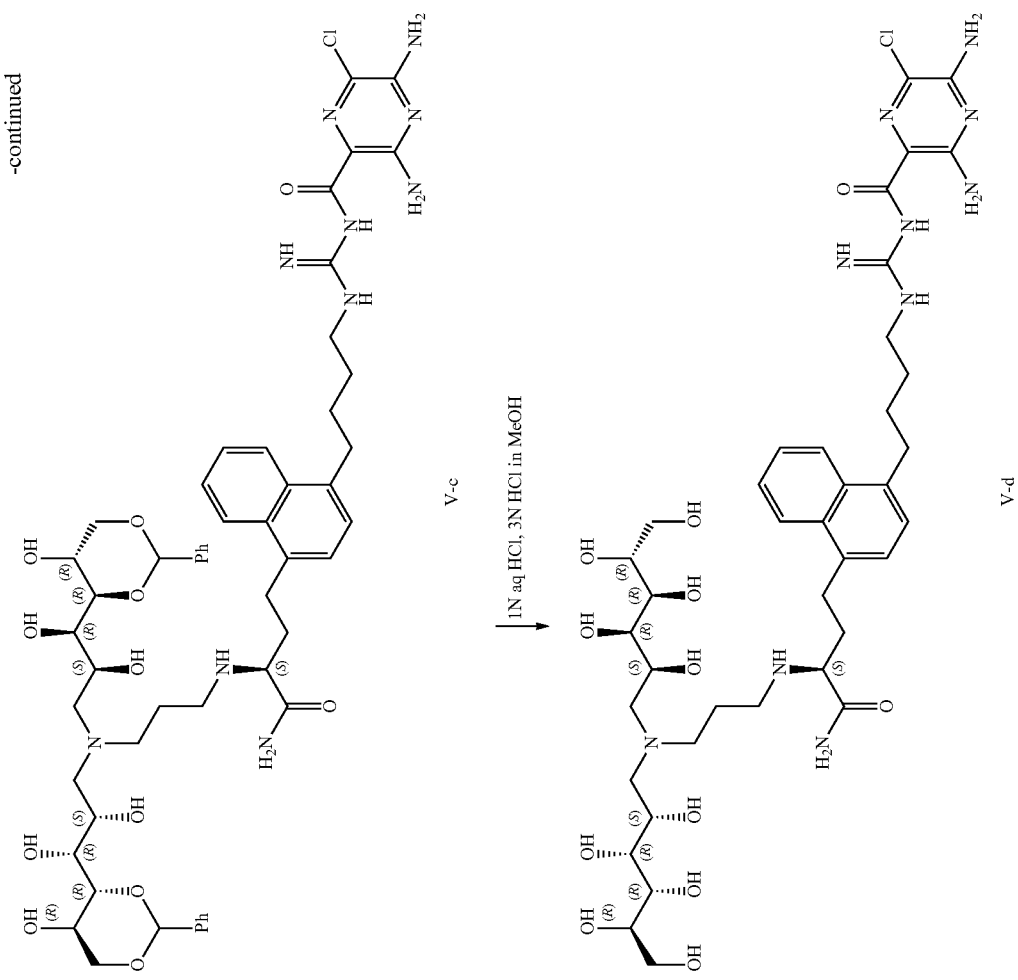

Preparation of V-a—(2S)-4-(4-(4-aminobutyl)naphthalen-1-yl)-2-(3-(bis((2S,3R)-2,3-dihydroxy-3-((4R,5R)-5-hydroxy-2-phenyl-1,3-dioxan-4-yl)propyl)amino)propylamino)butanamide acetate A suspension of IV-x (425 mg, 0.38 mmol) and 10% Pd/C (200 mg) in MeOH/AcOH (5.0 mL/1.0 mL) was subjected to hydrogenation conditions (1 atm) for 8 h at room temperature. The reaction mixture was filtered through celite and washed with MeOH. The filtrate was concentrated in vacuum and precipitated from MTBE/hexanes, to afford compound V-a as a colorless oil: $^1$H NMR (300 MHz, CD$_3$OD) δ 8.10-8.05 (m, 2H), 7.55-7.21 (m, 14H), 5.40 (s, 2H), 4.24-4.20 (m, 2H), 3.94-3.92 (m, 6H), 3.86-3.53 (m, 12H), 3.15-3.01 (m, 8H), 2.92-2.75 (m, 4H), 1.94 (s, 9H), 1.76-1.33 (m, 8H) □.

Preparation of V-c—3,5-diamino-N—(N-(4-(4-((3S)-4-amino-3-(3-(bis((2S,3R)-2,3-dihydroxy-3-((4R,5R)-5-hydroxy-2-phenyl-1,3-dioxan-4-yl)propyl)amino)propylamino)-4-oxobutyl)naphthalen-1-yl)butyl)carbamimidoyl)-6-chloropyrazine-2-carboxamide To a solution of compound V-a (356 mg, 0.34 mmol) and methyl 3,5-diamino-6-chloropyrazine-2-carbonylcarbamimidothioate hydroiodic acid salt (V-b, 213 mg, 0.54 mmol) in EtOH (8.0 mL) was added DIPEA (353 mg, 2.73 mmol) at room temperature. The reaction mixture was heated at 70° C. in a sealed tube for 2 h, then cooled to room temperature, and concentrated in vacuo. The residue was purified by column chromatography (silica gel, 10:1 CH$_2$Cl$_2$/MeOH, 8:2:0.2 CHCl$_3$/CH$_3$OH/NH$_4$OH) to afford compound V-c as a yellow solid: ESI-MS m/z 537 [C$_{53}$H$_{69}$ClN$_{10}$O$_{12}$+2H]$^{2+}$/2.

Preparation of V-d—3,5-diamino-N—(N-(4-(4-((S)-4-amino-3-(3-(bis((2S,3R,4R,5R)-2,3,4,5,6-pentahydroxyhexyl)amino)propylamino)-4-oxobutyl)naphthalen-1-yl)butyl)carbamimidoyl)-6-chloropyrazine-2-carboxamide hydrochloride A solution of compound V-c (120 mg, 0.111 mmol) in 1 N aq HCl (3.0 mL) and 3 N HCl in MeOH (3.0 mL) was stirred at room temperature for 3 h. The solvent was removed and the residue was purified by C-18 reverse phase Gold column to afford compound V-d as a yellow hygroscopic solid: $^1$H NMR (400 MHz, D$_2$O) δ 8.13 (d, J=8.4 Hz, 1H), 7.82 (d, J=9.2 Hz, 1H), 7.53-7.31 (m, 4H), 4.18-4.16 (m, 2H), 3.95 (br s, 1H), 3.78-3.74 (m, 6H), 3.62-3.58 (m, 4H), 3.36-3.29 (m, 6H), 3.22-3.18 (m, 2H), 3.08-3.04 (m, 6H), 2.17-2.14 (m, 4H), 1.85-1.73 (m, 4H); ESI-MS m/z 449 [C$_{39}$H$_{61}$ClN$_{10}$O$_{12}$+2H]$^{2+}$/2.

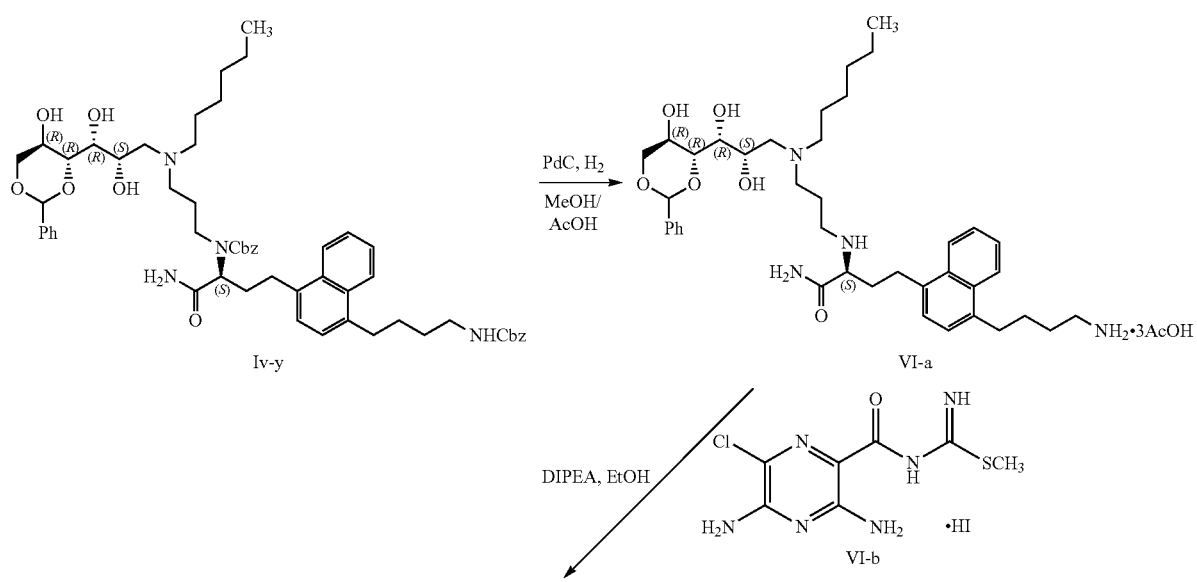

Scheme VI. Preparation of 3,5-diamino-N-(N-(4-(4-((S)-4-amino-3-(3-(hexyl((2S,3R,4R,5R)-2,3,4,5,6-pentahydroxyhexyl)amino)propylamino)-4-oxobutyl)napthalen-1-yl)butyl)carbamimidoyl)-6-chloropyrazine-2-carboxamide hydrochloride (VI-d).

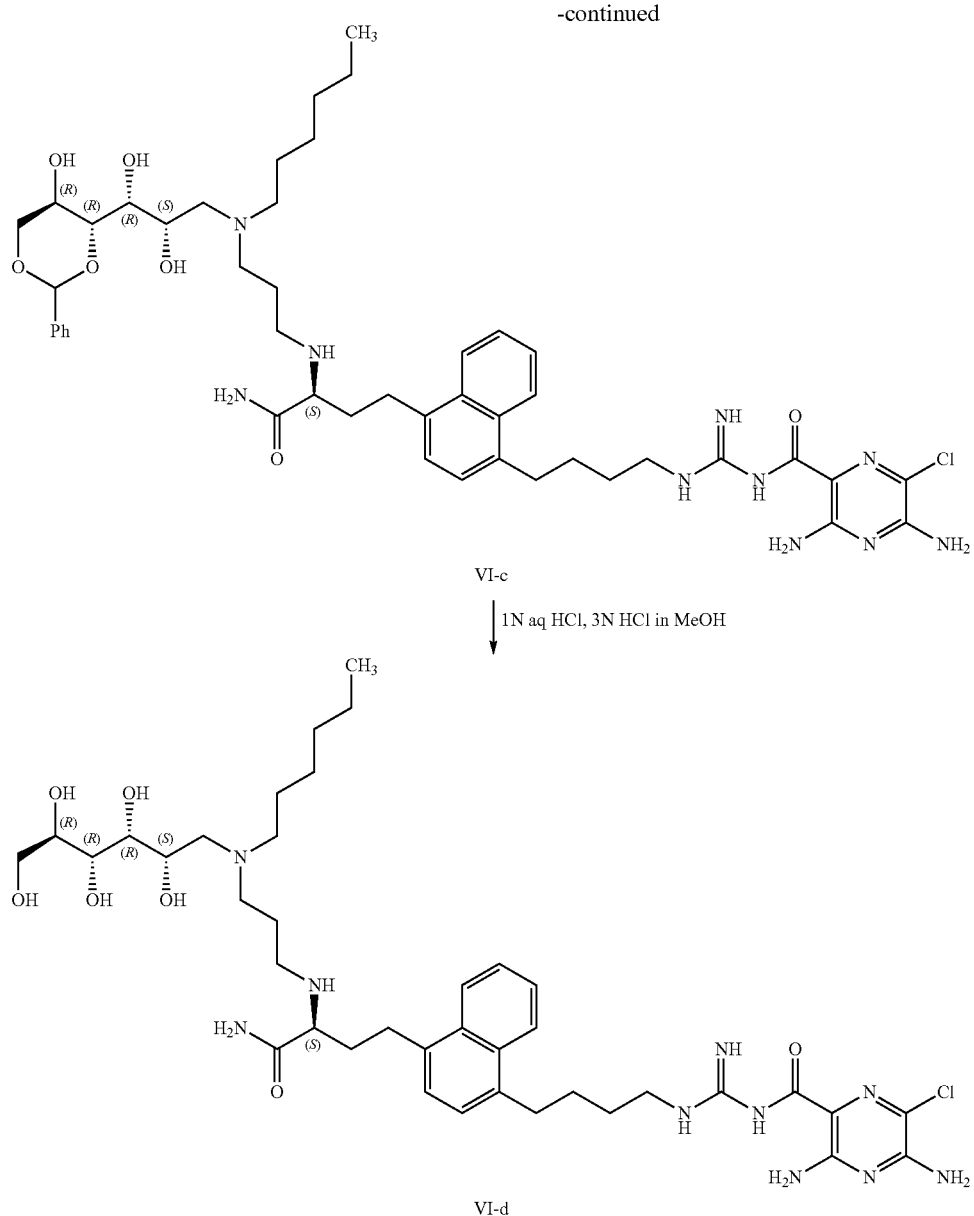

Preparation of VI-a—(2S)-4-(4-(4-aminobutyl)naphthalen-1-yl)-2-(3-(((2S,3R)-2,3-dihydroxy-3-((4R,5R)-5-hydroxy-2-phenyl-1,3-dioxan-4-yl)propyl)(hexyl)amino)propylamino)butanamide triacetate A suspension of IV-y (270 mg, 0.28 mmol) and 10% Pd/C (120 mg) in MeOH/AcOH (5.0 mL/1.0 mL) was subjected to hydrogenation conditions (1 atm) for 8 h at rt. The reaction mixture was filtered through celite and washed with MeOH. The filtrate was concentrated in vacuum to afford compound VI-a as a colorless oil: $^1$H NMR (300 MHz, CD$_3$OD) δ 8.09-8.05 (m, 2H), 7.54-7.21 (m, 9H), 5.46 (s, 1H), 4.24-4.21 (m, 2H), 3.95-3.94 (m, 2H), 3.79-3.59 (m, 5H), 3.15-3.07 (m, 6H), 2.96-2.89 (m, 2H), 2.76-2.75 (m, 2H), 1.94 (s, 9H), 1.90-1.62 (m, 10H), 1.28-1.22 (m, 6H), 0.78-0.76 (m, 3H) □

Preparation of Compound VI-c—3,5-diamino-N—(N-(4-(4-(((3S)-4-amino-3-(3-(((2S,3R)-2,3-dihydroxy-3-((4R,5R)-5-hydroxy-2-phenyl-1,3-dioxan-4-yl)propyl)(hexyl)amino)propylamino)-4-oxobutyl)naphthalen-1-yl)butyl)carbamimidoyl)-6-chloropyrazine-2-carboxamide To a solution of compound VI-a (209 mg, 0.24 mmol) and methyl 3,5-diamino-6-chloropyrazine-2-carbonylcarbamimidothioate hydroiodic acid salt (VI-b, 130 mg, 0.38 mmol) in EtOH (5.0 mL) was added DIPEA (250 mg, 1.92 mmol) at room temperature. The reaction mixture was heated at 70° C. in a sealed tube for 2 h, then cooled to rt, and concentrated in vacuo. The residue was purified by column chromatography (silica gel, 10:1 CH$_2$Cl$_2$/MeOH, 8:2:0.2 CHCl$_3$/CH$_3$OH/NH$_4$OH) to afford compound VI-c as a yellow solid: $^1$H NMR (400 MHz, CD$_3$OD) δ 8.08-8.06 (m, 2H), 7.50-7.41 (m, 4H), 7.28-7.26 (m, 5H), 5.48 (s, 1H), 4.23 (dd, J=10.4 Hz, 5.2 Hz, 1H), 3.90-3.88 (m, 3H), 3.75 (dd, J=9.6

Hz, 2.4 Hz, 1H), 3.58 (t, J=10.4 Hz, 1H), 3.20-3.12 (m, 5H), 2.70-2.48 (m, 7H), 1.88-1.62 (m, 8H), 1.43-1.41 (m, 2H), 1.26-1.17 (m, 6H), 0.83 (t, J=8.1 Hz, 3H).

Preparation of Compound VI-d—3,5-diamino-N—(N-(4-(4-((S)-4-amino-3-(3-(hexyl((2S,3R,4R,5R)-2,3,4,5,6-pentahydroxyhexyl)amino)propylamino)-4-oxobutyl)naphthalen-1-yl)butyl)carbamimidoyl)-6-chloropyrazine-2-carboxamide hydrochloride A solution of compound VI-c (98 mg, 0.108 mmol) in 1 N aq HCl (2.0 mL) and 3 N HCl in MeOH (2.0 mL) was stirred at rt for 2 h. The solvent was removed and the residue was purified by C-18 reverse phase Gold column to afford compound VI-d as a yellow hygroscopic solid: $^1$H NMR (400 MHz, D$_2$O) δ 8.12 (d, J=8.8 Hz, 1H), 7.83 (d, J=8.0 Hz, 1H), 7.51-7.30 (m, 4H), 4.14-4.12 (m, 1H), 3.76-3.58 (m, 7H), 3.39-2.90 (m, 14H), 2.17-1.62 (m, 10H), 1.28-1.19 (m, 6H), 0.78 (t, J=6.4 Hz, 3H); ESI-MS m/z 409 [C$_{39}$H$_{61}$ClN$_{10}$O$_7$+2H]$^{2+}$/2.

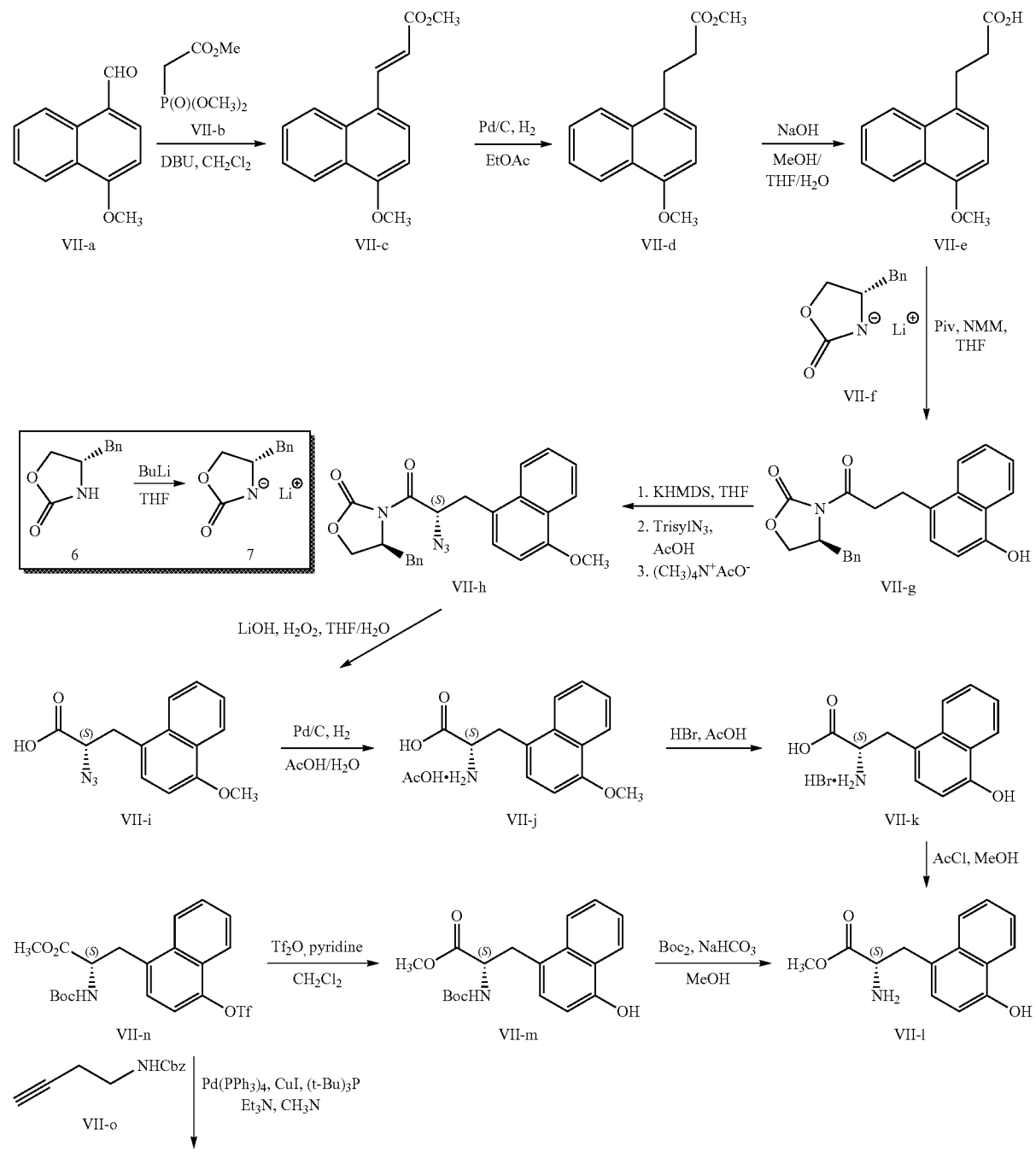

Scheme VII. Preparation of Hydrochloride Salt of 3,5-diamino-N-(N-(4-(4-((S)-3-amino-2-(3-(bis((2S,3R,4R,5R)-2,3,4,5,6-pentahydroxyhexyl)amino)propylamino)-3-oxopropyl)napthalen-1-yl)butyl)carbamimidoyl)-6-chloropyrazine-2-carboxamide (Compound VII-ee):

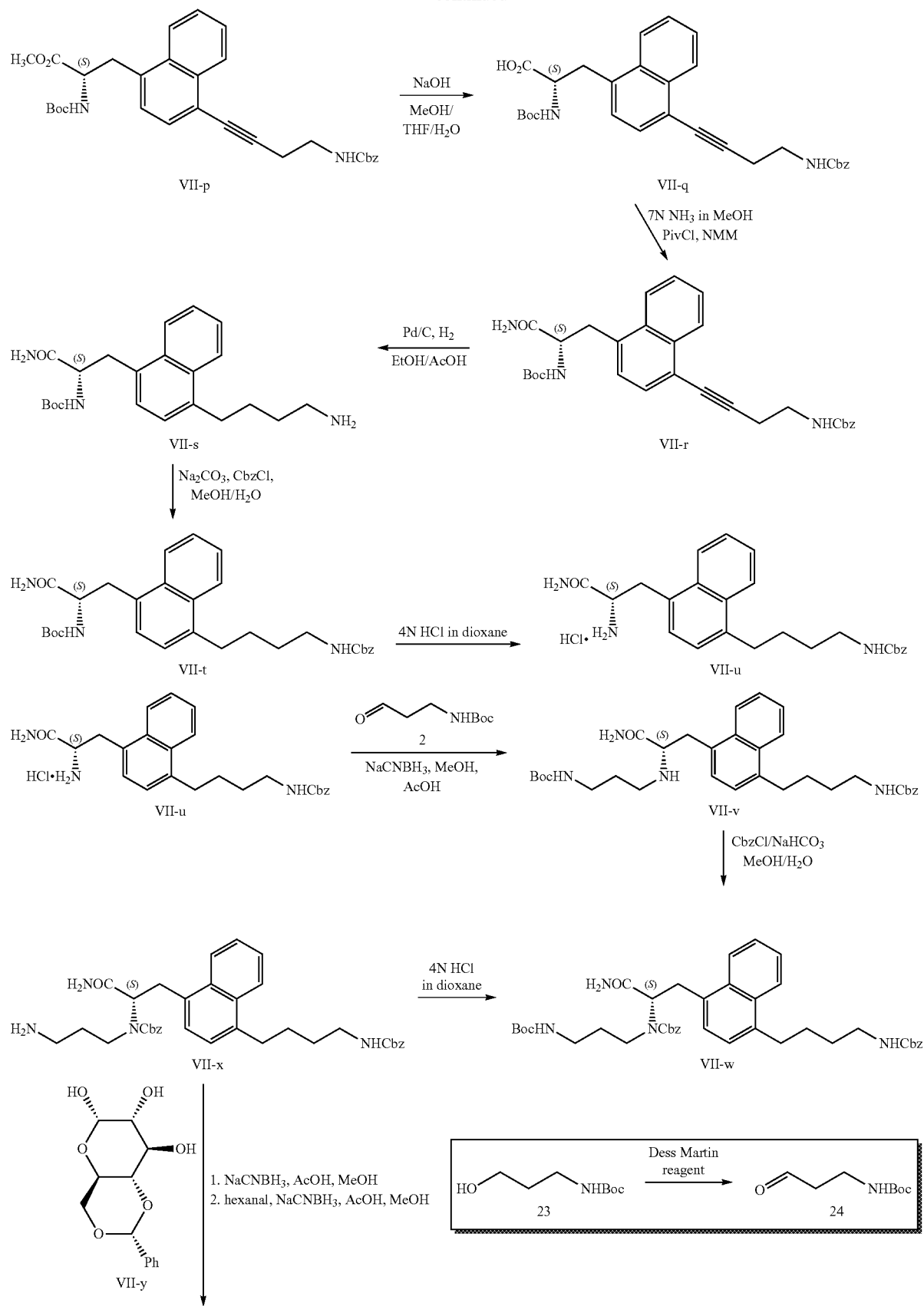

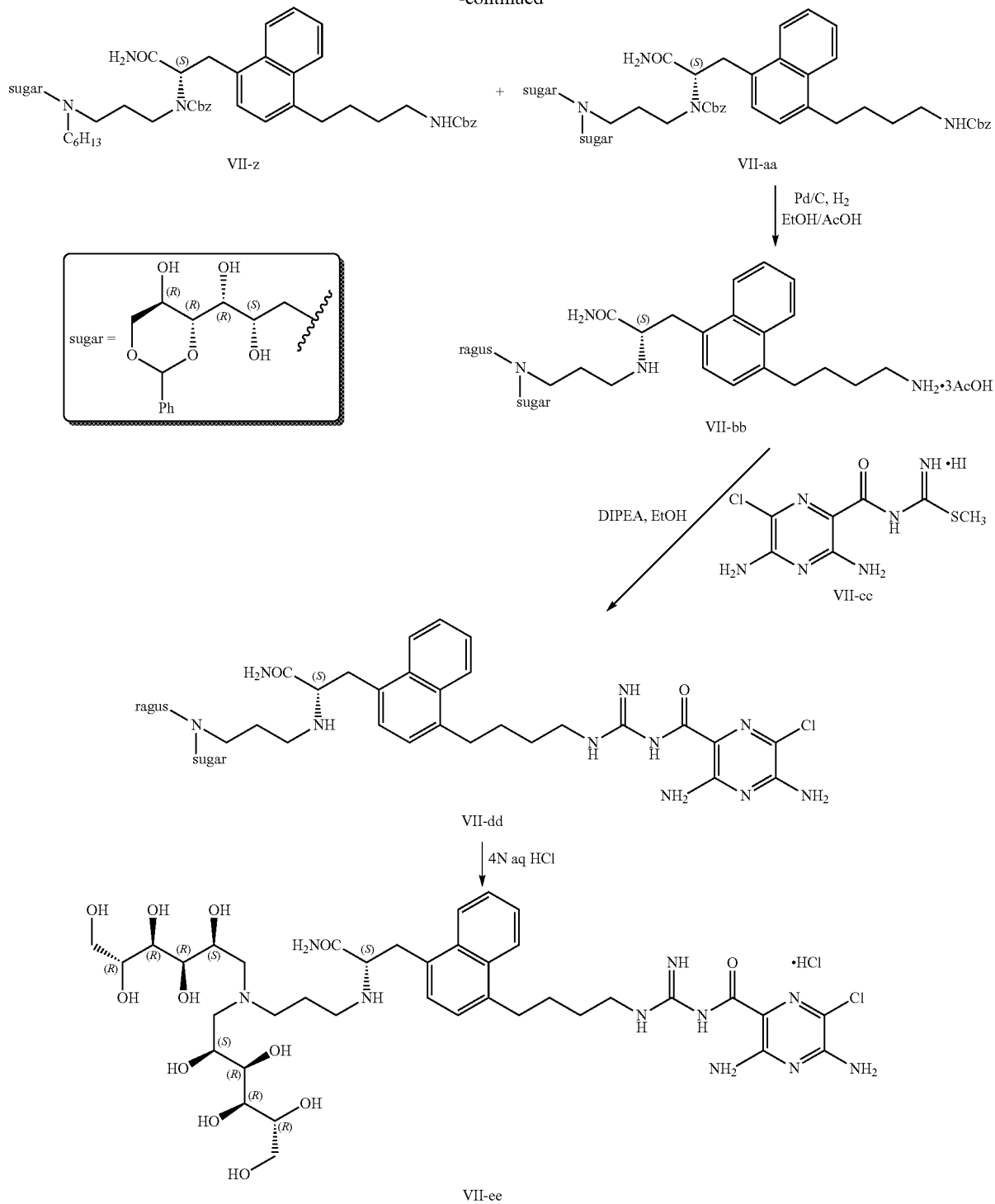

Preparation of Compound VII-c

Trimethyl phosphonoacetate VII-b (34.8 mL, 241 mmol) in 300 mL anhydrous $CH_2Cl_2$ was cooled to 0° C. and charged with DBU (30.5 mL, 322 mmol), and the mixture was stirred for 15 min. Aldehyde VII-a (25.0 g, 134 mmol) in 50 mL $CH_2Cl_2$ was charged dropwise. The reaction mixture was brought to room temperature, stirred for 36 h, and quenched with 100 mL of water. The mixture was partitioned, and the aqueous layer was extracted with $CH_2Cl_2$ (3×150 mL). The combined organics were washed with brine, dried ($Na_2SO_4$), filtered, and concentrated, and the residue was purified by silica-gel column chromatography (10:1 hexanes/ethyl acetate) to give the desired trans-α,β-unsaturated ester VII-c (32.0 g, 99%) as a white solid: $^1H$ NMR (400 MHz, $CDCl_3$): δ 8.45 (d, J=16.0 Hz, 1H), 8.29 (dd, J=8.4, 1.5 Hz, 1H), 8.14 (d, J=8.6 Hz, 1H), 7.70 (d, J=7.7 Hz, 1H), 7.57 (ddd, J=8.5, 7.0, 1.7 Hz, 1H), 7.49 (ddd, J=8.3, 6.7, 1.2 Hz, 1H), 6.78 (d, J=8.2 Hz, 1H), 6.43 (d, J=16.0 Hz, 1H), 3.99 (s, 3H), 3.83 (s, 3H).

Preparation of Compound VII-d

A suspension of compound VII-c (32.0 g, 132 mmol) and 10% Pd/C (5.0 g) in EtOAc (400 mL) was subjected to hydrogenation conditions (1 atm) for 16 h at room temperature. The reaction mixture was filtered through Celite and washed with MeOH. The filtrate was concentrated under vacuum to afford VII-d (32 g, 99%) as a white solid: $^1$H NMR (400 MHz, CDCl$_3$): δ 8.31 (d, J=8.2 Hz, 1H), 7.94 (d, J=8.6 Hz, 1H), 7.54 (ddd, J=8.4, 7.0, 1.5 Hz, 1H), 7.47 (ddd, J=8.3, 6.9, 1.3 Hz, 1H), 7.24 (d, J=8.2 Hz, 1H), 6.83 (d, J=7.7 Hz, 1H), 3.97 (s, 3H), 3.68 (s, 3H), 3.33 (t, J=7.6 Hz, 2 h), 2.72 (t, J=7.7 Hz, 2H).

Preparation of Compound VII-e

A solution of methyl ester VII-d (32.0 g, 131 mmol) in THF/MeOH/H$_2$O (200 mL/200 mL/75 mL) was charged with NaOH (31.5 g, 786 mmol) and the reaction mixture was stirred at room temperature for 1 h. The solvent was removed and pH was adjusted to 1 with 1 N aqueous HCl; a white solid precipitated, was filtered, washed with water, and dried under vacuum to afford acid VII-e (29.5 g, 98%) as a white solid: $^1$H NMR (400 MHz, DMSO-d$_6$): δ 12.15 (brs, 1H), 8.19 (dd, J=8.6, 1.1 Hz, 1H), 7.99 (d, J=8.4 Hz, 1H), 7.57 (ddd, J=8.2, 7.9, 1.3 Hz, 1H), 7.50 (ddd, J=8.4, 7.1, 1.5 Hz, 1H), 7.28 (d, J=7.9 Hz, 1H), 6.88 (d, J=8.1 Hz, 1H), 3.94 (s, 3H), 3.21 (t, J=7.6 Hz, 2H), 2.66 (t, J=7.7 Hz, 2H).

Preparation of Compound VII-g

A solution of compound VII-f (26.8 g, 151 mmol) in dry THF (300 mL) was charged with n-butyl lithium (76.0 mL, 2M solution in cyclohexane) dropwise at −78° C., and the reaction mixture was stirred for 1 h to give a solution of the lithium salt of compound VII-f. Another solution of compound VII-e (29 g, 126 mmol) in dry THF (300 mL) was charged with NMM (20.7 mL, 189 mmol) and PivCl (18.6 mL, 151 mmol) dropwise at −78° C. The reaction mixture was stirred for 1 min at the same temperature, and the prepared solution of compound VIM was added slowly at −78° C. The reaction mixture was stirred for another 10 min, stirred for 1 h at 0° C., stirred at room temperature for 30 min, quenched with saturated NH$_4$Cl, concentrated to remove THF, and partitioned between CH$_2$Cl$_2$ (1000 mL) and water (1000 mL). The aqueous layer was separated and extracted with CH$_2$Cl$_2$ (2×1000 mL). The combined organic extracts were dried over Na$_2$SO$_4$ and concentrated. The residue was purified by column chromatography (silica gel, CH$_2$Cl$_2$) to afford compound VII-g (16 g, 33%) as a white solid: $^1$H NMR (400 MHz, CDCl$_3$): δ 8.30 (dd, J=8.6, 1.3 Hz, 1H), 8.02 (d, J=8.2 Hz, 1H), 7.55 (ddd, J=8.5, 6.9, 1.6 Hz, 1H), 7.47 (ddd, J=8.2, 6.9, 1.2 Hz, 1H), 7.34-7.22 (m, 5H), 7.17 (d, J=7.7 Hz, 1H), 6.73 (d, J=8.0 Hz, 1H), 4.72-4.60 (m, 1H), 4.14 (d, J=2.4 Hz, 1H), 4.13 (s, 1H), 3.47-3.25 (m, 5H), 3.96 (s, 3H), 2.76 (dd, J=13.2, 9.6 Hz, 1H).

Preparation of Compound VII-h

A solution of compound VII-g (16.0 g, 41.1 mmol) in dry THF (500 mL) was charged with KHMDS (12.8 g, 61.7 mmol) portionwise at −78° C. After the resulting mixture was stirred for 30 min, trisyl azide (19.0 g, 61.7 mmol) was added and the reaction mixture was stirred for 5 min. Acetic acid (24.7 mL, 411 mmol) was added slowly at the same temperature, followed by tetramethyl ammonium acetate (10.9 g, 82.2 mmol). The reaction mixture was warmed to 24° C., stirred for 16 h, quenched with saturated NaHCO$_3$ (300 mL), concentrated to remove THF, and extracted with CH$_2$Cl$_2$ (2×500 mL). The combined organic extracts were dried over Na$_2$SO$_4$ and concentrated. The residue was purified by column chromatography (silica gel, 90:10 hexanes/EtOAc, followed by CH$_2$Cl$_2$) to afford compound VII-h (13.0 g, 74%) as a yellow solid: $^1$H NMR (400 MHz, CDCl$_3$): δ 8.29 (d, J=8.6 Hz, 1H), 8.05 (d, J=8.9 Hz, 1H), 7.56 (ddd, J=8.1, 6.7, 1.2 Hz, 1H), 7.46 (ddd, J=8.2, 6.9, 1.2 Hz, 1H), 7.38 (d, J=8.1 Hz, 1H), 7.33-7.20 (m, 3H), 7.18-7.12 (m, 2H), 6.75 (d, J=8.2 Hz, 1H), 5.47 (dd, J=8.4, 7.0 Hz, 1H), 4.44-4.35 (m, 1H), 4.02 (dd, J=9.2, 2.7 Hz, 1H), 3.93 (s, 3H), 3.74 (t, J=8.4 Hz, 1H), 3.66 (dd, J=1.41, 7.0 Hz, 1H), 3.46 (dd, J=14.3, 8.5 Hz, 1H), 3.24 (dd, J=13.4, 3.4 Hz, 1H), 2.75 (dd, J=13.6, 9.7 Hz, 1H).

Preparation of Compound VII-i

A solution of compound VII-h (26.0 g, 60.9 mmol) in THF/H$_2$O (100 mL/35 mL) was charged with H$_2$O$_2$ (41.4 mL, 366 mmol) followed by LiOH (5.11 g, 122 mmol) portionwise at 0° C. The reaction mixture was stirred for 10 min, stirred at room temperature for 1 h, quenched with saturated Na$_2$SO$_3$ (200 mL), concentrated under reduced pressure to remove THF, and washed with CH$_2$Cl$_2$ (500 mL). The aqueous layer was acidified with 1 N aqueous HCl and extracted with CH$_2$Cl$_2$ (2×500 mL). The combined organic extracts were dried over Na$_2$SO$_4$, concentrated, and triturated with MTBE to afford compound VII-i (13.5 g, 82%) as an off-white solid: $^1$H NMR (400 MHz, DMSO-d$_6$): δ 8.22 (dd, J=8.4, 1.4 Hz, 1H), 8.03 (d, J=8.4 Hz, 1H), 7.60 (ddd, J=8.2, 6.8, 1.4 Hz, 1H), 7.52 (ddd, J=8.2, 6.8, 1.3 Hz, 1H), 7.35 (d, J=8.0 Hz, 1H), 6.92 (d, J=8.0 Hz, 1H), 4.36 (dd, J=9.5, 5.0 Hz, 1H), 3.96 (s, 3H), 3.59 (dd, J=14.9, 5.1 Hz, 1H), 3.25 (dd, J=14.7, 8.9 Hz, 1H).

Preparation of Compound VII-j

A suspension of compound VII-ji (13.5 g, 49.6 mmol) and 10% Pd/C (1.35 g) in AcOH/H$_2$O (300 mL/100 mL) was subjected to hydrogenation conditions (1 atm) for 3 h at room temperature. The reaction mixture was filtered through Celite and washed with AcOH/H$_2$O followed by MeOH. The filtrate was concentrated under vacuum to afford acetic salt VII-j (12.0 g, 80%) as a yellow solid: ESI-MS m/z 246 [C$_{14}$H$_{15}$NO$_3$+H]$^+$.

Preparation of Compound VII-k

A solution of compound VII-j (12.0 g, 39.3 mmol) in acetic acid (130 mL) was charged with hydrobromic acid (130 mL) dropwise at room temperature and the reaction mixture was refluxed for 3 h. The reaction mixture was cooled to room temperature and concentrated. The crude brown residue VII-k (10.5 g, 86%) was directly used for the next step without any purification: $^1$H NMR (400 MHz, DMSO-d$_6$): δ 10.17 (brs, 1H), 8.32 (brs, 3H), 8.20 (dd, J=8.3, 1.5 Hz, 1H), 8.00 (d, J=8.5 Hz, 1H), 7.57 (ddd, J=8.2, 6.7, 1.2 Hz, 1H), 7.49 (ddd, J=8.2, 6.8, 1.1 Hz, 1H), 7.21 (d, J=7.7 Hz, 1H), 6.82 (d, J=7.7 Hz, 1H), 4.11-3.98 (m, 1H), 3.51-3.36 (m, 2H).

Preparation of Compound VII-l

Acetyl chloride (16.8 mL, 236 mmol) was added to dry methanol (250 mL) at 0° C., followed by compound VII-k (10.5 g, 33.7 mmol). The reaction mixture was refluxed for 4 h and concentrated. The residue was partitioned between $CH_2Cl_2$ (500 mL) and saturated $NaHCO_3$ (300 mL). The aqueous layer was separated and extracted with $CH_2Cl_2$ (2×300 mL). The combined organic extracts were dried over $Na_2SO_4$ and concentrated to afford compound VII-l (7.5 g, 91%) as a white solid: $^1$H NMR (400 MHz, DMSO-$d_6$): δ 9.97 (brs, 1H), 8.16 (d, J=8.4 Hz, 1H), 7.95 (d, J=8.6 Hz, 1H), 7.52 (ddd, J=8.1, 6.9, 1.2 Hz, 1H), 7.43 (t, J=6.7 Hz, 1H), 7.10 (d, J=7.9 Hz, 1H), 6.76 (d, J=7.9 Hz, 1H), 3.62 (t, J=6.8 Hz, 1H), 3.51 (s, 3H), 3.37-3.26 (m, 2H), 3.22 (dd, J=14.3, 6.7 Hz, 1H), 3.08 (t, J=14.3, 7.7, Hz, 1H).

Preparation of Compound VII-m

A solution of compound VII-l (7.5 g, 30.6 mmol) in MeOH/$H_2O$ (300 mL/100 mL) was charged with $NaHCO_3$ (25.7 g, 306 mmol) and $Boc_2O$ (10.0 g, 45.9 mmol) at 0° C. The resulting mixture was warmed to room temperature and stirred for 1 h. The reaction mixture was partitioned between $CH_2Cl_2$ (200 mL) and water (200 mL). The aqueous layer was separated and extracted with $CH_2Cl_2$ (2×400 mL). The combined organic extracts were washed with brine, dried over $Na_2SO_4$, and concentrated. Flash-column chromatography using 20% ethyl acetate/hexanes followed by $CH_2Cl_2$ gave compound VII-m (9.6 g, 91%) as a white solid: $^1$H NMR (300 MHz, CDCl3): δ 8.23 (d, J=8.2 Hz, 1H), 7.98 (d, J=8.2 Hz, 1H), 7.57-7.44 (m, 2H), 7.07 (d, J=8.0 Hz, 1H), 6.68 (d, J. 7.6 Hz, 1H), 6.55 (brs, 1H), 5.14-4.85 (brs, 1H), 4.77-4.51 (m, 1H), 3.78-3.31 (m, 5H), 1.40 (s, 6H), 1.10 (s, 3H).

Preparation of Compound VII-n

A solution of compound VII-m (12.9 g, 37.5 mmol) in pyridine (100 mL) was charged with triflate (9.5 mL, 56.3 mmol) at 0° C., and the reaction mixture was stirred at room temperature for 2 h. After concentration, the reaction mixture was partitioned between $CH_2Cl_2$ (100 mL) and water (50 mL). The aqueous layer was separated and extracted with $CH_2Cl_2$ (2×50 mL). The combined organic extracts were washed with brine, dried over $Na_2SO_4$, and concentrated to afford compound VII-n (22.0 g, crude) as a brown oil: $^1$H NMR (400 MHz, CDCl$_3$): δ 8.19-8.07 (m, 2H), 7.69-7.64 (m, 2H), 7.38 (d, J=8.1 Hz, 1H), 7.28 (d, J=7.9 Hz, 1H), 5.12-5.06 (brs, 1H), 4.78-4.67 (m, 1H), 3.68-3.46 (m, 5H), 1.39 (s, 8H), 1.25 (s, 1H).

Preparation of Compound VII-p

A solution of compound VII-n (22.0 g, crude, 37.51 mmol) in anhydrous $CH_3CN$ (250 mL) was charged with TEA (20.5 mL, 150 mmol), 10% (t-Bu)$_3$P in hexanes (15.0 mL, 7.50 mmol), benzyl but-3-ynylcarbamate (VII-o, 11.3 g, 56.3 mmol), and CuI (357 mg, 1.87 mmol) at room temperature. The resulting mixture was degassed with argon for 10 min and Pd(PPh$_3$)$_4$ (4.33 mg, 3.75 mmol) was charged rapidly in one portion. After degassing with argon for 5 min, the resulting mixture was refluxed for 16 h. The reaction mixture was concentrated under vacuum and the residue was purified by column chromatography (silica gel, 60:40 ethyl acetate/hexanes) to afford compound VII-p (14.0 g, 71% over two steps) as a brown oil: $^1$H NMR (400 MHz, CDCl$_3$): δ 8.33 (dd, J=7.5, 2.2 Hz, 1H), 8.07 (dd, J=7.5, 2.2 Hz, 1H), 7.58-7.51 (m, 2H), 7.52 (d, J=7.5 Hz, 1H), 7.35-7.29 (m, 5H), 7.19 (d, J=7.5 Hz, 1H), 5.16-5.12 (m, 1H), 5.13 (s, 2H), 5.07-4.99 (m, 1H), 4.74-4.65 (m, 1H), 3.59 (s, 3H), 3.91-3.42 (m, 2H), 3.53 (d, J=6.2 Hz, 2H), 2.79 (t, J=6.4 Hz, 2H), 1.39 (s, 8H), 1.25 (s, 1H).

Preparation of Compound VII-q

A solution of methyl ester VII-p (14.0 g, 26.5 mmol) in a mixture of THF (150 mL), methanol (150 mL), and water (75 mL) was charged with solid NaOH (6.33 g, 159 mmol) and the reaction mixture was stirred at room temperature for 2 h. When TLC of the reaction mixture showed completion of the reaction, the pH of the reaction mixture was brought to 9-10 by adding 1 N HCl (aqueous) and the organic solvent was removed. The pH of the aqueous part was adjusted to 5-6, and the resulting precipitate was extracted with dichloromethane. The aqueous part was extracted with $CH_2Cl_2$ (2×50 mL). The organic layers were combined, dried over $Na_2SO_4$ and concentrated to afford compound VII-q (13.0 g, 95%) as a brown solid: $^1$H NMR (400 MHz, DMSO-$d_6$): 8.32 (d, J=7.4 Hz, 1H), 8.13-8.05 (m, 1H), 7.58-7.48 (m, 4H), 7.38-7.29 (m, 5H), 5.21-5.15 (m, 1H), 5.12 (s, 2H), 5.07-4.93 (m, 1H), 4.70-4.54 (m, 1H), 3.77-3.62 (m, 1H), 3.57-3.35 (m, 2H), 2.84-2.68 (m, 2H), 1.37 (s, 9H).

Preparation of Compound VII-r

A solution of acid VII-q (4.00 g, 7.7 mmol) in THF (100 mL) was cooled to 0° C. in an ice bath. NMM (1.10 mL, 23.2 mmol) was added, followed by PivCl (1.10 mL, 9.30 mmol), and the reaction mixture was stirred at the same temperature for 2 h. NH$_3$ (7.0 N in methanol, 11.0 mL, 77.5 mmol) was added and the reaction mixture was stirred at 0° C. for 2 h, brought to room temperature, and stirred for 16 h. The organic solvent was removed. The residue was charged with water and extracted with $CH_2Cl_2$ (3×300 mL). The organic layers were combined, dried over $Na_2SO_4$, filtered, and concentrated. The residue was purified by column chromatography (3% methanol in chloroform) to afford amide VII-r (3.50 g, 88%) as a light yellow solid: $^1$H NMR (400 MHz, DMSO-d6) 8.29 (d, J=7.1 Hz, 1H), 8.21 (d, J=7.0 Hz, 1H), 7.63-7.52 (m, 4H), 7.36-7.30 (m, 6H), 6.91 (d, J=7.6 Hz, 1H), 5.05 (s, 2H), 4.23-4.22 (m, 1H), 3.61-3.60 (m, 1H), 3.53-3.48 (m, 1H), 3.16-3.06 (m, 1H), 2.74-2.68 (m, 2H), 1.24 (s, 9H).

Preparation of Compound VII-s

A suspension of compound VII-r (3.50 g, 6.8 mmol) and 10% Pd/C (700 mg) in EtOH (100 mL) and AcOH (20 mL) was subjected to hydrogenation conditions (1 atm) for 16 h at room temperature. The reaction mixture was filtered through Celite and washed with EtOH. The filtrate was concentrated under vacuum and triturated with MTBE/hexanes to afford acetic salt VII-s (3.0 g, 99%) as an off-white solid: $^1$H NMR (400 MHz, DMSO-d6) 8.24-8.21 (m, 1H), 8.10 (d, J=7.0 Hz, 1H), 7.56-7.54 (m, 2H), 7.31-7.26 (m, 2H), 4.44-4.42 (m, 1H), 3.75-3.68 (m, 1H), 3.64-3.59 (m, 1H), 3.24-3.19 (m, 2H), 3.13 (t, J=6.2 Hz 2H), 2.92 (t, J=6.2 Hz, 2H), 1.84-1.71 (m, 4H), 1.39 (s, 9H).

Preparation of Compound VII-t

A solution of amine VII-s (3.0 g, 6.74 mmol) in MeOH (100 mL) and water (50 mL) was charged with $Na_2CO_3$ (7.14 g, 67.4 mmol) at 0° C. and stirred for 10 min. Benzyl chloroformate (1.93 mL, 13.4 mmol) was added at the same temperature and the reaction mixture was stirred for 1 h, brought to room temperature, and stirred for another 1 h. The mixture was concentrated, the residue was dissolved in $CH_2Cl_2$ (200 mL), and the solution was washed with water (300 mL) and brine (300 mL). The organic layer was dried over $Na_2SO_4$, filtered, and concentrated. The residue was purified by column chromatography (3% methanol in chloroform) to afford amide VII-t (3.10 g, 89%) as a light yellow solid: ESI-MS m/z 520 $[C_{30}H_{37}N_3O_5+H]^+$.

Preparation of Compound VII-u

Compound VII-t (3.10 g, 5.80 mmol) was dissolved in 4 N HCl in dioxane (40 mL) at room temperature and the solution was stirred for 1 h. After concentration, amine salt VII-u (2.6 g, 99%) was obtained as a white solid, and was used directly for the next step: ESI-MS m/z 420 $[C_{25}H_{29}N_3O_3+H]^+$.

Preparation of Compound 2

A solution of 1 (10 g) in $CH_2Cl_2$ (100 mL) was cooled to 0° C. After 10 min, Dess-Martin periodinane (29 g) was added and the reaction mixture was stirred at room temperature for 2 h. 1 N NaOH (aqueous) was added and extracted with $CH_2Cl_2$ (3×300 mL). The organic layers were combined, dried over $Na_2SO_4$, filtered, and concentrated to afford aldehyde 2 (8.0 g, 80%) as a light yellow liquid.

Preparation of Compound VII-v

A solution of amine salt VII-u (3.70 g, 8.13 mmol), aldehyde (2) (1.7 g, 9.75 mmol), and acetic acid (4.88 mL) was added and stirred at room temperature for 10 min. Sodium cyanoborohydride (768 mg, 12.2 mmol) was added and the mixture stirred for 2 h. Additional 2 (0.3 equiv), AcOH (0.3 equiv), and $NaCNBH_3$ (0.3 equiv) were charged over 30 min. The reaction mixture was concentrated to dryness, and the residue was washed with saturated $NaHCO_3$ (200 mL) and extracted with EtOAc (3×300 mL). The organic layers were dried over $Na_2SO_4$, filtered, and concentrated. This crude product (VII-v, 8.0 g) was directly used for the next step without further purification, and product formation was confirmed by LCMS data: ESI-MS m/z 577 $[C_{33}H_{44}N_4O_5+H]^+$.

Preparation of Compound VII-w

A solution of amine VII-v (crude product 8.0 g) in MeOH (90 mL) and water (30 mL) was charged with $NaHCO_3$ (6.82 g, 81.3 mmol) at 0° C. and stirred for 10 min. Benzyl chloroformate (2.47 mL) was added and the reaction mixture was stirred for 1 h at the same temperature, brought to room temperature, and stirred for another 1 h. The mixture was concentrated, the residue was dissolved in $CH_2Cl_2$ (200 m L), and the solution was washed with water (300 mL) and brine (300 mL). The organic layer was dried over $Na_2SO_4$, filtered, and concentrated. This crude product VII-w (10.0 g) was directly used for the next step without further purification, and product formation was confirmed by LCMS data: ESI-MS m/z 711 $[C_{41}H_{50}N_4O_7+H]^+$.

Preparation of Compound VII-x

Compound VII-w (crude product, 10.0 g) was dissolved in 4 N HCl in dioxane (25 mL) at room temperature and the solution was stirred for 1 h. After concentration, amine salt was neutralized with aqueous $NaHCO_3$. The residue was purified by column chromatography (6% methanol in chloroform) to afford amine VII-x (2.50 g, 50% over three steps) as a light yellow solid: ESI-MS m/z 611 $[C_{36}H_{42}N_4O_5+H]^+$.

Preparation of Compounds VII-aa and VII-z

A solution of amine VII-x (2.50 g, 4.09 mmol) in methanol (50 mL) was charged with triol (VII-y) (4.39 g, 16.4 mmol) and acetic acid (2.45 mL) successively and stirred at room temperature for 10 min. Sodium cyanoborohydride (1.54 mg, 24.5 mmol) was added and the mixture stirred at room temperature for 24 h. Additional VII-y (2.0 equiv), AcOH (4.0 equiv), and $NaCNBH_3$ (3.0 equiv) were charged and the mixture stirred for 48 h. LC/MS showed 90% consumption of amine. Again VII-y (2.0 equiv), AcOH (4.0 equiv), and $NaCNBH_3$ (3.0 equiv) were added and the mixture stirred for 24 h. The reaction mixture was charged with hexanal (1.46 mL, 12.2 mmol) and $NaCNBH_3$ (1.26 g, 20.0 mmol), stirred for 2 h, and concentrated to dryness. The residue was washed with saturated $NaHCO_3$ (200 mL), and extracted with EtOAc (3×300 mL). The organic layers were dried over $Na_2SO_4$, filtered, and concentrated. Purification of compounds VII-aa and VII-z failed by normal chromatography using CMA system; reverse-phase chromatography using a C18 Gold column was used to get pure VII-z (810 mg, 21%) and VII-aa (1.10 g, 25%) respectively: ESI-MS m/z 947 $[C_{55}H_{70}N_4O_{10}+H]^+$; for VII-z and ESI-MS m/z 1115 $[C_{62}H_{74}N_4O_{15}+H]^+$ for VII-aa.

Preparation of Compound VII-bb

A suspension of VII-aa (1.10 g, 0.98) and 10% Pd/C (200 mg) in a mixture of EtOH (80 mL) and AcOH (20 mL) was degassed and subjected to hydrogenation conditions (1 atm) for 16 h at room temperature. The reaction mixture was filtered through a pad of Celite and was washed with MeOH. The filtrate was concentrated under vacuum to afford amine salt VII-bb (925 mg, 92%) as a white solid: ESI-MS m/z 847 $[C_{46}H_{62}N_4O_{11}+H]^+$.

Preparation of Compound VII-dd

A solution of amine salt VII-bb (925 mg, 0.95 mmol) and methyl 3,5-diamino-6-chloropyrazine-2-carbonylcarbamimidothioate (VII-cc, 561 mg, 1.44 mmol) in EtOH (10 mL) was charged with DIPEA (1.35 mL, 7.60 mmol) at room temperature. The reaction mixture was heated at 70° C. in a sealed tube for 2 h, cooled to room temperature, and concentrated in vacuo. The residue was purified by column chromatography (silica gel, 80:18:2 $CHCl_3/CH_3OH/NH_4OH$) to afford guanidine VII-dd (500 mg, 50%) as a yellow solid: $^1$H NMR (400 MHz, $CD_3OD$): δ 8.21-8.16 (m, 1H), 8.12-8.07 (m, 1H), 7.56-7.49 (m, 2H), 7.45-7.39 (m, 4H), 7.32-7.22 (m, 8H), 5.45 (s, 2H), 4.21 (dd, J=10.5, 5.3 Hz, 2H), 3.98-3.89 (m, 4H), 3.83 (dd, J=4.9, 2.5 Hz, 2H), 3.68 (dd, J=9.2, 2.5 Hz, 2H), 3.57 (t, J=10.5 Hz, 2H), 3.45-3.37 (m, 2H), 3.27 (t, J=7.7 Hz, 2H), 3.24-3.17 (m, 1H), 3.15-3.08 (m, 2H), 2.64-2.44 (m, 6H), 2.43-2.25 (m, 2H), 1.88-1.79 (m, 2H), 1.79-1.68 (m, 2H), 1.54-1.41 (m, 2H).

Preparation of the Hydrochloride Salt of 3,5-diamino-N—(N-(4-(4-((S)-3-amino-2-(3-(bis((2S,3R,4R,5R)-2,3,4,5,6-pentahydroxyhexyl)amino)propylamino)-3-oxopropyl)naphthalen-1-yl)butyl)carbamimidoyl)-6-chloropyrazine-2-carboxamide (Compound VII-ee)

4 N aqueous HCl (20 mL) was added to VII-dd (500 mg, 0.48 mmol) and the reaction mixture was stirred at room temperature for 2 h. The solvent was removed and the residue was purified by reverse-phase chromatography using a C18 Gold column to afford hydrochloric acid salt VII-ee (285 mg, 60%) as a yellow hygroscopic solid: $^1$H NMR (400 MHz, DMSO-$d_6$): δ 10.53 (brs, 1H), 10.29 (brs, 1H), 9.46 (brs, 1H), 9.32 (brs, 1H), 9.05-8.78 (m, 3H), 8.41-8.33 (m, 1H), 8.17-8.09 (m, 1H), 7.74 (s, 1H), 7.58 (dd, J=6.4, 3.2 Hz, 2H), 7.51 (s, 1H), 7.48-7.35 (m, 1H), 7.32 (d, J=7.8 Hz, 1H), 7.28 (d, J=7.3 Hz, 1H), 4.16-4.05 (m, 2H), 4.04-3.96 (m, 1H), 3.84 (dd, J=12.8, 3.3 Hz, 1H), 3.72 (d, J=5.8 Hz, 2H), 3.62 (d, J=2.8 Hz, 1H), 3.58 (d, J=2.8 Hz, 1H), 3.54-3.45 (m, 4H), 3.44-3.30 (m, 9H), 3.28-3.18 (m, 2H), 3.15-3.01 (m, 2H), 2.99-2.85 (m, 2H), 2.28-2.13 (m, 2H), 1.81-1.63 (m, 4H).

$^1$H NMR (400 MHz, CD$_3$OD): δ 8.25 (dd, J=8.5, 1.7 Hz, 1H), 8.16 (dd, J=8.1, 1.5 Hz, 1H), 7.64-7.54 (m, 2H), 7.37 (ABq, J=7.4 Hz, 2H), 4.25-4.17 (m, 3H), 3.88-3.84 (m, 2H), 3.83 (dd, J=13.8, 4.8 Hz, 1H), 3.79 (d, J=2.8 Hz, 1H), 3.76 (d, J=2.8 Hz, 1H), 3.73-3.63 (m, 5H), 3.61-3.50 (m, 3H), 3.49-3.42 (m, 4H), 3.41-3.35 (m, 3H), 3.23-3.06 (m, 4H), 2.36-2.23 (m, 2H), 1.93-1.77 (m, 4H).

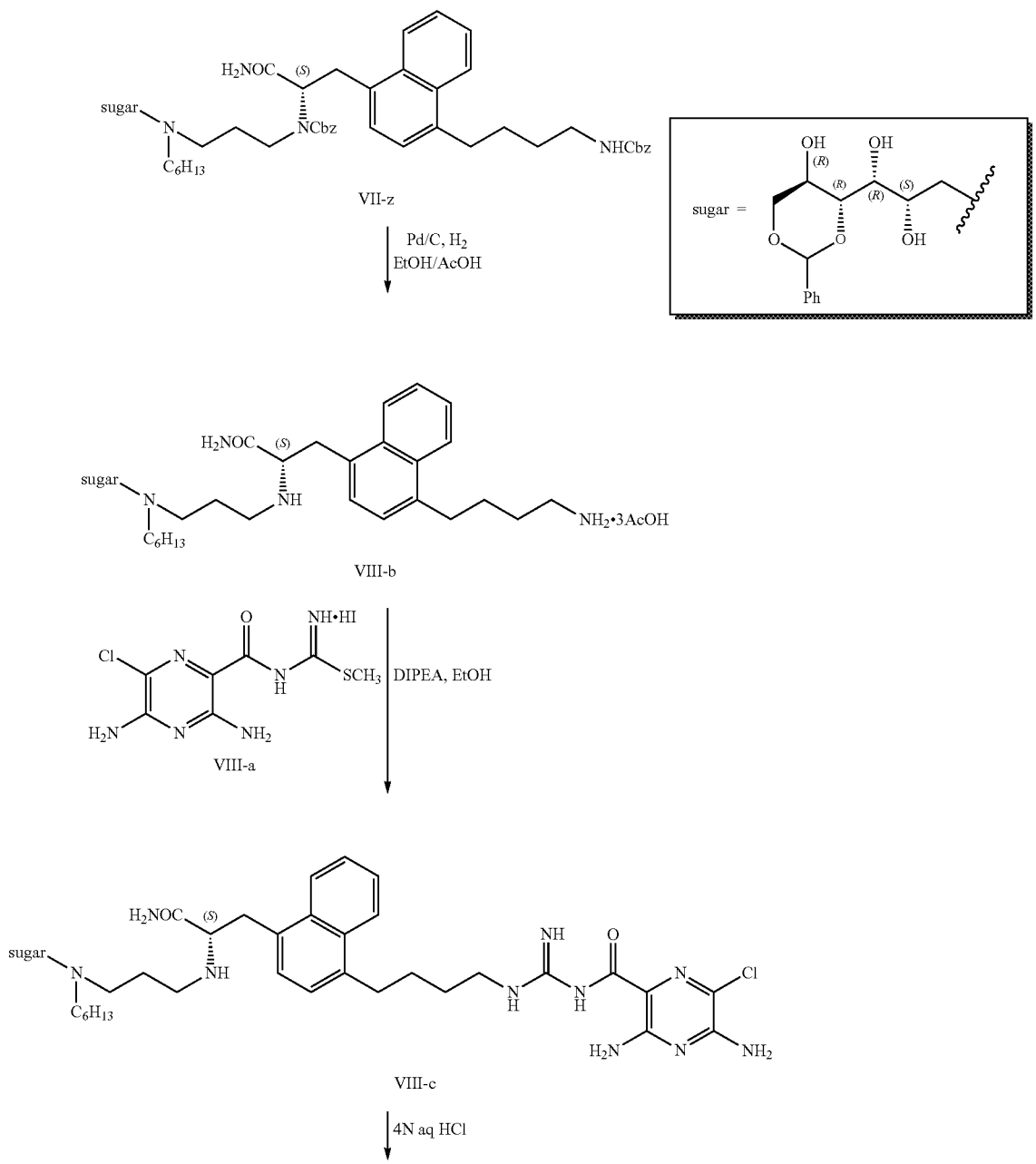

Scheme VIII. Preparation of 3,5-diamino-N-(N-(4-(4-((S)-3-amino-2-(3-(hexyl((2S,3R,4R,5R)-2,3,4,5,6-pentahydroxyhexyl)amino)propylamino)-3-oxopropyl)naphthalen-1-yl)butyl)carbamimidoyl)-6-chloropyrazine-2-carboxamide (VIIId)

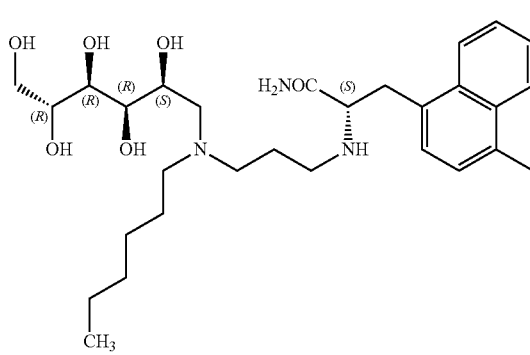
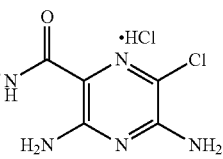

VIII-d

Preparation of Compound VIII-b

A suspension of VII-z (800 mg, 0.86) and 10% Pd/C (160 mg) in a mixture of EtOH (80 mL) and AcOH (20 mL) was degassed and subjected to hydrogenation conditions (1 atm) for 16 h at room temperature. The reaction mixture was filtered through a pad of Celite and washed with MeOH. The filtrate was concentrated under vacuum to afford amine salt VIII-b (670 mg, 91%) as a white solid: ESI-MS m/z 679 $[C_{39}H_{58}N_4O_6+H]^+$.

Preparation of Compound VIII-d

A solution of amine salt VIII-b (670 mg, 0.78 mmol) and methyl 3,5-diamino-6-chloropyrazine-2-carbonylcarbamimidothioate (VIII-a, 485 mg, 1.24 mmol) in EtOH (10 mL) was charged with DIPEA (1.10 mL, 6.24 mmol) at room temperature. The reaction mixture was heated at 70° C. in a sealed tube for 2 h, cooled to room temperature, and concentrated under vacuum. The residue was purified by column chromatography (silica gel, 80:18:2 $CHCl_3$/$CH_3OH$/$NH_4OH$) to afford guanidine VIII-c (360 mg, 52%) as a yellow solid: $^1$H NMR (400 MHz, $CD_3OD$): δ 8.24-8.18 (m, 1H), 8.14-8.07 (m, 1H), 7.56-7.48 (m, 2H), 7.47-7.40 (m, 2H), 7.32-7.22 (m, 5H), 5.50 (s, 1H), 4.23 (dd, J=10.8, 5.8 Hz, 1H), 4.00-3.91 (m, 1H), 3.86 (dd, J=5.4, 1.9 Hz, 1H), 3.73 (dd, J=9.5, 2.5 Hz, 1H), 3.59 (t, J=10.8 Hz, 2H), 3.46-3.37 (m, 2H), 3.12 (t, J=6.8 Hz, 2H), 3.24-3.17 (m, 1H), 2.67 (dd, J=13.8, 4.5 Hz, 1H), 2.55-2.26 (m, 8H), 1.90-1.70 (m, 4H), 1.51-1.41 (m, 2H), 1.36-1.08 (m, 9H), 0.86 (t, J=7.2 Hz, 3H).

Preparation of the Hydrochloride Salt of 3,5-diamino-N—(N-(4-(4-((S)-3-amino-2-(3-(hexyl((2S,3R,4R,5R)-2,3,4,5,6-pentahydroxyhexyl)amino)propylamino)-3-oxopropyl)naphthalen-1-yl)butyl)carbamimidoyl)-6-chloropyrazine-2-carboxamide (Compound VIII-d)

4 N aqueous HCl (20 mL) was added to VIII-dc (360 mg, 0.40 mmol) and the reaction mixture was stirred at room temperature for 2 h. The solvent was removed and the residue was purified by reverse-phase chromatography using a C18 Gold column to afford hydrochloric acid salt VIII-d (70 mg, 36%) as a yellow hygroscopic solid: $^1$H NMR (400 MHz, DMSO-$d_6$): δ 10.52 (s, 1H), 10.49-10.28 (m, 1H), 9.72-9.55 (m, 1H), 9.47-9.34 (m, 1H), 9.29 (brs, 1H), 9.01-8.74 (m, 2H), 8.43-8.35 (m, 1H), 8.20-8.11 (m, 1H), 7.73 (s, 1H), 7.62-7.55 (m, 2H), 7.52 (s, 1H), 7.47-7.37 (m, 2H), 7.32 (d, J=7.1 Hz, 1H), 7.27 (d, J=7.6 Hz, 1H), 3.73-3.67 (m, 2H), 3.60 (dd, J=10.6, 3.0 Hz, 1H), 3.55-3.45 (m, 2H), 3.44-3.22 (m, 3H), 3.31-3.22 (m, 3H), 3.20-3.00 (m, 5H), 2.98-2.86 (m, 2H), 2.24-2.08 (m, 2H), 1.79-1.61 (m, 6H), 1.36-1.22 (m, 6H), 0.88 (t, J=6.4 Hz, 3H).

$^1$H NMR (400 MHz, $CD_3OD$): δ 8.26 (d, J=8.4 Hz, 1H), 8.16 (dd, J=8.1, 1.3 Hz, 1H), 7.63-7.54 (m, 2H), 7.37 (q, J=7.2 Hz, 2H), 4.22-4.13 (m, 2H), 3.89-3.81 (m, 2H), 3.77 (dd, J=10.6, 3.1 Hz, 1H), 3.73-3.64 (m, 3H), 3.55-3.49 (m, 1H), 3.49-3.46 (m, 1H), 3.43-3.34 (m, 6H), 3.27-3.07 (m 5H). 2.32-2.17 (m, 2H), 1.93-1.71 (m, 6H), 1.46-1.33 (m, 6H), 0.93 (t, J=6.4 Hz, 3H).

Scheme IX 3,5-diamino-N-(N-(4-(6-((S)-3-amino-2-(3-(hexyl((2S,3R,4R,5R)-2,3,4,5,6-pentahydroxyhexyl)amino)propylamino)-3-oxopropyl)napthalen-2-yl)butyl)carbamimidoyl)-6-chloropyrazine-2-carboxamide

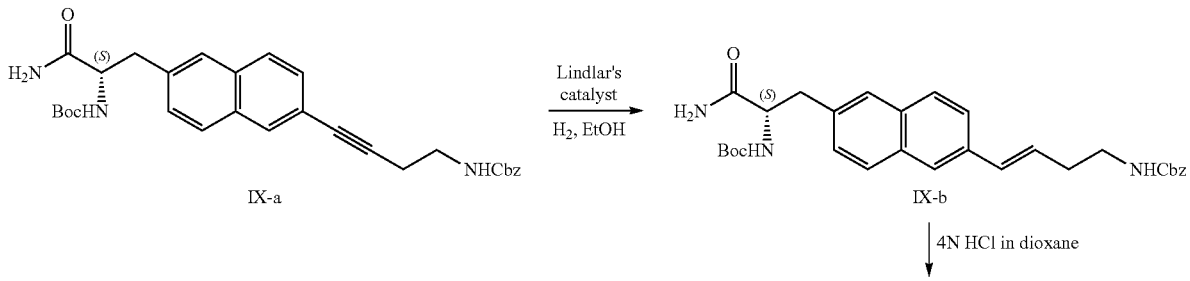

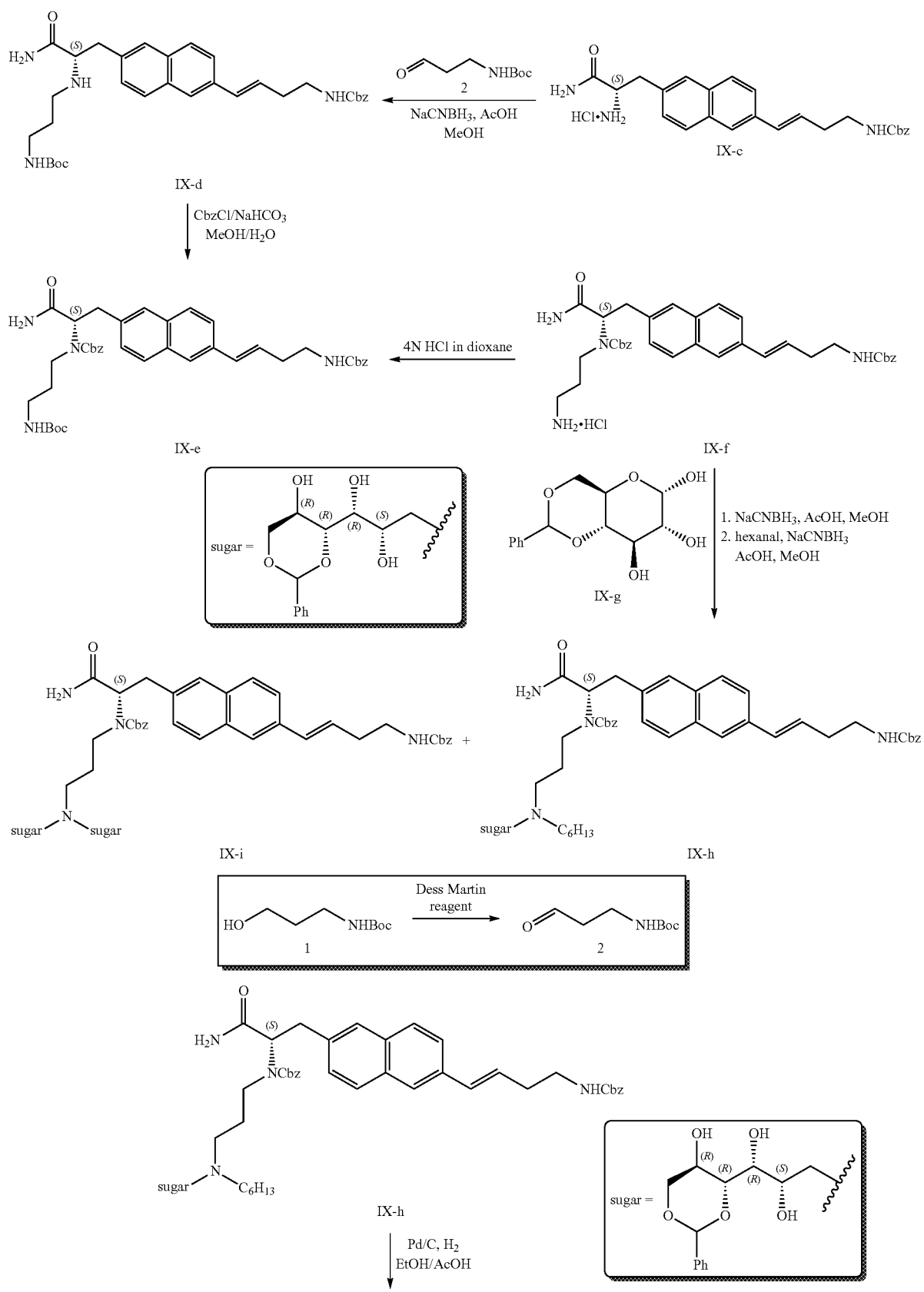

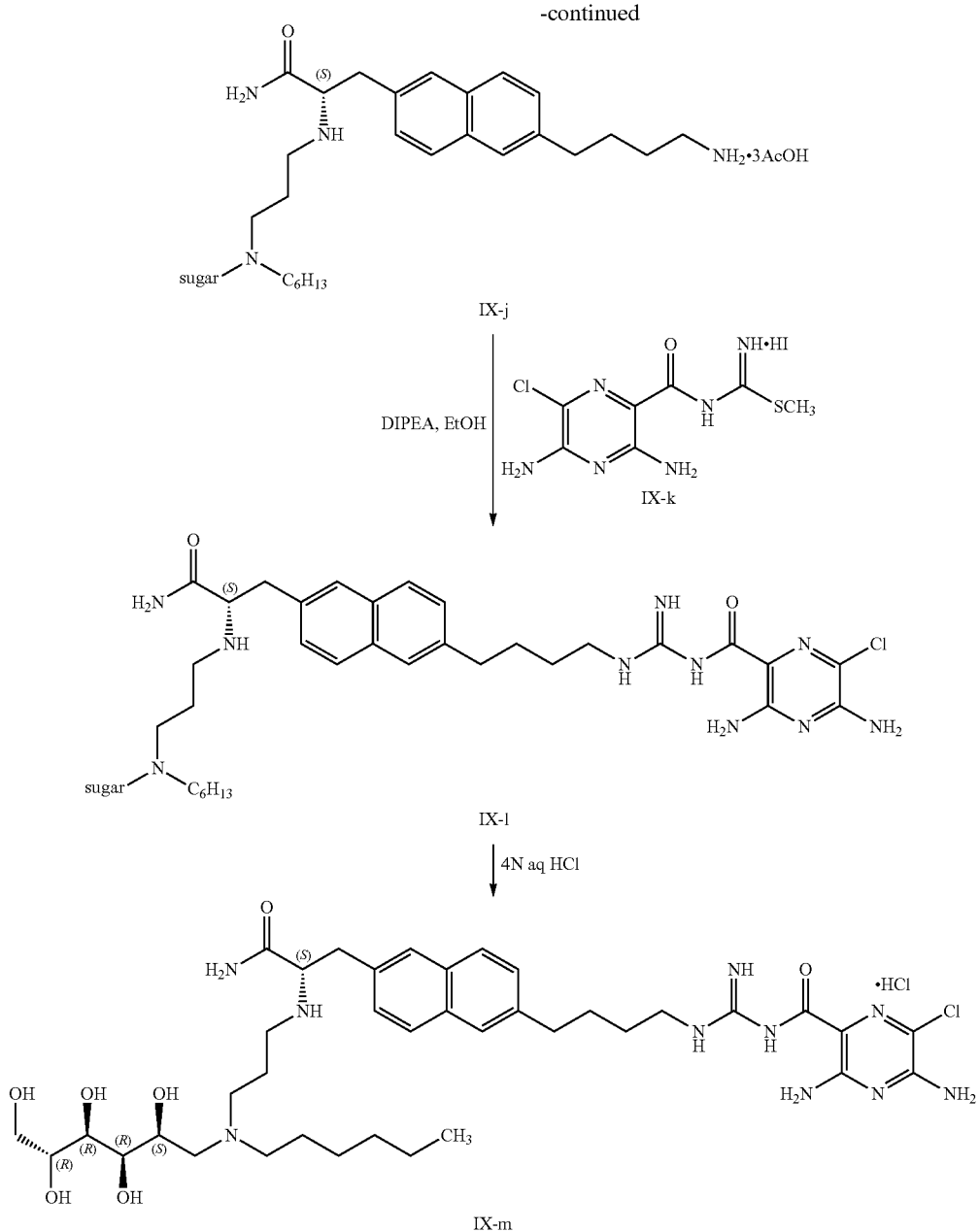

IX-m

Preparation of Compound IX-b

A suspension of IX-a (5.70 g, 11.0 mmol) and 10% Lindlar's Catalyst (1.0 g) in EtOH (100 mL) and THF (20 mL) was subjected to hydrogenation conditions (1 atm) for 36 h at room temperature. The reaction mixture was filtered through a plug of diatomaceous earth and the plug was washed with MeOH. The filtrate was concentrated in vacuum and the residue was purified by column chromatography (silica gel, 95:5 $CHCl_3/CH_3OH$) to afford compound IX-b (5.20 g, 92%) as a yellow solid: ESI-MS m/z 518 $[C_{30}H_{35}N_3O_5+H]^+$.

Preparation of Compound IX-c

Compound IX-b (5.20 g, 10.0 mmol) was dissolved in 4 N HCl in dioxane (40 mL) at room temperature and the solution was stirred for 2 h. After concentrated, amine salt IX-c (4.50 g, 99%) was obtained as a white solid: ESI-MS m/z 418 $[C_{25}H_{27}N_3O_3+H]^+$ 419.

Preparation of tert-butyl 3-oxopropylcarbamate 2

A solution of 1 (10 g) in $CH_2Cl_2$ (100 mL) was cooled to −0° C. and after 10 min Dess-Martin Periodane (29 g) was added and reaction mixture was stirred at the room temperature for 2 h. 1 N NaOH (aqueous) was added and extracted with $CH_2Cl_2$ (3×300 mL). The organic layers were combined, dried over $Na_2SO_4$, filtered, and concentrated to afford aldehyde 2 (9.0 g, 91%) as a light yellow liquid and directly used for next step.

Preparation of Compound IX-d

To a solution of amine salt IX-c (4.50 g, 10.0 mmol) in methanol (100 mL), aldehyde (2) (2.0 g, 12.0 mmol) acetic acid (6.0 mL) was added and stirred at rt for 10 min then sodium cyanoborohydride (942 mg, 15.0 mmol) was added and stirred at room temperature for 2 h. Additional 2 (0.3 equiv), AcOH (0.5 equiv), NaCNBH$_3$ (0.5 equiv) were added over the period of 2 h and this addition was repeated for three times until LC-MS showed >90% consumption of amine. The reaction mixture was concentrated to dryness, the residue was washed with saturated NaHCO$_3$ (200 mL), and extracted with EtOAc (3×300 mL). The organic layers were dried over Na$_2$SO$_4$, filtered, concentrated. The crude product IX-d (8.0 g) was confirmed by LC-MS analysis and directly used for the next step without further purification: ESI-MS m/z 575 [C$_{33}$H$_{42}$N$_4$O$_5$+H]$^+$.

Preparation of Compound IX-e

To a solution of amine IX-d (crude product 8.0 g) in MeOH (150 mL) and water (50 mL) was added NaHCO$_3$ (8.40 g, 100 mmol) at 0° C. and stirred for 10 min, then benzyl chloroformate (3.0 mL, 20.0 mmol) was added dropwise at same temperature and the reaction mixture was stirred for 2 h at same temperature then brought to room temperature and stirred for another 1 h. The mixture was concentrated, the residue was dissolved in CH$_2$Cl$_2$ (200 mL), and the solution was washed with water (300 mL) and brine (300 mL). The organic layer was dried over Na$_2$SO$_4$, filtered, and concentrated. This crude product IX-e (18.0 g) was confirmed by LC-MS analysis and directly used for the next step without further purification: ESI-MS m/z 709 [C$_{41}$H$_{48}$N$_4$O$_7$+H]$^+$.

Preparation of Compound IX-f

Compound IX-e (crude product, 18.0 g) was dissolved in 4 N HCl in dioxane (50 mL) at room temperature and the solution was stirred for 2 h. After concentrated, amine salt was neutralized with aqueous NaHCO$_3$. The residue was purified by column chromatography (6% methanol in chloroform) to afford amine IX-f (2.50 g, 41% over three steps) as a light yellow solid: ESI-MS m/z 609 [C$_{36}$H$_{40}$N$_4$O$_5$+H]$^+$.

Preparation of Compound IX-h and IX-i

To a solution of amine IX-f (2.50 g, 4.10 mmol) in methanol (100 mL), triol (IX-g) (3.30 g, 12.3 mmol), acetic acid (2.46 mL) were added successively and stirred at rt for 10 min then sodium cyanoborohydride (1.30 g, 20.5 mmol) were added and stirred at room temperature for 16 h. Additional IX-g (2.0 equiv), AcOH (5.0 equiv), NaCNBH$_3$ (3.0 equiv) were added over the period of 16 h and this addition was repeated for another time and stirred for 16 h, To this reaction mixture, hexanal (1.47 mL, 12.3 mmol), AcOH (0.7 mL), NaCNBH$_3$ (774 mg) were added and stirred for 1 h, The reaction mixture was concentrated to dryness, the residue was washed with saturated NaHCO$_3$ (200 mL), and extracted with EtOAc (3×300 mL). The organic layers were dried over Na$_2$SO$_4$, filtered, concentrated. Purification of compounds IX-h and IX-i were failed by normal chromatography using CMA system, then reverse phase column using C-18 gold was used to afford pure IX-h (1.30 g, 34%) and IX-i (1.43 g, 28%) respectively: ESI-MS m/z 945 [C$_{55}$H$_{68}$N$_4$O$_{10}$+H]$^+$ for IX-h and ESI-MS m/z 1113 [C$_{62}$H$_{72}$N$_4$O$_{15}$+H]$^+$ for IX-i.

Preparation of Compound IX-j

A suspension of IX-h (1.3 g, 1.37) and 10% Pd/C (400 mg) in a mixture of EtOH (100 mL) and AcOH (30 mL) was degassed and then subjected to hydrogenation conditions (1 atm) for 16 h at room temperature. The reaction mixture was filtered through a plug of diatomaceous earth and the plug was washed with MeOH. The filtrate was concentrated in vacuum to afford amine salt IX-j (1.15 g, 98%) as a white solid: ESI-MS m/z 679 [C$_{39}$H$_{58}$N$_4$O$_6$+H]$^+$ 679.

Preparation of Compound IX-l

To a solution of amine salt IX-j (1.15 g, 1.34 mmol) and methyl 3,5-diamino-6-chloropyrazine-2-carbonylcarbamimidothioate (IX-k, 834 mg, 2.14 mmol) in EtOH (20 mL) was added DIPEA (1.90 mL, 10.72 mmol) at room temperature. The reaction mixture was heated at 70° C. in a sealed tube for 2 h, then cooled to room temperature, and concentrated in vacuo. The residue was purified by column chromatography (silica gel, 80:18:2 CHCl$_3$/CH$_3$OH/NH$_4$OH) to afford guanidine IX-l (800 mg, 67%) as a yellow solid: $^1$H NMR (400 MHz, CD$_3$OD): δ 7.72 (dd, J=8.3, 2.7 Hz, 2H), 7.62 (d, J=8.6 Hz, 2H), 7.44 (d, J=7.4, 3.9 Hz, 2H), 7.38-7.32 (m, 2H), 7.32-7.27 (m, 3H), 5.51 (s, 1H), 4.25 (dd, J=10.8, 5.8 Hz, 1H), 4.04-3.93 (m, 2H), 3.89 (dd, J=5.3, 1.7 Hz, 1H), 3.74 (dd, J=9.2, 2.0 Hz, 1H), 3.61 (t, J=11.0 Hz, 1H), 3.45 (t, J=7.1 Hz, 1H), 3.17-3.05 (m, 1H), 2.95 (dd, J=13.8, 7.4 Hz, 1H), 2.83 (t, J=7.1 Hz, 2H), 2.80-2.69 (m, 3H), 2.67-2.56 (m, 2H), 2.54-2.44 (m, 3H), 1.87-1.78 (m, 2H), 1.76-1.67 (m, 2H), 1.64-1.54 (m, 2H), 1.36-1.17 (m, 6H), 1.16-1.01 (m, 4H), 0.85 (t, J=7.3 Hz, 3H).

Preparation of the Hydrochloride Salt of 3,5-diamino-N—(N-(4-(6-((S)-3-amino-2-(3-(hexyl((2S, 3R,4R,5R)-2,3,4,5,6-pentahydroxyhexyl)amino) propylamino)-3-oxopropyl)naphthalen-2-yl)butyl) carbamimidoyl)-6-chloropyrazine-2-carboxamide (Compound IX-m)

4 N aq HCl (25 mL) was added to IX-l (800 mg, 0.89 mmol) and reaction mixture was stirred at room temperature for 2 h. The solvent was removed the residue was purified by reverse phase column using C-18 Gold column to afford hydrochloric acid salt IX-m (500 mg, 62%) as a yellow hygroscopic solid: $^1$H NMR (400 MHz, DMSO-d$_6$) 10.51 (brs, 1H), 9.29 (brs, 1H), 8.94 (brs, 1H), 8.82 (brs, 1H), 7.77 (dd, J=8.7, 3.1 Hz, 2H), 7.68 (d, J=10.7 Hz, 2H), 7.59 (brs, 1H), 7.47-7.34 (m, 4H), 7.17 (brs, 1H), 5.97-5.09 (m 3H), 4.64 (brs, 1H), 4.44 (brs, 1H), 3.96 (brs, 1H), 3.69 (d, J=11.1 Hz, 1H), 3.56-3.49 (m, 1H), 3.48-3.40 (m, 2H), 3.17-2.90 (m, 6H), 2.84-2.66 (m, 1H), 2.78 (t, J=7.5 Hz, 2H), 1.75-1.67 (m, 2H), 1.65-1.55 (m, 2H), 1.30-1.07 (m, 6H), 0.85 (t, J=7.2 Hz, 3H).

$^1$H NMR (400 MHz, CD$_3$OD) 7.77 (d, J=8.5 Hz, 2H), 7.70 (s, 1H), 7.65 (s, 1H), 7.40 (dt, J=8.6, 1.7 Hz, 2H), 4.15-4.08 (m, 1H), 3.83-3.77 (m, 2H), 3.76-3.64 (m, 4H), 3.37 (t, J=7.1 Hz, 2H), 3.24 (d, J=10.6 Hz, 2H), 3.20-3.08 (m, 4H), 2.85 (t, J=7.4 Hz, 2H), 2.97-2.76 (m, 5H), 1.95-1.80 (m, 4H), 1.79-1.70 (m, 2H), 1.55 (brs, 1H), 1.35-1.12 (m, 6H), 1.45-1.36 (m, 1H), 0.90 (t, J=7.1 Hz, 3H).

Scheme X.
3,5-diamino-N-(N-(4-(6-((S)-3-amino-2-(3-bis((2S,3R,4R,5R)-2,3,4,5,6-pentahydroxyhexyl)amino)propylamino)-3-oxopropyl)naphthalen-2-yl)butyl)carbamimidoyl)-6-chloropyrazine-2-carboxamide
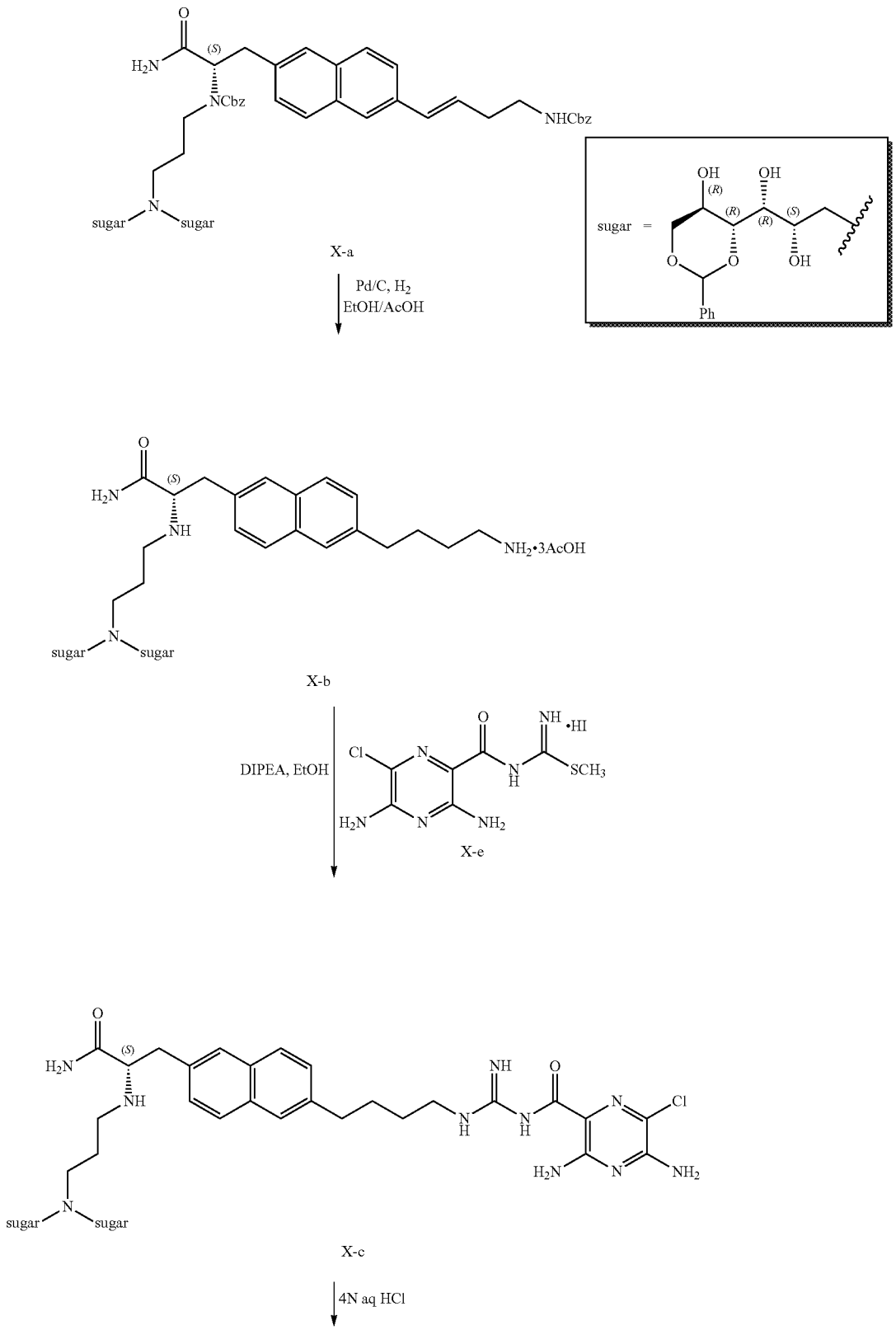

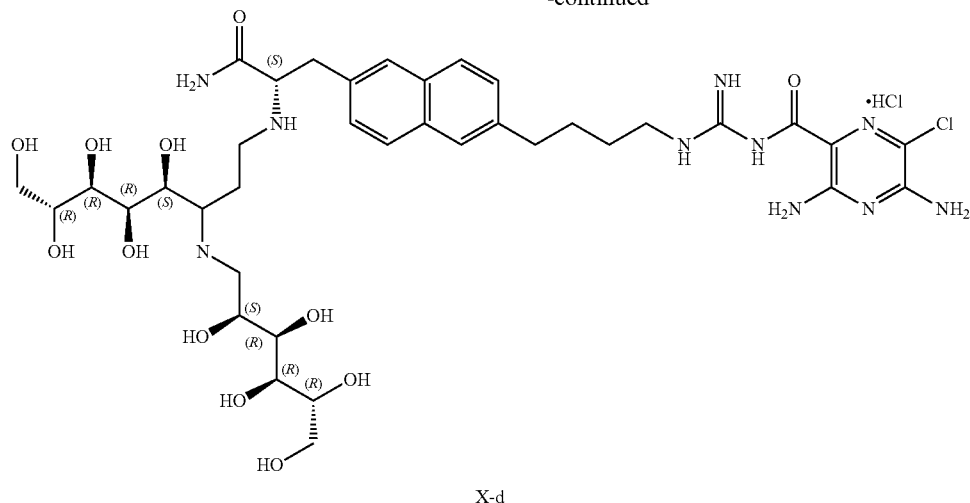

X-d

Preparation of Compound X-b

A suspension of X-a (1.43 g, 1.28) and 10% Pd/C (400 mg) in a mixture of EtOH (100 mL) and AcOH (40 mL) was degassed and then subjected to hydrogenation conditions (1 atm) for 16 h at room temperature. The reaction mixture was filtered through a plug of diatomaceous earth and the plug was washed with MeOH. The filtrate was concentrated in vacuum to afford amine salt X-b (1.30 g, 99%) as a white solid: ESI-MS m/z 847 $[C_{46}H_{62}N_4O_{11}+H]^+$.

Preparation of Compound X-c

To a solution of amine salt X-b (1.30 g, 1.26 mmol) and methyl 3,5-diamino-6-chloropyrazine-2-carbonylcarbamimidothioate (X-e, 788 mg, 2.02 mmol) in EtOH (20 mL) was added DIPEA (1.79 mL, 10.0 mmol) at room temperature. The reaction mixture was heated at 70° C. in a sealed tube for 2 h, then cooled to room temperature, and concentrated in vacuo. The residue was purified by column chromatography (silica gel, 80:18:2 $CHCl_3/CH_3OH/NH_4OH$) to afford guanidine X-c (900 mg, 68%) as a yellow solid: $^1$H NMR (400 MHz, $CD_3OD$): δ 7.70 (d, J=8.1 Hz, 2H), 7.59 (s, 2H), 7.46-7.39 (m, 4H), 7.34-7.24 (m, 8H), 5.45 (s, 2H), 4.21 (dd, J=10.7, 5.5 Hz, 2H), 3.99-3.88 (m, 6H), 3.82 (dd, J=5.3, 2.4 Hz, 2H), 3.67 (dd, J=9.8, 2.9 Hz, 2H), 3.57 (t, J=10.6, 2H), 3.23 (t, J=6.7 Hz, 2H), 3.06 (dd, J=13.4, 6.6 Hz, 1H), 2.93 (dd, J=13.6, 7.5 Hz, 1H), 2.79 (t, J=7.6 Hz, 2H), 2.63-2.45 (m, 5H), 2.44-2.36 (m, 2H), 1.84-1.73 (m, 2H), 1.70-1.60 (m, 2H), 1.57-1.44 (m, 2H).

Preparation of the Hydrochloride Salt of 3,5-diamino-N—(N-(4-(6-((S)-3-amino-2-(3-(bis((2S,3R, 4R,5R)-2,3,4,5,6-pentahydroxyhexyl)amino)propylamino)-3-oxopropyl)naphthalen-2-yl)butyl) carbamimidoyl)-6-chloropyrazine-2-carboxamide (Compound X-d)

4 N aq HCl (30 mL) was added to X-c (900 mg, 0.85 mmol) and reaction mixture was stirred at room temperature for 2 h. The solvent was removed the residue was purified by reverse phase column using C-18 Gold column to afford hydrochloric acid salt X-d (590 mg, 70%) as a yellow hygroscopic solid: $^1$H NMR (400 MHz, DMSO-$d_6$) 10.51 (brs, 1H), 9.81 (brs, 1H), 9.29 (brs, 1H), 8.94 (brs, 1H), 8.83 (brs, 1H), 7.94 (brs, 1H), 7.80 (brs, 1H), 7.78 (brs, 1H), 7.71 (brs, 1H), 7.68 (brs, 1H), 7.59 (brs, 1H), 7.46-7.35 (m, 4H). 5.47 (brs, 2H), 4.84 (brs, 1H), 4.69-4.54 (m, 3H), 4.43 (brs, 1H), 4.18-3.98 (m, 3H), 3.74-3.67 (m, 2H), 3.63-3.61 (m, 1H), 3.60-3.56 (m, 1H), 3.55-3.38 (m, 6H), 3.27-3.09 (m, 3H), 3.02-2.86 (m, 2H), 2.79 (t, J=7.1 Hz, 2H), 2.25-2.09 (m, 2H), 1.79-1.67 (m, 2H), 1.65-1.54 (m, 2H).

$^1$H NMR (400 MHz, $CD_3OD$) 7.79 (brs, 1H), 7.77 (brs, 1H), 7.74 (brs, 1H), 7.66 (brs, 1H), 7.40 (dt, J=6.8, 1.6 Hz, 2H), 4.24-4.12 (m, 3H), 3.86-3.82 (m, 2H), 3.80 (d, J=3.2 Hz, 1H), 3.77 (d, J=3.4 Hz, 1H), 3.74-3.63 (m, 6H0, 3.52-3.33 (m, 6H), 3.36 (t, J=6.9 Hz, 2H), 3.28-3.21 (m, 2H), 3.15-3.07 (m, 2H), 2.86 (t, J=7.1 Hz, 2H), 2.28-2.04 (m, 2H), 1.90-1.80 (m, 2H), 1.79-1.70 (m, 2H).

Preparation of 1,4-tetralinyl tyrosine derivatives
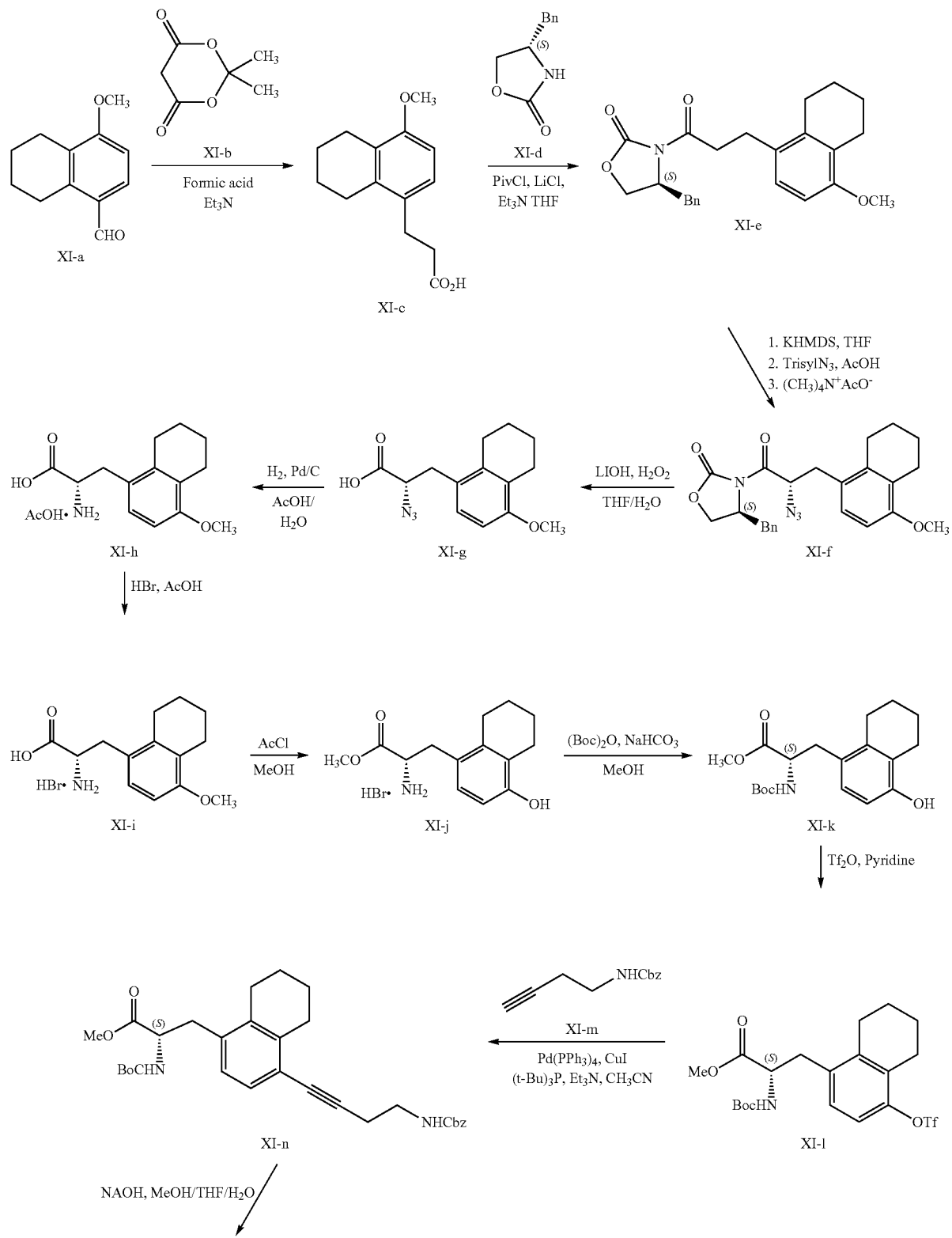
Scheme XI 3,5-diamino-N-(N-(4-(4-((S)-3-amino-2-(3-(bis((2S,3R,4R,5R)-2,3,4,5,6-pentahydroxyhexyl)amino)propylamino)-3-oxopropyl)-5,6,7,8-tetrahydronaphthalen-1-yl)butyl)carbamimidoyl)-6-chloropyrazine-2-carboxamide

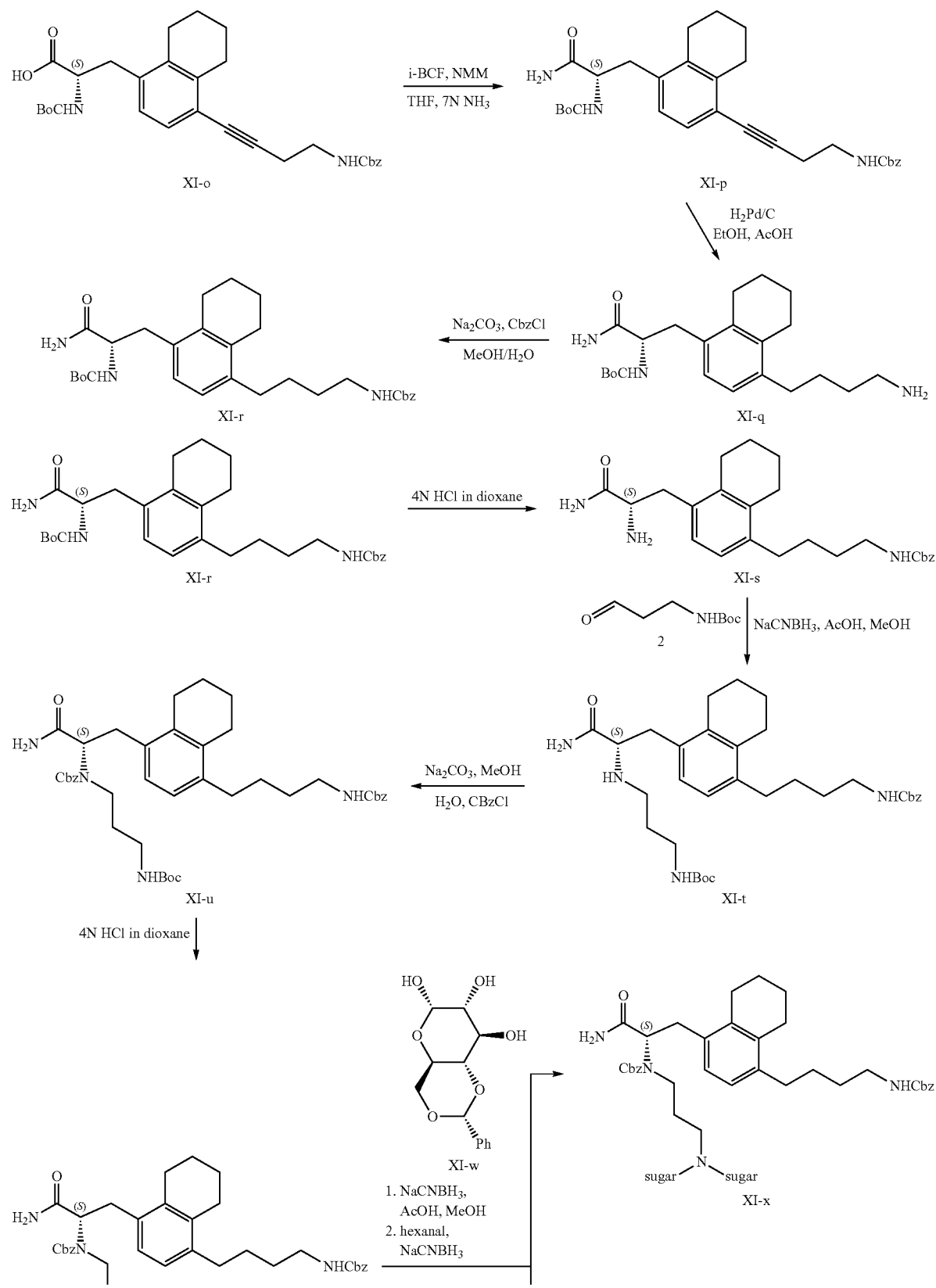
-continued

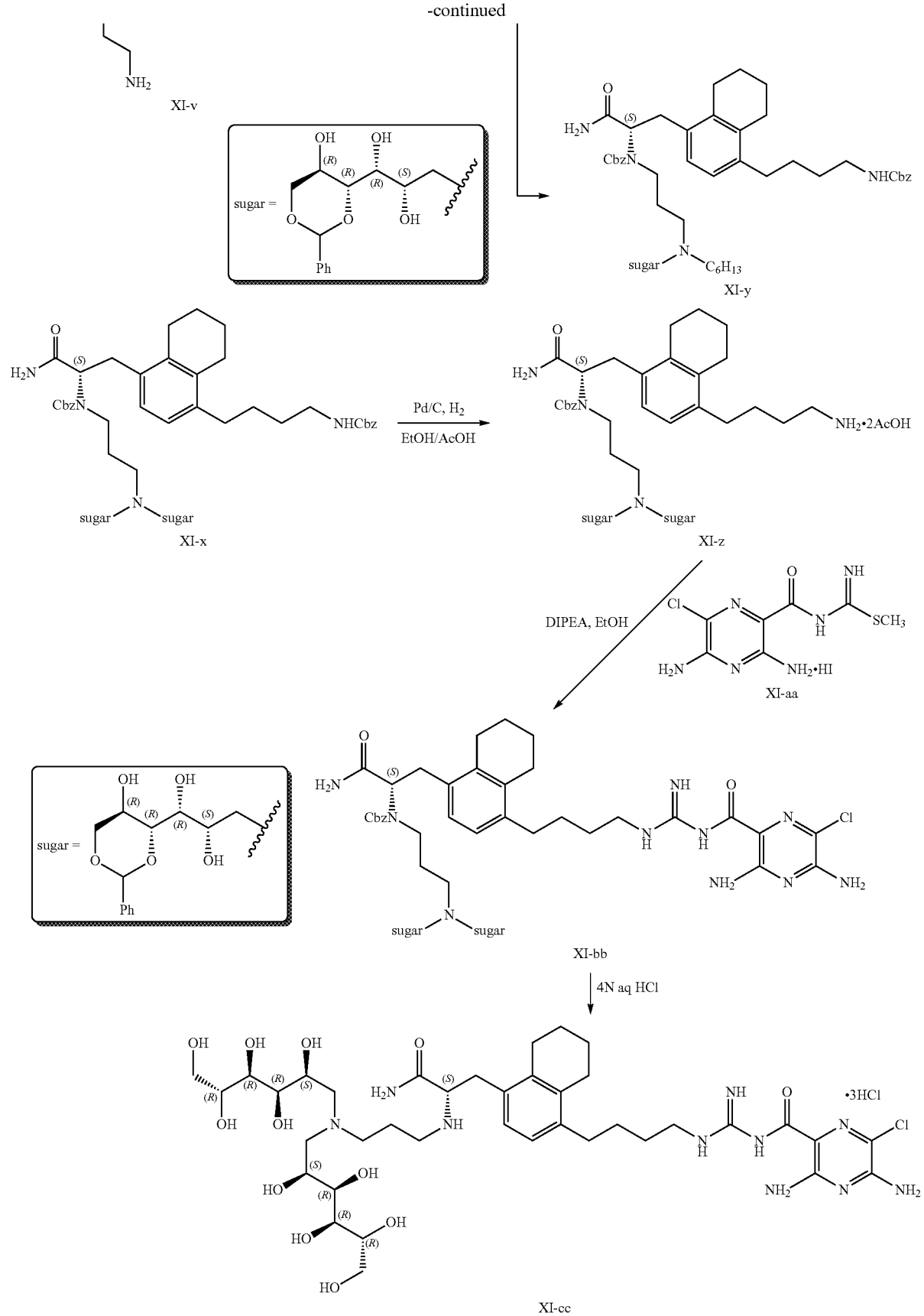

Preparation of Compound XI-c

TEA (340 mL) was added slowly to formic acid (150 mL) at 0° C. After the addition of TEA, compound XI-a (76.4 g, 401.6 mmol) and compound XI-b (59.2 g, 415.0 mL) were added. The reaction mixture was heated to reflux for 12 h, cooled down to room temperature, and poured into ice water (600 mL). The pH of the solution was adjusted to 11 by the addition of aqueous NaOH (70 g) in water (1.4 L). The resulting solution was extracted with EtOAc (600 mL for 3 times) and acidified to pH 2-3. The white precipitate was filtered and dried under vacuum at 50° C. to afford compound XI-c (74.6 g, 79%) as an off-white solid. $^1$H NMR (400 MHz, MeOD-d$_4$): δ 6.92 (d, J=8.4 Hz, 1H), 6.67 (dd, J=8.4 Hz, 8.4 Hz, 1H), 3.75 (s, 3H), 2.81 (t, J=7.6 Hz, 2H), 2.67 (t, J=6.0 Hz, 2H), 2.62 (t, J=6.0 Hz, 2H), 2.49 (t, J=7.6 Hz, 2H), 1.78-1.73 (m, 4H).

Preparation of Compound XI-e

A solution of compound XI-c (36 g, 153.8 mmol) in dry THF (400 mL) was charged with TEA (56 mL, 400.0 mmol) and pivaloyl chloride (22.7 mL, 184.6 mmol) dropwise at −10° C. The mixture was stirred for 40 min at −10° C. followed by the addition of compound XI-d (32.7 g, 184.6 mmol) and the solution of LiCl (8.5 g, 184.6 mmol) in THF (200 mL). The reaction mixture was warmed to room temperature, stirred for 12 h, quenched with saturated NaHCO$_3$, concentrated to remove THF, and partitioned between EtOAc (1000 mL) and water (1000 mL). The aqueous layer was separated and extracted with EtOAc (2×800 mL). The combined organic extracts were washed with brine, dried over Na$_2$SO$_4$ and concentrated. The residue was recrystallized from EtOAc/hexane (3:1, V/V) to afford compound XI-e (40.7 g, 78%) as a white solid. $^1$H NMR (400 MHz, CDCl$_3$): δ 7.32-7.25 (m, 3H), 7.20 (d, J=8.0 Hz, 1H), 7.02 (d, J=8.0 Hz, 1H), 6.63 (d, J=8.0 Hz, 1H), 4.68-4.62 (m, 1H), 4.18-4.16 (m, 2H), 3.79 (s, 3H), 3.31 (dd, J=13.6, 3.2 Hz, 1H), 3.23-3.16 (m, 2H), 2.95-2.91 (m, 2H), 2.78-2.71 (m, 3H), 2.66 (t, J=7.5 Hz, 2H), 1.80-1.75 (m, 4H).

Preparation of Compound XI-f

A solution of compound XI-e (25.0 g, 63.5 mmol) in dry THF (500 mL) was charged with KHMDS (18.0 g, 95.3 mmol) portionwise at −78° C. After the resulting mixture was stirred for 30 min, trisyl azide (25.0 g, 82.6 mmol) was added and the reaction mixture was stirred for 2-3 min. Acetic acid (19.1 g, 317.5 mmol) was added at the same temperature, followed by potassium acetate (31.0 g, 317.5 mmol). The reaction mixture was warmed to 27° C., stirred for 16 h, and quenched with brine (500 mL). The aqueous layer was separated and extracted with EtOAc (3×500 mL). The combined organic extracts were washed with saturated NaHCO$_3$ and brine, dried over Na$_2$SO$_4$, and concentrated. The residue was purified by column chromatography (silica gel, 90:10 hexane/EtOAc) to afford compound XI-f (15.0 g, 60%) as a colorless oil. $^1$H NMR (400 MHz, CDCl$_3$): δ 7.34-7.28 (m, 3H), 7.25-7.20 (m, 2H), 7.01 (d, J=8.4 Hz, 1H), 6.61 (d, J=8.4 Hz, 1H), 5.36 (t, J=7.6 Hz, 1H), 4.55-4.45 (m, 1H), 4.10 (dd, J=9.2, 2.4 Hz, 1H), 3.94 (t, J=8.4 Hz, 1H), 3.78 (s, 3H), 3.30 (dd, J=11.2, 3.2 Hz, 1H), 3.12 (dd, J=8.0, 2.4 Hz, 2H), 2.81-2.72 (m, 3H), 2.63 (t, J=6.4 Hz, 2H), 1.80-1.73 (m, 4H).

Preparation of Compound XI-g

A solution of compound XI-f (22.0 g, 50.6 mmol) in THF/H$_2$O (450 mL/150 mL) was charged with H$_2$O$_2$ (25 mL, 253 mmol) followed by LiOH (4.7 g, 111 mmol) portionwise at 0° C. The reaction mixture was stirred for 3 h at the same temperature, quenched with saturated Na$_2$SO$_3$ (300 mL), concentrated under reduced pressure to remove THF, and washed with CH$_2$Cl$_2$ (200 mL). The aqueous layer was acidified with 2 N aqueous HCl and extracted with CH$_2$Cl$_2$ (2×250 mL). The combined organic extracts were dried over Na$_2$SO$_4$ and concentrated to afford compound XI-g (11.0 g, 79%) as an off-white solid. The crude product was directly used for the next step without purification.

Preparation of Compound XI-h

A suspension of compound XI-g (10.0 g, 36.3 mmol) and 10% Pd/C (3.50 g) in AcOH/H$_2$O (200 mL/50 mL) was subjected to hydrogenation conditions (1 atm) for 12 h at room temperature. The reaction mixture was filtered through celite and washed with MeOH. The filtrate was concentrated under vacuum to afford acetic salt XI-h (8.0 g, 88%) as a yellow solid. The crude product was directly used for the next step without purification.

Preparation of Compound XI-i

A solution of compound XI-h (13.0 g, 52.3 mmol) in acetic acid (150 mL) was charged with 40% hydrobromic acid (150 mL) dropwise at room temperature and the reaction mixture was refluxed for 4 h. The reaction mixture was cooled to room temperature and concentrated. The residue was diluted with H$_2$O (15 mL), slightly basified with ammonia and crystallized overnight to afford compound XI-i (15.0 g, 90%) as a brown solid. The product was characterized by LC/MS and used for the next step without purification. ESI-MS m/z 236 [C$_{13}$H$_{17}$NO$_3$+H]$^+$.

Preparation of Compound XI-j

Acetyl chloride (26.0 g, 332 mmol) was added to dry methanol (210 mL) at 0° C. followed by compound XI-i (15.0 g, 47.4 mmol). The reaction mixture was refluxed for 4 h and concentrated. The residue was partitioned between CH$_2$Cl$_2$ (300 mL) and saturated NaHCO$_3$ (300 mL). The aqueous layer was separated and extracted with CH$_2$Cl$_2$ (2×300 mL). The combined organic extracts were dried over Na$_2$SO$_4$ and concentrated to afford compound XI-j (15.0 g, crude) as colorless oil. The crude product was characterized by LC/MS and used for the next step without purification. ESI-MS m/z 250 [C$_{14}$H$_{19}$NO$_3$+H]$^+$.

Preparation of Compound XI-k

A solution of compound XI-j (15.0 g, 47.0 mmol) in MeOH/H$_2$O (160 mL/160 mL) was charged with NaHCO$_3$ (17.0 g, 200.0 mmol) and Boc$_2$O (12.8 g, 60.0 mmol) at 0° C. The resulting mixture was allowed to warm to room temperature and stirred for 3 h. The reaction mixture was partitioned between CH$_2$Cl$_2$ (200 mL) and water (200 mL). The aqueous layer was separated and extracted with CH$_2$Cl$_2$ (2×200 mL). The combined organic extracts were washed with brine, dried over Na$_2$SO$_4$, and concentrated to give compound XI-k (9.0 g, 50% over three steps from compound XI-h) as a colorless oil. $^1$H NMR (400 MHz, CDCl$_3$): δ 6.77 (d, J=8.4 Hz, 1H), 6.55 (d, J=8.4 Hz, 1H), 4.95 (d, J=8.0 Hz, 1H), 4.70 (s, 1H), 4.50 (t, J=6.5 Hz, 1H), 3.69 (s, 3H), 3.42 (dd, J=14.0, 6.0 Hz, 1H), 2.89-2.84 (m, 1H), 2.68-2.63 (m, 4H), 1.79 (t, J=3.2 Hz, 4H), 1.40 (s, 9H).

Preparation of Compound XI-1

A solution of compound XI-k (9.40 g, 26.9 mmol) in pyridine (100 mL) was charged with triflate (11.4 g, 40.4 mmol) at 0° C., and the reaction mixture was stirred at room temperature for 2 h. After concentration, the reaction mixture was partitioned between $CH_2Cl_2$ (300 mL) and water (300 mL). The aqueous layer was separated and extracted with $CH_2Cl_2$ (2×300 mL). The combined organic extracts were washed with brine, dried over $Na_2SO_4$, and concentrated to afford compound XI-1 (9.10 g, 71%) as a brown oil. $^1H$ NMR and LC-MS data is consistent with product. $^1H$ NMR (400 MHz, $CDCl_3$): δ 7.29-7.26 (m, 2H), 5.04 (d, J=7.8 Hz, 1H), 4.56 (d, J=7.2 Hz, 1H), 3.68 (s, 3H), 3.12-3.04 (m, 1H), 2.95-2.90 (m, 1H), 2.80-2.73 (m, 4H), 1.83-1.79 (m, 4H), 1.38 (s, 9H).

Preparation of Compound XI-n

A solution of compound XI-1 (9.10 g, 18.9 mmol) in anhydrous $CH_3CN$ (100 mL) was charged with TEA (7.6 g, 75.6 mmol), $(t-Bu)_3P$ in hexanes (0.76 g, 3.78 mmol), benzyl but-3-ynylcarbamate (XI-m, 5.74 g, 28.3 mmol), and CuI (180 mg, 0.94 mmol) at room temperature. The resulting mixture was degassed with argon for 3 min and $Pd(PPh_3)_4$ (2.18 g, 1.89 mmol) was added rapidly in one portion. After degassing with argon for 5 min, the resulting mixture was refluxed for 4 h. The reaction mixture was concentrated under vacuum and the residue was purified by column to afford compound XI-n (7.50 g, 74% over two steps) as a brown oil. $^1H$ NMR and LC-MS data is consistent with product. $^1H$ NMR (300 MHz, $CDCl_3$): δ 7.36-7.25 (m, 5H), 7.15 (d, J=7.8 Hz, 1H), 6.83 (d, J=7.8 Hz, 1H), 5.12 (br s, 3H), 4.97 (d, J=7.6 Hz, 1H), 4.52 (d, J=6.8 Hz, 1H), 3.67 (s, 3H), 3.46-3.40 (m, 2H), 3.11-3.04 (m, 1H), 2.95-2.83 (m, 3H), 2.68-2.64 (m, 4H), 1.77-1.75 (m, 4H), 1.39 (s, 9H).

Preparation of Compound XI-o

A solution of methyl ester XI-n (7.50 g, 14.04 mmol) in $THF/MeOH/H_2O$ (50 mL/50 mL/25 mL) was charged with NaOH (1.12 g, 28.08 mmol) and the reaction mixture was stirred at room temperature for 1 h. The pH value was adjusted to 9 with 1 N aqueous HCl and the organic solvent was removed. The pH value of the residue was adjusted to 5, and the suspension was partitioned between $CH_2Cl_2$ (200 mL) and water (200 mL). The aqueous layer was separated and extracted with $CH_2Cl_2$ (2×200 mL). The combined organic extracts were dried over $Na_2SO_4$ and concentrated to afford compound XI-o (6.50 g, 90%) as a brown solid. $^1H$ NMR (400 MHz, DMSO-$d_6$): δ 7.44 (t, J=5.8 Hz, 1H), 7.33-7.28 (m, 5H), 7.15 (d, J=8.4 Hz, 1H), 7.09 (d, J=7.8 Hz, 1H), 6.99 (d, J=7.8 Hz, 1H), 5.02 (br s, 2H), 4.07-4.01 (m, 1H), 3.61-3.58 (m, 1H), 3.24-3.15 (m, 2H), 3.02-2.97 (m, 1H), 2.79-2.75 (m, 3H), 2.66-2.64 (m, 2H), 2.58 (t, J=7.0, Hz, 2H), 1.73-1.69 (m, 4H), 1.31 (s, 9H).

Preparation of Compound XI-p

A solution of acid XI-o (6.50 g, 12.5 mmol) in THF (200 mL) was charged with NMM (1.89 g, 18.75 mmol) and i-BCF (2.04 g, 15.0 mmol) at 0° C. The reaction mixture was stirred at the same temperature for 1 h and $NH_3$ (7.0 N in methanol, 29.4 mL, 206 mmol) was added dropwise. The reaction mixture continued to stir at 0° C. for 2 h, warmed to room temperature, and stirred for 1 h. After concentration, the residue was partitioned between $CH_2Cl_2$ (100 mL) and water (100 mL). The aqueous layer was separated and extracted with $CH_2Cl_2$ (2×100 mL). The combined organic extracts were dried over $Na_2SO_4$ and concentrated. The residue was washed with MTBE to afford amide XI-p (5.90 g, 70%) as a yellow solid. $^1H$ NMR (400 MHz, DMSO-$d_6$): δ 7.44 (t, J=5.8 Hz, 1H), 7.33-7.28 (m, 5H), 7.15 (d, J=8.4 Hz, 1H), 7.09 (d, J=7.8 Hz, 1H), 6.99 (d, J=7.8 Hz, 1H), 5.02 (s, 2H), 4.12-4.05 (m, 1H), 3.62-3.53 (m, 1H), 3.25-3.13 (m, 3H), 2.94-2.88 (m, 1H), 2.74-2.67 (m, 4H), 2.60 (t, J=7.0, Hz, 2H), 1.74-1.69 (m, 4H), 1.31 (s, 9H).

Preparation of Compound XI-q

A suspension of compound XI-p (5.90 g, 11.3 mmol) and 10% Pd/C (59 mg) in EtOH (100 mL)/AcOH (20 mL) was subjected to hydrogenation conditions (1 atm) for 16 h at room temperature. The reaction mixture was filtered through celite and washed with EtOH. The filtrate was concentrated under vacuum and washed with MTBE/hexanes to afford acetic salt XI-q (6.50 g, crude) as a colorless liquid. ESI-MS m/z 390 $[C_{22}H_{35}N_3O_3+H]^+$.

Preparation of Compound XI-r

A stirred solution of compound XI-q (6.50 g, crude) in MeOH (300 mL)/water (100 mL) was charged with $Na_2CO_3$ and CbzCl (4.20 g, 25.06 mmol) at 0° C. and stirred at the same temperature for 1 h. The reaction mixture was stirred for 1 h at room temperature and the solvent was removed and partitioned between $CH_2Cl_2$ (500 mL) and water (100 mL). The aqueous layer was separated and extracted with $CH_2Cl_2$ (2×100 mL). The combined organic extracts were washed with brine, dried over $Na_2SO_4$, and concentrated to afford compound XI-r (3.90 g, 66% over two steps) as a yellow solid. $^1H$ NMR (300 MHz, $CDCl_3$): δ 7.37-7.32 (m, 5H), 6.96-6.89 (m, 2H), 5.65 (br s, 1H), 5.29 (br s, 1H), 5.08 (s, 2H), 4.71-4.69 (m, 1H), 4.31-4.28 (m, 1H), 3.21 (t, J=6.2 Hz, 2H), 3.11-2.95 (m, 2H), 2.74 (br s, 2H), 2.67 (br s, 2H), 2.54 (br s, 2H), 1.73-1.69 (m, 4H), 1.40 (s, 9H).

Preparation of Compound XI-s

A solution of compound XI-r (3.90 g, 7.45 mmol) in dioxane was charged with 4 N HCl in dioxane (30 mL) and the reaction mixture was stirred for 4 h at room temperature. The solvent was removed under vacuum and the residue was washed with MTBE to afford compound XI-s (3.0 g, 95%) as a yellow oil. $^1H$ NMR (300 MHz, $CD_3OD$): δ 7.33-7.25 (m, 5H), 7.00-6.97 (m, 2H), 5.05 (s, 2H), 4.00-3.92 (m, 1H), 3.20-2.98 (m, 4H), 2.77-2.65 (m, 4H), 2.57 (br s, 2H), 1.81-1.77 (m, 4H), 1.55-1.54 (m, 4H).

Preparation of Compound XI-t

A solution of compound XI-s (3.0 g, 7.09 mmol) and aldehyde 2 (1.47 g, 8.51 mmol) in MeOH (100 mL) was charged with acetic acid (5.0 mL) and the reaction mixture was stirred at room temperature for 10 min. Sodium cyanoborohydride (670 mg, 10.63 mmol) was added and the solution continued to stir at room temperature for 1 h. Additional compound 2 (0.3 equiv), AcOH (0.5 equiv), and NaCNBH$_3$ (0.5 equiv) were added and stirred for 1 h. After concentration, the residue was partitioned between EtOAc (300 mL) and saturated NaHCO$_3$ (200 mL). The aqueous layer was separated and extracted with EtOAc (2×300 mL). The combined organic extracts were dried over Na$_2$SO$_4$ and concentrated. The residue XI-t (3.50 g, crude) was directly used for the next step without further purification.

Preparation of Compound XI-u

A solution of compound XI-t [3.50 g, crude in MeOH/H$_2$O (100 mL/50 mL)] was charged with saturated Na$_2$CO$_3$ at 0° C. and the solution was stirred for 10 min. Benzyl chloroformate (1.53 g, 9.05 mmol) was added dropwise and the reaction mixture was stirred for 1 h at 0° C., warmed to room temperature, and stirred for 1 h. After concentration, the residue was dissolved in CH$_2$Cl$_2$ (200 mL), then washed with water (300 mL) and brine (300 mL). The organic layer was dried over Na$_2$SO$_4$ and concentrated and purified by column to afford XI-u (3.20 g, 65% over two steps) as a yellow oil. $^1$H NMR (300 MHz, CD$_3$OD): δ 7.32-7.26 (m, 13H), 6.91-6.73 (m, 3H), 5.15-4.95 (m, 4H), 4.48-4.31 (m, 1H), 3.63-3.51 (m, 1H), 3.17-3.03 (m, 9H), 2.87-2.67 (m, 4H), 2.57 (br s, 7H), 1.76-1.63 (m, 7H), 1.53-1.52 (m, 6H), 1.48-1.39 (br s, 20H).

Preparation of Compound XI-v

Compound XI-u (3.20 g, 4.48 mmol) was dissolved in 4 N HCl in dioxane (50 mL) at room temperature and the solution was stirred for 2 h. After concentration, the residue was washed with MTBE to afford compound XI-v (2.50 g, 92%) as an off-white solid. $^1$H NMR (300 MHz, CD$_3$OD): δ 7.33-7.28 (m, 9H), 6.92-6.73 (m, 2H), 5.12-4.99 (m, 4H), 4.57-4.52 (m, 1H), 3.71-3.60 (m, 1H), 3.20-3.03 (m, 7H), 2.81-2.53 (m, 8H), 1.89-1.71 (m, 6H), 1.53 (br s, 4H).

Preparation of Compounds XI-x and XI-y

A solution of compound XI-v (2.50 g, 4.07 mmol) and triol XI-w (2.18 g, 8.14 mmol) in methanol (10 mL) was charged with acetic acid (2.5 mL) and the reaction mixture was stirred at room temperature for 10 min. Sodium cyanoborohydride (370 mg, 6.15 mmol) was added and the solution continued to stir at room temperature for 24 h. Additional compound XI-w (2.0 equiv), AcOH (10 equiv), and NaCNBH$_3$ (1.5 equiv) were added and the solution continued to stir at room temperature for 24 h. Hexanal (2.00 mL, 20.3 mmol), AcOH (1.10 mL), and NaCNBH$_3$ (370 mg, 6.15 mmol) were added and the reaction mixture was stirred for 2 h. After concentration, the residue was partitioned between EtOAc (300 mL) and saturated NaHCO$_3$ (200 mL). The aqueous layer was separated and extracted with EtOAc (2×300 mL). The combined organic extracts were dried over Na$_2$SO$_4$ and concentrated. The residue was purified by C18 reverse phase Gold column to afford compound XI-x (310 mg, 7%) and compound XI-y (510 mg, 14%) as white solids. $^1$H NMR for compound XI-x (400 MHz, CD$_3$OD): δ 7.44 (br s, 5H), 7.32-7.28 (m, 16H), 6.83-6.77 (m, 2H), 5.53-5.45 (m, 2H), 5.18-5.04 (m, 4H), 4.45 (br s, 1H), 4.23-4.14 (m, 2H), 3.97-3.91 (m, 6H), 3.83 (br s, 6H), 3.69 (br s, 2H), 3.58 (t, J=8.0 Hz, 2H), 3.17-3.04 (m, 5H), 2.76-2.51 (m, 12H), 1.79-1.64 (m, 4H), 1.50 (br s, 6H). $^1$H NMR for compound XI-y (400 MHz, CD$_3$OD): δ 7.45 (br s, 2H), 7.34-7.26 (m, 14H), 6.79-6.75 (m, 2H), 5.50 (br s, 1H), 5.05 (m, 4H), 4.55-4.44 (m, 1H), 4.25-4.21 (m, 1H), 3.98-3.92 (m, 3H), 3.75-3.57 (m, 3H), 3.20-3.29 (m, 6H), 2.66-2.45 (m, 10H), 1.75-1.67 (m, 5H), 1.53 (br s, 6H), 1.28-1.18 (m, 10H), 0.86 (t, J=7.0 Hz, 3H).

Preparation of Compound XI-z

A suspension of XI-x (310 mg, 0.273 mmol) and 10% Pd/C (30 mg) in EtOH/AcOH (50 mL/10 mL) was subjected to hydrogenation conditions (1 atm) for 16 h at room temperature. The reaction mixture was filtered through celite and washed with EtOH. The filtrate was concentrated under vacuum and precipitated from MTBE/hexanes to afford compound XI-z (205 mg, 87%) as a colorless oil. $^1$H NMR (400 MHz, CD$_3$OD): δ 7.47-7.43 (m, 4H), 7.32-7.27 (m, 6H), 6.93-6.89 (m, 2H), 5.52 (s, 2H), 4.27-4.15 (m, 4H), 3.99-3.86 (m, 4H), 3.76-3.73 (m, 2H), 3.16-3.09 (m, 3H), 3.02-2.82 (m, 6H), 2.78-2.69 (m, 7H), 2.59 (t, J=7.6 Hz, 2H), 1.80-1.71 (m, 5H), 1.69-1.53 (m, 5H).

Preparation of Compound XI-bb

A solution of compound XI-z (205 mg, 0.205 mmol) and methyl 3,5-diamino-6-chloropyrazine-2-carbonylcarbamimidothioate hydroiodic acid salt (XI-aa, 85 mg, 0.328 mmol) in EtOH (25 mL) was charged with DIPEA (211 mg, 1.64 mmol) at room temperature. The reaction mixture was heated at 70° C. in a sealed tube for 2 h, cooled to room temperature, and concentrated in vacuo. The residue was purified by column chromatography (silica gel, 10:1 CH$_2$Cl$_2$/MeOH, 8:2:0.2 CHCl$_3$/CH$_3$OH/NH$_4$OH) to afford compound XI-bb (160 mg, 63%) as a yellow solid. $^1$H NMR (300 MHz, CD$_3$OD): δ 7.46-7.42 (m, 4H), 7.30-7.28 (m, 6H), 6.89 (br s, 2H), 5.47 (s, 2H), 4.24-4.19 (m, 2H), 3.99-3.83 (m, 6H), 3.71-3.53 (m, 5H), 2.83-2.73 (m, 6H), 2.64-2.52 (m, 8H), 1.77 (br s, 4H), 1.66-1.55 (m, 6H).

Preparation of the Hydrochloride Salt of 3,5-diamino-N—(N-(4-(4-((S)-3-amino-2-(3-(bis((2S,3R,4R,5R)-2,3,4,5,6-pentahydroxyhexyl)amino)propylamino)-3-oxopropyl)-5,6,7,8-tetrahydronaphthalen-1-yl)butyl)carbamimidoyl)-6-chloropyrazine-2-carboxamide (Compound XI-cc)

A solution of compound XI-bb (160 mg, 0.134 mmol) in 4 N aqueous HCl (5.0 mL) was stirred at room temperature for 3 h. The solvent was removed and the residue was purified by C18 reverse phase Gold column to afford compound XI-cc (75 mg, 56%) as a yellow hygroscopic solid. $^1$H NMR (400 MHz, CD$_3$OD): δ 6.99 (s, 2H), 4.22-4.18 (m, 2H), 3.97-3.91 (m, 1H), 3.85-3.64 (m, 11H), 3.50-3.35 (m, 10H), 3.12-3.06 (m, 4H), 2.80-2.75 (m, 4H), 2.63 (t, J=7.8 Hz, 2H), 2.20 (br, s, 2H), 1.81-1.64 (m, 8H).

Scheme XII
3,5-diamino-N-(N-(4-((S)-3-amino-2-(3-(hexyl((2S,3R,4R,5R)-2,3,4,5,6-pentahydroxyhexyl)amino)propylamino)-3-oxopropyl)-5,6,7,8-tetrahydronaphthalen-1-yl)butyl)carbamimidoyl)-6-chloropyrazine-2-carboxamide
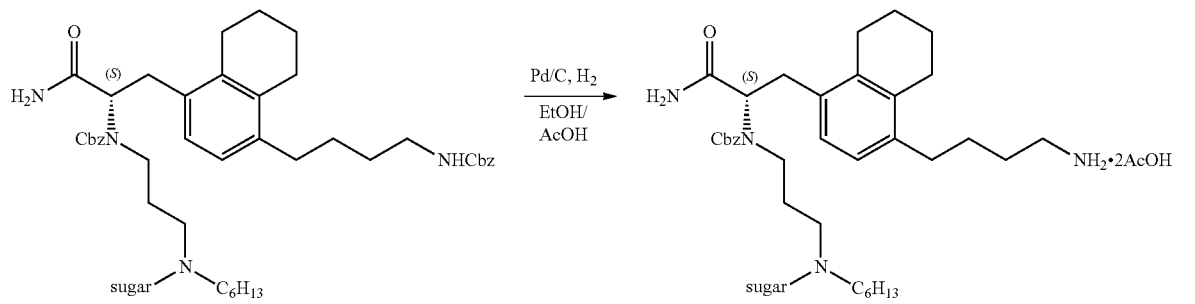
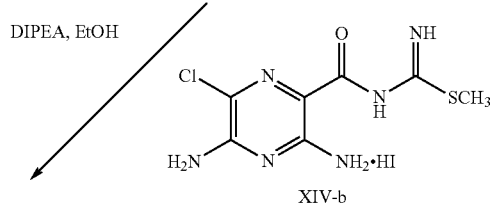
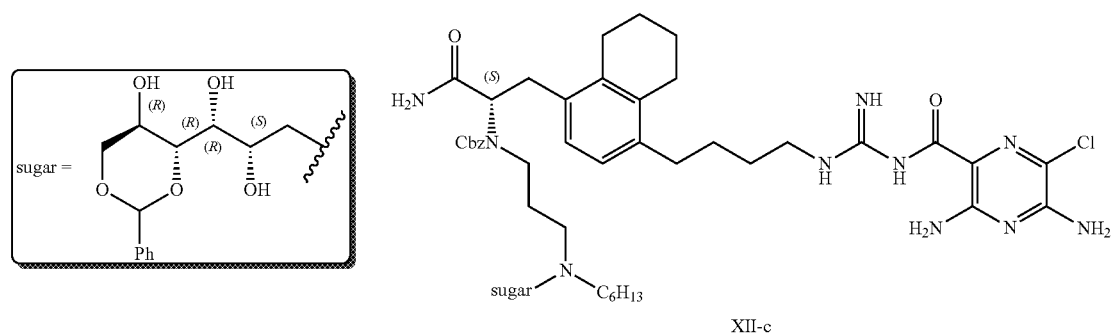
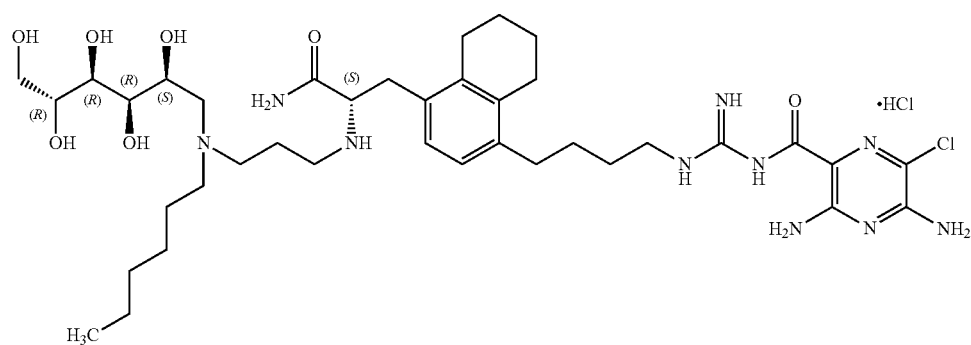

Preparation of Compound XII-a

A suspension of XI-y (510 mg, 0.529 mmol) and 10% Pd/C (150 mg) in EtOH/AcOH (50 mL/10 mL) was subjected to hydrogenation conditions (1 atm) for 16 h at room temperature. The reaction mixture was filtered through celite and washed with EtOH. The filtrate was concentrated under vacuum and precipitated from MTBE/hexanes to afford compound XII-a (290 mg, 85%) as a colorless oil. $^1$H NMR (300 MHz, CD$_3$OD): δ 7.49-7.46 (m, 2H), 7.33-7.31 (m, 3H), 6.93 (br s, 2H), 5.57 (s, 1H), 4.29-4.14 (m, 2H), 4.03-3.94 (m, 2H), 3.81-3.57 (m, 2H), 3.25-3.15 (m, 6H), 3.09-2.83 (m, 7H), 2.72-2.57 (m, 8H), 1.80-1.55 (m, 12H), 1.31-1.25 (m, 16H), 0.89 (t, J=6.6 Hz, 3H).

Preparation of Compound XII-c

A solution of compound XII-a (290 mg, 0.349 mmol) and methyl 3,5-diamino-6-chloropyrazine-2-carbonylcarbamimidothioate hydroiodic acid salt (XII-b, 145 mg, 0.560 mmol) in EtOH (25 mL) was charged with DIPEA (360 mg, 2.79 mmol) at room temperature. The reaction mixture was heated at 70° C. in a sealed tube for 2 h, cooled to room temperature, and concentrated in vacuo. The residue was purified by column chromatography (silica gel, 10:1 CH$_2$Cl$_2$/MeOH, 8:2:0.2 CHCl$_3$/CH$_3$OH/NH$_4$OH) to afford compound XII-c (250 mg, 65%) as a yellow solid. $^1$H NMR (300 MHz, CD$_3$OD): δ 7.45-7.44 (m, 2H), 7.30-7.28 (m, 3H), 6.91 (br s, 2H), 5.51 (s, 1H), 5.47 (s, 1H), 4.26-4.21 (m, 1H), 4.00-3.86 (m, 3H), 3.76-3.53 (m, 2H), 3.27-3.22 (m, 3H), 2.93-2.67 (m, 7H), 2.62-2.32 (m, 9H), 1.78 (br s, 4H), 1.67-1.50 (m, 6H), 1.36-1.11 (m, 8H), 0.86 (t, J=6.6 Hz, 3H).

Preparation of the Hydrochloride Salt of 3,5-diamino-N—(N-(4-(4-((S)-3-amino-2-(3-(hexyl((2S,3R,4R,5R)-2,3,4,5,6-pentahydroxyhexyl)amino)propylamino)-3-oxopropyl)-5,6,7,8-tetrahydronaphthalen-1-yl)butyl)carbamimidoyl)-6-chloropyrazine-2-carboxamide (Compound XII-d)

A solution of compound XII-c (250 mg, 0.267 mmol) in 4 N aqueous HCl (5.0 mL) was stirred at room temperature for 3 h. The solvent was removed and the residue was purified by C18 reverse phase Gold column to afford compound XII-d (125 mg, 55%) as a yellow hygroscopic solid. $^1$H NMR (400 MHz, CD$_3$OD): δ 6.98 (s, 2H), 4.18-4.14 (m, 1H), 3.84-3.76 (m, 2H), 3.71-3.64 (m, 4H), 3.38-3.35 (m, 4H), 3.23-2.99 (m, 7H), 2.80-2.75 (m, 4H), 2.63 (t, J=7.8 Hz, 2H), 2.15-2.09 (m, 2H), 1.81-1.64 (m, 10H), 1.38 (br, s, 6H), 0.93 (t, J=7.0 Hz, 3H).

Preparation of 2,6-naphthyl homotyrosine derivatives

Scheme XIII
3,5-diamino-N-(N-(4-(6-((S)-4-amino-3-(bis((2S,3R,4R,5R)-2,3,4,5,6-pentahydroxyhexyl)amino)propylamino)-4-oxobutyl)naphthalen-2-yl)butyl)carbamimidoyl)-6-chloropyrazine-2-carboxamide

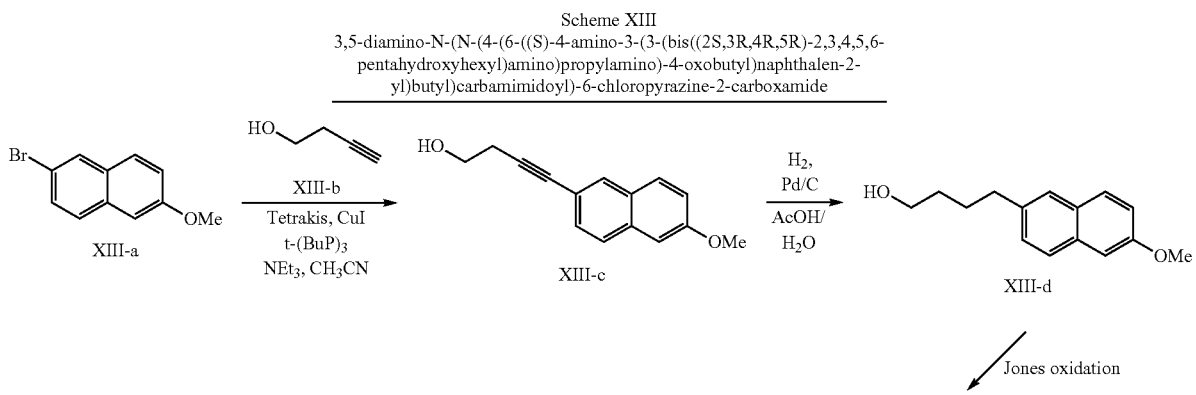

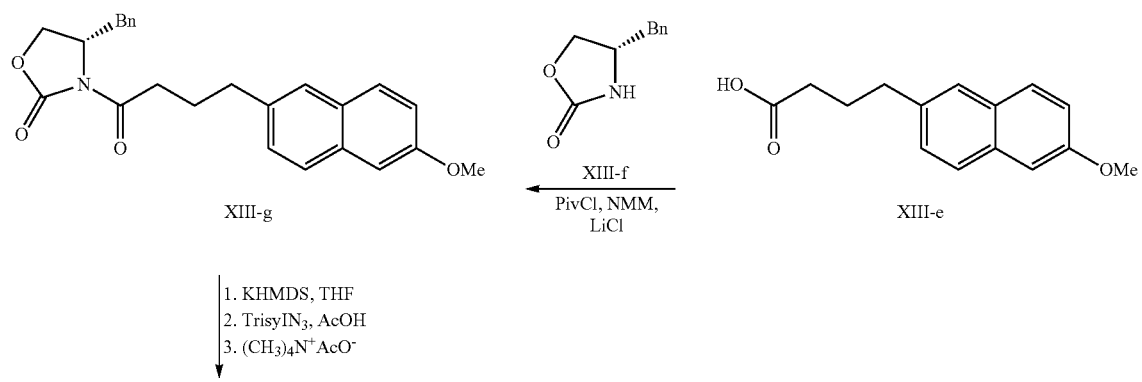

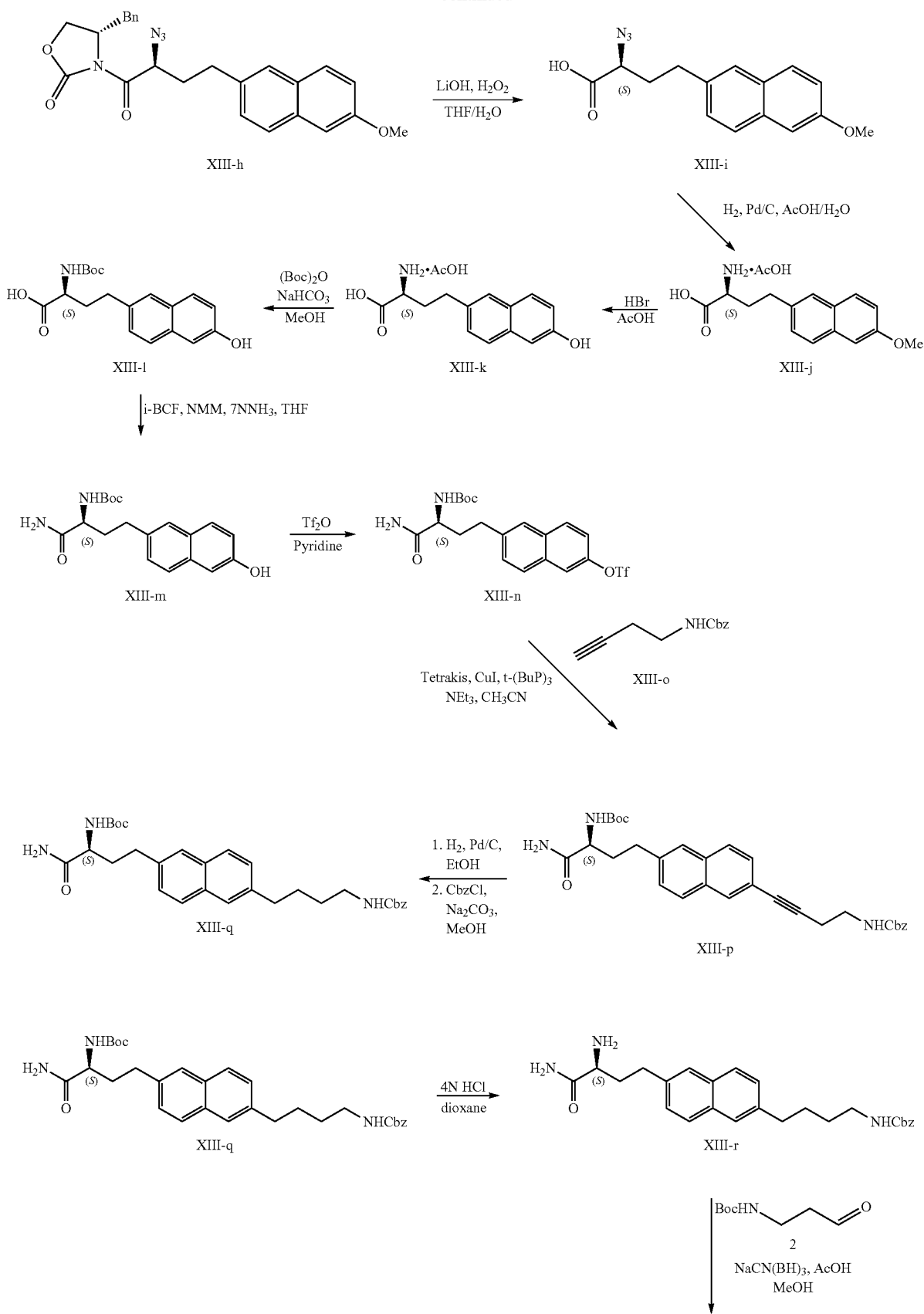

-continued
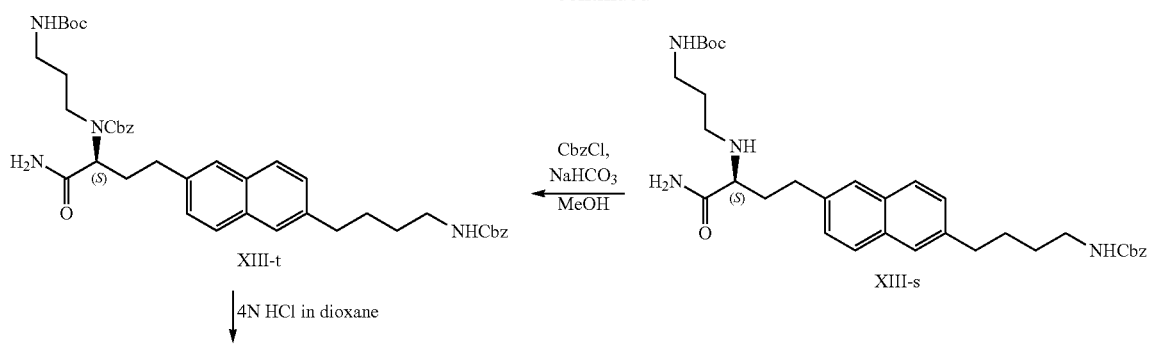
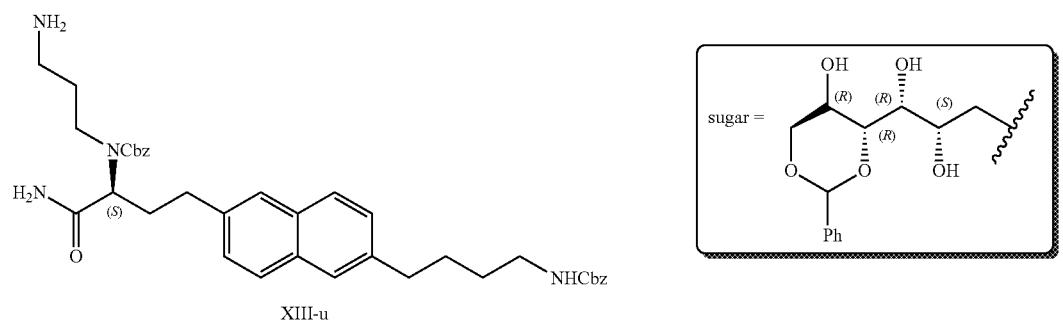
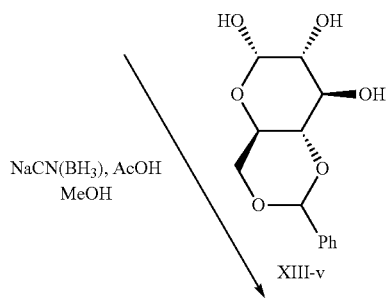
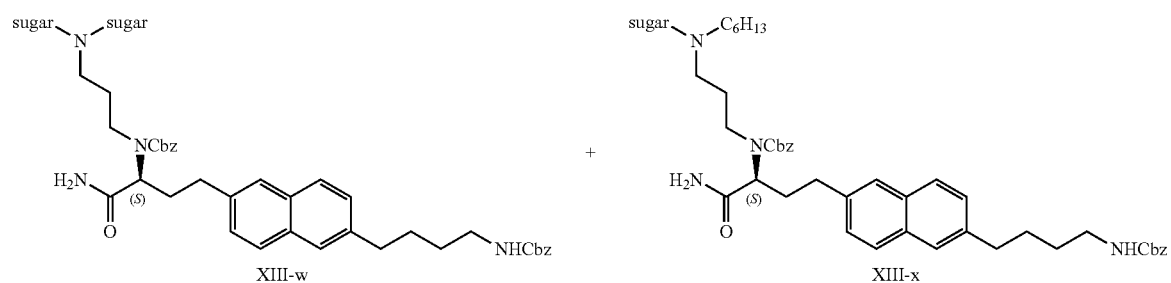

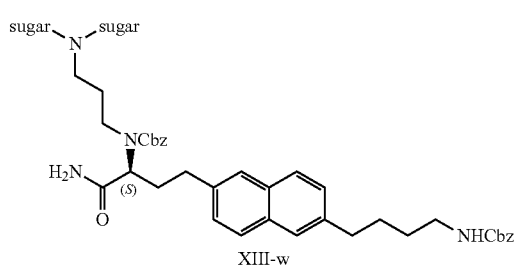

XIII-w

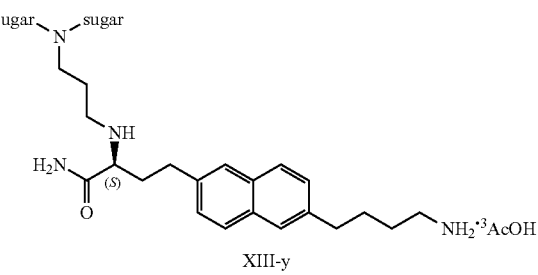

XIII-y

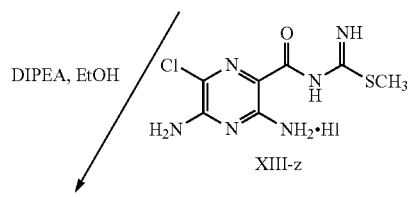

XIII-z

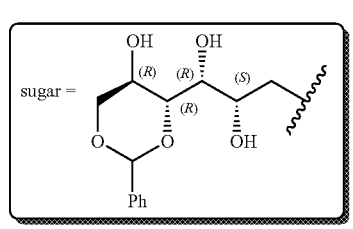

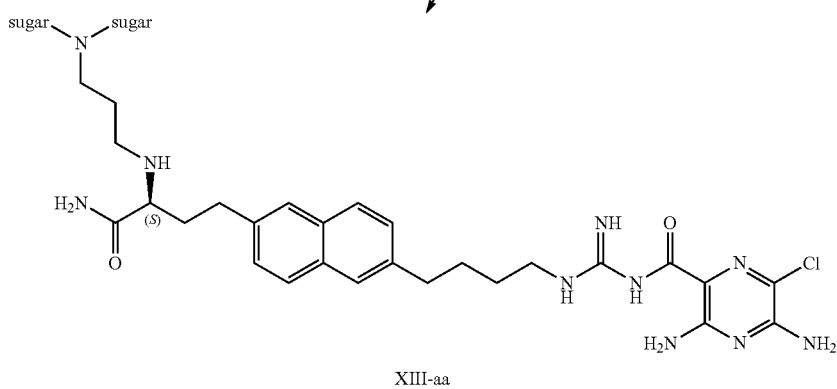

XIII-aa

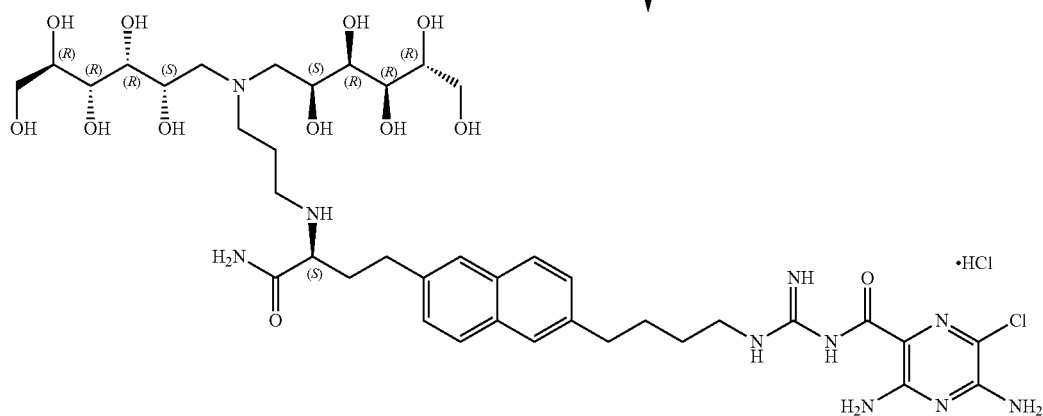

XIII-bb

Preparation of Compound XIII-c

A solution of compound XIII-a (10.0 g, 42.1) in anhydrous CH₃CN (200 mL) was charged with TEA (17.0 g, 168.7 mmol), 10% (t-Bu)₃P in hexanes (1.70 g, 8.42 mmol), but-3-yn-1-ol (XIII-b, 4.42 g, 63.1 mmol), and CuI (400 mg, 2.10 mmol) at room temperature. The resulting mixture was degassed with argon for 3 min and Pd(PPh₃)₄ (4.86 g, 4.21 mmol) was added rapidly in one portion. After degassing with argon for 5 min, the resulting mixture was refluxed for 4 h. The reaction mixture was concentrated under vacuum and the residue was purified by column (silica gel, 80:20 hexanes/EA) to afford compound XIII-c (7.20 g, 76%) as a yellow solid. $^1$H NMR and LC-MS data is consistent with product. $^1$H NMR (300 MHz, CDCl₃): δ 7.85 (br s, 1H), 7.68-7.63 (m, 2H), 7.44-7.40 (m, 1H), 7.16-7.08 (m, 2H), 3.87-3.81 (m, 2H), 3.91 (s, 3H), 2.73 (t, J=6.2 Hz, 2H), 1.85 (t, J=6.2 Hz, 2H).

Preparation of Compound XIII-d

A suspension of compound XIII-c (7.20 g, 31.7 mmol) and 10% Pd/C (2.16 g) in EtOH (50 mL)/AcOH 10 mL) was subjected to hydrogenation conditions (1 atm) for 16 h at room temperature. The reaction mixture was filtered through celite and washed with EtOH. The filtrate was concentrated under vacuum, basified with saturated $Na_2CO_3$, and extracted with ethyl acetate. The organic layer was washed with water and brine, and the organic phase was concentrated under reduced pressure to afford XIII-d (5.20 g, 71%) as an yellow solid, which was directly used for the next step. $^1H$ NMR and LC-MS data is consistent with product. $^1H$ NMR (300 MHz, $CDCl_3$): δ 7.65 (d, J=8.4 Hz, 2H), 7.53 (br s, 1H), 7.30-7.25 (m, 2H), 7.12-7.10 (m, 2H), 3.90 (s, 3H), 3.67 (t, J=6.4 Hz, 2H), 2.77 (t, J=7.2 Hz, 2H), 1.82-1.70 (m, 2H), 1.68-1.58 (m, 2H).

Preparation of Compound XIII-e

A stirred solution of compound XIII-d (5.20 g, 22.5 mmol) in acetone (100 mL) was charged with freshly prepared Jones reagent (1.3 equiv) dropwise at room temperature. The reaction mixture was stirred for another 30 min at room temperature and Jones reagent (0.5 equiv) was added to complete the reaction. The acetone was decanted from the reaction mixture and the solid chromium salts were washed with excess acetone. The acetone layers were combined, quenched with IPA, and concentrated under reduced pressure to get crude solid. This solid was purified by acid/base treatment to afford pure compound XIII-e (4.20 g, 76%) as off-white solid. $^1H$ NMR and LC-MS data is consistent with product. $^1H$ NMR (300 MHz, DMSO-$d_6$): δ 12.04 (s, 1H), 7.76-7.72 (m, 2H), 7.59 (br s, 1H), 7.33-7.26 (m, 2H), 7.14-7.10 (m, 1H), 3.85 (s, 3H), 2.71 (t, J=7.4 Hz, 2H), 2.24 (t, J=7.4 Hz, 2H), 1.92-1.82 (m, 2H).

Preparation of Compound XIII-g

A solution of compound XIII-e (4.20 g, 17.1 mmol) in dry THF (50 mL) was charged with triethylamine (4.30 g, 42.8 mmol) and pivaloyl chloride (2.46 g, 20.5 mmol) followed by lithium chloride (860 mg, 20.5 mmol). Compound XIII-f (3.6 g, 20.5 mmol) was added at −25° C., and the reaction mixture was stirred for 2 hours at room temperature. After completion of the reaction, the reaction mixture was evaporated and the residue was triturated with 1N NaOH. The aqueous layer was separated and extracted with dichloromethane (2×500 mL). The combined organic extracts were dried over $Na_2SO_4$ and concentrated. The residue was purified by MTBE and hexane washings to afford compound XIII-g (5.50 g, 79%) as an off-white solid. $^1H$ NMR and LC-MS data is consistent with product. $^1H$ NMR (400 MHz, $CDCl_3$): δ 7.77-7.63 (m, 2H), 7.58 (br s, 1H), 7.33-7.23 (m, 5H), 7.18-7.16 (m, 2H), 7.13-7.10 (m, 2H), 4.62-4.56 (m, 1H), 4.12-4.07 (m, 2H), 3.26-3.22 (m, 1H), 3.08-2.94 (m, 2H), 2.86-2.82 (m, 2H), 2.72-2.66 (m, 1H), 2.15-2.07 (m, 2H).

Preparation of Compound XIII-h

A solution of compound XIII-g (11.2 g, 27.79 mmol) in dry THF (300 mL) was charged with KHMDS (7.18 g, 36.1 mmol) portionwise at −78° C. After the resulting mixture was stirred for 30 min, trisyl azide (12.8 g, 41.68 mmol) was added and the reaction mixture was stirred for 2-3 min. Acetic acid (10.0 g, 166.7 mmol) was added slowly at the same temperature, followed by tetramethylammonium acetate (14.7 g, 111.1 mmol). The mixture was warmed to 27° C., stirred for 4 h, quenched with saturated $NaHCO_3$ (300 mL), concentrated to remove THF, and extracted with EtOAc (2×500 mL). The combined organic extracts were dried over $Na_2SO_4$ and concentrated. The residue was purified by column chromatography (silica gel, 70:30 hexane/EtOAc) to afford compound XIII-h (8.10 g, 65%) as a colorless oil, which was directly used for the next step. LC-MS data is consistent with product.

Preparation of Compound XIII-i

A solution of compound XIII-h (8.10 g, 18.2 mmol) in THF/$H_2O$ (100 mL/25 mL) was charged with $H_2O_2$ (3.7 g, 109.2 mmol) followed by LiOH (1.56 g, 36.4 mmol) portionwise at 0° C. The reaction mixture was stirred for 1 h at the same temperature, quenched with saturated $Na_2SO_3$ (200 mL), concentrated under reduced pressure to remove THF, and washed with $CH_2Cl_2$ (200 mL). The aqueous layer was acidified with 1 N aqueous HCl and extracted with $CH_2Cl_2$ (2×250 mL). The combined organic extracts were dried over $Na_2SO_4$, concentrated, and washed with MTBE to afford compound XIII-i (4.10 g, 80%) as an off-white solid, which was directly used for the next step. LC-MS data is consistent with product.

Preparation of Compound XIII-j

A suspension of compound XIII-i (4.10 g, 14.3 mmol) and 10% Pd/C (410 Mg) in AcOH/$H_2O$ (50 mL/15 mL) was subjected to hydrogenation conditions (1 atm) for 3 h at room temperature. The reaction mixture was filtered through celite and washed with MeOH. The filtrate was concentrated under vacuum to afford acetic salt XIII-j (3.40 g, 91%) as a white solid, which was directly used for the next step. LC-MS data is consistent with product.

Preparation of Compound XIII-k

A solution of compound XIII-j (3.40 g, 13.1 mmol) in acetic acid (30 mL) was charged with hydrobromic acid (30 mL) dropwise at room temperature and the reaction mixture was refluxed for 4 h. The reaction mixture was cooled to room temperature and concentrated. The residue was concentrated under reduced pressure to afford compound XIII-k (2.60 g, 81%) as a brown solid. $^1H$ NMR and LC-MS data is consistent with product. $^1H$ NMR (400 MHz, $CD_3OD$): δ 7.72-7.59 (m, 3H), 7.45-7.27 (m, 1H), 7.19-7.03 (m, 1H), 4.01 (t, J=5.8 Hz, 1H), 2.99-2.81 (m, 2H), 2.38-2.14 (m, 2H).

Preparation of Compound XIII-l

A solution of compound XIII-k (13.8 g, 56.3 mmol) in MeOH/$H_2O$ (160 mL/100 mL) was charged with $NaHCO_3$ (4.50 g, 112.6 mmol) and $Boc_2O$ (14.7 g, 67.5 mmol) at 0° C. The resulting mixture was warmed to room temperature and stirred for 3 h. The reaction mixture was partitioned between $CH_2Cl_2$ (200 mL) and water (200 mL). The aqueous layer was separated and extracted with $CH_2Cl_2$ (2×200 mL). The combined organic extracts were washed with brine, dried over $Na_2SO_4$, and concentrated to give compound XIII-l (14.0 g, 73%) as a white solid. $^1H$ NMR and LC-MS data is consistent with product. $^1H$ NMR (400 MHz, DMSO-$d_6$): δ 12.43 (br s, 1H), 9.58 (br s, 1H), 7.66-7.58 (m, 2H), 7.52 (br s, 1H), 7.26-7.21 (m, 2H), 7.07-7.02 (m, 2H), 3.88-3.82 (m, 1H), 2.79-2.64 (m, 2H), 2.01-1.86 (m, 2H), 1.40 (s, 9H).

Preparation of Compound XIII-m

A solution of acid XIII-l (13.7 g, 39.7 mmol) in THF (150 mL) was charged with DIPEA (7.68 g, 59.5 mmol) and $T_3P$ (18.9 g, 59.5 mmol) at 0° C. The reaction mixture was stirred at the same temperature for 1 h and $NH_3$ (7.0 N in methanol, 29.4 mL, 206 mmol) was added dropwise. The reaction mixture was stirred at 0° C. for 1 h, warmed to room temperature, and stirred for 1 h. After concentration, the residue was partitioned between $CH_2Cl_2$ (100 mL) and water (100 mL). The aqueous layer was separated and extracted with $CH_2Cl_2$ (2×100 mL). The combined organic extracts were dried over $Na_2SO_4$ and concentrated. The residue was washed with MTBE to afford amide XIII-m (7.20 g, 53%) as a pale yellow solid. $^1$H NMR and LC-MS data is consistent with product. $^1$H NMR (300 MHz, DMSO-$d_6$): δ 9.60 (s, 1H), 7.66-7.51 (m, 3H), 7.28-7.16 (m, 4H), 7.06-6.94 (m, 4H), 6.15 (br s, 1H), 3.90-3.82 (m, 1H), 2.84-2.58 (m, 2H), 1.98-1.80 (m, 2H), 1.40 (s, 9H).

Preparation of Compound XIII-n

A solution of compound XIII-m (7.20 g, 20.9 mmol) in pyridine (70 mL) was charged with triflate (8.90 g, 31.3 mmol) at 0° C., and the reaction mixture was stirred at room temperature for 1 h. After concentration, the reaction mixture was partitioned between $CH_2Cl_2$ (300 mL) and water (300 mL). The aqueous layer was separated and extracted with $CH_2Cl_2$ (2×300 mL). The combined organic extracts were washed with brine, dried over $Na_2SO_4$, and concentrated to afford compound XIII-n (6.80 g, 69%) as a brown solid, which was directly used for the next step. LC-MS data is consistent with product.

Preparation of Compound XIII-p

A solution of compound XIII-n (6.80 g, 14.2) in anhydrous $CH_3CN$ (150 mL) was charged with TEA (5.7 g, 57.1 mmol), 10% (t-Bu)$_3$P in hexanes (0.57 g, 2.84 mmol), benzyl but-3-ynylcarbamate (XIII-o, 4.30 g, 21.5 mmol), and CuI (134 mg, 0.71 mmol) at room temperature. The resulting mixture was degassed with argon for 3 min and Pd(PPh$_3$)$_4$ (1.60 g, 1.42 mmol) was added rapidly in one portion. After degassing with argon for 5 min, the resulting mixture was refluxed for 4 h. The reaction mixture was concentrated under vacuum and the residue was purified by column (silica gel, 80:20 hexanes/EA) to afford compound XIII-p (4.50 g, 60%) as a brown solid. $^1$H NMR and LC-MS data is consistent with product. $^1$H NMR (300 MHz, CD$_3$OD): δ 7.83 (s, 1H), 7.72-7.60 (m, 3H), 7.43-7.24 (m, 7H), 5.10 (s, 2H), 4.04 (br s, 1H), 3.37 (t, J=6.8 Hz, 2H), 2.85-2.75 (m, 2H), 2.64 (t, J=6.8 Hz, 2H), 2.20-1.90 (m, 2H), 1.45 (s, 9H).

Preparation of Compound XIII-q

A suspension of compound XIII-p (4.50 g, 8.50 mmol) and 10% Pd/C (135 mg) in EtOH (500 mL)/AcOH (10 mL) was subjected to hydrogenation conditions (1 atm) for 16 h at room temperature. The reaction mixture was filtered through celite and washed with EtOH. The filtrate was concentrated under vacuum and washed with MTBE/hexanes to afford acetic salt (4.20 g, crude) as an off-white solid, which was directly used for the next step. LC-MS data is consistent with product.

Preparation of Compound XIII-q

A stirred solution of crude compound from XIII-q (4.20 g, crude) in MeOH/$H_2O$ (100 mL/500 mL) was charged with saturated $Na_2CO_3$ and CbzCl (2.68 g, 15.7 mmol) at 0° C. and stirred at the same temperature for 1 h. The reaction mixture was stirred for 1 h at room temperature. The solvent was removed and the mixture was partitioned between $CH_2Cl_2$ (500 mL) and water (100 mL). The aqueous layer was separated and extracted with $CH_2Cl_2$ (2×100 mL). The combined organic extracts were washed with brine, dried over $Na_2SO_4$, and concentrated to afford compound XIII-q (2.80 g, 62% over two steps) as a yellow oil, which was directly used for the next step. LC-MS data is consistent with product.

Preparation of Compound XIII-r

A solution of compound XIII-q (2.80 g, 5.25 mmol) in dioxane was charged with 4 N HCl in dioxane (30 mL) and the reaction mixture was stirred for 4 h at room temperature. The solvent was removed under vacuum and the residue was washed with MTBE to afford compound XIII-r (1.90 g, 82%). $^1$H NMR and LC-MS data is consistent with product. $^1$H NMR (400 MHz, CD$_3$OD): δ 7.75-7.69 (m, 2H), 7.64-7.54 (m, 2H), 7.36-7.25 (m, 8H), 5.04 (s, 2H), 3.98 (t, J=6.4 Hz, 1H), 3.14 (t, J=6.8 Hz, 2H), 2.87 (t, J=7.8 Hz, 2H), 2.77 (t, J=7.4 Hz, 2H), 2.33-2.15 (m, 2H), 1.75-1.68 (m, 2H), 1.58-1.51 (m, 2H).

Preparation of Compound XIII-s

A solution of compound XIII-r (1.90 g, 4.38 mmol) and aldehyde 2 (910 g, 5.26 mmol) in MeOH (80 mL) was charged with acetic acid (2.6 g, 43.8 mmol) and the reaction mixture was stirred at room temperature for 10 min. Sodium cyanoborohydride (413 mg, 6.57 mmol) was added and the solution continued to stir at room temperature for 1 h. Additional compound 2 (0.3 equiv), AcOH (0.5 equiv), and NaCNBH$_3$ (0.5 equiv) were added and stirred for 1 h. After concentration, the residue was partitioned between EtOAc (300 mL) and saturated NaHCO$_3$ (200 mL). The aqueous layer was separated and extracted with EtOAc (2×300 mL). The combined organic extracts were dried over Na$_2$SO$_4$ and concentrated to afford the crude residue XIII-s (2.50 g), which was directly used for the next step. LC-MS data is consistent with product.

Preparation of Compound XIII-t

A solution of compound XIII-s (2.50 g, crude in MeOH/$H_2O$ (80 mL/30 mL) was charged with saturated Na$_2$CO$_3$ at 0° C. and the solution was stirred for 10 min. Benzyl chloroformate (1.0 g, 6.30 mmol) was added dropwise and the reaction mixture was stirred for 1 h at 0° C., warmed to room temperature, and stirred for 1 h. After concentration, the residue was dissolved in CH$_2$Cl$_2$ (200 mL), then washed with water (300 mL) and brine (300 mL). The organic layer was dried over Na$_2$SO$_4$, concentrated, and purified by column chromatography to afford XIII-t (1.90 g, 62% over two steps), which was directly used for the next step. LC-MS data is consistent with product.

Preparation of Compound XIII-u

Compound XIII-t (1.90 g, 2.62 mmol) was dissolved in 4 N HCl in dioxane (30 mL) at room temperature and the solution was stirred for 2 h. After concentration, the residue was washed with MTBE to afford compound XIII-u (1.30 g, 82%) as an off-white solid. $^1$H NMR and LC-MS data is consistent with product. $^1$H NMR (300 MHz, CD$_3$OD): δ 7.69-7.63 (m, 2H), 7.56-7.55 (m, 2H), 7.35-7.21 (m, 16H), 5.15-5.04 (m, 5H), 4.59-4.45 (m, 2H), 3.75-3.59 (m, 9H), 3.57-3.34 (m, 3H), 3.20-3.12 (m, 5H), 3.08-2.94 (m, 6H), 2.76 (t, J=7.4 Hz, 4H), 2.35-2.15 (m, 3H), 2.02-1.81 (m, 6H), 1.76-1.49 (m, 4H).

Preparation of Compound XIII-w and XIII-x

A solution of compound XIII-u (1.30 mg, 2.08 mmol) and triol XIII-v (1.08 g, 4.16 mmol) in methanol (80 mL) was charged with acetic acid (1.2 g, 20.8 mmol) and the reaction mixture was stirred at room temperature for 10 min. Sodium cyanoborohydride (193 mg, 3.12 mmol) was added and the solution continued to stir at room temperature for 24 h. Additional compound XIII-x (2.0 equiv), AcOH (4.0 equiv), and NaCNBH$_3$ (3.0 equiv) were added and the solution continued to stir at room temperature for 24 h. Hexanal (1.0 mL, 10.4 mmol), AcOH (1.10 mL), and NaCNBH$_3$ (193 mg, 3.12 mmol) were added and the reaction mixture was stirred for 2 h. After concentration, the residue was partitioned between EtOAc (300 mL) and saturated NaHCO$_3$ (200 mL). The aqueous layer was separated and extracted with EtOAc (2×300 mL). The combined organic extracts were dried over Na$_2$SO$_4$ and concentrated. The residue was purified by C18 reverse phase Gold column to afford compound XIII-w (550 mg, 25%) and compound XIII-x (400 mg, 21%) as white solids. $^1$H NMR and LC-MS data is consistent with product.

$^1$H NMR for compound XIII-w (300 MHz, CD$_3$OD): δ 7.67-7.65 (m, 2H), 7.55-7.40 (m, 3H), 7.31-7.26 (m, 22H), 5.42-5.29 (m, 2H), 5.04 (s, 4H), 4.21-4.15 (m, 2H), 3.94-3.84 (m, 6H), 3.68-3.50 (m, 5H), 3.14 (t, J=6.8 Hz, 2H), 2.78-2.61 (m, 10H), 1.73-1.68 (m, 4H), 1.58-1.51 (m, 2H).

$^1$H NMR for compound XIII-x (400 MHz, CD$_3$OD): δ 7.68 (d, J=7.4 Hz, 2H), 7.53-7.49 (m, 2H), 7.42-7.27 (m, 16H), 5.48-5.42 (m, 1H), 5.11 (br s, 2H), 5.04 (s, 2H), 4.50-4.38 (m, 1H), 4.23-4.19 (m, 1H), 3.97-3.88 (m, 3H), 3.75-3.48 (m, 3H), 3.13-3.10 (m, 3H), 2.78-2.71 (m, 5H), 2.48-2.29 (m, 5H), 2.15-2.02 (m, 1H), 1.80-1.51 (m, 6H), 1.33-1.14 (m, 6H), 0.82 (t, J=6.8 Hz, 3H).

Preparation of Compound XIII-z

A suspension of XIII-y (550 mg, 0.487 mmol) and 10% Pd/C (165 mg) in EtOH/AcOH (50 mL/10 mL) was subjected to hydrogenation conditions (1 atm) for 8 h at room temperature. The reaction mixture was filtered through celite and washed with EtOH. The filtrate was concentrated under vacuum and precipitated from MTBE/hexanes to afford compound XIII-z (400 mg, 95%) as a colorless oil. $^1$H NMR (300 MHz, CD$_3$OD): δ 7.73-7.56 (m, 4H), 7.41-7.23 (m, 14H), 5.45 (s, 2H), 4.25-4.13 (m, 5H), 3.98-3.83 (m, 5H), 3.74-3.50 (m, 6H), 3.13-2.98 (m, 5H), 3.00-2.71 (m, 10H), 1.82-1.66 (m, 7H).

Preparation of Compound XIII-aa

A solution of compound XIII-z (400 mg, 0.465 mmol) and methyl 3,5-diamino-6-chloropyrazine-2-carbonylcarbamimidothioate hydroiodic acid salt (XIII-aa, 193 mg, 0.744 mmol) in EtOH (50 mL) was charged with DIPEA (480 mg, 3.72 mmol) at room temperature. The reaction mixture was heated at 70° C. in a sealed tube for 2 h, cooled to room temperature, and concentrated in vacuo. The residue was purified by column chromatography (silica gel, 10:1 CH$_2$Cl$_2$/MeOH, 8:2:0.2 CHCl$_3$/CH$_3$OH/NH$_4$OH) to afford compound XIII-bb (350 mg, 70%) as a yellow solid. $^1$H NMR (300 MHz, CD$_3$OD): δ 7.72-7.67 (m, 2H), 7.60 (d, J=9.6 Hz, 2H), 7.44-7.41 (m, 4H), 7.34-7.26 (m, 8H), 5.49 (s, 1H), 5.45 (s, 2H), 4.24-4.18 (m, 2H), 3.99-3.90 (m, 4H), 3.85-3.82 (m, 2H), 3.71-3.68 (m, 2H), 3.56 (t, J=10.5 Hz, 2H), 3.16-3.06 (m, 1H), 2.85-2.74 (m, 4H), 2.68-2.62 (m, 4H), 2.58-2.47 (m, 3H), 1.98-1.81 (m, 6H), 1.70-1.58 (m, 4H).

Preparation of the Hydrochloride Salt of 3,5-diamino-N—(N-(4-(6-((S)-4-amino-3-(3-(bis((2S,3R,4R,5R)-2,3,4,5,6-pentahydroxyhexyl)amino)propylamino)-4-oxobutyl)naphthalen-2-yl)butyl)carbamimidoyl)-6-chloropyrazine-2-carboxamide (XIII-bb)

A solution of compound XIII-aa (350 mg, 0.326 mmol) in 1 N aqueous HCl (5.0 mL) was stirred at room temperature for 3 h. The solvent was removed and the residue was purified by C18 reverse phase Gold column to afford compound XIII-bb (250 mg, 86%) as a yellow hygroscopic solid. $^1$H NMR (400 MHz, CD$_3$OD): δ 7.75 (d, J=7.8 Hz, 2H), 7.60 (br, s, 2H), 7.37-7.32 (m, 2H), 4.16 (br, s, 2H), 3.81-3.75 (m, 4H), 3.73-3.63 (m, 6H), 3.48-3.44 (m, 2H), 3.37-3.34 (m, 7H), 3.13-3.10 (m, H), 2.85 (t, J=2 Hz, 4H), 2.25-2.15 (m, 3H), 1.92-1.69 (m, 4H).

Scheme XIV
3,5-diamino-N-(N-(4-(6-((S)-4-amino-3-(3-(hexyl((2S,3R,4R,5R)-2,3,4,5,6-pentahydroxyhexyl)amino)propylamino)-4-oxobutyl)naphthalen-2-yl)butyl)carbamimidoyl)-6-chloropyrazine-2-carboxamide
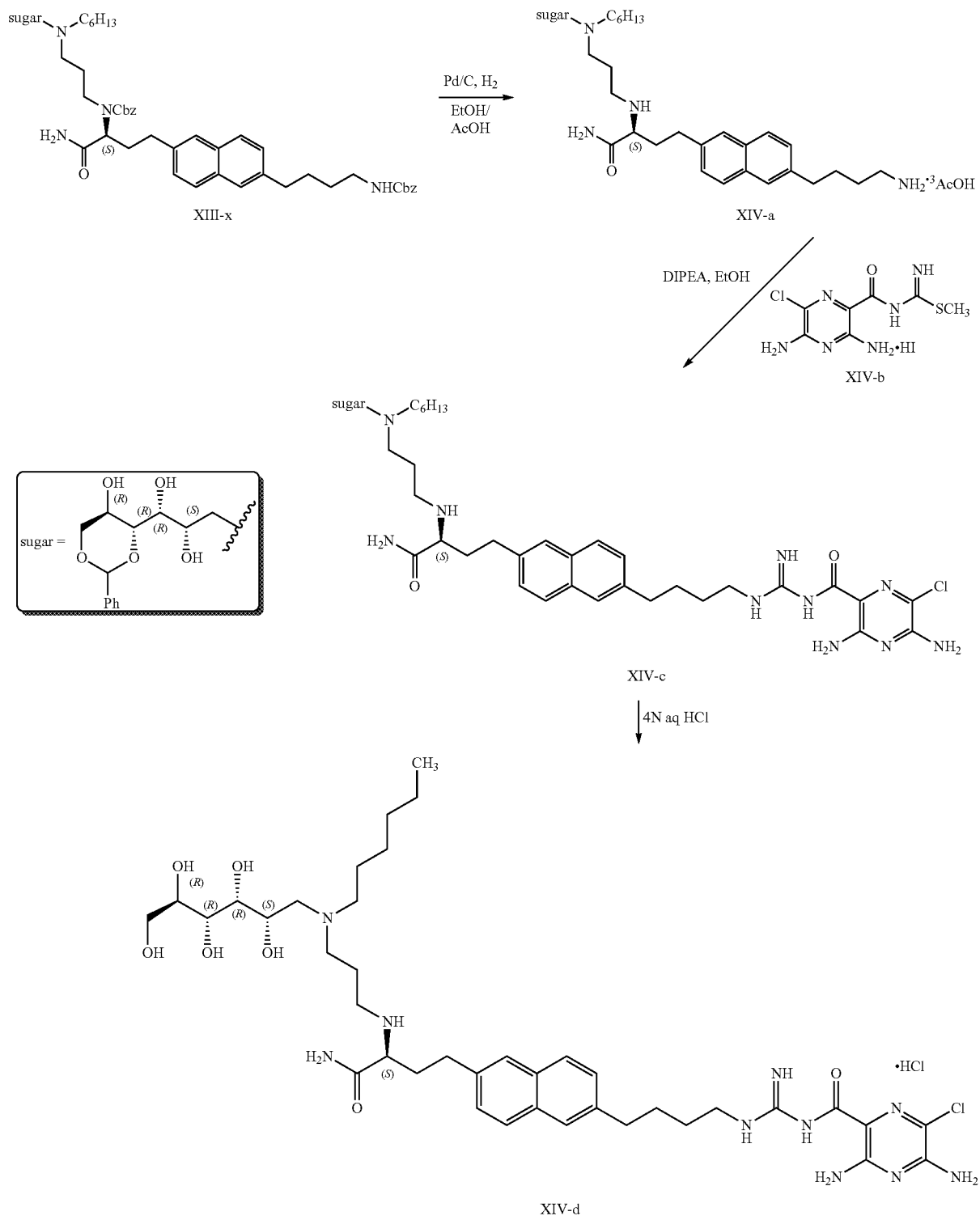

Preparation of XIV-a

A suspension of XIII-x (400 mg, 0.416 mmol) and 10% Pd/C (120 mg) in EtOH/AcOH (50 mL/10 mL) was subjected to hydrogenation conditions (1 atm) for 16 h at room temperature. The reaction mixture was filtered through celite and washed with MeOH.

The filtrate was concentrated under vacuum to afford compound XIV-a (270 mg, 93%) as a colorless oil. $^1$H NMR (400 MHz, CD$_3$OD): δ 7.73 (d, J=8.2 Hz, 2H), 7.62 (d, J=6.2 Hz, 2H), 7.48-7.39 (m, 3H), 7.36-7.24 (m, 6H), 5.52 (s, 1H), 4.23-4.15 (m, 2H), 4.00-3.94 (m, 2H), 3.80-3.77 (m, 1H), 3.64-3.57 (m, 2H), 3.22-3.07 (m, 4H), 3.04-2.91 (m, 3H), 2.85-2.75 (m, 6H), 1.82-1.77 (m, 4H), 1.73-1.54 (m, 5H), 1.33-1.11 (m, 10H), 0.82 (t, J=6.8 Hz, 3H).

Preparation of XIV-c

A solution of compound XIV-a (270 mg, 0.390 mmol) and methyl 3,5-diamino-6-chloropyrazine-2-carbonylcarbamimidothioate hydroiodic acid salt (XIV-b, 163 mg, 0.62 mmol) in EtOH (50 mL) was charged with DIPEA (402 mg, 3.12 mmol) at room temperature. The reaction mixture was heated at 70° C. in a sealed tube for 2 h, cooled to room temperature, and concentrated in vacuo. The residue was purified by column chromatography (silica gel, 10:1 CH$_2$Cl$_2$/MeOH, 8:2:0.2 CHCl$_3$/CH$_3$OH/NH$_4$OH) to afford compound XIV-c (180 mg, 57%) as a yellow solid. $^1$H NMR (400 MHz, CD$_3$OD): δ 7.71-7.68 (m, 2H), 7.60-7.59 (m, 2H), 7.46-7.42 (m, 2H), 7.34-7.25 (m, 5H), 5.50 (s, 1H), 4.25-4.21 (m, 1H), 4.01-3.88 (m, 3H), 3.76-3.71 (m, 1H), 3.63-3.55 (m, 1H), 3.15-3.09 (m, 1H), 2.84-2.73 (m, 5H), 2.61-2.43 (m, 8H), 2.02-1.79 (m, 4H), 1.73-1.59 (m, 4H), 1.43-1.41 (m, 2H), 1.29-1.15 (m, 8H), 2.02-1.79 (m, 4H), 1.73-1.59 (m, 4H), 1.43-1.41 (m, 2H), 1.29-1.15 (m, 8H), 0.84 (t, J=6.8 Hz, 3H).

Preparation of the Hydrochloride Salt of 3,5-diamino-N—(N-(4-(6-((S)-4-amino-3-(3-(hexyl((2S,3R,4R,5R)-2,3,4,5,6-pentahydroxyhexyl)amino)propylamino)-4-oxobutyl)naphthalen-2-yl)butyl)carbamimidoyl)-6-chloropyrazine-2-carboxamide (XIV-d)

A solution of compound XIV-c (180 mg, 0.199 mmol) in 4 N aqueous HCl (2.0 mL) was stirred at room temperature for 2 h. The solvent was removed and the residue was purified by C18 reverse phase Gold column to afford compound XIV-d (82 mg, 50%) as a yellow hygroscopic solid. $^1$H NMR (400 MHz, CD$_3$OD): δ 7.75 (d, J=8.4 Hz, 2H), 7.66 (d, J=8.4 Hz, 2H), 7.38 (t, J=7.8 Hz, 2H), 4.18-4.16 (m, 1H), 4.04-4.02 (m, 1H), 3.85-3.76 (m, 2H), 3.71-3.64 (m, 3H), 3.48-3.46 (m, 1H), 3.38-3.34 (m, 8H), 3.25-3.08 (m, 5H), 2.92-2.81 (m, 4H), 1.38 (br s, 6H), 0.93 (t, J=6.6 Hz, 3H).

Scheme XV
3,5-diamino-N-(4-(4-((S)-4-amino-3-(3-(bis((2S,3R,4R,5R)-2,3,4,5,6-pentahydroxyhexyl)amino)propylamino)-4-oxobutyl)-5,6,7,8-tetrahydronaphthalen-1-yl)butyl)carbamimidoyl)-6-chloropyrazine-2-carboxamide (XV-dd):

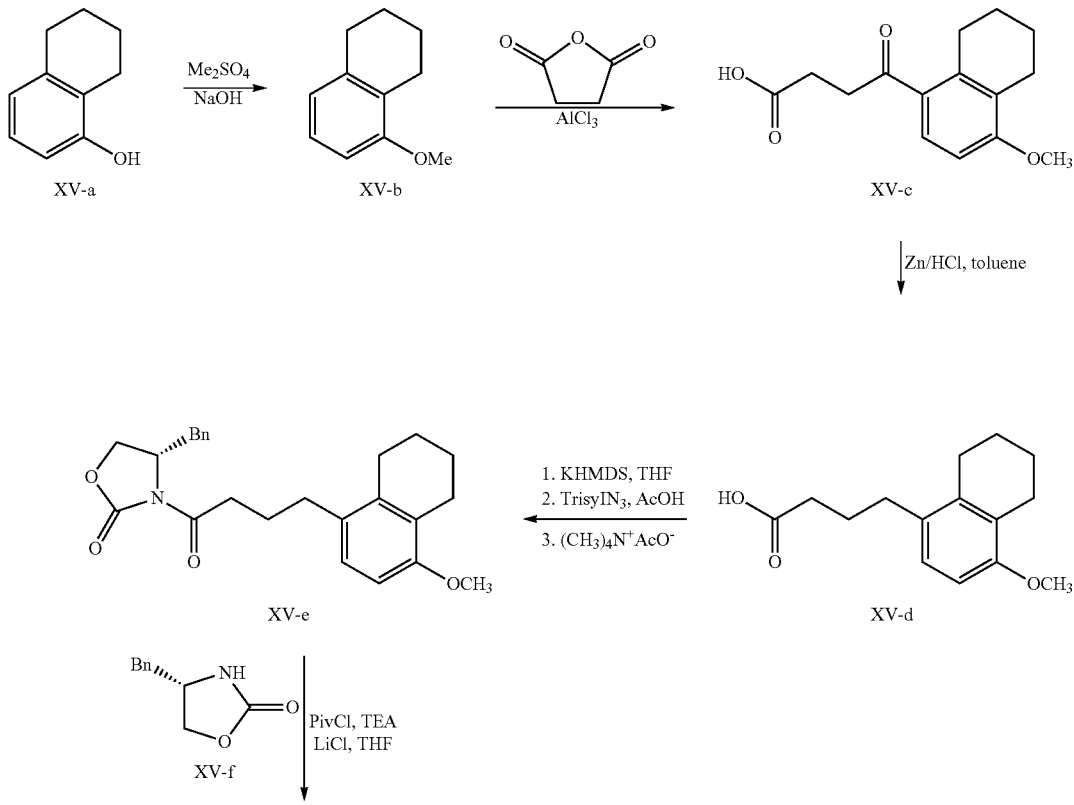

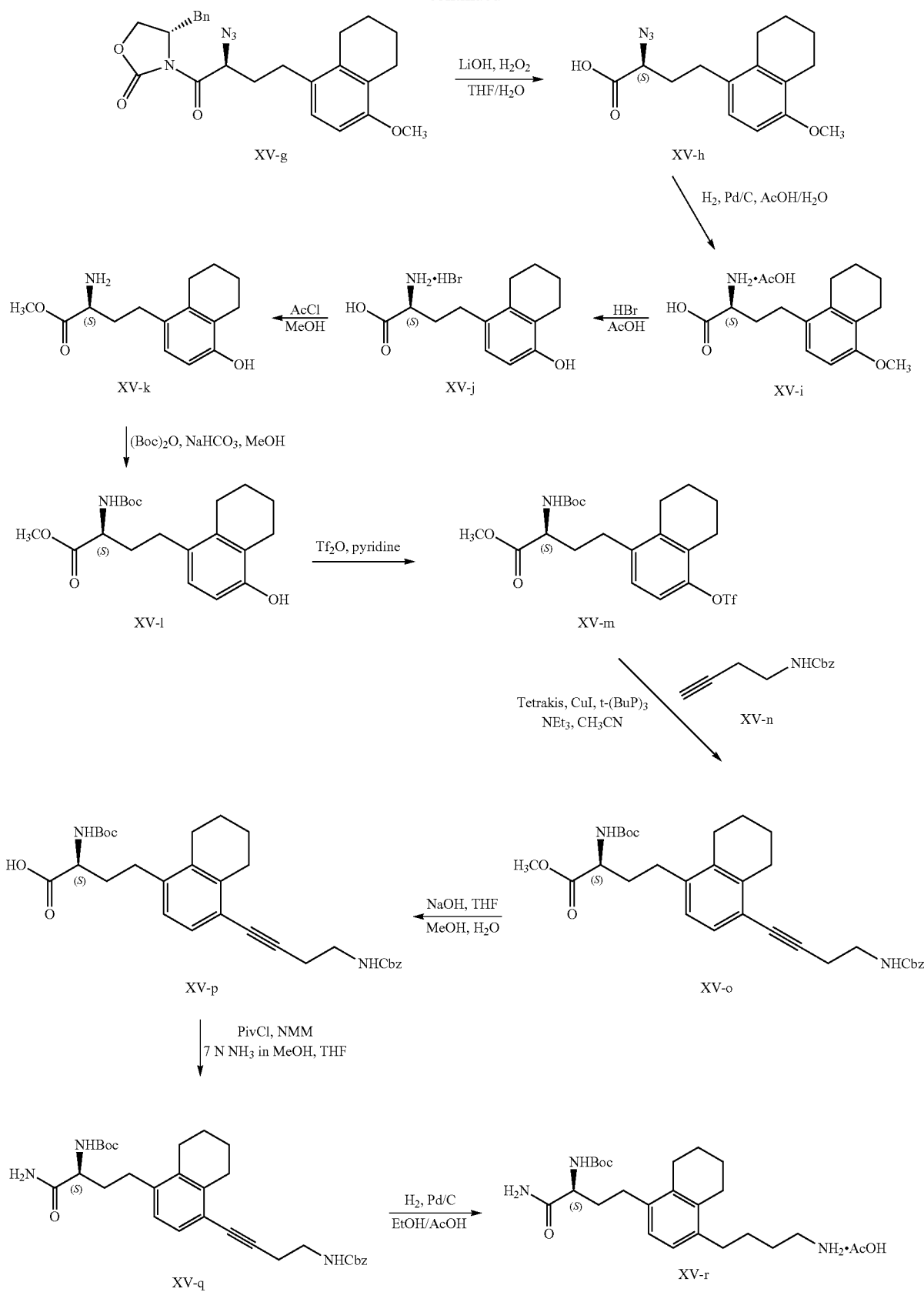

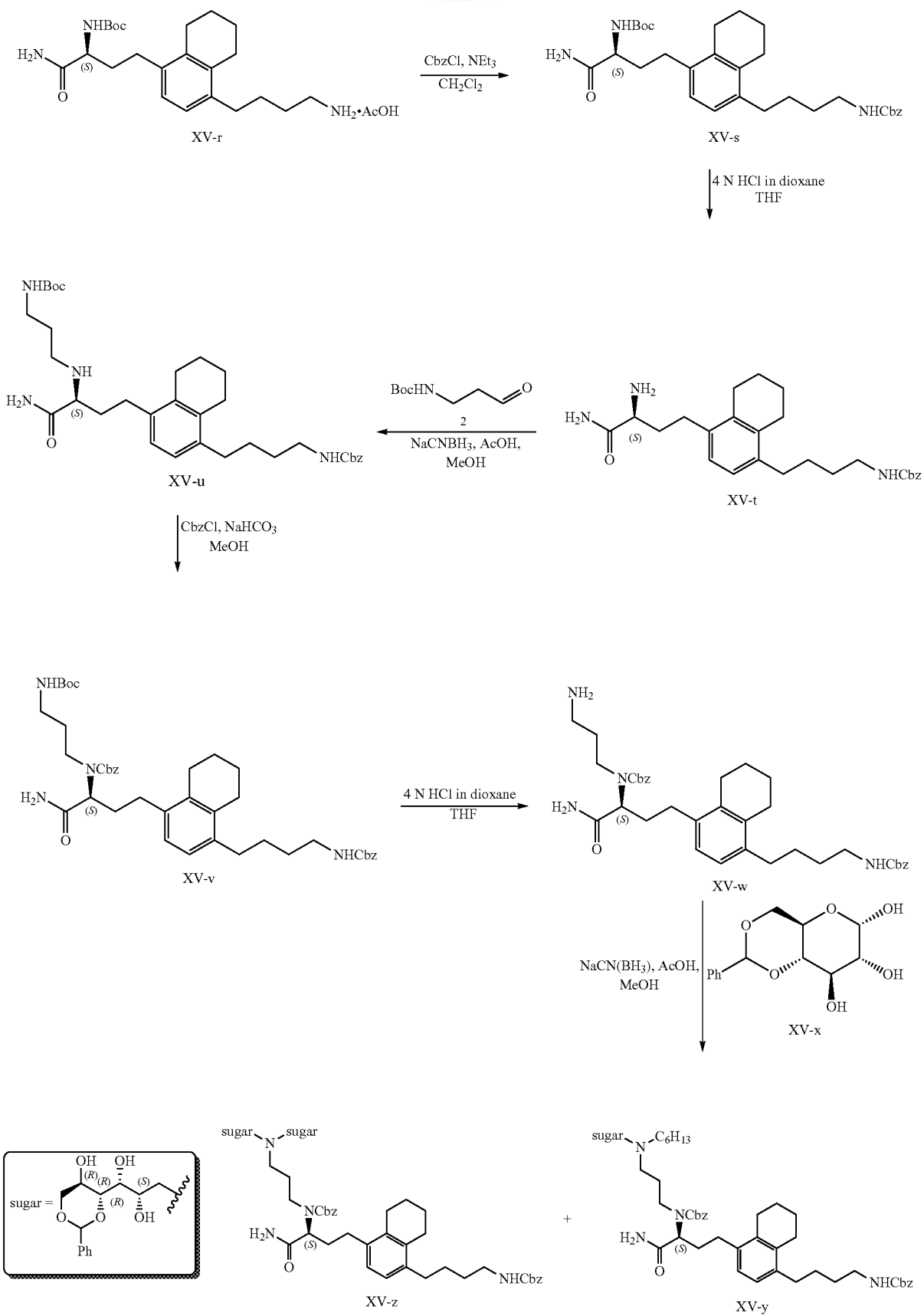

-continued

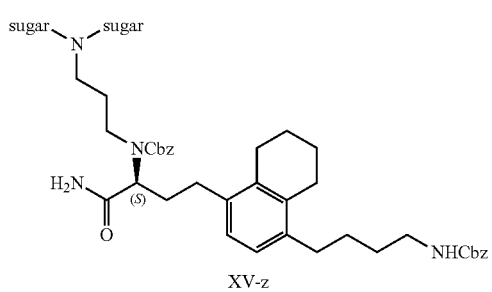

XV-z

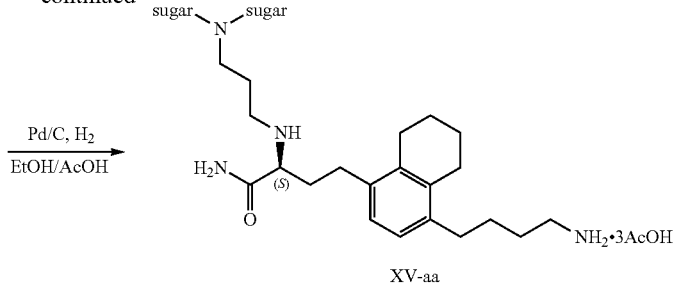

XV-aa

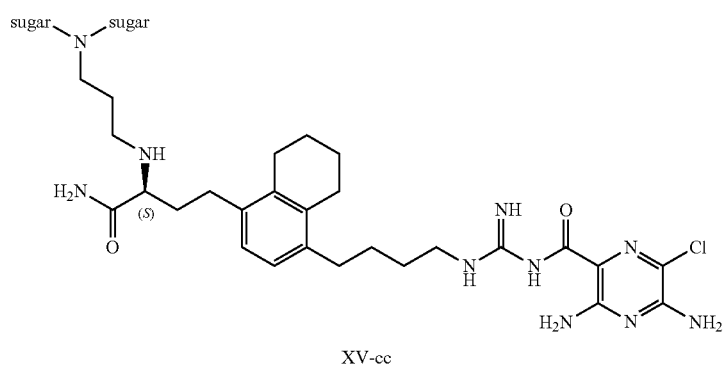

XV-cc

↓ 4 N aq HCl

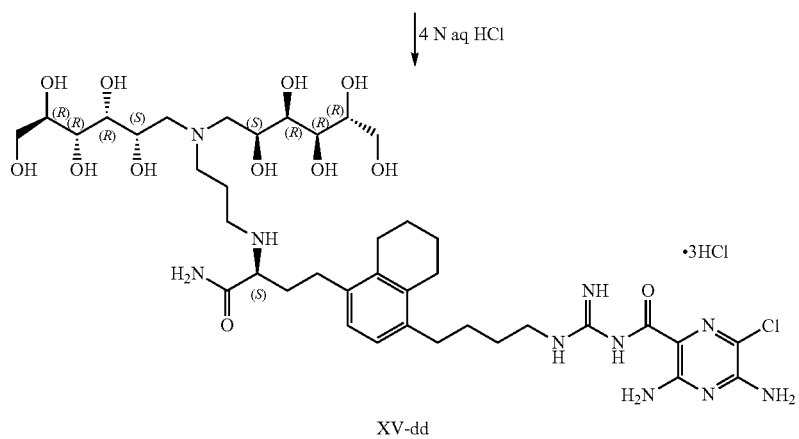

XV-dd

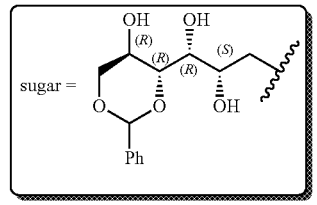

Preparation of Compound XV-b

A solution of compound XV-a (100 g, 674 mmol) in dry THF (600 mL) was charged with dimethyl sulfate (102 g, 809 mmol) followed by NaOH (32.4 g, 809 mmol) at 0° C. The resulting reaction mixture was stirred at room temperature for 3 hours. After completion of the reaction, the reaction mixture was concentrated to remove the solvent and diluted with water. The aqueous layer was extracted with ethyl acetate (2×500 mL). The combined organic extracts were dried over $Na_2SO_4$ and concentrated. The residue was purified by column chromatography (silica gel, 90:10 hexane/EtOAc) to afford compound XV-b (108 g, 98%) as a colorless oil. $^1$H NMR (400 MHz, $CDCl_3$): δ7.05 (t, J=7.8 Hz, 1H), 6.69 (d, J=7.6 Hz, 1H), 6.64 (d, J=7.9 Hz, 1H), 3.80 (s, 3H), 2.74 (t, J=6.2 Hz, 2H), 2.64 (t, J=6.2 Hz, 2H), 1.81-1.71 (m, 4H).

Preparation of Compound XV-c

A solution of succinic anhydride (12.3 g, 123 mmol) in $CH_2Cl_2$ (150 mL) was charged with $AlCl_3$ (18.4 g, 138 mmol) portionwise at 0° C. After 10 minutes, compound XV-b (20.0 g, 123 mmol) dissolved in $CH_2Cl_2$ (50 mL) was added to the reaction mixture at the same temperature. The reaction mixture was stirred at room temperature for 3 hours. After completion of the reaction, the reaction mixture was poured into ice-cold water and acidified with HCl. The reaction mixture was filtered through a Celite pad to remove Al(OH)$_3$ and washed with hot ethyl acetate. The aqueous layer was extracted with ethyl acetate. The solvent was concentrated to get a solid, and the compound was further purified by triturating with hexane washing to get compound XV-c (22.3 g, 69%) as a white solid. $^1$H NMR and LC-MS data is consistent with product. $^1$H NMR (400 MHz, CD$_3$OD): δ ☐7.68 (d, J=8.7 Hz, 1H), 6.80 (d, J=8.7 Hz, 1H), 3.86 (s, 3H), 3.16 (t, J=6.4 Hz, 2H), 2.90 (t, J=6.4 Hz, 2H), 2.67-2.60 (m, 4H), 1.78-1.64 (m, 4H).

Preparation of Compound XV-d

A solution of compound XV-c (30 g, 114 mmol) in toluene (300 mL) was charged with concentrated hydrochloric acid (300 mL) followed by Zn dust (74.8 g, 1145 mmol) portionwise at room temperature. The reaction mixture was heated to reflux for 3 h, cooled down to room temperature, and filtered through Celite. After the filtrate was concentrated to 50%, the resulting precipitate was filtered and dried to afford compound XV-d (24.0 g, 85%) as an off-white solid. $^1$H NMR and LC-MS data is consistent with product. $^1$H NMR (400 MHz, CD$_3$OD): δ ☐6.90 (d, J=8.4 Hz, 1H), 6.63 (d, J=8.4 Hz, 1H), 3.75 (s, 3H), 2.67 (t, J=5.9 Hz, 2H), 2.61 (t, J=5.9 Hz, 2H), 2.57-2.49 (m, 2H), 2.35-2.28 (m, 2H), 1.85-1.68 (m, 4H).

Preparation of Compound XV-e

A solution of compound XV-d (20 g, 80.6 mmol) in dry THF (500 mL) was charged with Et$_3$N (28 mL, 96.8 mmol), PivCl (11.9 mL, 96.7 mmol), and LiCl (3.418 g, 96.8 mmol), followed by compound XV-f (17.1 g, 96.8 mmol) at −25° C., and the reaction mixture was stirred for 2 hours at room temperature. After completion of the reaction, the reaction mixture was evaporated and the residue was treated with 1 N NaOH. The aqueous layer was separated and extracted with dichloromethane (2×500 mL). The combined organic extracts were dried over Na$_2$SO$_4$ and concentrated. The residue was purified by triturating with MTBE and hexane to get compound XV-e (26 g, 79%) as a solid. $^1$H NMR (400 MHz, CDCl$_3$): δ ☐7.37-7.27 (m, 3H), 7.23-7.15 (m, 2H), 6.98 (d, J=8.5 Hz, 1H), 6.63 (d, J=8.5 Hz, 1H), 4.70-4.61 (m, 1H), 4.21-4.11 (m, 2H), 3.78 (s, 3H), 3.30 (dd, J=9.7 Hz, 1H), 3.14-2.79 (m, 3H), 2.80-2.52 (m, 7H), 2.05-1.88 (m, 2H), 1.89-1.64 (m, 4H).

Preparation of Compound XV-g

A solution of compound XV-e (30.0 g, 73.7 mmol) in dry THF (300 mL) was charged with KHMDS (19.1 g, 95.8 mmol) portionwise at −78° C. After the resulting mixture was stirred for 30 min, trisyl azide (34.2 g, 110.6 mmol) was added and the reaction mixture was stirred for 2-3 min. Acetic acid (26.5 g, 442 mmol) was added slowly at the same temperature followed by tetramethylammonium acetate (29.5 g, 221 mmol). The reaction mixture was warmed to 27° C., stirred for 4 h, quenched with saturated NaHCO$_3$ (300 mL), concentrated to remove THF, and extracted with EtOAc (2×500 mL). The combined organic extracts were dried over Na$_2$SO$_4$ and concentrated. The residue was purified by column chromatography (silica gel, 70:30 hexane/EtOAc) to afford compound XV-g (18.3 g, 55%) as a colorless oil. $^1$H NMR (400 MHz, CDCl$_3$): δ 7.37-7.27 (m, 3H), 7.23-7.18 (m, 2H), 6.96 (d, J=8.4 Hz, 1H), 6.62 (d, J=8.4 Hz, 1H), 5.03-4.98 (m, 1H), 4.61-4.54 (m, 2H), 4.23-4.10 (m, 2H), 3.77 (s, 3H), 3.32 (dd, J=10.3 Hz, 1H), 2.86-2.77 (m, 2H), 2.73-2.61 (m, 5H), 2.17-2.07 (m, 1H), 2.05-1.95 (m, 1H), 1.82-1.70 (m, 4H).

Preparation of Compound XV-h

A solution of compound XV-g (40.5 g, 20.0 mmol) in THF/H$_2$O (150 mL/50 mL) was charged with H$_2$O$_2$ (61.4 mL, 542 mmol) followed by LiOH (7.57 g, 181 mmol) portionwise at 0° C. The reaction mixture was stirred for 1 h at the same temperature, quenched with saturated aqueous Na$_2$SO$_3$ (200 mL), concentrated under reduced pressure to remove THF, and washed with CH$_2$Cl$_2$ (200 mL). The aqueous layer was acidified with 1 N aqueous HCl and extracted with CH$_2$Cl$_2$ (2×250 mL). The combined organic extracts were dried over Na$_2$SO$_4$, concentrated, and triturated with MTBE to afford compound XV-h (20.0 g, 77%) as an off-white solid. $^1$H NMR (300 MHz, CD$_3$OD): δ ☐6.91 (d, J=8.4 Hz, 1H), 6.64 (d, J=8.4 Hz, 1H), 3.93 (dd, J=7.9, 4.1 Hz, 1H), 3.74 (s, 3H), 2.72-2.55 (m, 6H), 2.08-1.83 (m, 2H), 1.81-1.63 (m, 4H).

Preparation of Compound XV-i

A suspension of compound XV-h (41.0 g, 144 mmol) and 10% Pd/C (8.0 g) in AcOH/H$_2$O (480 mL/160 mL) was subjected to hydrogenation conditions (1 atm) for 16 h at room temperature. The reaction mixture was filtered through Celite and washed with MeOH. The filtrate was concentrated under vacuum to afford acetic salt XV-i (40.0 g, 86%) as a yellow solid. $^1$H NMR (400 MHz, DMSO-d$_6$): δ 6.98 (d, J=8.8 Hz, 1H), 6.69 (d, J=8.8 Hz, 1H), 3.97 (t, J=6.3 Hz, 1H), 3.76 (s, 3H), 2.76-2.55 (m, 7H), 2.14-1.99 (m, 2H), 1.84-1.67 (m, 5H), 1.93 (s, 3H).

Preparation of Compound XV-j

A solution of compound XV-i (41.3 g, 128 mmol) in acetic acid (250 mL) was charged with hydrobromic acid (250 mL) dropwise at room temperature and the reaction mixture was refluxed for 16 h. The reaction mixture was cooled to room temperature and concentrated. The residue was diluted with H$_2$O (15 mL), slightly basified with ammonia, and crystallized overnight to afford compound XV-j (40.0 g, 95%) as a brown solid. $^1$H NMR (400 MHz, DMSO-d$_6$): δ ☐8.35 (brs, 1H), 6.74 (d, J=7.7 Hz, 1H), 6.56 (d, J=7.7 Hz, 1H), 4.01-3.90 (m, 1H), 2.55-2.38 (m, 4H), 2.05-1.85 (m, 2H), 1.78-1.56 (m, 6H), Preparation of Compound XV-k Acetyl chloride (60.5 mL, 852 mmol) was added to dry methanol (400 mL) at 0° C., followed by compound XV-j (40.0 g, 122 mmol). The reaction mixture was refluxed for 3 h and concentrated. The residue was partitioned between CH$_2$Cl$_2$ (500 mL) and saturated NaHCO$_3$ (300 mL). The aqueous layer was separated and extracted with CH$_2$Cl$_2$ (2×300 mL). The combined organic extracts were dried over Na$_2$SO$_4$ and concentrated to afford compound XV-k (30.0 g, 83%) as a colorless oil. $^1$H NMR (400 MHz, CD$_3$OD): δ 6.77 (d, J=8.2 Hz, 1H), 6.50 (d, J=8.2 Hz, 1H), 3.72 (s, 3H), 3.51 (t, J=6.2 Hz, 1H), 2.70-2.57 (m, 4H), 2.53 (t, J=8.5 Hz, 2H), 1.83-1.69 (m, 6H).

Preparation of Compound XV-l

A solution of compound XV-k (30.0 g, 114 mmol) in MeOH/H$_2$O (300 mL/100 mL) was charged with NaHCO$_3$ (39.0 g, 456 mmol) and Boc$_2$O (30.0 g, 137 mmol) at 0° C. The resulting mixture was warmed to room temperature and stirred for 3 h. The reaction mixture was partitioned between CH$_2$Cl$_2$ (200 mL) and water (200 mL). The aqueous layer was separated and extracted with CH$_2$Cl$_2$ (2×200 mL). The combined organic extracts were washed with brine and dried over Na$_2$SO$_4$, and the residue was purified by column chromatography (silica gel, 70:30 hexanes/EA) to afford compound XV-l (31.0 g, 85%) as a colorless oil. $^1$H NMR (400 MHz, CDCl$_3$): δ ☐6.80 (d, J=8.0 Hz, 1H), 6.56 (d, J=8.0 Hz, 1H), 5.32 (brs, 1H), 5.29 (s, 1H), 4.45-4.30 (m, 1H), 3.73 (s, 3H), 2.69-2.43 (m, 6H), 1.88-1.72 (m, 6H), 1.46 (s, 9H).

Preparation of Compound XV-m

A solution of compound XV-l (31.0 g, 85.4 mmol) in pyridine (70 mL) was charged with triflate (21.5 mL, 128 mmol) at 0° C., and the reaction mixture was stirred at room temperature for 1 h. After concentration, the reaction mixture was partitioned between CH$_2$Cl$_2$ (300 mL) and water (300 mL). The aqueous layer was separated and extracted with CH$_2$Cl$_2$ (2×300 mL). The combined organic extracts were washed with brine, dried over Na$_2$SO$_4$, and concentrated to afford compound XV-m (41.0 g crude) as a brown oil. $^1$H NMR (400 MHz, CDCl$_3$): δ ☐7.01 (s, 2H), 5.22-5.11 (m, 1H), 4.44-4.34 (m, 1H), 3.74 (s, 3H), 2.78 (t, J=6.0 Hz, 2H), 2.71-2.52 (m, 4H), 2.16-2.02 (m, 1H), 1.89-1.73 (m, 5H), 1.45 (s, 9H).

Preparation of Compound XV-o

A solution of compound XV-m (41.0 g, crude) in anhydrous CH$_3$CN (400 mL) was charged with TEA (46.8 mL, 342 mmol), 10% (t-Bu)$_3$P in hexanes (34.5 mL, 17.0 mmol), benzyl but-3-ynylcarbamate (XV-n, 20.6 g, 103 mmol), and CuI (0.81 g, 4.26 mmol) at room temperature. The resulting mixture was degassed with argon for 3 min and Pd(PPh$_3$)$_4$ (9.86 g, 8.53 mmol) was added rapidly in one portion. After degassing with argon for 5 min, the resulting mixture was refluxed for 16 h. The reaction mixture was concentrated under vacuum and the residue was purified by column (silica gel, 80:20 hexanes/EA) to afford compound XV-o (25 g, 54% over two steps) as a brown oil. $^1$H NMR (400 MHz, CDCl$_3$): δ 7.38-7.31 (m, 5H), 7.15 (d, J=7.9 Hz, 1H), 6.88 (d, J=7.9 Hz, 1H), 5.19-5.05 (m, 4H), 4.43-4.31 (m, 1H), 3.73 (s, 3H), 3.47-3.37 (m, 2H), 2.82 (t, J=6.7 Hz, 2H), 2.69-2.55 (m, 5H), 2.13-2.00 (m, 1H), 1.82-1.70 (m, 6H), 1.45 (s, 9H).

Preparation of Compound XV-p

A solution of methyl ester XV-o (23.0 g, 42.0 mmol) in THF/MeOH/H$_2$O (200 mL/200 mL/65 mL) was charged with NaOH (10.0 g, 252 mmol) and the reaction mixture was stirred at room temperature for 1 h. The pH value was adjusted to 9 with 1 N aqueous HCl and the organic solvent was removed. The pH value of the residue was adjusted to 5, and the suspension was partitioned between CH$_2$Cl$_2$ (200 mL) and water (200 mL). The aqueous layer was separated and extracted with CH$_2$Cl$_2$ (2×200 mL). The combined organic extracts were dried over Na$_2$SO$_4$ and concentrated to afford compound XV-p (16.0 g, 72%) as a brown solid. $^1$H NMR (400 MHz, CD$_3$OD): δ 7.38-7.20 (m, 5H), 7.09 (d, J=8.6 Hz, 1H), 6.89 (d, J=8.5 Hz, 1H), 5.08 (s, 2H), 4.16-4.02 (m, 1H), 3.34 (t, J=7.3 Hz, 2H), 2.81 (t, J=6.4 Hz, 2H), 2.70-2.58 (m, 6H), 2.08-1.93 (m, 1H), 1.90-1.81 (m, 1H), 1.80-1.68 (m, 4H), 1.45 (s, 9H).

Preparation of Compound XV-q

A solution of acid XV-p (11.0 g, 20.6 mmol) in THF (200 mL) was charged with NMM (3.39 mL, 31.0 mmol) and PivCl (3.0 mL, 24.7 mmol) at 0° C. The reaction mixture was stirred at the same temperature for 1 h and NH$_3$ (7.0 N in methanol, 29.4 mL, 206 mmol) was added dropwise. The reaction mixture continued to stir at 0° C. for 1 h, was warmed to room temperature, and stirred for 1 h. After concentration, the residue was partitioned between CH$_2$Cl$_2$ (100 mL) and water (100 mL). The aqueous layer was separated and extracted with CH$_2$Cl$_2$ (2×100 mL). The combined organic extracts were dried over Na$_2$SO$_4$ and concentrated. The residue was triturated with MTBE to afford amide XV-q (12.0 g, crude) as a yellow solid. $^1$H NMR (400 MHz, CD$_3$OD): δ 7.35-7.22 (m, 5H), 7.09 (d, J=8.3 Hz, 1H), 6.88 (d, J=8.3 Hz, 1H), 5.07 (s, 2H), 4.09-3.97 (m, 1H), 3.39 (t, J=6.9 Hz, 2H), 2.80 (t, J=6.5 Hz, 2H), 2.70-2.56 (m, 6H), 1.82-1.67 (m, 6H), 1.45 (s, 9H).

Preparation of Compound XV-r

A suspension of compound XV-q (12.0 g, crude) and 10% Pd/C (2.50 g) in EtOH (300 mL)/AcOH 960 mL) was subjected to hydrogenation conditions (1 atm) for 16 h at room temperature. The reaction mixture was filtered through Celite and washed with EtOH. The filtrate was concentrated under vacuum and triturated with MTBE/hexanes to afford acetic salt XV-r (12.0 g, crude) as an off-white solid. This product was directly used for the next step. [M+H]$^+$ 264.

Preparation of Compound XV-s

A stirred solution of compound XV-r (12.0 g, crude) in MeOH (300 mL)/water (100 mL) was charged with Na$_2$CO$_3$ (21.8 g, 206 mmol) and CbzCl (6.27 mL, 41.2 mmol) at 0° C. and stirred at the same temperature for 1 h. The reaction mixture was stirred for 1 h at room temperature, and the solvent was removed and partitioned between CH$_2$Cl$_2$ (500 mL) and water (100 mL). The aqueous layer was separated and extracted with CH$_2$Cl$_2$ (2×100 mL). The combined organic extracts were washed with brine, dried over Na$_2$SO$_4$, and concentrated to afford compound XV-s (15.0 g, crude) as yellow oil. This product was directly used for the next step. [M+H]$^+$ 538.

Preparation of Compound XV-t

A solution of compound XV-s (15.0 g, crude) was charged with 4 N HCl in dioxane (60 mL) and the reaction mixture was stirred for 1 h at room temperature. The solvent was removed under vacuum and the residue was triturated with MTBE to afford compound XV-t (15.0 g, crude). This product was directly used for the next step. [M+H]$^+$ 438.

Preparation of Compound XV-u

A solution of compound XV-t (15.0 g, crude) and aldehyde 2 (4.27 g, 24.2 mmol) in MeOH (100 mL) was charged with acetic acid (12.5 mL) and the reaction mixture was stirred at room temperature for 10 min. Sodium cyanoborohydride (1.94 g, 30.9 mmol) was added and the solution continued to stir at room temperature for 1 h. Additional compound XV-u (0.3 equiv), AcOH (0.5 equiv), and NaCNBH$_3$ (0.5 equiv) were added and stirred for 1 h. After concentration, the residue was partitioned between EtOAc (300 mL) and saturated NaHCO$_3$ (200 mL). The aqueous layer was separated and extracted with EtOAc (2×300 mL). The combined organic extracts were dried over Na$_2$SO$_4$ and concentrated. The residue (20 g, crude) was directly used for the next step without further purification. [M+H]$^+$ 595.

Preparation of Compound XV-w

A solution of compound XV-u (20 g, crude in MeOH/H$_2$O (300 mL/100 mL) was charged with Na$_2$CO$_3$ (21.8 g, 206 mmol) at 0° C. and the solution was stirred for 10 min. Benzyl chloroformate (6.77 mL, 41.2 mmol) was added dropwise and the reaction mixture was stirred for 1 h at 0° C., warmed to room temperature, and stirred for 1 h. After concentration, the residue was dissolved in CH$_2$Cl$_2$ (200 mL) and washed with water (300 mL) and brine (300 mL). The organic layer was dried over Na$_2$SO$_4$ and concentrated. The residue (20 g, crude) was directly used for the next step without further purification. [M+Na]$^+$ 752.

Preparation of Compound XV-w

Compound XV-v (20 g, crude) was dissolved in 4 N HCl in dioxane (50 mL) at room temperature and the solution was stirred for 2 h. After concentration, the residue was triturated with MTBE, neutralized with aqueous NaHCO$_3$, and purified by flash-column chromatography using CMA system to afford compound XV-w (3.50 g, 27% over 7 steps) as an off-white solid. $^1$H NMR (400 MHz, CD$_3$OD): δ 7.43-7.24 (m, 10H), 6.83 (s, 2H), 5.16 (s, 2H), 5.05 (s, 2H), 4.54-4.42 (m, 1H), 3.58-3.44 (m, 1H), 3.42-3.33 (m, 2H), 3.15-3.10 (m, 2H), 3.00-2.86 (m, 2H), 2.71-2.57 (m, 4H), 2.56-2.45 (m, 5H), 2.32-1.87 (m, 2H), 1.79-1.65 (m, 4H), 1.59-1.48 (m, 4H).

Preparation of Compound XV-y and XV-z

A solution of compound XV-w (3.50 mg, 5.57 mmol) and triol XV-x (6.00 g, 22.3 mmol) in methanol (50 mL) was charged with acetic acid (3.35 mL) and the reaction mixture was stirred at room temperature for 10 min. Sodium cyanoborohydride (1.40 g, 22.3 mmol) was added and the solution continued to stir at room temperature for 24 h. Additional compound XV-x (2.0 equiv), AcOH (4.0 equiv), and NaCNBH$_3$ (3.0 equiv) were added and the solution continued to stir at room temperature for 24 h. Hexanal (2.00 mL, 16.8 mmol), AcOH (1.10 mL), and NaCNBH$_3$ (1.75 g, 27.9 mmol) were added and the reaction mixture was stirred for 2 h. After concentration, the residue was partitioned between EtOAc (300 mL) and saturated NaHCO$_3$ (200 mL). The aqueous layer was separated and extracted with EtOAc (2×300 mL). The combined organic extracts were dried over Na$_2$SO$_4$ and concentrated. The residue was purified by C18 reverse phase Gold column to afford compound XV-z (2.50 g, 40%) and compound XV-y (1.30 g, 24%) as white solids: $^1$H NMR (400 MHz, CD$_3$OD): δ □7.51-7.19 (m, 20H), 6.87-6.74 (m, 2H), 5.51-5.32 (m, 2H), 5.16-5.20 (m, 2H), 4.45-4.25 (m, 1H), 4.20 (dd, J=10.8, 5.6 Hz, 2H), 4.00-3.90 (m, 3H), 3.89-3.80 (m, 2H), 3.75-3.63 (m, 2H), 3.55 (t, J=11.3 Hz, 2H), 3.11 (t, J=6.5 Hz, 2H), 2.80-2.36 (m, 12H), 2.20-2.01 (m, 1H), 1.99-1.83 (m, 1H), 1.82-1.62 (m, 6H), 1.57-1.44 (m, 4H), 1.41-1.21 (m, 2H), 0.94-0.86 (m, 1H).

Preparation of Compound XV-aa

A suspension of XV-z (2.50 g, 2.20 mmol) and 10% Pd/C (500 mg) in EtOH/AcOH (100 mL/20 mL) was subjected to hydrogenation conditions (1 atm) for 16 h at room temperature. The reaction mixture was filtered through celite and washed with MeOH. The filtrate was concentrated under vacuum and triturated with MTBE/hexanes to afford compound XV-aa (2.20 g, 96%) as a white solid. $^1$H NMR (400 MHz, CD$_3$OD): δ 7.45-7.38 (m, 4H), 7.30-7.24 (m, 6H), 6.87 (s, 2H), 5.47 (s, 2H), 4.23 (dd, J=10.9, 5.7 Hz, 2H), 4.17-4.10 (m, 2H), 3.98-3.90 (m, 2H), 3.84 (dd, J=5.1, 2.3 Hz, 2H), 3.72 (dd, J=9.4, 2.3 Hz, 2H), 3.65-3.54 (m, 4H), 3.13-2.96 (m, 4H), 2.93-2.81 (m, 2H), 2.80-2.47 (m, 11H), 0.95 (s, 9H), 1.81-1.54 (m, 10H), 1.40-1.23 (m, 2H).

Preparation of XV-cc

A solution of compound XV-aa (2.20 g, 2.10 mmol) and methyl 3,5-diamino-6-chloropyrazine-2-carbonylcarbamimidothioate hydroiodic acid salt (XV-bb, 1.30 g, 3.36 mmol) in EtOH (15 mL) was charged with DIPEA (2.98 mL, 16.8 mmol) at room temperature. The reaction mixture was heated at 70° C. in a sealed tube for 2 h, cooled to room temperature, and concentrated in vacuo. The residue was purified by column chromatography (silica gel, 10:1 CH$_2$Cl$_2$/MeOH, 8:2:0.2 CHCl$_3$/CH$_3$OH/NH$_4$OH) to afford compound XV-cc (1.24 g, 55%) as a yellow solid. $^1$H NMR (400 MHz, CD$_3$OD): δ 7.45-7.39 (m, 4H), 7.35-7.24 (m, 6H), 6.88 (s, 2H), 5.47 (s, 2H), 4.21 (dd, J=10.7, 5.3 Hz, 2H), 4.00-3.89 (m, 4H), 3.85 (dd, J=5.1, 2.5 Hz, 2H), 3.70 (dd, J=9.3, 2.5 Hz, 2H), 3.57 (t, J=10.7 Hz, 2H), 3.24 (t, J=6.8 Hz, 2H), 3.08 (t, J=6.4 Hz, 1H), 2.74-2.41 (m, 16H), 1.80-1.70 (m, 6H), 1.71-1.52 (m, 6H).

Preparation of the Hydrochloride Salt of 3,5-diamino-N—(N-(4-(4-((S)-4-amino-3-(3-(bis((2S,3R,4R,5R)-2,3,4,5,6-pentahydroxyhexyl)amino)propylamino)-4-oxobutyl)-5,6,7,8-tetrahydronaphthalen-1-yl)butyl)carbamimidoyl)-6-chloropyrazine-2-carboxamide (XV-dd)

Compound XV-cc (1.24 g, 1.15 mmol) was charged with 4 N aqueous HCl (50 mL) and the mixture was stirred at room temperature for 2 h. The solvent was removed and the residue was purified by C18 reverse phase Gold column to afford compound XV-dd (700 mg, 61%) as a yellow hygroscopic solid. $^1$H NMR (400 MHz, DMSO-d$_6$): δ 10.50 (brs, 1H), 9.67-9.54 (m, 1H), 9.25 (t, J=5.4 Hz, 1H), 9.14-9.02 (m, 1H), 8.94-8.87 (m, 2H), 8.86-8.72 (m, 1H), 8.23 (brs, 1H), 7.81 (brs, 2H), 7.42 (s, 3H), 6.91 (ABq, J=7.8 Hz, 2H), 5.54-5.38 (m, 1), 5.02-4.22 (m, 3H), 4.11-4.00 (m, 2H), 3.95-3.84 (m, 1H), 3.71 (d, J=5.0 Hz, 2H), 3.59 (dd, J=10.7, 2.4 Hz, 2H), 3.54-3.44 (m, 5H), 3.44 (dd, J=10.9, 5.4 Hz, 2H), 3.42-3.16 (m, 13H), 3.03-2.82 (m, 2H), 2.70-2.58 (m, 3H), 2.54 (d, J=9.4 Hz, 1H), 2.23-2.10 (m, 2H), 2.09-2.06 (m, 1H), 2.00-1.90 (m, 1H), 1.76-1.67 (m, 4H), 1.65-1.48 (m, 5H), $^1$H NMR (400 MHz, CD$_3$OD): δ 6.94 (s, 2H), 4.25-4.18 (m, 2H), 4.03 (t, J=6.2 Hz, 1H), 3.86 (d, J=4.6 Hz, 2H), 3.78 (dd, J=10.6, 2.3 Hz, 2H), 3.75-3.62 (m, 6H), 3.61-3.51 (m, 2H), 3.50-3.41 (m, 4H), 3.36 (t, J=7.3 Hz, 2H), 3.21-3.09 (m, 2H), 2.77-2.68 (m, 4H), 2.68-2.60 (m, 4H), 2.33-2.21 (m, 2H), 2.16-2.05 (m, 2H), 1.83-1.76 (m, 4H), 1.75-1.71 (m, 2H), 1.70-1.61 (m, 2H).

HRMS [M+H]$^+$ calculated C$_{39}$H$_{66}$ClN$_{10}$O$_{12}$: 901.4506. and found 901.4553.

Scheme XVI. The Synthesis of the Hydrochloride Salt 3,5-diamino-N-(N-(4-(4-((S)-3-amino-2-(3-(bis((2S,3R,4R,5R)-2,3,4,5,6-pentahydroxyhexyl)amino)propylamino)-3-oxopropyl)phenyl)butyl)carbamimidoyl)-6-chloropyrazine-2-carboxamide (XVI-ee)

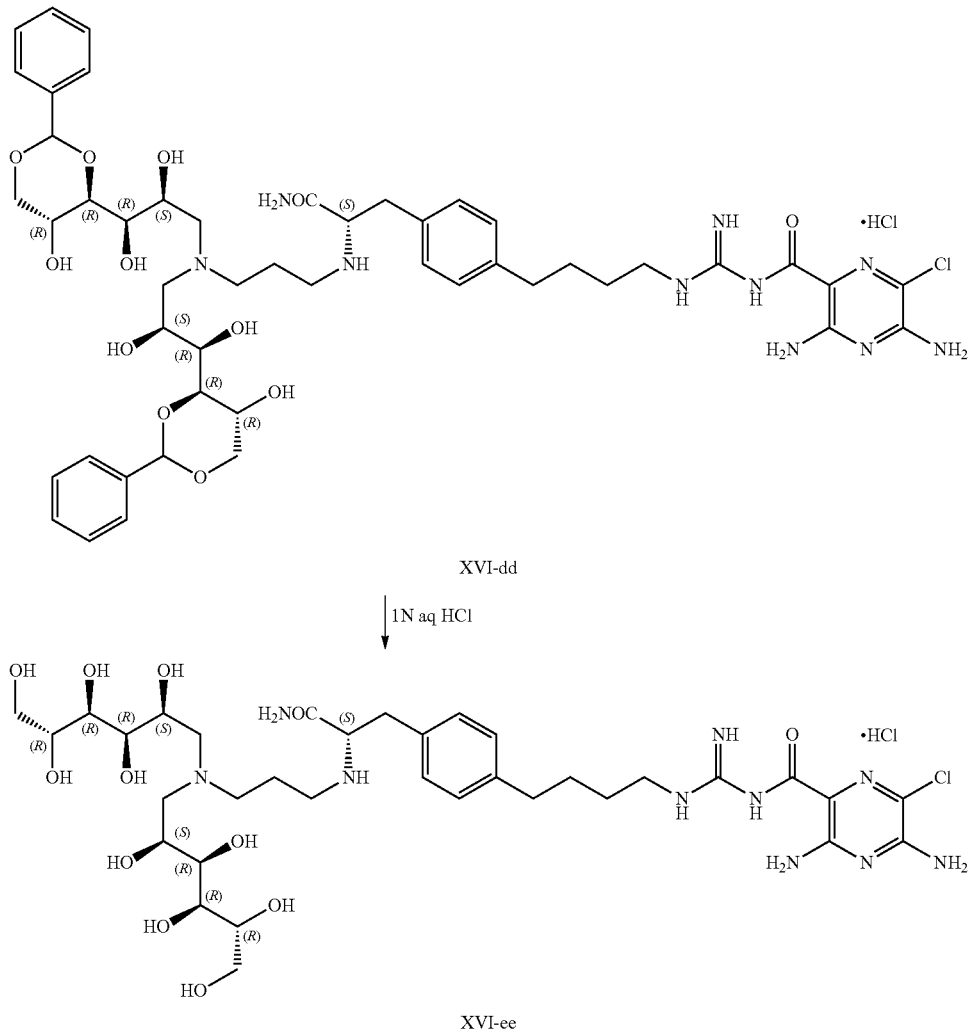

XVI-dd 1N aq HCl

XVI-ee

Scheme XVII. The Synthesis of the Hydrochloride Salt of 3,5-diamino-N-(N-(4-(4-((S)-3-amino-2-(3-(hexyl((2S,3R,4R,5R)-2,3,4,5,6-pentahydroxyhexyl)amino)propylamino)-3-oxopropyl)phenyl)butyl)carbamimidoyl)-6-chloropyrazine-2-carboxamide (XVII-d):

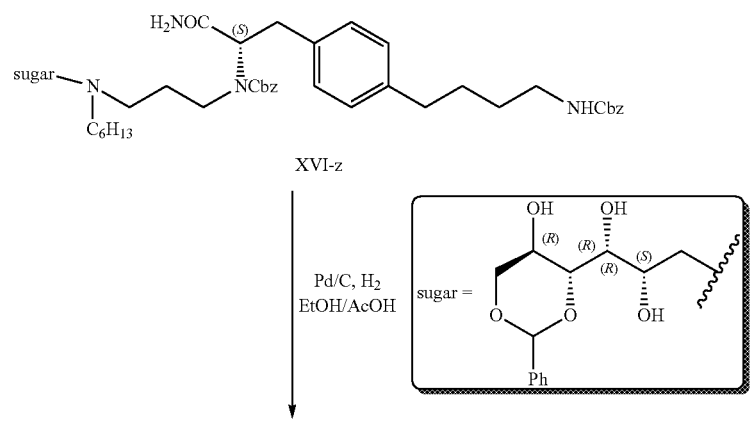

XVI-z

Pd/C, H₂
EtOH/AcOH

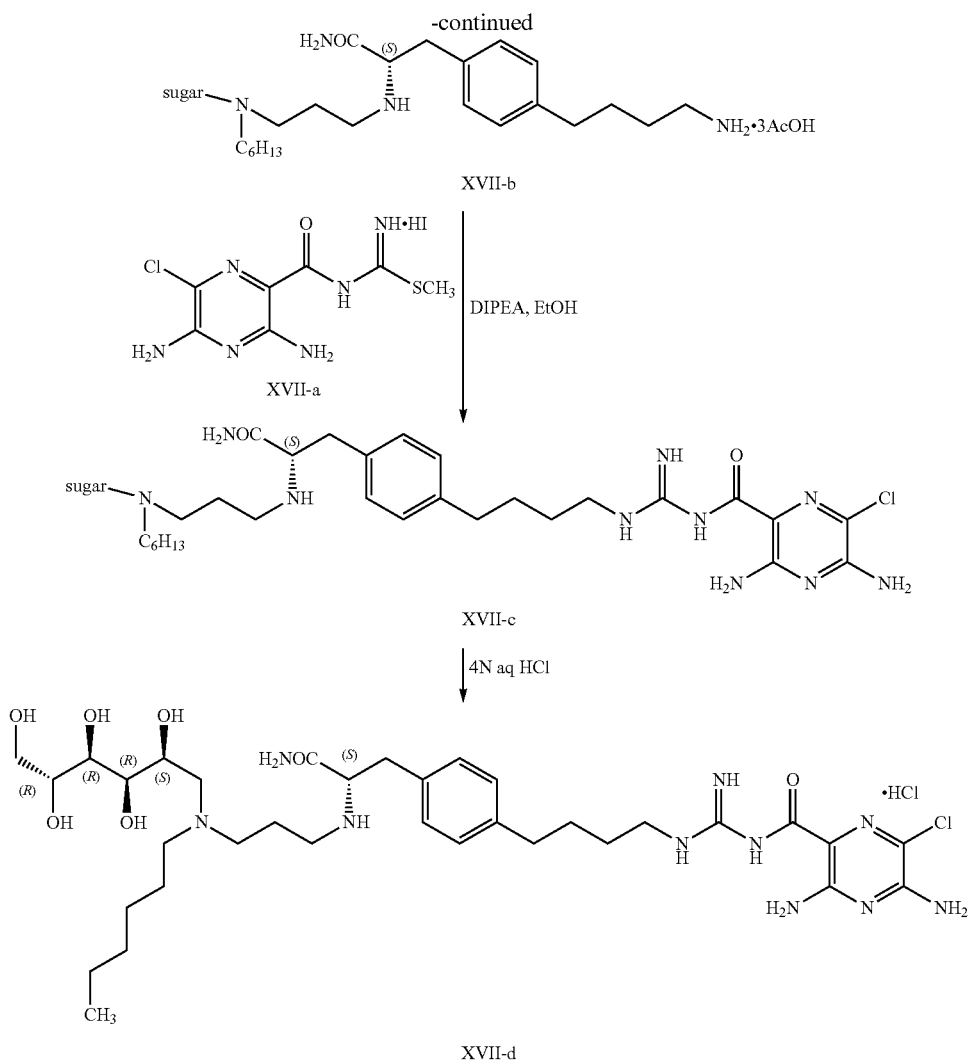

XVII-b

XVII-a

XVII-c

XVII-d

Several assays may be used to characterize the compounds of the present invention. Representative assays are discussed below.

Assay 1. In Vitro Measure of Sodium Channel Blocking Activity and Reversibility

One assay used to assess mechanism of action and/or potency of the compounds of the present invention involves the determination of lumenal drug inhibition of airway epithelial sodium currents measured under short circuit current ($I_{SC}$) using airway epithelial monolayers mounted in Ussing chambers. This assay is described in detail in Hirsh, A. J., Zhang, J., Zamurs, A., et al. Pharmacological properties of N-(3,5-diamino-6-chloropyrazine-2-carbonyl)-N'-4-[4-(2,3-dihydroxypropoxy)phenyl]butyl-guanidine methanesulfonate (552-02), a novel epithelial sodium channel blocker with potential clinical efficacy for CF lung disease. J. Pharmacol. Exp. Ther. 2008; 325(1): 77-88. Cells obtained from freshly excised human, dog, sheep or rodent airways are seeded onto porous 0.4 micron Snapwell™ Inserts (CoStar), cultured at air-liquid interface (ALI) conditions in hormonally defined media, and assayed for sodium transport activity ($I_{SC}$) while bathed in Krebs Bicarbonate Ringer (KBR) in Using chambers. All test drug additions are to the lumenal bath with half-log dose addition protocols (from $1\times10^{-11}$ M to $3\times10^{-5}$ M), and the cumulative change in $I_{SC}$ (inhibition) recorded. All drugs are prepared in dimethyl sulfoxide as stock solutions at a concentration of $1\times10^{-2}$ M and stored at $-20°$ C. Eight preparations are typically run in parallel; two preparations per run incorporate amiloride and/or benzamil as positive controls. After the maximal concentration ($5\times10^{-5}$ M) is administered, the lumenal bath is exchanged three times with fresh drug-free KBR solution, and the resultant $I_{SC}$ measured after each wash for approximately 5 minutes in duration. Reversibility is defined as the percent return to the baseline value for sodium current after the third wash. All data from the voltage clamps are collected via a computer interface and analyzed off-line.

Dose-effect relationships for all compounds are considered and analyzed by the Prism 3.0 program. $IC_{50}$ values, maximal effective concentrations, and reversibility are calculated and compared to amiloride and benzamil as positive controls. The potency of the sodium channel blocking activity of representative compounds relative to amiloride in freshly excised cell from canine airways is shown in Table 1.

TABLE 1

Inhibition of Short-Circuit Current by Compound
(Ia) in canine bronchial epithelial (CBE) cells (IC$_{50}$ nM)

| Compound Number | Potency of Sodium Channel Blockade IC$_{50}$ (nM) |
|---|---|
| Amiloride | 781 |
| II-d | 10.6 |
| III-d | 2.6 |
| Vd | 24 |
| VI-d | 14.3 |
| XIII-bb | 12.5 |
| XIV-d | 6.0 |
| XV-dd | 7.3 |
| XVI-ee | 35.6 |
| XVII-d | 2.9 |
| VIIee | 40.8 |
| VIII-d | 8.8 |
| X-d | 27.4 |
| IX-m | 11.3 |
| XI-cc | 5.5 |
| XII-d | 8.4 |

Assay 2. Mucociliary Clearance (MCC) Studies in Sheep

The animal model that has been used most often to measure changes in MCC is the sheep model. The effect of compounds for enhancing mucociliary clearance (MCC) can be measured using an in vivo model described by Sabater et al., Journal of Applied Physiology, 1999, pp. 2191-2196, incorporated herein by reference.

In these studies, adult sheep were restrained and nasally intubated with an endotracheal tube. Aerosolized test articles were administered over 10-15 minutes to sheep. Radiolabeled $^{99m}$Tc-sulfur colloid (TSC, 3.1 mg/mL; containing approximately 20 mCi) was then administered at a specified time four or eight hours after test article. The radiolabeled aerosol was administered through the endotracheal tube for about 5 minutes. The sheep were then extubated, and total radioactive counts in the lung were measured every 5 minutes for a 1-hour observation period. The rate of radiolabel clearance from the lung is representative of the MCC rate in the animal. The advantage of this system is that it closely simulates the human lung environment. The model also allows for the collection of simultaneous PK/PD information through plasma and urine sampling over the test period. There are also several techniques to measure the drug concentrations on the airway surface during the MCC measurements. These include the collection of exhaled breath condensates or a filter paper method to obtain ASL via bronchoscopy.

The ovine model described above was used to evaluate the in vivo effects (efficacy/durability) of aerosol-delivered Compound II-d on MCC. Treatments consisting of either 4 mL of Compound II-d, Comparative Example 1, (S)-3,5-diamino-6-chloro-N—(N-(4-(4-(2,3-diamino-3-oxopropoxy)phenyl)butyl)carbamimidoyl)pyrazine-2-carboxamide, vehicle (sterile distilled H$_2$O), or test agent in combination with HS were tested. To determine if combining HS with Compound II-d MCC, HS was administered immediately following Compound II-d administration. Test solutions were aerosolized using a Raindrop nebulizer at a flowrate of eight liters per minute and connected to a dosimetry system consisting of a solenoid valve and a source of compressed air (20 psi). The deposited dose of drug in sheep lungs after an aerosol administration using the Raindrop nebulizer is estimated to be 8-15% of the dose. Using a Raindrop nebulizer, radiolabeled TSC was administered over approximately 3 minutes either 4 or 8 hours after drug treatment to evaluate efficacy/durability. Radioactive counts were measured in a central region in the right lung at 5 min intervals for one hour with a gamma camera. Three methods of analysis were utilized, 1) initial rate of clearance (slope) over the first 30 min fitted using linear regression 2) area under the curve for % clearance over time over one hour, and 3) the maximum clearance obtained in one hour.

The effect of Compound II-d at 0.024 nmol/kg, 0.24 nmol/kg and 2.4 nmol/kg were tested and compared to vehicle (4 mL sterile H$_2$O) on sheep MCC four hour post-dosing (FIG. 1). The analyses of effects are shown in Table 2. At all doses tested, Compound II-d enhanced MCC compared to vehicle control. The 0.24 nmol/kg dose was considered to be a maximum (100%) MCC effect at the top of the dose response curve as illustrated in FIG. 2. The ED$_{50}$ dose for Compound II-d was approximately 0.024 nmo/kg. Importantly, doses as high as 24 nmol/kg (1,000 times the ED$_{50}$) exhibited no increase in plasma potassium (a marker for hyperkalemia) as seen in FIG. 2.

TABLE 2

MCC in Sheep at 4 h Post-dose of Compound (Ia) or Vehicle

| Compound II-d Dose | Initial Slope (4.0-4.5 h) | AUC (% Cl-h) | Maximum Clearance |
|---|---|---|---|
| 0.24 nmol/kg (3 µM) | 41.9 ± 3.7* (4) | 19.8 ± 1.4* (4) | 34.4 ± 2.9* (4) |
| 0.024 nmol/kg (300 nM) | 26.5 ± 1.4* (4) | 11.5 ± 0.9* (4) | 20.5 ± 1.0* (4) |
| Vehicle (H$_2$O) 4 mL | 17.2 ± 6.8 (8) | 7.3 ± 1.5 (8) | 12.2 ± 2.9 (8) |

Data are reported as the mean ± SD (n)
*Indicates significance (p < 0.05) from vehicle.

FIG. 3 demonstrates that the potent, in vivo effect on sheep MCC carries over to the napthyl series of compounds as well.

Assay 3. Airway Surface Liquid Drug (ASL) Clearance and Metabolism by Human Airway Epithelium The disappearance of Compound II-d from the apical surface and airway epithelial metabolism were assessed in human bronchial epithelial (HBE) cells (Table 3). In these experiments 25 µL of a 25 µM solution of ENaC blocker was added to the apical surface of HBE cells grown at an air/liquid interface, and the drug concentration in the apical and basolateral compartment was measured over 2 h by UPLC. After 2 h incubation of Compound II-d on the apical surface (37° C.), no metabolites were detected on either the apical or basolateral sides and no Compound II-d was detectable on the basolateral side.

TABLE 3

Apical Disappearance and Metabolism of Compound II-d and Related Compounds vs. Comparative Example 1 in HBE

| Compound | % of Initial Drug Mass on Apical Side (Parent and metabolite, 2 h) | % of Apical Mass as Metabolites (2 h) | % of Initial Apical Mass on Basolateral Side (2 h) | % on Basolateral Side as Metabolites (2 h) |
|---|---|---|---|---|
| II-d | 88.0 ± 021% | None | 1.6 ± 0.15% | None |

Values represent the mean ± SD

Assay 4. Airway Hydration and Sodium Channel Block (In Vitro Model)

Parion Sciences has developed experimental models for assessing airway hydration in cell cultures (Hirsh, A. J., Sabater, J. R., Zamurs, A., et. al. Evaluation of second generation amiloride analogs as therapy for CF lung disease. J. Pharmacol. Exp. Ther. 2004; 311(3): 929-38. Hirsh, A. J., Zhang, J., Zamurs, A., et al. Pharmacological properties of N-(3,5-diamino-6-chloropyrazine-2-carbonyl)-N'-4-[4-(2,3-dihydroxy propoxy)phenyl]butyl-guanidine methanesulfonate (552-02), a novel epithelial sodium channel blocker with potential clinical efficacy for CF lung disease. J. Pharmacol. Exp. Ther. 2008; 325(1): 77-88).

Primary CBE cells are plated onto collagen-coated, porous membranes maintained at an air-liquid interface to assess maintenance of surface liquid volume over time. At the start of the experiment, each 12 mm snapwell insert was removed from the plate containing air-liquid interface culture media, blotted dry, weighed, and 50 µL of vehicle (0.1% DMSO), or ENaC blocker (10 µM in 0.1% DMSO) applied to the apical surface and the mass was recorded. The inserts were immediately returned to a transwell plate (500 µL, Krebs Ringer Bicarbonate (KRB), pH 7.4 in lower chamber) and placed in a 37° C., 5% $CO_2$ incubator. To reduce artifact due to an apical carbohydrate osmotic gradient upon water loss, glucose was not included in the apical buffer. Compound (1a) was tested and compared to vehicle, and the mass of ASL was monitored serially from 0-8 or 24 h. The mass of surface liquid was converted to volume in µL. Data are reported as % initial volume (100%=50 µL).

The duration of sodium transport inhibition was determined indirectly by measuring the buffer retained after a 50 µl volume of experimental buffer was added to the apical surface of CBE cells. Only 12.5±12.1% of vehicle (buffer) remained on the surface after 8 hours and a small increase in surface liquid retention was seen with 10 µM amiloride in the vehicle (25±19.2% after 8 hours). In comparison, Compound II-d significantly increased apical surface liquid retention, maintaining 112±11% (n=6) of the surface liquid over 8 hours.

To test Compound II-d further, the duration of incubation was increased from eight to 24 hours. Amiloride was not tested over 24 hours as the majority of the effect was gone after eight hours. After 24 hours, only 11% of the vehicle buffer remained whereas, Compound II-d maintained 70.6±8.0% (n=42) of surface liquid over 24 hours, a loss of only 16% relative to the 8-hour measure, suggesting Compound II-d exhibits a durable effect on liquid retention.

COMPARATIVE EXAMPLES

The present compounds of Formula (A) are more potent and/or absorbed less rapidly from mucosal surfaces, especially airway surfaces, compared to known sodium channel blockers, such as amiloride and third generation compounds such as Comparative Example 1 described below. Therefore, the compounds of Formula (A) have a longer half-life on mucosal surfaces compared to these know compounds as evidenced by the data shown in Table 4. The disappearance of Compound II-d from the apical surface and airway epithelial metabolism were assessed in HBE and compared to Comparative Example 1 (Table 4). In these experiments 25 µL of a 25 µM solution of ENaC blocker was added to the apical surface of HBE cells grown at an air/liquid interface, and the drug concentration in the apical and basolateral compartment was measured over 2 h by UPLC. After 2 h incubation of the compounds of this present invention on the apical surface (37° C.), no metabolites were detected on either the apical or basolateral sides and only small amounts of these compounds were detectable on the basolateral side. In contrast, most of Comparative Example 1 was eliminated from the apical side with 83% metabolized to the less active carboxylic acid, (S)-2-amino-3-(4-(4-(3-(3,5-diamino-6-chloropyrazine-2-carbonyl)guanidino)butyl) phenoxy)propanoic acid, structure below.

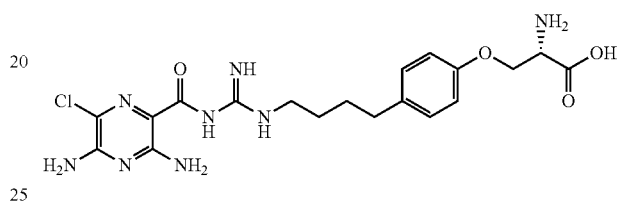

TABLE 4

Apical Disappearance and Metabolism of Compound II-d and Related Compounds vs. Comparative Example 1 in HBE

| Compound | % of Initial Drug Mass on Apical Side (Parent and metabolite, 2 h) | % of Apical Mass on Metabolites (2 h) | % of Initial Apical Mass on Basolateral Side (2 h) | % on Basolateral Side as Metabolites (2 h) |
|---|---|---|---|---|
| II-d | 88.0 ± 21% | None | 1.6 ± 0.15% | None |
| Comparative Example 1 | 41.6 ± 7.6% (8% Parent) | 83.0 ± 03.5% | 8.3 ± 0.2 (1% Parent) | 94.7 ± 1.0% |
| III-d | 53.8 ± 5.9% | none | 3.5 ± 2.2% | None |
| V-d | 25.6 ± 5.1% | none | 9.3 ± 0.86% | None |
| VI-d | 67.3 ± 25.6% | None | 1.2 ± 0.5% | None |
| XIII-bb | 72.6 ± 2.9% | None | 4.2 ± 1.9% | None |
| XIV-d | 62.2 ± 14.9% | None | 0.32 ± 0.6% | None |
| XV-dd | 39.4 ± 6.7% | None | 1.81 ± 1.6% | None |
| XVI-ee | 77.7 ± 12.2% | None | 14.9 ± 1.4% | None |
| XVII-d | 76.6 ± 14.7% | None | 1.9 ± 1.7% | None |
| VII-ee | 66.8 ± 14.1% | None | 6.4 ± 2.1% | None |
| VIII-d | 62.7 ± 4.7% | None | 2.0 ± 0.8% | None |
| X-d | 66.9 ± 22.9% | None | 5.0 ± 3.3% | None |
| IX-m | 61.3 ± 7.7% | None | 1.1 ± 0.2% | None |
| XI-cc | 55.6 ± 17.7% | None | 1.8 ± 0.3% | None |
| XII-d | 31.4 ± 17.4% | None | 9.6 ± 6.3% | None |

Values represent the mean ± SD

Comparative Example 1, (S)-3,5-diamino-6-chloro-N—(N-(4-(4-(2,3-diamino-3-oxopropoxy)phenyl)butyl)carbamimidoyl)pyrazine-2-carboxamide, having the structure:

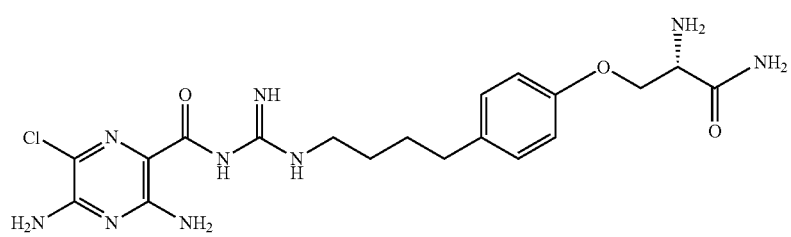 [SMILES: N=C(NCCCCc1ccc(OC[C@H](N)C(N)=O)cc1)NC(=O)c1nc(Cl)c(N)nc1N]

is claimed, described or within the disclosures of WO 2003/070182 (U.S. Pat. Nos. 6,858,615; 7,186,833; 7,189, 719; 7,192,960; and 7,332,496), as sodium channel blockers having useful medicinal properties and can be prepared by methods described therein and others known in the art.

The compound of Comparative Example 1 can be seen on page 15 of US 2005/0080093 and as Compound 2 on page 90 of WO 2008/031048, and as Compound 2 on pages 42-43 of WO 2008/031028. In order to have useful activity in treating Cystic Fibrosis and C.O.P.D a compound must have properties that will cause enhancement of mucociliary clearance (MCC) at doses that do not elevate plasma potassium which will eventually lead to hyperkalemia, a serious and dangerous condition, upon multiple dosing. It must therefore be avoided in this class of compounds, which are known to elevate plasma potassium if they are significantly excreted by the kidney. In order to evaluate this potential, it is beneficial to have MCC activity in vivo and not cause elevation of plasma potassium at the useful dose. One model to assess this is the sheep MCC model described below.

As can be seen from the Table 5 and FIG. 4 the $ED_{50}$ for Comparative Example 1 in the sheep MCC model is approximately 240 nmol/kg (3 mM) using three different measures (slope, AUC and Maximum Clearance). At this dose, which would be a clinically active dose, Comparative Example 1 causes a rise in plasma potassium (FIG. 5) which on repeat dosing will lead to hyperkalemia. Thus, Comparative Example I is unacceptable for human use while Compound II-d produces a safe and effective MCC with a benefit to risk ratio greater than 1000 in this model.

TABLE 5

MCC in Sheep at 4 h Post-dose of vehicle, Comparative Example 1 or Compound II-d

| Dose | Initial Slope (4.0-4.5 h) | AUC (% Cl × h) | Maximum Clearance |
|---|---|---|---|
| Comparative Example 1 240 nmol/kg (3 mM) | 32.2 ± 7.3* (6) | 14.1 ± 2.2* (6) | 22.9 ± 2.1* (6) |
| Comparative Example 1 24 nmol/kg (300 μM) | 14.5 ± 1.3 (3) | 6.9 ± 1.0 (3) | 14.6 ± 0.9 (3) |
| Compound II-d 0.024 nmol/kg (300 nM) | 26.5 ± 1.4* (4) | 11.5 ± 0.9* (4) | 20.5 ± 1.0* (4) |
| Vehicle H₂O (4 mL) | 17.2 ± 6.8 (8) | 7.3 ± 1.5 (8) | 12.2 ± 2.9 (8) |

FIG. 6 graphs the percentage mucus clearance over time by Compound II-d and Comparative Example 1, as described in the MCC model, above. A similar percentage mucus clearance was provided by Compound II-d at a 10,000-fold lower dose than seen with Comparative Example 1. Compound II-d provided a maximal effect in a clinically relevant dose range.

FIG. 7 illustrates the significant increase in plasma potassium levels at an efficacious dose seen in the plasma of the sheep receiving Comparative Example 1 in the MCC study. Compound II-d is 10,000 times more potent in sheep MCC than Comparative Example 1 with no elevation of Plasma K at doses as high as 24 nmol/kg (1000 times the ED50 dose), whereas Comparative Example 1 has elevations of plasma K at the approximate ED50 dose of 3 mM (FIGS. 6 and 7). This, again, demonstrates the unique and unexpected potency and safety advantage of Compound II-d as seen in Table 6 with a Therapeutic Index of 10,000-100,000 times greater renal safety than Comparative Example 1.

TABLE 6

Therapeutic Ratio (Benefit/Risk)

| Compound | MCC Highest Submaximal Dose | Top Dose in Sheep with no Elevation of Plasma Potassium | Therapeutic Ratio |
|---|---|---|---|
| Comparative Example 1 | 3 mM | 300 μM | 0.1 |
| II-d | 300 nM | 300 μM | 1,000 |
| Ratio | 10,000 | 1 | 10,000 |

That which is claimed is:

1. A compound of Formula (A):

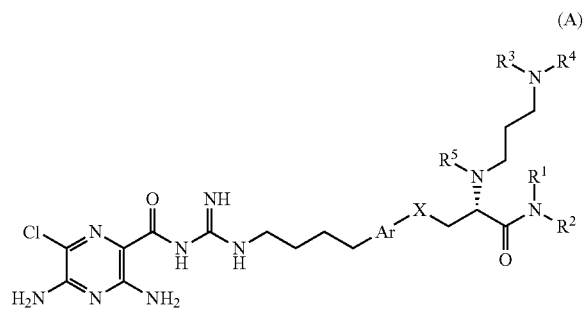

(A)

wherein:

Ar is a moiety selected from the group consisting of:

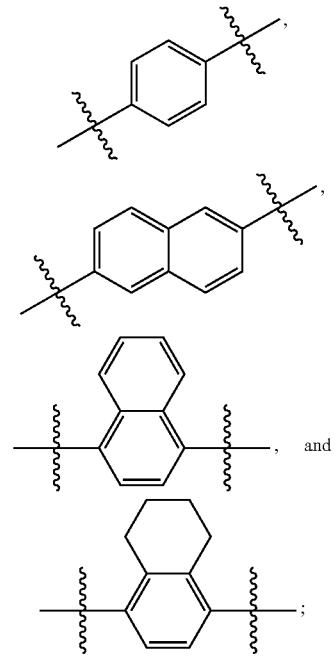

, and

;

X is selected from the group consisting of —CH₂—, —O—, and —S—;

$R^1$ and $R^2$ are independently selected from the group consisting of H and $C_1$-$C_6$ alkyl, or $R^1$ and $R^2$ together with the nitrogen atom to which they are bound form a 5-membered or 6-membered heterocyclic ring optionally containing one additional ring heteroatom selected from N and O;

R³ is an alkyl group having from 3 to 8 carbon atoms or a polyhydroxylated alkyl group having from 3 to 8 carbon atoms;
R⁴ is a polyhydroxylated alkyl group having from 3 to 8 carbon atoms; and
R⁵ is H or $C_1$-$C_3$ alkyl;
or a pharmaceutically acceptable salt thereof.
2. The compound of claim 1, which is represented by any one of Formulae (B)-(G):
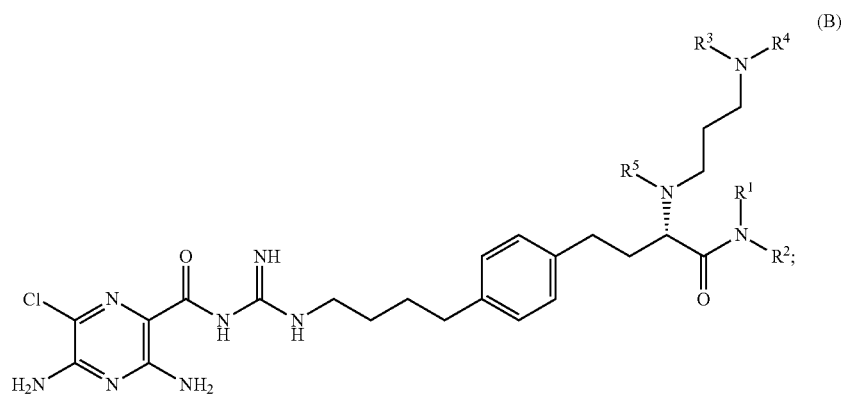
(B)
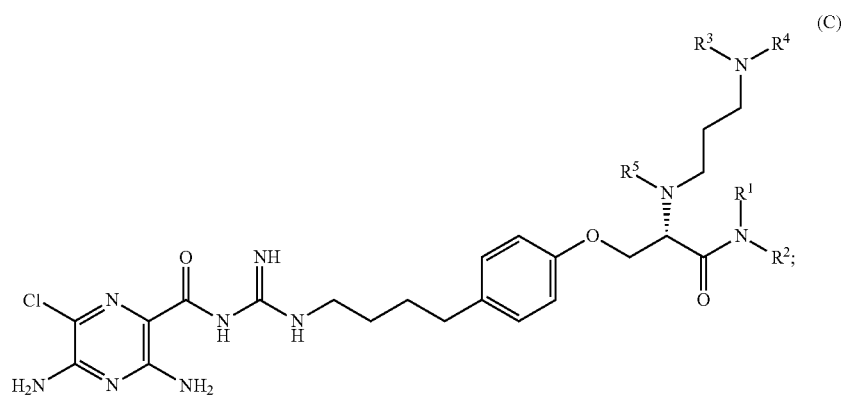
(C)
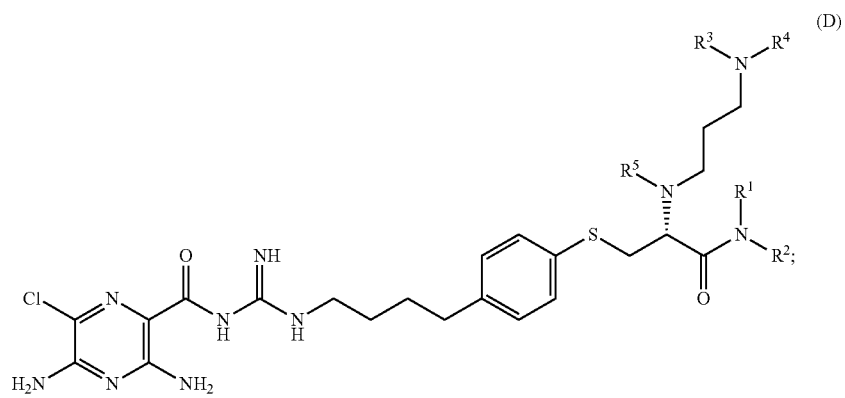
(D)

-continued

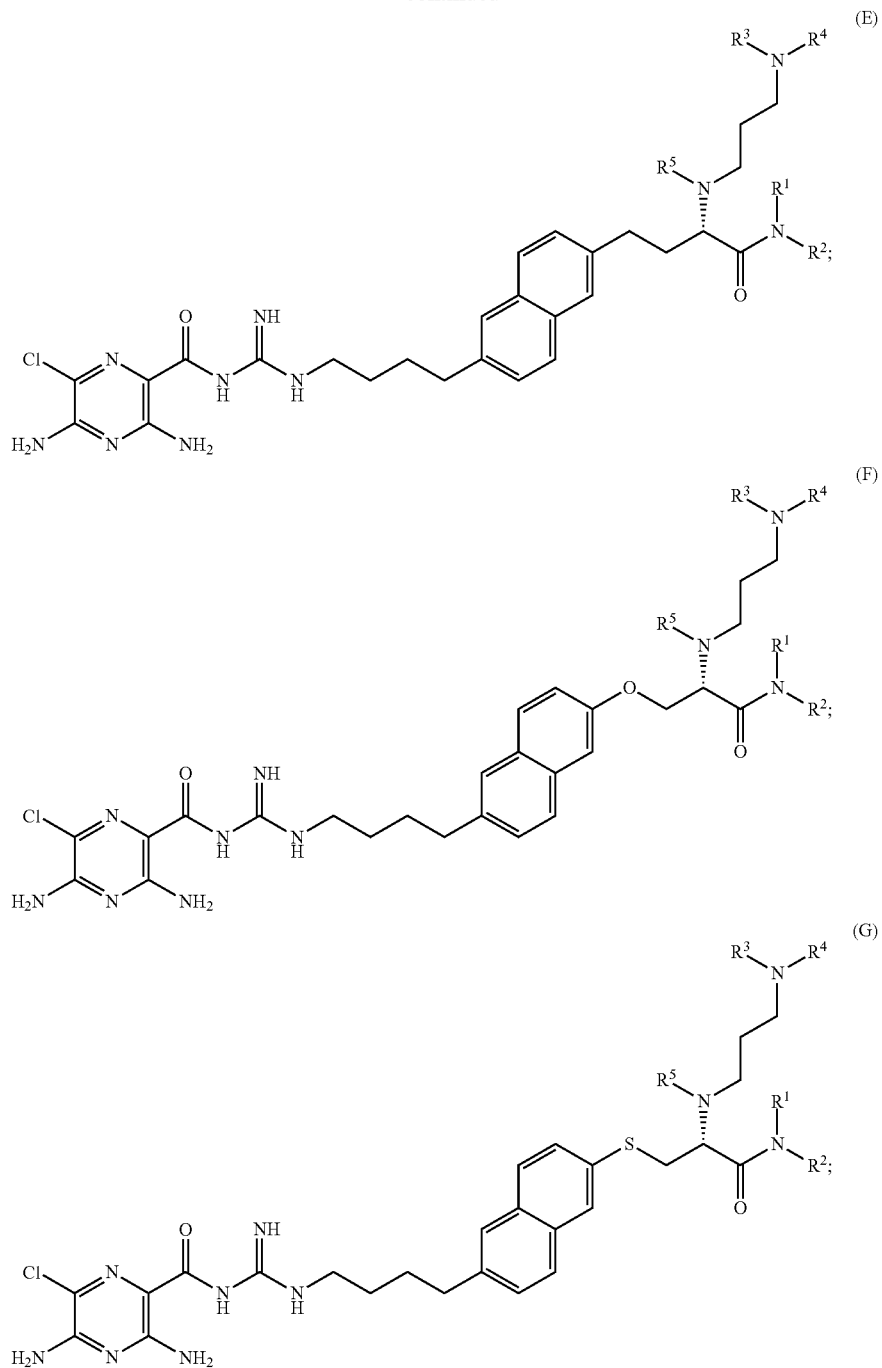

wherein:

R¹ and R² are independently H or $C_1$-$C_6$ alkyl, or R¹ and R² together with the nitrogen atom to which they are bound form a 5-membered or 6-membered heterocyclic ring optionally containing one additional ring heteroatom selected from N and O;

R³ is an alkyl group having from 3 to 8 carbon atoms or a polyhydroxylated alkyl group having from 3 to 8 carbon atoms;

R⁴ is a polyhydroxylated alkyl group having from 3 to 8 carbon atoms; and

R⁵ is H or $C_1$-$C_3$ alkyl;

or a pharmaceutically acceptable salt thereof.

3. The compound of claim 1, wherein R³ is a polyhydroxylated alkyl group represented by the formula —$CH_2$—$(CHR^5)_n$, wherein n is an integer selected from 2, 3, 4, 5, 6, and 7; and R⁵ is independently in each instance H or OH, with the proviso that at least two of the R⁵ groups are OH, or a pharmaceutically acceptable salt thereof.

4. The compound of claim 1, wherein the polyhydroxylated alkyl group is represented by the formula —$CH_2$—CHOH—$(CHR^6)_m$, wherein m is an integer selected from 1, 2, 3, 4, 5, and 6; and R⁶ is independently in each instance H or OH, with the proviso that at least one of the $R^6$ groups is OH, or a pharmaceutically acceptable salt thereof.

5. The compound of claim 1, wherein the polyhydroxylated alkyl group is represented by the formula —CH$_2$—(CHOH)$_n$—CH$_2$OH, wherein n is an integer selected from 1, 2, 3, 4, 5, and 6; or a pharmaceutically acceptable salt thereof.

6. The compound of claim 1, wherein the polyhydroxylated alkyl group is represented by the formula:

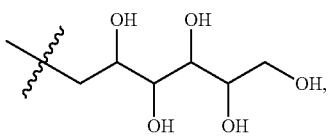 [SMILES: *CC(O)C(O)C(O)C(O)CO]

or a pharmaceutically acceptable salt thereof.

7. The compound of claim 1, wherein the polyhydroxylated alkyl group is represented by the formula:

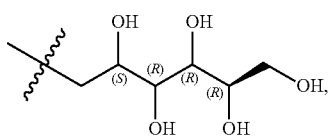

or a pharmaceutically acceptable salt thereof.

8. The compound of claim 1, wherein the compound is selected from one of the following:

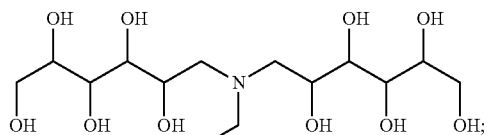

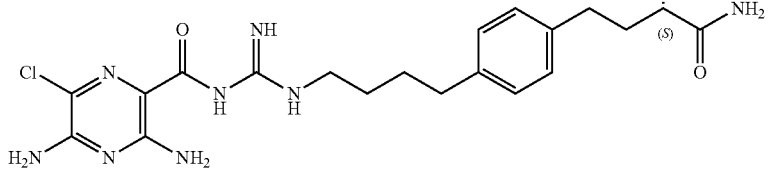

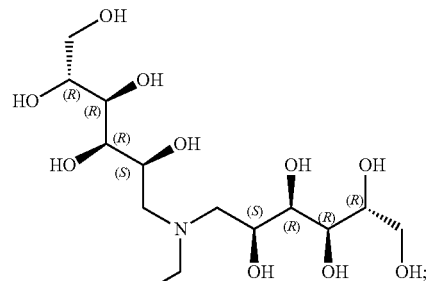

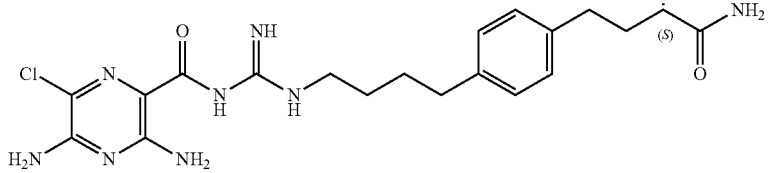

-continued
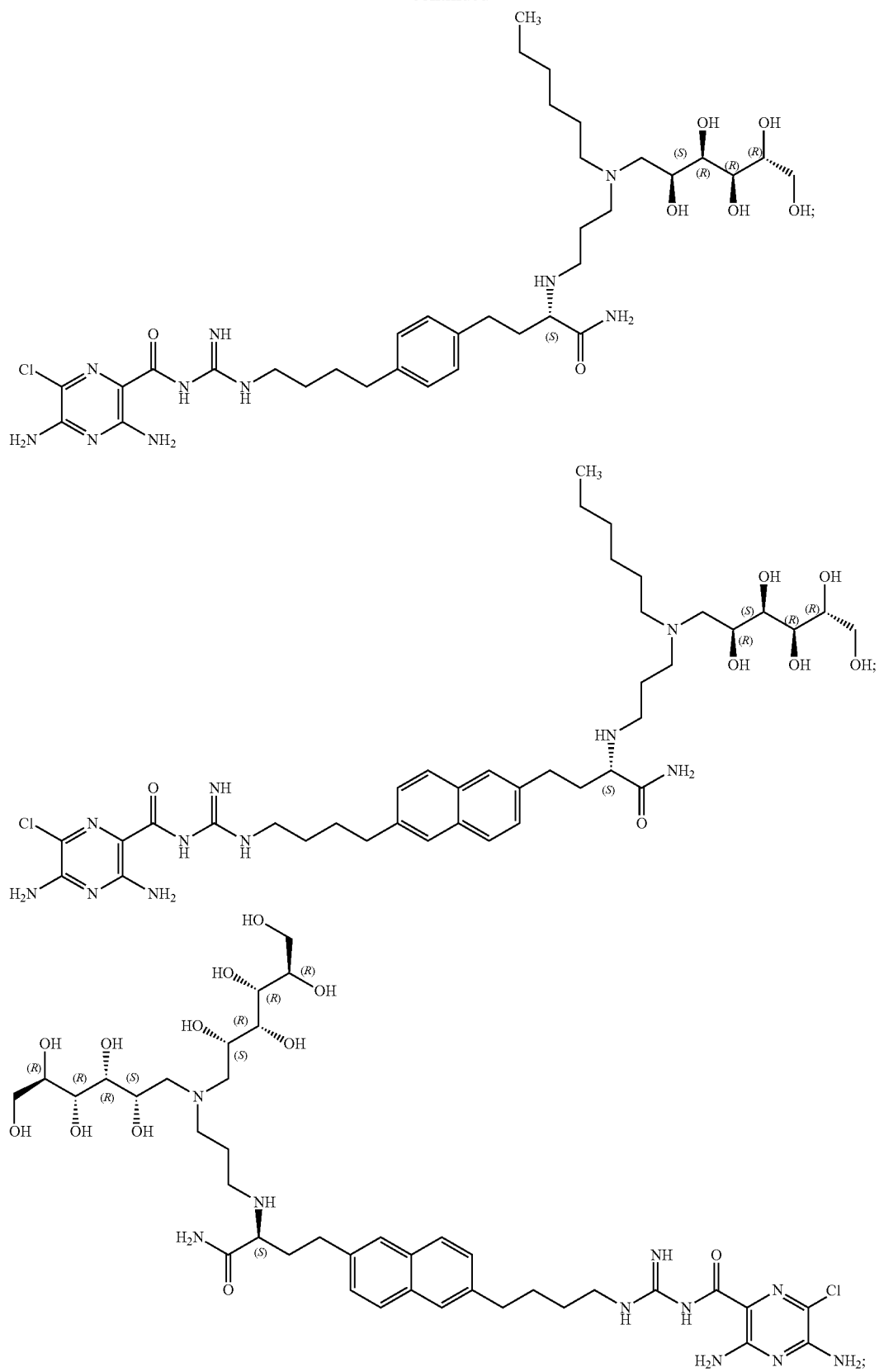

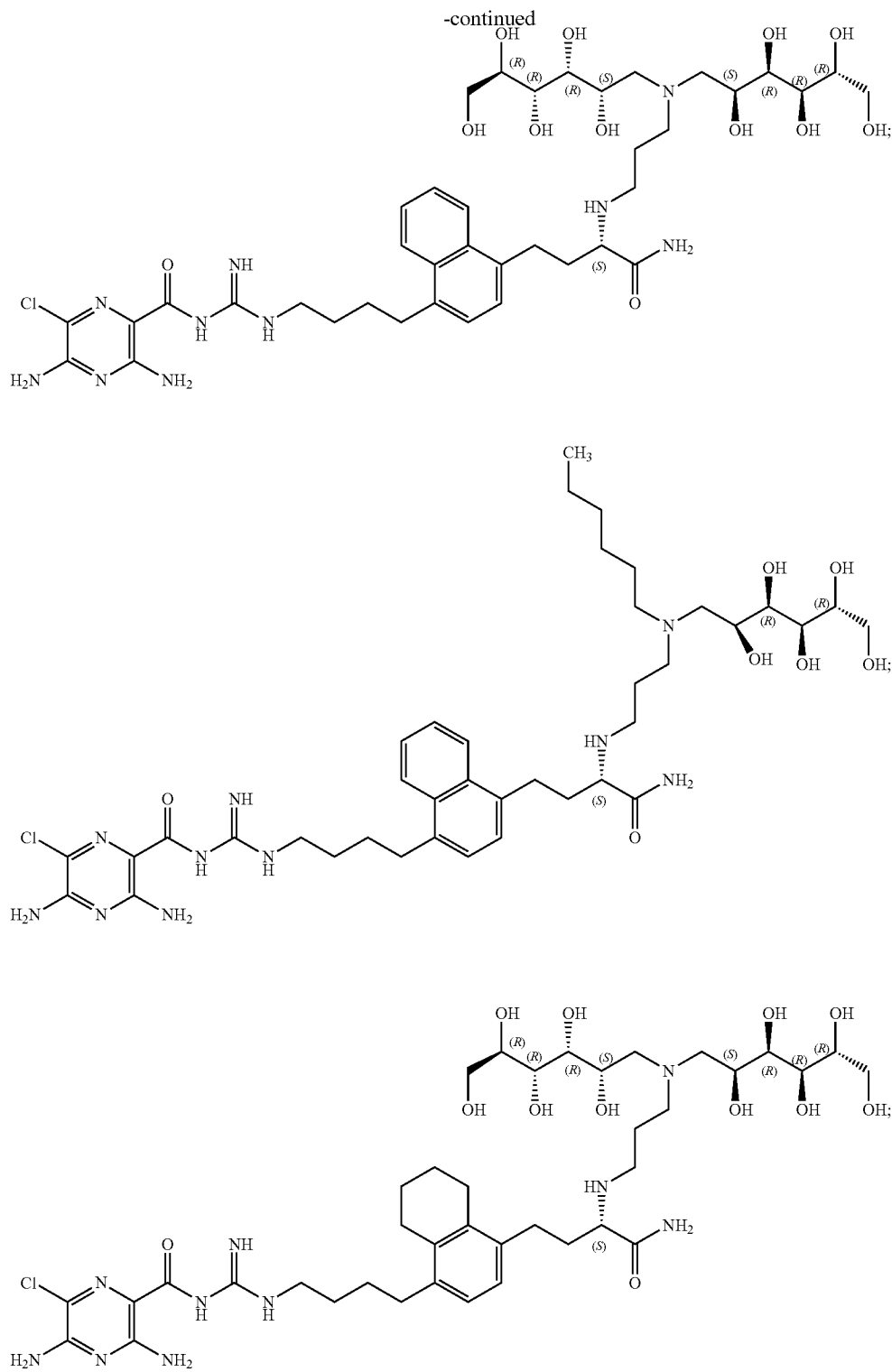

and pharmaceutically acceptable salts thereof.

9. A pharmaceutical composition comprising a pharmaceutically effective amount of a compound of claim 1, or a pharmaceutically acceptable salt thereof, and a pharmaceutically acceptable carrier or excipient.

10. The composition of claim 9, wherein said composition is suitable for inhalation.

11. The composition of claim 10, which is a solution for aerosolization and administration by nebulizer, metered dose inhaler, or dry powder inhaler.

12. The pharmaceutical composition of claim 9, further comprising an osmolyte.

13. The pharmaceutical composition of claim 12, wherein the osmolyte is hypertonic saline.

14. A compound of one of the following formulae:
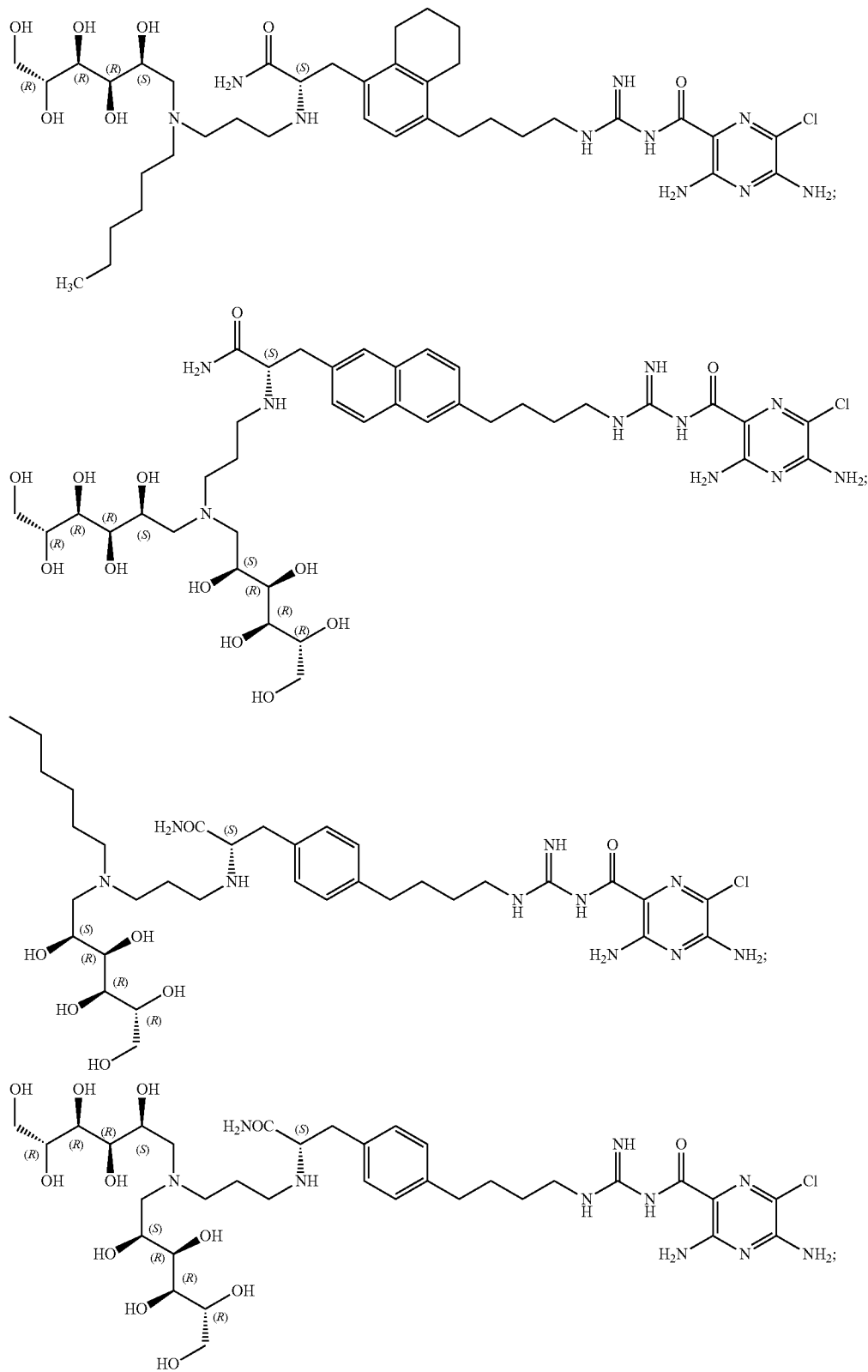

-continued

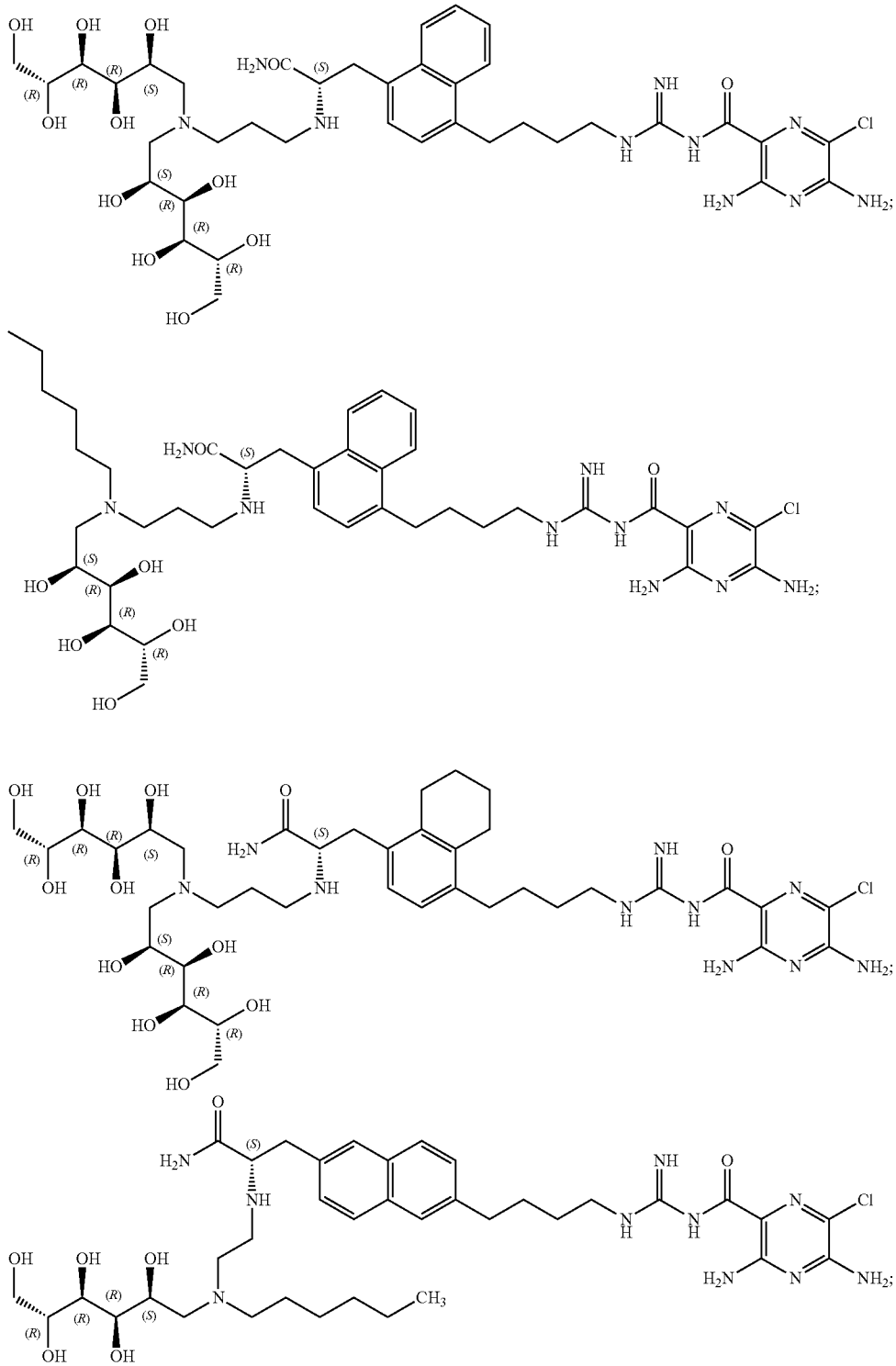

or a pharmaceutically acceptable salt thereof.

15. A pharmaceutical composition comprising a pharmaceutically effective amount of a compound of claim 14, or a pharmaceutically acceptable salt thereof, and a pharmaceutically acceptable carrier or excipient.

16. The pharmaceutical composition of claim 15, further comprising an osmolyte.

17. The pharmaceutical composition of claim 16, wherein the osmolyte is hypertonic saline.

18. The compound of claim 1, wherein the compound is represented by any one of Formulae (H)-(M):
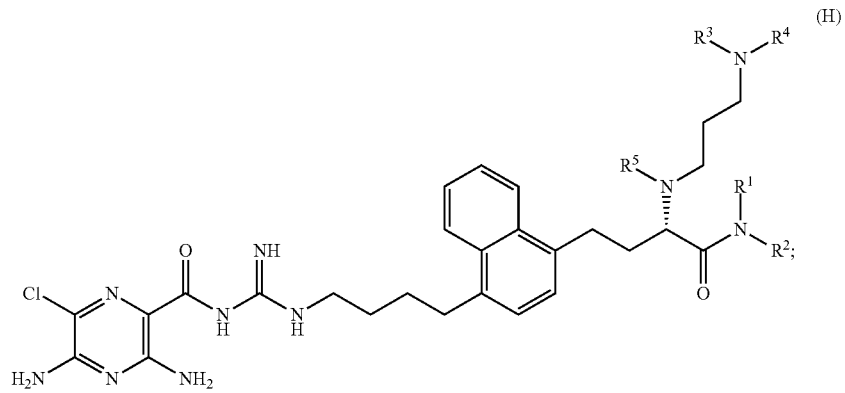
(H)
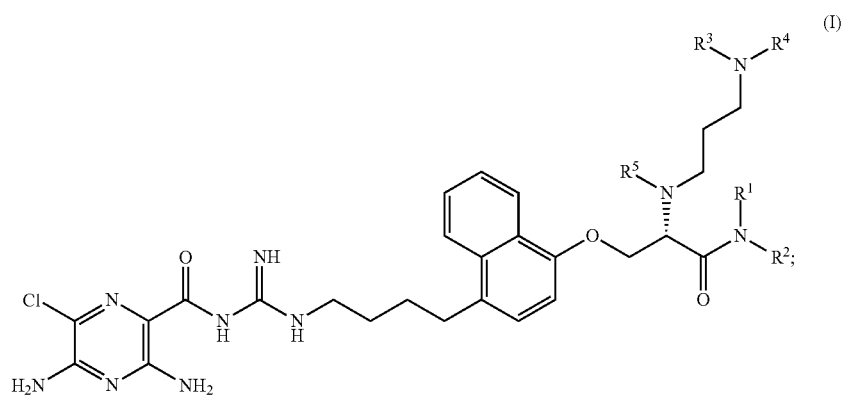
(I)
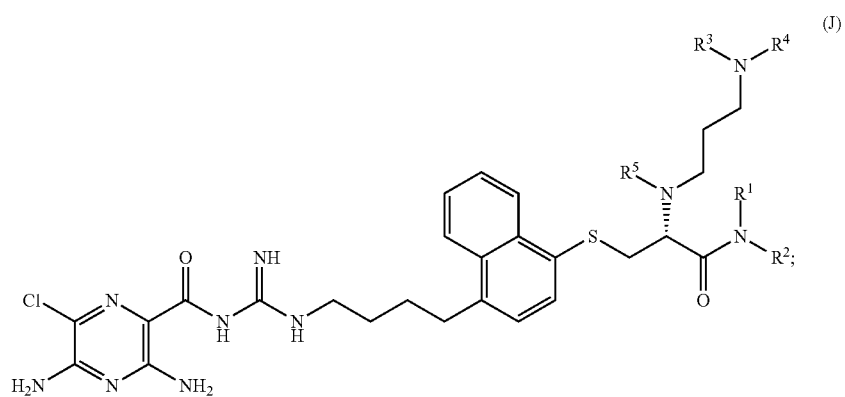
(J)
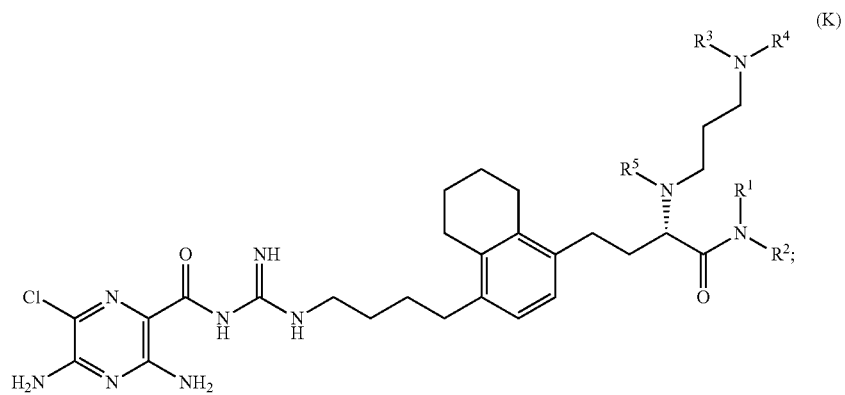
(K)

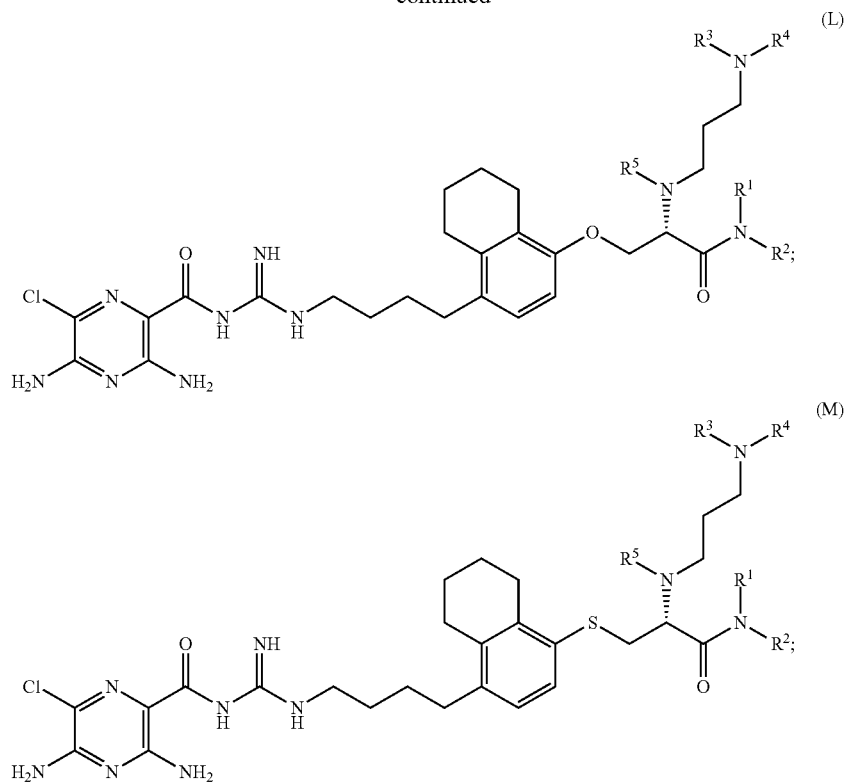

wherein:
- $R^1$ and $R^2$ are independently H or $C_1$-$C_6$ alkyl, or $R^1$ and $R^2$ together with the nitrogen atom to which they are bound form a 5-membered or 6-membered heterocyclic ring optionally containing one additional ring heteroatom selected from N and O;
- $R^3$ is an alkyl group having from 3 to 8 carbon atoms or a polyhydroxylated alkyl group having from 3 to 8 carbon atoms;
- $R^4$ is a polyhydroxylated alkyl group having from 3 to 8 carbon atoms; and
- $R^5$ is H or $C_1$-$C_3$ alkyl;

or a pharmaceutically acceptable salt thereof.

19. A compound of one of the following formulae:

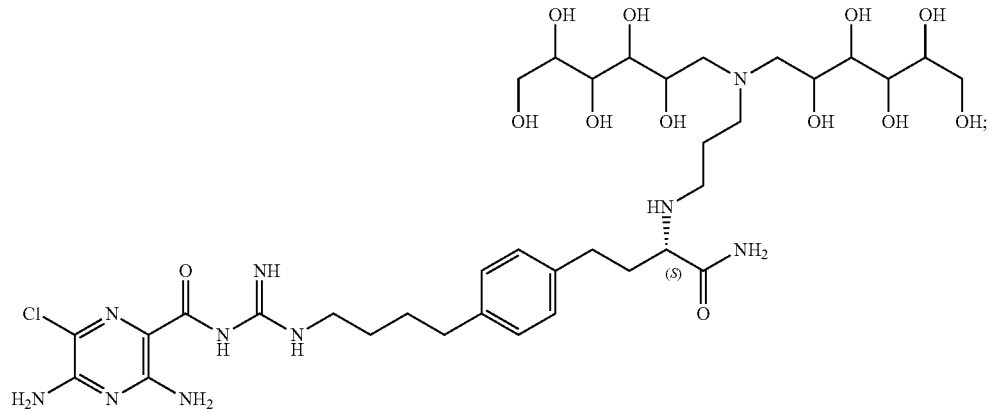

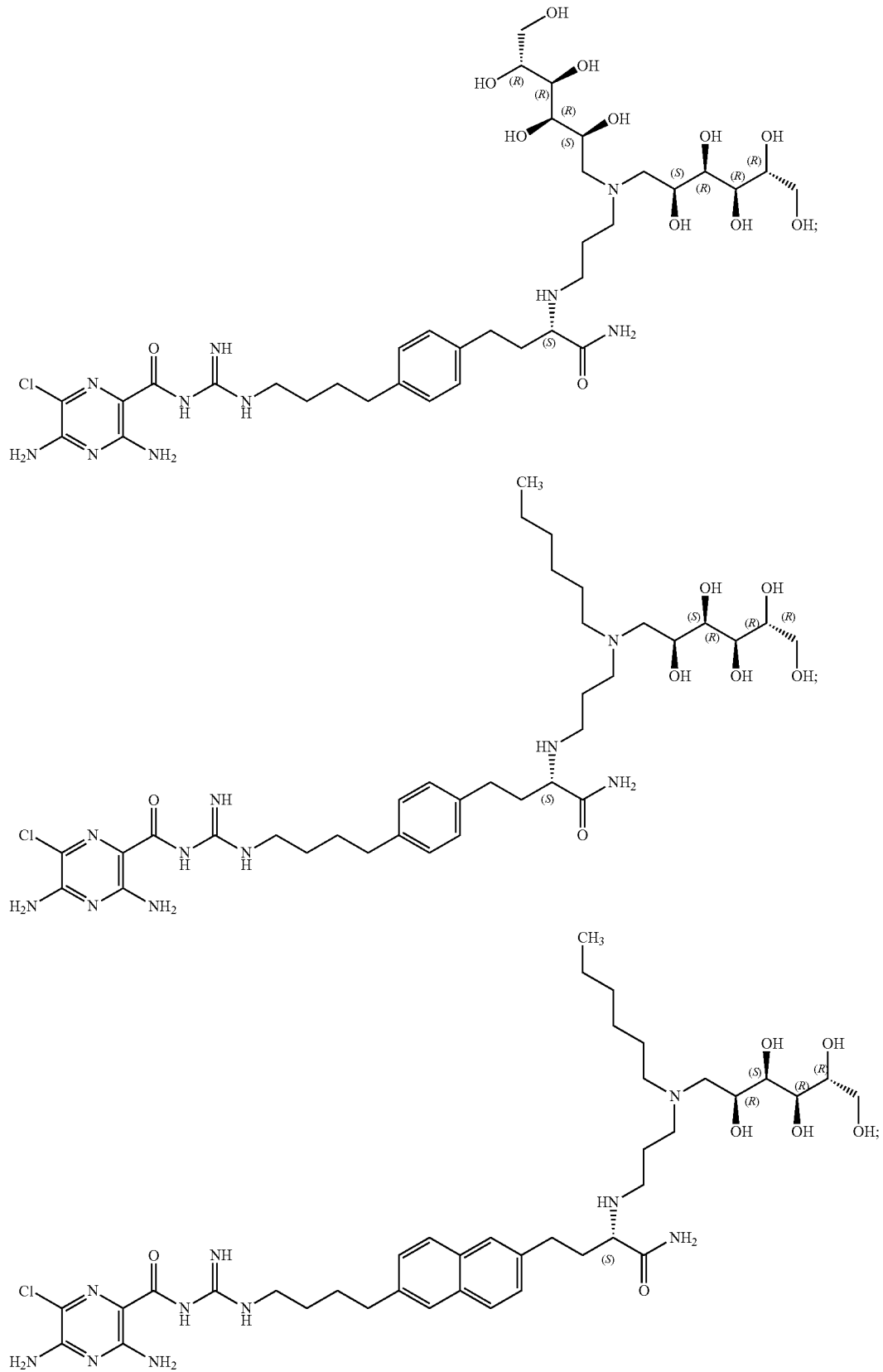

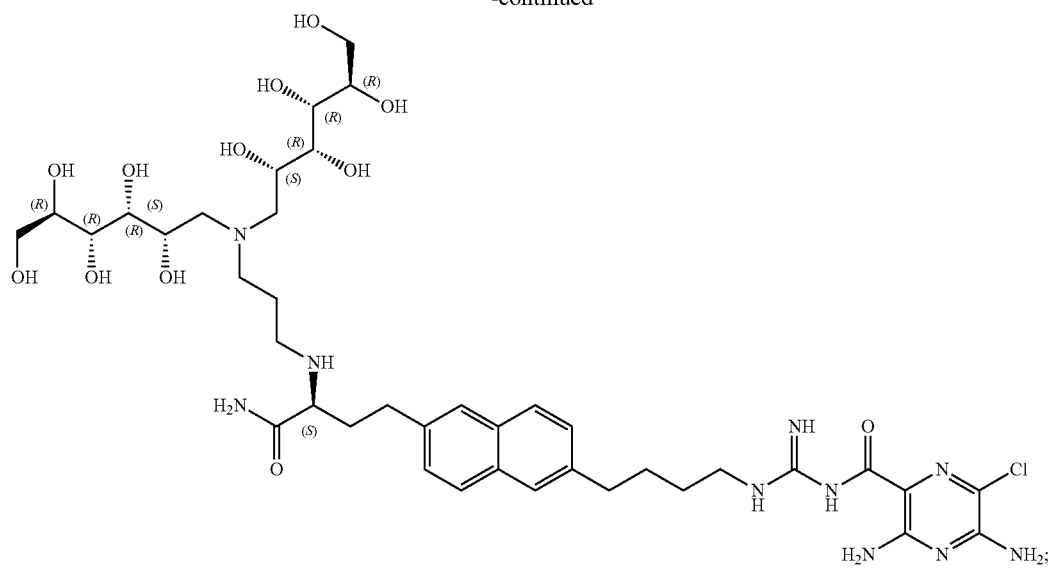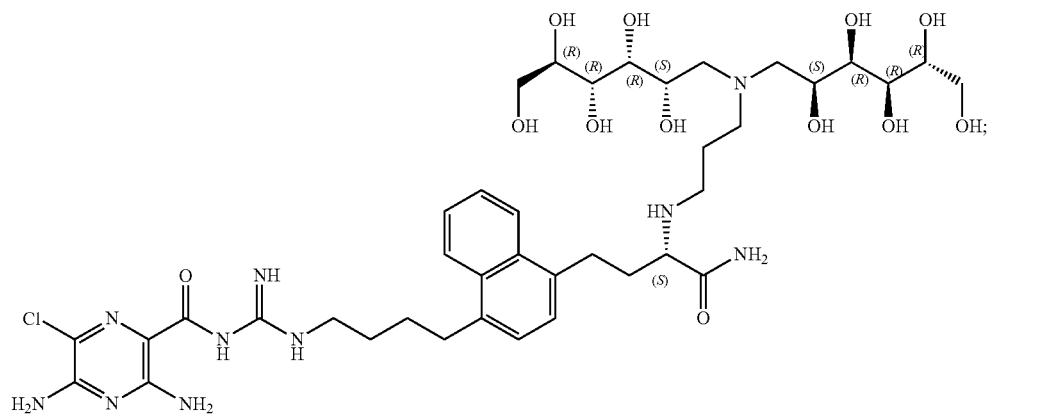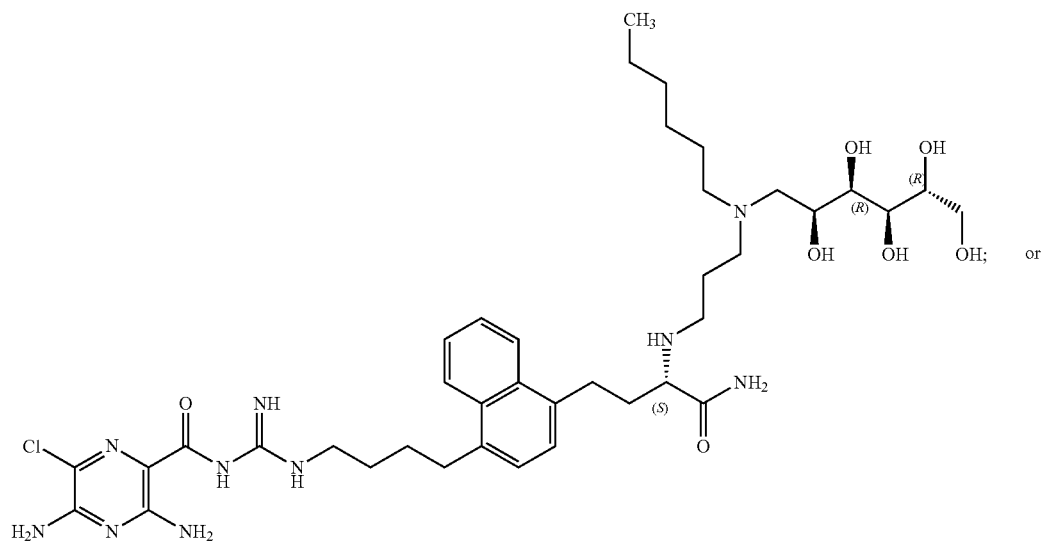

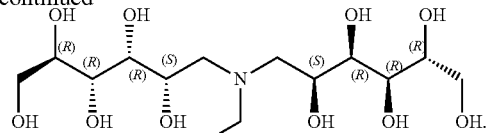
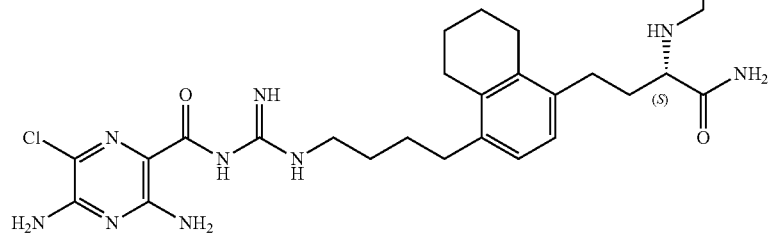
20. A compound of one of the following formulae:
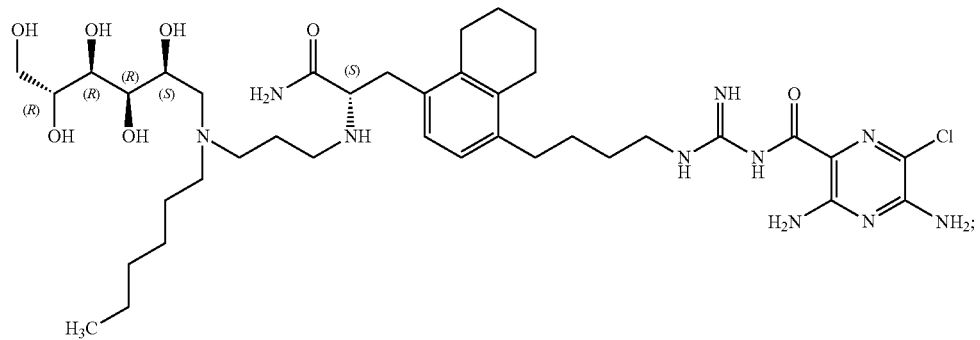
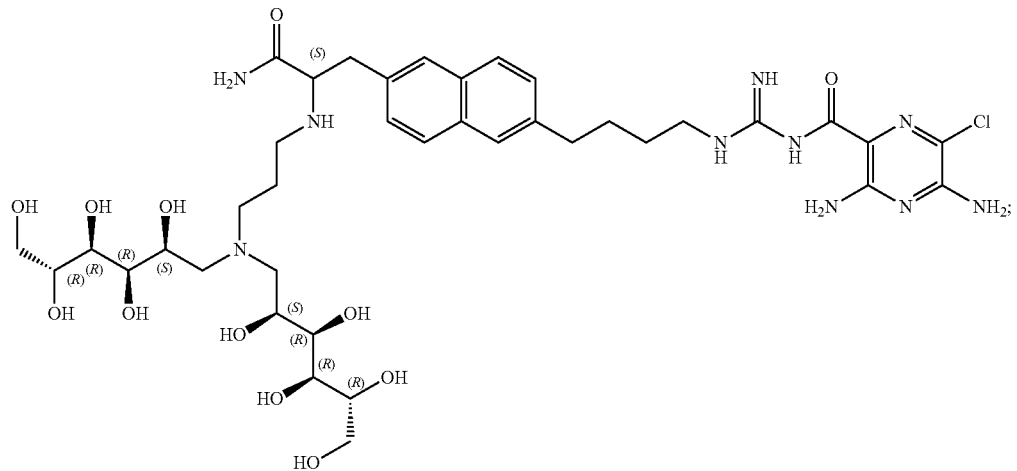

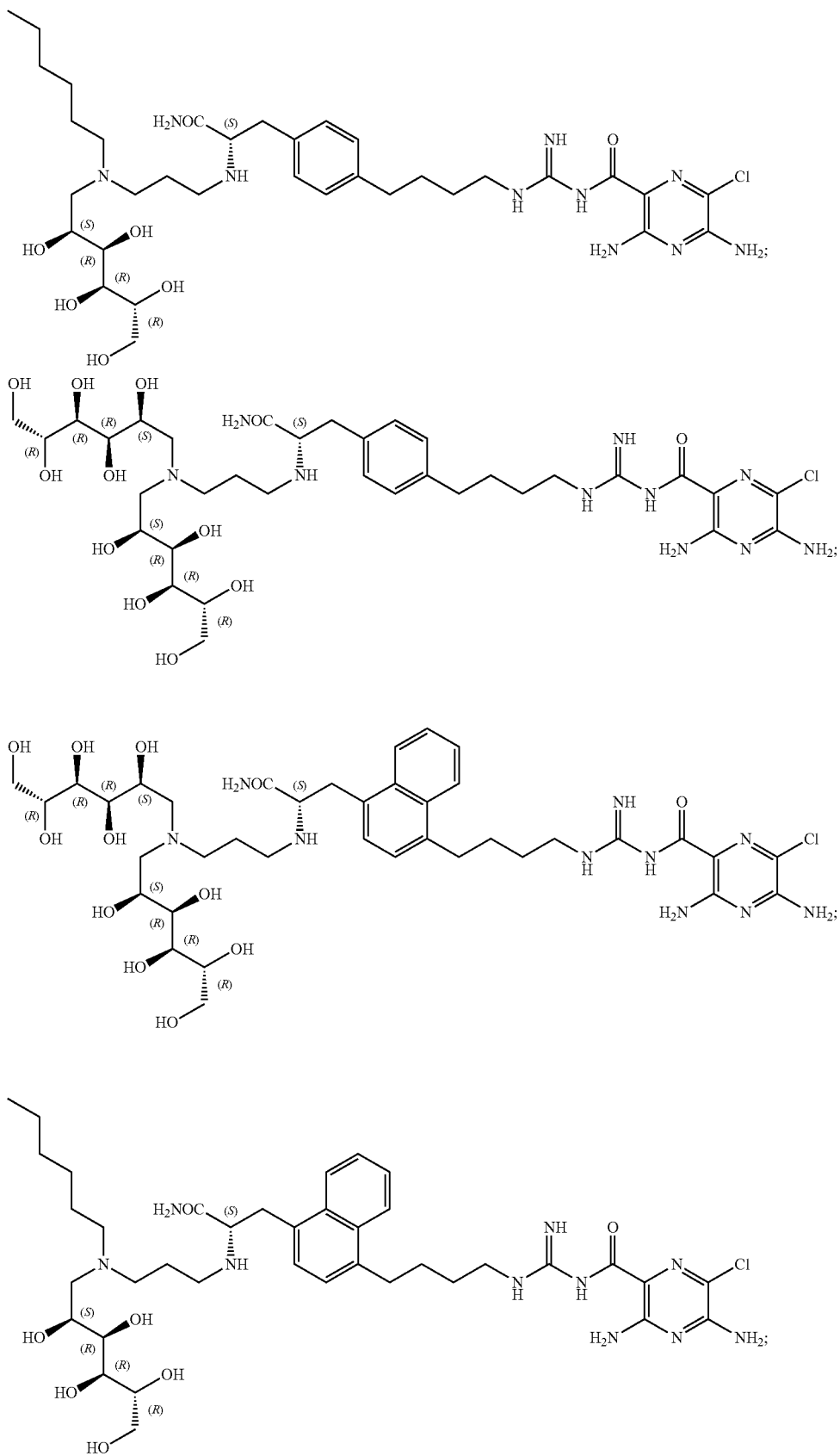

-continued
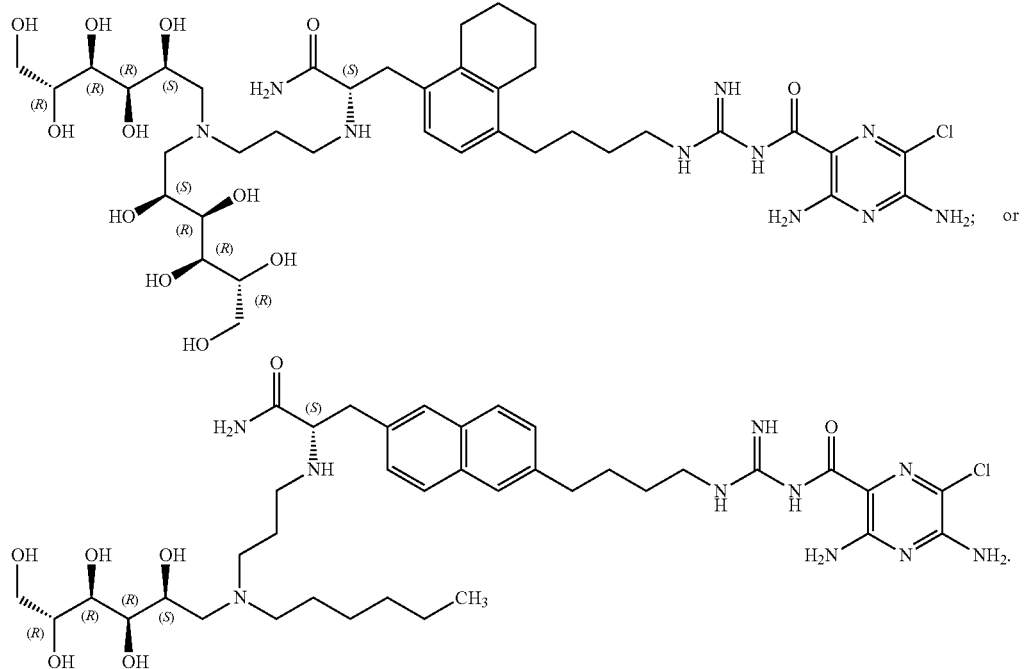
* * * * *

UNITED STATES PATENT AND TRADEMARK OFFICE
CERTIFICATE OF CORRECTION

Page 1 of 2

PATENT NO. : 9,695,134 B2
APPLICATION NO. : 14/592480
DATED : July 4, 2017
INVENTOR(S) : Michael R. Johnson It is certified that error appears in the above-identified patent and that said Letters Patent is hereby corrected as shown below:

In the Claims

In Claim 14, at Column 197, the structure:

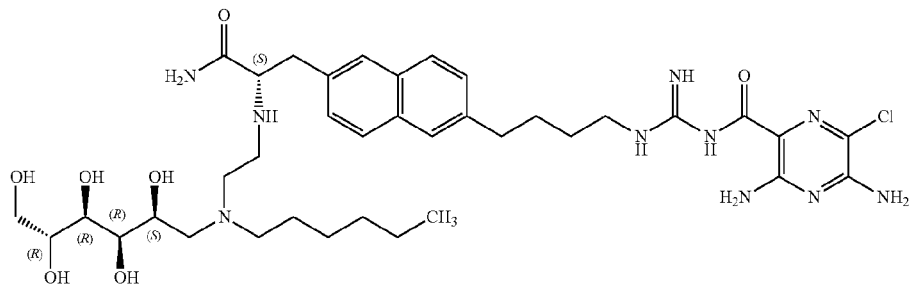

Should be replaced by the structure:

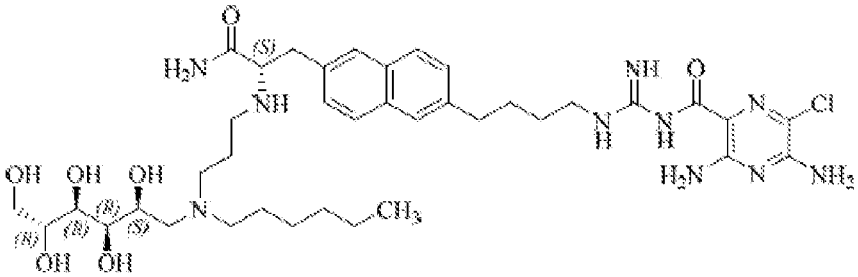

Signed and Sealed this
Fifth Day of September, 2017

In Claim 20, at Column 207, the structure:
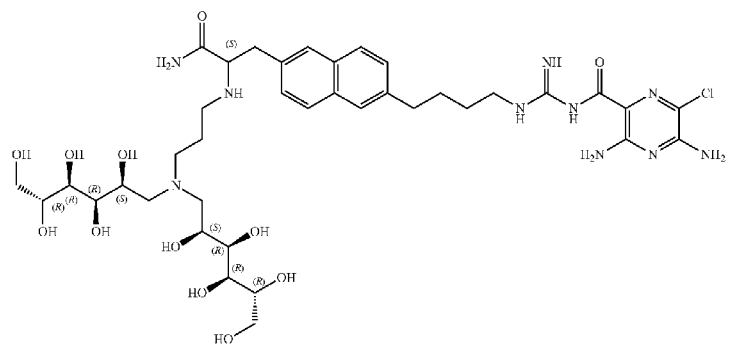
Should be replaced by the structure:
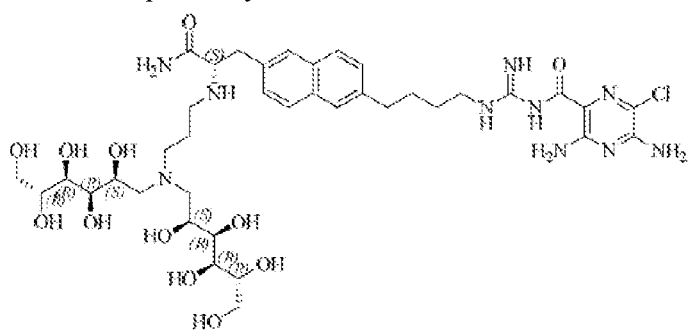

Joseph Matal
*Performing the Functions and Duties of the
Under Secretary of Commerce for Intellectual Property and
Director of the United States Patent and Trademark Office*